US009493450B2

(12) United States Patent
Wu et al.

(10) Patent No.: US 9,493,450 B2
(45) Date of Patent: Nov. 15, 2016

(54) CYCLOPROPYLAMINES AS LSD1 INHIBITORS

(71) Applicant: Incyte Corporation, Wilmington, DE (US)

(72) Inventors: Liangxing Wu, Wilmington, DE (US); Chunhong He, Chadds Ford, PA (US); Leah C. Konkol, Wilmington, DE (US); Ding-Quan Qian, Newark, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 14/620,884

(22) Filed: Feb. 12, 2015

(65) Prior Publication Data
US 2015/0225394 A1    Aug. 13, 2015

Related U.S. Application Data

(60) Provisional application No. 61/939,458, filed on Feb. 13, 2014, provisional application No. 62/061,258, filed on Oct. 8, 2014.

(51) Int. Cl.
| | | |
|---|---|---|
| *C07D 417/14* | (2006.01) | |
| *C07D 211/58* | (2006.01) | |
| *C07D 401/04* | (2006.01) | |
| *C07D 401/14* | (2006.01) | |
| *C07D 205/04* | (2006.01) | |
| *C07D 211/34* | (2006.01) | |
| *C07D 405/14* | (2006.01) | |
| *C07D 405/12* | (2006.01) | |
| *C07D 413/06* | (2006.01) | |
| *C07D 211/98* | (2006.01) | |

(52) U.S. Cl.
CPC ........... *C07D 417/14* (2013.01); *C07D 205/04* (2013.01); *C07D 211/34* (2013.01); *C07D 211/58* (2013.01); *C07D 211/98* (2013.01); *C07D 401/04* (2013.01); *C07D 401/14* (2013.01); *C07D 405/12* (2013.01); *C07D 405/14* (2013.01); *C07D 413/06* (2013.01)

(58) Field of Classification Search
CPC .................................................. C07D 417/14
See application file for complete search history.

(56) References Cited

U.S. PATENT DOCUMENTS

| | | | |
|---|---|---|---|
| 5,658,857 A | 8/1997 | Andree et al. | |
| 7,468,375 B2 * | 12/2008 | Dress et al. | 514/300 |
| 8,115,000 B2 | 2/2012 | Rajagopalan et al. | |
| 8,853,408 B2 | 10/2014 | Johnson | |
| 2002/0151549 A1 | 10/2002 | Hayakawa et al. | |
| 2004/0023972 A1 | 2/2004 | Sundermann et al. | |
| 2004/0058938 A1 | 3/2004 | Cullmann et al. | |
| 2004/0082635 A1 | 4/2004 | Hashimoto et al. | |
| 2004/0082781 A1 | 4/2004 | Hibi et al. | |
| 2004/0220189 A1 | 11/2004 | Sun et al. | |
| 2005/0009832 A1 | 1/2005 | Sun et al. | |
| 2005/0113283 A1 | 5/2005 | Solow-Cordero et al. | |
| 2006/0178399 A1 | 8/2006 | Nishizawa et al. | |
| 2007/0004772 A1 | 1/2007 | Sun et al. | |
| 2008/0249154 A1 | 10/2008 | Ohmoto et al. | |
| 2009/0203690 A1 | 8/2009 | Akritopoulou-Zanze et al. | |
| 2009/0318436 A1 | 12/2009 | Albrecht et al. | |
| 2010/0113441 A1 | 5/2010 | Siegel et al. | |
| 2011/0105457 A1 | 5/2011 | Taniyama et al. | |
| 2011/0112067 A1 | 5/2011 | Hartmann et al. | |
| 2012/0220582 A1 | 8/2012 | Mitchell et al. | |
| 2012/0283266 A1 | 11/2012 | Ortega Munoz et al. | |
| 2012/0322877 A1 | 12/2012 | Casero et al. | |
| 2013/0035377 A1 | 2/2013 | Minucci et al. | |
| 2013/0040946 A1 | 2/2013 | Siegel et al. | |
| 2013/0090386 A1 | 4/2013 | Ortega Munoz et al. | |
| 2013/0095067 A1 | 4/2013 | Baker et al. | |
| 2013/0109751 A1 | 5/2013 | Salvatore | |
| 2013/0197013 A1 | 8/2013 | Fyfe et al. | |
| 2013/0203754 A1 | 8/2013 | Yang et al. | |
| 2013/0217878 A1 | 8/2013 | Lizuka et al. | |
| 2013/0231342 A1 | 9/2013 | Munoz et al. | |
| 2013/0303545 A1 | 11/2013 | Maes et al. | |
| 2014/0011857 A1 | 1/2014 | Casero et al. | |
| 2014/0018393 A1 | 1/2014 | Johnson et al. | |
| 2014/0094445 A1 | 4/2014 | Vakayalapati et al. | |
| 2014/0206757 A1 | 7/2014 | Shi et al. | |
| 2014/0213657 A1 | 7/2014 | Munoz et al. | |
| 2014/0228405 A1 | 8/2014 | Tomita et al. | |
| 2014/0256742 A1 | 9/2014 | Baker et al. | |
| 2014/0343118 A1 | 11/2014 | McCafferty et al. | |
| 2015/0065434 A1 | 3/2015 | Woster et al. | |
| 2015/0065495 A1 | 3/2015 | Vankayalapati et al. | |
| 2015/0133564 A1 | 5/2015 | Oh et al. | |

(Continued)

FOREIGN PATENT DOCUMENTS

| | | |
|---|---|---|
| CA | 2831143 | 10/2012 |
| CA | 2844525 | 2/2013 |

(Continued)

OTHER PUBLICATIONS

Patani et. al. "Bioisosterism: A Rational Approach in Drug Design" Chemical Reviews 1996, 96, 3147-3176.*
Wakefield, Basil "Fluorinated Pharmaceuticals" Innovations in Pharmaceutical Technology 2003, 74, 76-78, Online "http://web.archive.org/web/20030905122408/http://www.iptonline.com/articles/public/IPTFOUR74NP.pdf." (accessed via Wayback machine Nov. 20, 2009 showing web availability as of Sep. 2003).*

(Continued)

*Primary Examiner* — David K. O'Dell
(74) *Attorney, Agent, or Firm* — Fish & Richardson P.C.

(57) ABSTRACT

The present invention is directed to cyclopropylamine derivatives which are LSD1 inhibitors useful in the treatment of diseases such as cancer.

33 Claims, No Drawings

(56) References Cited

U.S. PATENT DOCUMENTS

| | | | |
|---|---|---|---|
| 2015/0225375 A1 | 8/2015 | Wu et al. | |
| 2015/0225379 A1 | 8/2015 | Wu et al. | |
| 2015/0225401 A1 | 8/2015 | Wu et al. | |
| 2015/0232436 A1 | 8/2015 | Baker et al. | |
| 2016/0009711 A1 | 1/2016 | Wu et al. | |
| 2016/0009712 A1 | 1/2016 | Wu et al. | |
| 2016/0009720 A1 | 1/2016 | Wu et al. | |
| 2016/0009721 A1 | 1/2016 | Wu et al. | |

FOREIGN PATENT DOCUMENTS

| | | |
|---|---|---|
| CA | 02887598 * | 4/2014 |
| CN | 103054869 | 4/2013 |
| CN | 103124724 | 5/2013 |
| CN | 103373996 | 10/2013 |
| CN | 103893163 | 7/2014 |
| CN | 103933036 | 7/2014 |
| CN | 103961340 | 8/2014 |
| CN | 104119280 | 10/2014 |
| DE | 102006041292 | 3/2008 |
| EP | 0404190 | 12/1990 |
| EP | 0430385 | 6/1991 |
| EP | 2524918 | 11/2012 |
| EP | 2740474 | 6/2014 |
| EP | 2743256 | 6/2014 |
| FR | 2662163 | 11/1991 |
| FR | 2920090 | 2/2009 |
| FR | 2920091 | 2/2009 |
| JP | 2000319277 | 11/2000 |
| JP | 2000319278 | 11/2000 |
| JP | 2001006877 | 1/2001 |
| JP | 2001035664 | 2/2001 |
| JP | 2001057292 | 2/2001 |
| JP | 2001114780 | 4/2001 |
| JP | 2005089352 | 4/2005 |
| JP | 2010070503 | 4/2010 |
| JP | WO 2013/022047 | 3/2015 |
| WO | WO 8804298 | 6/1988 |
| WO | WO 9325553 | 12/1993 |
| WO | WO 9418198 | 8/1994 |
| WO | WO 9924434 | 5/1999 |
| WO | WO 0127119 | 4/2001 |
| WO | WO 0183481 | 8/2001 |
| WO | WO 02/00196 | 1/2002 |
| WO | WO 0206286 | 1/2002 |
| WO | WO 0234748 | 5/2002 |
| WO | WO 0238562 | 5/2002 |
| WO | WO 02051831 | 7/2002 |
| WO | WO 02072549 | 9/2002 |
| WO | WO 03006471 | 1/2003 |
| WO | WO 03044021 | 5/2003 |
| WO | WO 03062392 | 7/2003 |
| WO | WO 2004017950 | 3/2004 |
| WO | WO 2004021989 | 3/2004 |
| WO | WO 2004058762 | 7/2004 |
| WO | WO 2004/072081 | 8/2004 |
| WO | WO 2004074290 | 9/2004 |
| WO | WO 2004089380 | 10/2004 |
| WO | WO 2004089416 | 10/2004 |
| WO | WO 2004/096131 | 11/2004 |
| WO | WO 2004/108692 | 12/2004 |
| WO | WO 2005007658 | 1/2005 |
| WO | WO 2005/025558 | 3/2005 |
| WO | WO 2005035532 | 4/2005 |
| WO | WO 2005042537 | 5/2005 |
| WO | WO 2005044793 | 5/2005 |
| WO | WO 2005097052 | 10/2005 |
| WO | WO 2006015263 | 2/2006 |
| WO | WO 2006018727 | 2/2006 |
| WO | WO 2006038116 | 4/2006 |
| WO | WO 2006057946 | 6/2006 |
| WO | WO 2006058752 | 6/2006 |
| WO | WO 2006073938 | 7/2006 |
| WO | WO 2006074041 | 7/2006 |
| WO | WO 2006/113704 | 10/2006 |
| WO | WO 2006/138695 | 12/2006 |
| WO | WO 2006131003 | 12/2006 |
| WO | WO 2006135667 | 12/2006 |
| WO | WO 2006135795 | 12/2006 |
| WO | WO 2006138657 | 12/2006 |
| WO | WO 2006138695 | 12/2006 |
| WO | WO 2006138734 | 12/2006 |
| WO | WO 2007022529 | 2/2007 |
| WO | WO 2007028051 | 3/2007 |
| WO | WO 2007058942 | 5/2007 |
| WO | WO 2007/074491 | 7/2007 |
| WO | WO 2007095588 | 8/2007 |
| WO | WO 2007113226 | 10/2007 |
| WO | WO 2007/149478 | 12/2007 |
| WO | WO 2007145921 | 12/2007 |
| WO | WO 2008/005423 | 1/2008 |
| WO | WO 2008005262 | 1/2008 |
| WO | WO 2008005908 | 1/2008 |
| WO | WO 2008008539 | 1/2008 |
| WO | WO 2008011560 | 1/2008 |
| WO | WO 2008027812 | 3/2008 |
| WO | WO 2008037607 | 4/2008 |
| WO | WO 2008045393 | 4/2008 |
| WO | WO 2008/064157 | 5/2008 |
| WO | WO 2008056176 | 5/2008 |
| WO | WO 2008065198 | 6/2008 |
| WO | WO 2008113559 | 9/2008 |
| WO | WO 2008/125111 | 10/2008 |
| WO | WO 2008130951 | 10/2008 |
| WO | WO 2008141239 | 11/2008 |
| WO | WO 2008/157752 | 12/2008 |
| WO | WO 2008154241 | 12/2008 |
| WO | WO 2008156614 | 12/2008 |
| WO | WO 2009010530 | 1/2009 |
| WO | WO 2009017701 | 2/2009 |
| WO | WO 2009017954 | 2/2009 |
| WO | WO 2009023179 | 2/2009 |
| WO | WO 2009045753 | 4/2009 |
| WO | WO 2009047514 | 4/2009 |
| WO | WO 2009085230 | 7/2009 |
| WO | WO 2009085980 | 7/2009 |
| WO | WO 2009091374 | 7/2009 |
| WO | WO 2009/114512 | 9/2009 |
| WO | WO 2009114180 | 9/2009 |
| WO | WO 2009128520 | 10/2009 |
| WO | WO 2010010184 | 1/2010 |
| WO | WO 2010010187 | 1/2010 |
| WO | WO 2010010188 | 1/2010 |
| WO | WO 2010010189 | 1/2010 |
| WO | WO 2010019899 | 2/2010 |
| WO | WO 2010033906 | 3/2010 |
| WO | WO 2010/043721 | 4/2010 |
| WO | WO 2010036380 | 4/2010 |
| WO | WO 2010048149 | 4/2010 |
| WO | WO 2010064020 | 6/2010 |
| WO | WO 2010/084160 | 7/2010 |
| WO | WO 2010088368 | 8/2010 |
| WO | WO 2010091067 | 8/2010 |
| WO | WO 2010/108059 | 9/2010 |
| WO | WO 2010104306 | 9/2010 |
| WO | WO 2010113942 | 10/2010 |
| WO | WO 2010119264 | 10/2010 |
| WO | WO 2010/136438 | 12/2010 |
| WO | WO 2010/144571 | 12/2010 |
| WO | WO 2010151711 | 12/2010 |
| WO | WO 2011022439 | 2/2011 |
| WO | WO 2011/033265 | 3/2011 |
| WO | WO 2011/035941 | 3/2011 |
| WO | WO 2011/042217 | 4/2011 |
| WO | WO 2011050245 | 4/2011 |
| WO | WO 2011089400 | 7/2011 |
| WO | WO 2011097607 | 8/2011 |
| WO | WO 2011/106105 | 9/2011 |
| WO | WO 2011/106106 | 9/2011 |
| WO | WO 2011112766 | 9/2011 |
| WO | WO 2011113606 | 9/2011 |
| WO | WO 2011113862 | 9/2011 |
| WO | WO 2011/121137 | 10/2011 |
| WO | WO 2011/131576 | 10/2011 |

(56) References Cited

FOREIGN PATENT DOCUMENTS

| WO | WO 2011/131697 | 10/2011 | | |
|----|----|----|----|----|
| WO | WO 2011/143365 | 11/2011 | | |
| WO | WO 2011141713 | 11/2011 | | |
| WO | WO 2011160548 | 12/2011 | | |
| WO | WO 2012003392 | 1/2012 | | |
| WO | WO 2012007345 | 1/2012 | | |
| WO | WO 2012/013727 | 2/2012 | | |
| WO | WO 2012/013728 | 2/2012 | | |
| WO | WO 2012016133 | 2/2012 | | |
| WO | WO 2012/034116 | 3/2012 | | |
| WO | WO 2012/042042 | 4/2012 | | |
| WO | WO 2012/047852 | 4/2012 | | |
| WO | WO 2012052730 | 4/2012 | | |
| WO | WO 2012052745 | 4/2012 | | |
| WO | WO 2012054233 | 4/2012 | | |
| WO | WO 2012/071469 | 5/2012 | | |
| WO | WO 2012/072713 | 6/2012 | | |
| WO | WO 2012/080476 | 6/2012 | | |
| WO | WO 2012080230 | 6/2012 | | |
| WO | WO 2012080232 | 6/2012 | | |
| WO | WO 2012080234 | 6/2012 | | |
| WO | WO 2012080236 | 6/2012 | | |
| WO | WO 2012080729 | 6/2012 | | |
| WO | WO 2012088411 | 6/2012 | | |
| WO | WO 2012088438 | 6/2012 | | |
| WO | WO 2012100229 | 7/2012 | | |
| WO | WO 2012/107498 | 8/2012 | | |
| WO | WO 2012/107499 | 8/2012 | | |
| WO | WO 2012116237 | 8/2012 | | |
| WO | WO 2012129562 | 9/2012 | | |
| WO | WO 2012/135113 | 10/2012 | | |
| WO | WO 2012/156531 | 11/2012 | | |
| WO | WO 2012/156537 | 11/2012 | | |
| WO | WO 2012147890 | 11/2012 | | |
| WO | WO 2012/177606 | 12/2012 | | |
| WO | WO 2012176856 | 12/2012 | | |
| WO | WO 2013/010380 | 1/2013 | | |
| WO | WO 2013/025805 | 2/2013 | | |
| WO | WO 2013022047 A1 * | 2/2013 | ........... | A61K 31/167 |
| WO | WO 2013/033515 | 3/2013 | | |
| WO | WO 2013/033688 | 3/2013 | | |
| WO | WO 2013/053690 | 4/2013 | | |
| WO | WO 2013/057320 | 4/2013 | | |
| WO | WO 2013/057322 | 4/2013 | | |
| WO | WO 2013/074390 | 5/2013 | | |
| WO | WO 2013/085877 | 6/2013 | | |
| WO | WO 2013147711 | 10/2013 | | |
| WO | WO 2014/002051 | 1/2014 | | |
| WO | WO 2014009296 | 1/2014 | | |
| WO | WO 2014/058071 | 4/2014 | | |
| WO | WO 2014078479 | 5/2014 | | |
| WO | WO 2014/084298 | 6/2014 | | |
| WO | WO 2014/085613 | 6/2014 | | |
| WO | WO 2014/086790 | 6/2014 | | |
| WO | WO 2014/127350 | 8/2014 | | |
| WO | WO 2014138791 | 9/2014 | | |
| WO | WO 2014/164867 | 10/2014 | | |
| WO | WO 2014/194280 | 12/2014 | | |
| WO | WO 2014/205213 | 12/2014 | | |
| WO | WO 2015/031564 | 3/2015 | | |
| WO | WO 2015/089192 | 6/2015 | | |
| WO | WO 2015/156417 | 10/2015 | | |
| WO | WO 2015/181380 | 12/2015 | | |

OTHER PUBLICATIONS

Pitt "Heteroaromatic Rings of the Future" J. Med. Chem. 2009, 52, 2952-2963.*
Pozharskii et. al. Heterocycles in Life and Society Wiley, 1997, pp. 1-6.*
Rotili "Targeting Histone Demethylases: A New Avenue for the Fight against Cancer" J Genes & Cancer 2(6) 663-679.*
Blom et al., "Preparative LC-MS Purification: Improved Compound-Specific Method Optimization," J. Comb. Chem., 2004, 6(6): 874-883.
"LSD1 inhibitors of Lysine specific demethylase 1, a novel target in neurodegenerative disease," Powerpoint presentation, Oryzon, Feb. 2011, 42 pages.
Abdulla et al., "Natural Polyphenols Inhibit Lysine-Specific Demethylase-1 in vitro," Journal of Biochemical and Pharamcological Research, Mar. 2013, 1: 56-63.
Adamo et al., "LSD1 and pluripotency: a new player in the network," Cell Cycle, Oct. 2011, 10(19): 3215-6.
Adamo et al., "LSD1 regulates the balance between self-renewal and differentiation in human embryonic stem cells," Nat. Cell Biol, Jun. 2011, 13(6): 652-9.
Anand and Marmorstein, "Structure and mechanism of lysine-specific demethylase enzymes," J Biol Chem, Dec. 2007, 282(49): 35425-9.
Baron et al., "Molecular Mimicry and Ligand Recognition in Binding and Catalysis by the Histone Demethylase LSD1-CoREST Complex," Structure, Feb. 2011, 19: 212-220.
Bauer et al., "Reawakening fetal hemoglobin: prospects for new therapies for the β-globin disorders," Blood, Oct. 2012, 120(15): 3945-53.
Beck and Blanpain, "Unravelling cancer stem cell potential," Nat Rev Cancer, Oct. 2013, 13(10): 727-38.
Benelkebir et al., "Enantioselective synthesis of tranylcypromine analogues as lysine demethylase (LSD1) inhibitors," Bioorganic & Medicinal Chemistry, 2011, 19: 3709-3716.
Bennani-Baiti et al., "Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma," Hum Pathol, Aug. 2012, 43(8): 1300-7.
Berge and Robiette, "Development of a Regioselective N-Methylation of (Benz)imidazoles Providing the More Sterically Hindered Isomer," The Journal of Organic Chemistry, 2013, A-D.
Berge et al., "Pharmaceutical salts," J Pharm Sci, 1977, 66(1): 1-19.
Binda et al., "Biochemical, Structural, and Biological Evaluation of Tranylcypromine Derivatives as Inhibitors of Histone Demethylases LSD1 and LSD2," J. Am. Chem. Soc., 2010, 132: 6827-6833.
Binda et al., "Molecular Insights into Human Monoamine Oxidase B Inhibition by the Glitazone Antidiabetes Drugs," ACS Med. Chem. Letter, 2012, 3: 39-42.
Blom et al., "Optimizing Preparative LC/MS Configurations and Methods for Parallel Synthesis Purification," J. Comb. Chem., 2003, 5(5): 670-683.
Blom, "Two-Pump at-Column-Dilution Configuration for Preparative Liquid Chomratography—Mass Spectrometry," J. Comb. Chem, 2002, 4(4): 295-301.
Cain, "AML takes LSD1," SciBX, Apr. 2012, 1-3.
Cao et al., "One-Pot Regiospecific Synthesis of Imidazo[1,2-a]pyridines: A Novel, Metal-Free, Three-Component Reaction for the Formation of C—N, C—O, and C—S Bonds," Org. Lett., 2013, A-D.
Chen and Flies, "Molecular mechanisms of T cell co-stimulation and co-inhibition," Nat Rev Immunol, Apr. 2013, 13(4): 227-42.
Chen et al., "Crystal structure of human histone lysine-specific demethylase 1 (LSD1)," Proc Natl Acad Sci USA, Sep. 2006, 103(38): 13956-61.
Chen et al., "Lysine-specific histone demethylase 1 (LSD1): A potential molecular target for tumor therapy," Crit Rev Eukaryot Gene Expre, 2012, 22(1): 53-9.
Cho et al., "Demethylation of RB regulator MYPT1 by histone demethylase LSD1 promotes cell cycle progression in cancer cells," Cancer Res., Feb. 2011, 71(3): 655-60.
Clevers, "The cancer stem cell: premises, promises and challenges," Nat Med., Mar. 2011, 17(3): 313-9.
Crea et al., "The emerging role of histone lysine demethylases in prostate cancer," Mol Cancer, Aug. 2012, 11:52.
Cui et al., "The LSD1 inhibitor RN-1 induces fetal hemoglobin synthesis and reduces disease pathology in sickle cell mice," Blood, 2015, 1-31.
Culhane and Cole, "LSD1 and the chemistry of histone demethylation," Current Opinion in Chemical Biology, 2007, 11: 561-568.

(56) References Cited

OTHER PUBLICATIONS

Culhane et al., "A Mechanism-Based Inactivator for Histone Demethylase LSD1," J. Am. Chem. Soc., 2006, 128: 4536-4537.

Culhane et al., "Comparative Analysis of Small Molecules and Histone Substrate Analogues as LSD1 Lysine Demethylase Inhibitors," J. Am. Chem. Soc., 2010, 132: 3164-3176.

Dancy et al., "Azalysine Analogues as Probes for Protein Lysine Deacetylation and Demethylation," J. Am. Chem. Soc., 2012, 5138-5148.

Dawson and Kouzarides, "Cancer epigenetics: from mechanism to therapy," Cell, Jul. 2012, 150(1): 12-27.

Dhanak, "Cracking the Code: The Promise of Epigenetics," ACS Med. Chem. Letter, 2012, 3: 521-523.

Ding et al., "LSD1-mediated epigenetic modification contributes to proliferation and metastasis of colon cancer," Br J Cancer, Aug. 2013, 109(4): 994-1003.

Dulla et al., "Synthesis and evaluation of 3-amino/guanidine substituted phenyl oxazoles as a novel class of LSD1 inhibitors with anti-proliferative properties," The Royal Society of Chemistry, 2013, 1-25.

Ellsworth et al., "Reductions in log P Improved Protein Binding and Clearance Predictions Enabling the Prospective Design of Cannabinoid Receptor (CB1) Antagonists with Desired Pharmacokinetic Properties," J. Med. Chem., 2013, 56: 9586-9600.

Fiskus et al., "Pre-Clinical Efficacy of Combined Therapy with LSD1 Antagonist SP-2509 and Pan-Histone Deacetylase Inhibitor Against AML Blast Pregenitor Cells," 54th ASH Annual Meeting and Exposition, session 604, poster abstract, Dec. 2012, [retrieved on May 1, 2013]. Retrieved from the Internet at URL: https://ash.confex.com/ash/2012/webprogram/Paper53429.html, 2 pages.

Forneris et al., "LSD1: oxidative chemistry for multifaceted functions in chormatin regulation," Cell Press, Mar. 2008, 181-189.

Forneris, F., et al., Structural basis of LSD1-CoREST selectivity in histone H3 recognition. J Biol Chem, 2007. 282(28): p. 20070-4.

Ge et al., "Pd-Catalyzed α-Arylation of α,α-Difluoroketones with Aryl Bromides and Chlorides. A Route to Difluoromethylarenes," J. Am. Chem. Soc., 2014, A-D.

Gonzalez et al., "Selective and Potent Morpholinone Inhibitors of the MDM2-p53 Protein-Protein Interaction," J. Med. Chem., 2013, A-Q.

Gooden et al., "Facile synthesis of substituted trans-2-arylcyclopropylamine inhibitors of the human histone demethylase LSD1 and monoamine oxidases A and B," Bioorganic & Medicinal Chemistry Letters, 2008, 18: 3047-3051.

Greaves and Gribben, "The role of B7 family molecules in hematologic malignancy," Blood, Jan. 2013, 121(5): 734-44.

Gui et al., "C—H Methylation of Heteroarenes Inspired by Radical SAM Methyl Transferase," J. Am. Chem. Soc., 2014, A-D.

Hakimi et al., "A core-BRAF35 complex containing histone deacetylase mediates repression of neuronal-specific genes," Proc Natl Acad Sci USA, May 2002, 99(11): 7420-5.

Hamada et al., "Design, Synthesis, Enzyme-Inhibitory Activity, and Effect on Human Cancer Cells of a Novel Series of Jumonji Domain-Containing Protein 2 Histone Demethylase Inhibitors," J. Med. Chem., 2010, 52: 5629-5638.

Hamilton et al., "Comparison of a Direct and Indirect Method for Measuring Flavins-Assessing Flavin Status in Patients Receiving Total Parenteral Nutrition," The Open Clinical Chemistry Journal, 2009, 2: 42-48.

Han et al., "Synergistic re-activation of epigenetically silenced genes by combinatorial inhibition of DNMTs and LSD1 in cancer cells," pLoS One, Sep. 2013, 8(9): e75136.

Harris et al., "The histone demethylase KDM1A sustains the oncogenic potential of MLL-AF9 leukemia stem cells," Cancer Cell, Apr. 2012, 21(4): 473-87.

Hayami et al., "Overexpression of LSD1 contributes to human carcinogenesis through chromatin regulation in various cancers," Int J Cancer, Feb. 2011, 128(3): 574-86.

Hazeldine et al., "Low Molecular Weight Amidoximes that Act as Potent Inhibitors of Lysine-Specific Demethylase 1," J. Med. Chem., 2012, 55: 7378-7391.

Hesp et al., "Expedient Synthesis of α-Heteroaryl Piperidines Using a Pd-Catalyzed Suzuki Cross-Coupling—Reduction Sequence," Org. Lett., 2013, A-C.

Hicken et al., "Discovery of a Novel Class of Imidazo[1,2-a]Pyridines with Potent PDGFR Activity and Oral Bioavailability," ACS Med. Chem. Lett., 2013, A-F.

Hitchin et al., "Development and evaluation of selective, reversible LSD1 inhibitors derived from fragments," Med. Chem. Commun., 2013, 4: 1513-1522.

Hoffmann et al., "The role of histone demethylases in cancer therapy," Molecular Oncology, 2012, 6: 683-703.

Hou and Yu, "Structural insights into histone lysine demethylation," Current Opinion in Structural Biology, 2010, 20: 739-748.

Hruschka et al., "Fluorinated phenylcyclopropylamines. Part 5: Effects of electron-withdrawing or -donating aryl substituents on the inhibition of monoamine oxidases A and B by 2-aryl-2-fluorocyclopropylamines," Bioorganic & Medicinal Chemistry, 2008, 16: 7148-7166.

Huang et al., "p53 is regulated by the lysine demethylase LSD1," Nature, Sep. 2007, 449(7158): 105-8.

Jalluri, Drug Analysis Table, LSD1 KDM1a Cortellis Update, retrieved on May 6, 2013, 3 pages.

Kahl et al., "Androgen Receptor Coactivators Lysine-Specific Histone Demethylase 1 and Four and a Half LIM Domain Protein 2 Predict Risk of Prostate Cancer Recurrence," Cancer Res., 2006, 66(23): 11341-7.

Kakizawa et al., "Histone H3 peptide based LSD1-selective inhibitors," Bioorganic & Medicinal Chemistry Letters, 2015, 25: 1925-1928.

Karytinos et al., "A novel mammalian flavin-dependent histone demethylase," J Biol Chem, Jan. 2009, 284(26): 17775-82.

Kelly and Lipshutz, "Chemoselective Reductions of Nitroaromatics in Water at Room Temperature," Org. Lett., 2013, A-D.

Khan et al., "An Overview of Phenylcyclopropylamine Derivatives: Biochemical and Biological Significance and Recent Developments," Medicinal Research Reviews, 2012, 874-910.

Khoury et al., "Efficient Assembly of Iminodicarboxamides by a "Truly" Four-Component Reaction," Angew. Chem. Int. Ed., 2012, 51: 10280-10283.

Kinzel et al., "Identification of MK-5710 ((8aS)-8a-methyl-1,3-dioxo-2-[(1S,2R)-2-phenylcyclo-propyl]-N-(1-phenyl-1H-pyrazol-5-yl)hexahydro-imidazo[1,5-a]pyrazine-7(1H)-carboxamide), a potent smoothened antagonist for use in Hedgehog pathway dependent malignancies, part 2," Bioorg Med Chem Lett, Aug. 2011, 21(15): 4429-35.

Kjer-Nielsen et al., "MR1 presents microbial vitamin B metabolites to MAIT cells," Nature, Nov. 2012, 491: 717-725.

Kong et al , "Immunohistochemical expression of RBP2 and LSD1 in papillary thyroid carcinoma," Rom J Morphol Embryol, 2013, 54(3): 499-503.

Konovalov and Garcia-Bassets, "Analysis of the levels of lysine-specific demethylase 1 (LSD1) mRNA in human ovarian tumors and the effects of chemical LSD1 inhibitors in ovarian cancer cell lines," J Ovarian Res, Oct. 2013, 6(1): 75.

Kontaki and Talianidis, "Lysine methylation regulates E2F1-induced cell death," Mol Cell, Jul. 2010, 39(1): 152-60.

Kooistra and Helin, "Molecular mechanisms and potential functions of histone demethylases," Nat Rev Mol Cell Biol, Apr. 2012, 13(5): 297-311.

Kutz et al., "3,5-Diamino-1,2,4-triazoles as a novel scaffold for potent, reversible LSD1 (KDM1A) inhibitors," Med. Chem. Commun., 2014, 5: 1863-1870.

Lan et al., "Recognition of unmethylated histone H3 lysine 4 links BHC80 to LSD1-mediated gene repression," Nature, 2007, 718-723.

Larsen and Hartwig, "Iridium-Catalyzed C—H Borylation of Heteroarenes: Scope, Regioselectivity, Application to Late-Stage Functionalization, and Mechanism," J. Am. Chem. Soc., 2013, A-M.

(56) References Cited

OTHER PUBLICATIONS

Lee et al., "Functional interplay between histone demethylase and deacetylase enzymes," Mol Cell Biol, Sep. 2006, 26(17): 6395-402.
Liang et al., "A Novel Selective LSD1/KDM1A Inhibitor Epigenetically Blocks Herpes Simplex Virus Lytic Replication and Reactivation from Latency," mBio, 2013, 4(1): 1-9.
Liang et al., "Inhibition of the histone demethylase LSD1 blocks alpha-herpesvirus lytic replication and reactivation from latency," Nat Med., Nov. 2009, 15(11): 1312-7.
Liang et al., "Targeting the JMJD2 histone demethylases to epigenetically control herpesvirus infection and reactivation from latency," Sci Transl Med., Jan. 2013, 5(167): 167ra5.
Lim et al., "Lysine-specific demethylase 1 (LSD1) is highly expressed in ER-negative breast cancers and a biomarker predicting aggressive biology," Carcinogenesis, Mar. 2010, 31(3): 512-20.
Liu and Nefzi, "Solid-Phase Synthesis of N-Substituted Pyrrolidinone-Tethered N-Substituted Piperidines via Ugi Reaction," J. Comb. Chem., 2010, 12: 566-570.
Lund and van Lohuizen, "Epigenetics and cancer," Genes Dev., Oct. 2004, 18(19): 2315-35.
Lv et al., "Over-Expression of LSD1 Promotes Proliferation, Migration and Invasion in Non-Small Cell Lung Cancer," PLoS ONE, Apr. 2012, 7(4): 1-8, e35065.
Lynch et al., "CD86 expression as a surrogate cellular biomarker for pharmacological inhibition of the histone demethylase lysine-specific demethylase 1," Anal Biochem, Nov. 2013, 442(1): 104-6.
Merck KGaA, "Product comparison- EMD4Biosciences," Comparison of LSD1 inhibitors, EMD Millipore USA, retrieved on May 6, 2013, 3 pages.
Metzger et al., "LSD1 demethylates repressive histone marks to promote androgen-receptor-dependent transcription," Nature, Sep. 2005, 437(7057): 436-9.
Mimasu et al., "Structurally Designed trans-2-Phenylcyclopropylamine Derivatives Potently Inhibit Histone Demethylase LSD1/KDM1," Biochemistry, 2010, 49: 6494-6503.
Moon et al., "Copper-Catalyzed Chan-Lam Coupling between Sulfonyl Azides and Boronic Acids at Room Temperature," Org. Lett., 2013, A-D.
Moormann et al., "Potential Antisecretory Antidiarrheals. 2. $\alpha_2$-Adrenergic 2-[(Aryloxy)alkyl]imidazolines," American Chemical Society, 1990, 33: 614-626.
Mosammaparast and Shi, "Reversal of histone methylation: biochemical and molecular mechanisms of histone demethylases," Annu Rev Biochem, 2010, 79: 155-79.
Mulder et al., "Development of a Safe and Economical Synthesis of Methyl 6-Chloro-5-(trifluoromethyl)nicotinate: Trifluoromethylation on Kilogram Scale," Org. Process Res. Dev., 2013, 940-945.
Ogasawara et al., "Lysine-Specific Demethylase 1-Selective Inactivators: Protein-Targeted Drug Delivery Mechanism," Angew. Chem. Int. Ed., 2013, 52: 8620-8624.
Ogasawara et al., "Lysine-Specific Demethylase 1-Selective Inactivators: Protein-Targeted Drug Delivery Mechanism," 2013, Supporting Information.
Portela and Esteller, "Epigenetic modifications and human disease," Nat Biotechnol, Oct. 2010, 28(10): 1057-68.
*Remington's Pharmaceutical Sciences*, 17th Ed., (Mack Publishing Company, Easton, 1985), p. 1418.
Roberston et al., "Expanding the Druggable Space of the LSD1/CoREST Epigenetic Target: New Potential Binding Regions for Drug-Like Molecules, Peptides, Protein Partners, and Chromatin," PLOS, Jul. 2013, 9(7): 1-10.
Rotilli and Mai, "Targeting Histone Demethylases: A New Avenue for the Fight against Cancer," Genes and Cancer, 2011, 2(6): 663-679.
Sakane et al., "Activation of HIV transcription by the viral Tat protein requires a demethylation step mediated by lysine-specific demethylase 1 (LSD1/KDM1)," PLoS Pathog., Aug. 2011, 7(8):e1002184.

Salarius Pharmaceuticals (Non confidential pharmaceutical package), Oncology Epigenetic Therapy Sp-2528, an Inhibitor of Lysine-Specific Demethylase 1 (LSD1), Jan. 2012, 28 pages.
Samann et al., "Full Functionalization of the Imidazole Scaffold by Selective Metalation and Sulfoxide/Magnesium Exchange," Angew. Chem. Int. Ed., 2013, 52: 1-6.
Sankaran and Orkin, "The switch from fetal to adult hemoglobin," Cold Spring Harb Perspect Med., Jan. 2013, 3(1): a011643.
Sareddy et al., "KDM1 is a novel therapeutic target for the treatment of gliomas," Oncotarget, Jan. 2013, 4(1): 18-28.
Schenk et al., "Inhibition of the LSD1 (KDM1A) demethylase reactivates the all-trans-retinoic acid differentiation pathway in acute myeloid leukemia," Nat Med, Mar. 2012, 18(4): 605-11.
Schmitt et al., "Nonpeptidic Propargylamines as Inhibitors of Lysine Specific Demethylase 1 (LSD1) with Cellular Activity," J. Med. Chem., 2013, A-I.
Schulte et al., "Lysine-Specific Demethylase 1 Is Strongly Expressed in Poorly Differentiated Neuroblastoma: Implications for Therapy," Cancer Res, 2009, 69(5): 2065-71.
Senecal et al., "A General, Practical Palladium-Catalyzed Cyanation of (Hetero) Aryl Chlorides and Bromides," Angew. Chem. Int. Ed., 2013, 52: 1-6.
Serce et al., "Elecated expression of LSD1 (Lysine-specific demethylase 1) during tumour progression from re-invasive to invasive ductal carcinoma of the breast," BMC Clin Pathol, Aug. 2012, 12:13.
Sharma et al., "(Bis)urea and (Bis)thiourea Inhibitors of Lysine-Specific Demethylase 1 as Epigenetic Modulators," J. Med. Chem., 2010, 53: 5197-5212.
Shen and Laird, "Interplay between the cancer genome and epigenome," Cell, Mar. 2013, 153(1): 38-55.
Shi et al., "Histone demethylation mediated by the nuclear amine oxidase homolog LSD1," Cell, Dec. 2004, 119(7): 941-53.
Shi et al., "Lysine-specific demethylase 1 is a therapeutic target for fetal hemoglobin induction," Nat Med, Mar. 2013, 19(3): 291-4.
Shi et al., "Regulation of LSD1 Histone Demethylase Activity by Its Associated Factors," Molecular Cell, Sep. 2005, 19: 857-864.
Singh et al, "Inhibition of LSD1 sensitizes gliobastoma cells to histone deacetylase inhibitors," Neuro Oncol, Aug. 2011, 13(8): 894-903.
Sippl et al., "Target-based development of novel lysine histone demethylase one (LSD1) inhibitors," Dissertation, Martin-Luther-University Halle- Wittenberg, Institute of Pharmaceutical Chemistry, defended on Dec. 3, 2014, 152 pages.
Son et al., "Structure of human monoamine oxidase A at 2.2-A resolution: The control of opening the entry for substrates/inhibitors," PNAS, Apr. 2008, 105(15): 5739-5744.
Stavropoulos et al., "Crystal structure and mechanism of human lysine-specific demethylase-1," Nat Struct Mol Biol, Jul. 2006, 13(7): 626-32.
Suikki et al., "Genetic alterations and changes in expression of histone demethylases in prostate cancer," Prostate, Jun. 2010, 70(8): 889-96.
Sun et al., "Histone demethylase LSD1 regulates neural stem cell proliferation," Mol Cell Biol, Apr. 2010, 30(8): 1997-2005.
Suzuki and Miyata, "Lysine Demethylases Inhibitors," J. Med. Chem., 2011, 54: 8236-8250.
Szewczuk et al., "Mechanistic Analysis of a Suicide Inactivator of Histone Demethylase LSD1," Biochemistry, 2007, 46: 6892-6902.
Szostak et al., "Highly Chemoselective Reduction of Amides (Primary, Secondary, Tertiary) to Alcohols using $SmI_2$/Amine/$H_2O$ under Mild Conditions," J. Am. Chem. Soc., 2013, A-D.
Theisen et al., "Reversible inhibition of lysine specific demethylase 1 is a novel anti-tumor strategy for poorly differentiated endometrial carcinoma," BMC Cancer, 2014, 14:752 1-12.
Tortorici et al., "Protein Recognition by Short Peptide Reversible Inhibitors of the Chromatin-Modifying LSD1/CoREST Lysine Demethylase," ACS Chem. Biol., 2013, A-F.
Ueda and Nagasawa, "Facile Synthesis of 1,2,4-Triazoles via a Copper-Catalyzed Tandem Addition—Oxidative Cyclization," J. Am. Chem. Soc., 2009, 131: 15080-15081.

(56) References Cited

OTHER PUBLICATIONS

Ueda et al., "Identification of Cell-Active Lysine Specific Demethylase 1-Selective Inhibitors," J. Am. Chem. Soc., 2009, 131: 17536-17537.
Vianello et al., "Synthesis, biological activity and mechanistic insights of 1-substituted cyclopropylamine derivatives: A novel class of irreversible inhibitors of histone demethylase KDM1A," European Journal of Medicinal Chemistry, 2014, 86: 352-363.
Waldmann and Schneider, "Targeting histone modifications—epigenetics in cancer," Curr Opin Cell Biol, Apr. 2013, 25(2): 184-9.
Wang et al., "Novel Histone Demethylase LSD1 Inhibitors Selectively Target Cancer Cells with Pluripotent Stem Cell Properties," Cancer Res, Dec. 2011, 7238-7249.
Wang et al., "The lysine demethylase LSD1 (KDM1) is required for maintenance of global DNA methylation," Nat Genet, Jan. 2009, 41(1): 125-9.
Wen et al., "Triptolide induces cell-cycle arrest and apoptosis of human multiple myeloma cells in vitro via altering expression of histone demethylase LSD1 and JMJD2B," Acta Pharmacologica Sinica, 2012, 33: 109-119.
Wengryniuk et al., "Regioselective Bromination of Fused Heterocyclic N-Oxides," American Chemical Society, 2013, 15(4): 792-795.
Willmann et al., "Impairment of prostate cancer cell growth by a selective and reversible lysine-specific demethylase 1 inhibitor," Int. J. Cancer, 2012, 131: 2704-2709.
Xu et al., "Corepressor-dependent silencing of fetal hemoglobin expression by BCL11A," Proc Natl Acad Sci USA, Apr. 2013, 110(16): 6518-23.
Yang et al., "Reversible methylation of promoter-bound STAT3 by histone-modifying enzymes," Proc Natl Acad Sci USA, Dec. 2010, 107(50): 21499-504.
Yang et al., "Structural Basis for the Inhibition of the LSD1 Histone Demethylase by the Antidepressant trans-2-Phenylcyclopropylamine," Biochemistry, 2007, 46: 8058-8065.
Yang et al., "Structural basis of histone demethylation by LSD1 revealed by suicide inactivation," Nature Structural & Molecular Biology, Jun. 2007, 14(6): 535-539.
Yoshida et al., "Fluorinated Phenylcyclopropylamines. 1. Synthesis and Effect of Fluorine Substitution at the Cyclopropane Ring on Inhibition of Microbial Tyramine Oxidase," J. Med. Chem., 2004, 47: 1796-1806.
You et al., "CoREST is an integral component of the CoREST-human histone deacetylase complex," Proc Natl Acad Sci USA, Feb. 2001, 98(4): 1454-8.
Yu et al., "High expression of lysine-specific demethylase 1 correlates with poor prognosis of patients with esophageal squamous cell carcinoma," Biochem Biophys Res Commun, Jul. 2013, 437(2): 192-8.
Zhang et al., "Pluripotent stem cell protein Sox2 confers sensitivity to LSD1 inhibition in cancer cells," Cell Rep, Oct. 2013, 5(2): 445-57.
Zheng et al., "A Systematic Review of Histone Lysine-Specific Demethylase 1 and Its Inhibitors," 2015, 1-40.
Dhudshia et al., "Diastereoselective allylation and crotylation of N-unsubstituted imines derived from ketones," Chem Commun, 2005, 5551-5553.
Ganesan, "Targeting Epigenetic Demethylation," University of East Anglia (School of Pharmacy), PowerPoint presentation, Presented from the World Epigenetics Summit, London, Jul. 24, 2012, 26 pages.
Huang et al., "Rhodium(III)-Catalyzed Direct Selective C(5)-H Oxidative Annulations of 2-Substituted Imidazoles and Alkynes by Double C—H Activation," Organic Letters, Feb. 2013, 15(8): 1878-1881.
International Search Report and Written Opinion in International Application No. PCT/US2015/015635, dated May 8, 2015, 10 pages.
International Search Report and Written Opinion in International Application No. PCT/US2015/015663, dated May 6, 2015, 10 pages.
International Search Report and Written Opinion in International Application No. PCT/US2015/015706, dated May 6, 2015, 16 pages.
International Search Report and Written Opinion in International Application No. PCT/US2015/015600, dated May 18, 2015, 9 pages.
International Search Report and Written Opinion in International Application No. PCT/US2015/039734, dated Sep. 18, 2015, 14 pages.
International Search Report and Written Opinion in International Application No. PCT/US2015/039724, dated Sep. 15, 2015, 14 pages.
International Search Report and Written Opinion in International Application No. PCT/US2015/039718, dated Sep. 15, 2015, 13 pages.
Kettle et al., "Diverse Heterocyclic Scaffolds as Allosteric Inhibitors of AKT," Journal of Medicinal Chemistry, Mar. 2012, 55(3): 1261-1273.
Lynch et al., "LSD1 Inhibition: A therapeutic strategy in cancer?," Expert Opinion on Therapeutic Targets, 2012, 16(12): 1239-1249.
Neelamegam et al., "Brain-Penetrant LSD1 Inhibitors Can Block Memory Consolidation," ACS Chem. Neurosci., 2012, 3:120-128.
Potts et al., "The mass spectra of somes-triazolo[4,3-a]pyrazines," Organic Mass Spectrometry, Jun. 1971, 5(6): 663-674.
Rostom et al., "A facile synthesis of some 3-cyano-1,4,6-trisubstituted-2(1)-pyridinones and their biological evaluation as anticancer agents," Medicinal Chemistry Research, Oct. 2010, 20(8): 1260-1272.
Search Report, May 30, 2014, 6 pages.
Search Report, May 30, 2014, 109 pages.
Search Report, Jun. 3, 2014, 7 pages.
Yu et al., "Energetic factos determining the binding of type I inhibitors to c-Met kinase: experimental studies and quantum mechanical calculations," Acta Pharmacologica Sinica, Nov. 2013, 34(11): 1475-1783.
Dhudshia and Thadani, "Diastereoselective allylation and crotylation of N-unsubstituted imines derived from ketones," Chem. Commun., 2005, 33 pages.
Guiles et al. "preparation of triazolopyrimidine derivatives as P2T receptor antagonists," CA130:168386 (1999).
Neelamegam et al., "Brain-penetrant LSD1 inhibitors can block memory consolidation," Supplementary Data, 2012, 24 pages.
Improper Markush Fed. Reg. 76(27) p. 7612-75, slide 1, 64-67 (2011).
International Preliminary Report on Patentability in International Application No. PCT/US2015/015635, dated Aug. 16, 2016, 8 pages.

* cited by examiner

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: synthetic peptide

<400> SEQUENCE: 1

Gln Thr Ala Arg Lys Ser Thr Gly Gly Lys Ala Pro Arg Lys Gln Leu
1               5                   10                  15

Ala Gly Gly Lys
            20
```

CYCLOPROPYLAMINES AS LSD1 INHIBITORS

FIELD OF THE INVENTION

The present invention relates to enzyme inhibitors, which selectively modulate demethylase, and uses therefor. Particular embodiments contemplate compounds and disease indications amenable to treatment by modulation of lysine specific demethylase-1 (LSD1).

BACKGROUND OF THE INVENTION

Epigenetic modifications can impact genetic variation but, when dysregulated, can also contribute to the development of various diseases (Portela, A. and M. Esteller, *Epigenetic modifications and human disease*. Nat Biotechnol, 2010. 28(10): p. 1057-68; Lund, A. H. and M. van Lohuizen, *Epigenetics and cancer*. Genes Dev, 2004. 18(19): p. 2315-35). Recently, in depth cancer genomics studies have discovered many epigenetic regulatory genes are often mutated or their own expression is abnormal in a variety of cancers (Dawson, M. A. and T. Kouzarides, *Cancer epigenetics: from mechanism to therapy*. Cell, 2012. 150(1): p. 12-27; Waldmann, T. and R. Schneider, *Targeting histone modifications—epigenetics in cancer*. Curr Opin Cell Biol, 2013. 25(2): p. 184-9; Shen, H. and P. W. Laird, *Interplay between the cancer genome and epigenome*. Cell, 2013. 153(1): p. 38-55). This implies epigenetic regulators function as cancer drivers or are permissive for tumorigenesis or disease progression. Therefore, deregulated epigenetic regulators are attractive therapeutic targets.

One particular enzyme which is associated with human diseases is lysine specific demethylase-1 (LSD1), the first discovered histone demethylase (Shi, Y., et al., *Histone demethylation mediated by the nuclear amine oxidase homolog LSD1*. Cell, 2004. 119(7): p. 941-53). It consists of three major domains: the N-terminal SWIRM which functions in nucleosome targeting, the tower domain which is involved in protein-protein interaction, such as transcriptional co-repressor, co-repressor of RE1-silencing transcription factor (CoREST), and lastly the C terminal catalytic domain whose sequence and structure share homology with the flavin adenine dinucleotide (FAD)-dependent monoamine oxidases (i.e., MAO-A and MAO-B) (Forneris, F., et al., *Structural basis of LSD1-CoREST selectivity in histone H3 recognition*. J Biol Chem, 2007. 282(28): p. 20070-4; Anand, R. and R. Marmorstein, *Structure and mechanism of lysine-specific demethylase enzymes*. J Biol Chem, 2007. 282(49): p. 35425-9; Stavropoulos, P., G. Blobel, and A. Hoelz, *Crystal structure and mechanism of human lysine-specific demethylase-1*. Nat Struct Mol Biol, 2006. 13(7): p. 626-32; Chen, Y., et al., *Crystal structure of human histone lysine-specific demethylase 1* (LSD1). Proc Natl Acad Sci USA, 2006. 103(38): p. 13956-61). LSD1 also shares a fair degree of homology with another lysine specific demethylase (LSD2) (Karytinos, A., et al., *A novel mammalian flavin-dependent histone demethylase*. J Biol Chem, 2009. 284(26): p. 17775-82). Although the biochemical mechanism of action is conserved in two isoforms, the substrate specificities are thought to be distinct with relatively small overlap. The enzymatic reactions of LSD1 and LSD2 are dependent on the redox process of FAD and the requirement of a protonated nitrogen in the methylated lysine is thought to limit the activity of LSD1/2 to mono- and di-methylated at the position of 4 or 9 of histone 3 (H3K4 or H3K9). These mechanisms make LSD1/2 distinct from other histone demethylase families (i.e. Jumonji domain containing family) that can demethylate mono-, di-, and tri-methylated lysines through alpha-ketoglutarate dependent reactions (Kooistra, S. M. and K. Helin, *Molecular mechanisms and potential functions of histone demethylases*. Nat Rev Mol Cell Biol, 2012. 13(5): p. 297-311; Mosammaparast, N. and Y. Shi, *Reversal of histone methylation: biochemical and molecular mechanisms of histone demethylases*. Annu Rev Biochem, 2010. 79: p. 155-79).

Methylated histone marks on K3K4 and H3K9 are generally coupled with transcriptional activation and repression, respectively. As part of corepressor complexes (e.g., CoREST), LSD1 has been reported to demethylate H3K4 and repress transcription, whereas LSD1, in nuclear hormone receptor complex (e.g., androgen receptor), may demethylate H3K9 to activate gene expression (Metzger, E., et al., *LSD1 demethylates repressive histone marks to promote androgen-receptor-dependent transcription*. Nature, 2005. 437(7057): p. 436-9; Kahl, P., et al., *Androgen receptor coactivators lysine-specific histone demethylase 1 and four and a half LIM domain protein 2 predict risk of prostate cancer recurrence*. Cancer Res, 2006. 66(23): p. 11341-7). This suggests the substrate specificity of LSD1 can be determined by associated factors, thereby regulating alternative gene expressions in a context dependent manner. In addition to histone proteins, LSD1 may demethylate non-histone proteins. These include p53 (Huang, J., et al., *p53 is regulated by the lysine demethylase LSD1*. Nature, 2007. 449(7158): p. 105-8), E2F (Kontaki, H. and I. Talianidis, *Lysine methylation regulates E2F1-induced cell death*. Mol Cell, 2010. 39(1): p. 152-60), STAT3 (Yang, J., et al., *Reversible methylation of promoter-bound STAT3 by histone-modifying enzymes*. Proc Natl Acad Sci USA, 2010. 107(50): p. 21499-504), Tat (Sakane, N., et al., *Activation of HIV transcription by the viral Tat protein requires a demethylation step mediated by lysine-specific demethylase 1 (LSD1/KDM1)*. PLoS Pathog, 2011. 7(8): p. e1002184), and myosin phosphatase target subunit 1 (MYPT1) (Cho, H. S., et al., *Demethylation of RB regulator MYPT1 by histone demethylase LSD1 promotes cell cycle progression in cancer cells*. Cancer Res, 2011. 71(3): p. 655-60). The lists of non-histone substrates are growing with technical advances in functional proteomics studies. These suggest additional oncogenic roles of LSD1 beyond in regulating chromatin remodeling. LSD1 also associates with other epigenetic regulators, such as DNA methyltransferase 1 (DNMT1) (Wang, J., et al., *The lysine demethylase LSD1 (KDM1) is required for maintenance of global DNA methylation*. Nat Genet, 2009. 41(1): p. 125-9) and histone deacetylases (HDACs) complexes (Hakimi, M. A., et al., *A core-BRAF35 complex containing histone deacetylase mediates repression of neuronal-specific genes*. Proc Natl Acad Sci USA, 2002. 99(11): p. 7420-5; Lee, M. G., et al., *Functional interplay between histone demethylase and deacetylase enzymes*. Mol Cell Biol, 2006. 26(17): p. 6395-402; You, A., et al., *CoREST is an integral component of the CoREST-human histone deacetylase complex*. Proc Natl Acad Sci USA, 2001. 98(4): p. 1454-8). These associations augment the activities of DNMT or HDACs. LSD1 inhibitors may therefore potentiate the effects of HDAC or DNMT inhibitors. Indeed, preclinical studies have shown such potential already (Singh, M. M., et al., *Inhibition of LSD1 sensitizes glioblastoma cells to histone deacetylase inhibitors*. Neuro Oncol, 2011. 13(8): p. 894-903; Han, H., et al., *Synergistic re-activation of epigenetically silenced genes by combinatorial inhibition of DNMTs and LSD1 in cancer cells*. PLoS One, 2013. 8(9): p. e75136).

LSD1 has been reported to contribute to a variety of biological processes, including cell proliferation, epithelial-mesenchymal transition (EMT), and stem cell biology (both embryonic stem cells and cancer stem cells) or self-renewal and cellular transformation of somatic cells (Chen, Y., et al., *Lysine-specific histone demethylase 1 (LSD1): A potential molecular target for tumor therapy*. Crit Rev Eukaryot Gene Expr, 2012. 22(1): p. 53-9; Sun, G., et al., *Histone demethylase LSD1 regulates neural stem cell proliferation*. Mol Cell Biol, 2010. 30(8): p. 1997-2005; Adamo, A., M. J. Barrero, and J. C. Izpisua Belmonte, *LSD1 and pluripotency: a new player in the network*. Cell Cycle, 2011. 10(19): p. 3215-6; Adamo, A., et al., *LSD1 regulates the balance between self-renewal and differentiation in human embryonic stem cells*. Nat Cell Biol, 2011. 13(6): p. 652-9). In particular, cancer stem cells or cancer initiating cells have some pluripotent stem cell properties that contribute the heterogeneity of cancer cells. This feature may render cancer cells more resistant to conventional therapies, such as chemotherapy or radiotherapy, and then develop recurrence after treatment (Clevers, H., *The cancer stem cell: premises, promises and challenges*. Nat Med, 2011. 17(3): p. 313-9; Beck, B. and C. Blanpain, *Unravelling cancer stem cell potential*. Nat Rev Cancer, 2013. 13(10): p. 727-38). LSD1 was reported to maintain an undifferentiated tumor initiating or cancer stem cell phenotype in a spectrum of cancers (Zhang, X., et al., *Pluripotent Stem Cell Protein Sox2 Confers Sensitivity to LSD1 Inhibition in Cancer Cells*. Cell Rep, 2013. 5(2): p. 445-57; Wang, J., et al., *Novel histone demethylase LSD1 inhibitors selectively target cancer cells with pluripotent stem cell properties*. Cancer Res, 2011. 71(23): p. 7238-49). Acute myeloid leukemias (AMLs) are an example of neoplastic cells that retain some of their less differentiated stem cell like phenotype or leukemia stem cell (LSC) potential. Analysis of AML cells including gene expression arrays and chromatin immunoprecipitation with next generation sequencing (ChIP-Seq) revealed that LSD1 may regulate a subset of genes involved in multiple oncogenic programs to maintain LSC (Harris, W. J., et al., *The histone demethylase KDM1A sustains the oncogenic potential of MLL-AF9 leukemia stem cells*. Cancer Cell, 2012. 21(4): p. 473-87; Schenk, T., et al., *Inhibition of the LSD1 (KDM1A) demethylase reactivates the all-trans-retinoic acid differentiation pathway in acute myeloid leukemia*. Nat Med, 2012. 18(4): p. 605-11). These findings suggest potential therapeutic benefit of LSD1 inhibitors targeting cancers having stem cell properties, such as AMLs.

Overexpression of LSD1 is frequently observed in many types of cancers, including bladder cancer, NSCLC, breast carcinomas, ovary cancer, glioma, colorectal cancer, sarcoma including chondrosarcoma, Ewing's sarcoma, osteosarcoma, and rhabdomyosarcoma, neuroblastoma, prostate cancer, esophageal squamous cell carcinoma, and papillary thyroid carcinoma. Notably, studies found over-expression of LSD1 was significantly associated with clinically aggressive cancers, for example, recurrent prostate cancer, NSCLC, glioma, breast, colon cancer, ovary cancer, esophageal squamous cell carcinoma, and neuroblastoma. In these studies, either knockdown of LSD1 expression or treatment with small molecular inhibitors of LSD1 resulted in decreased cancer cell proliferation and/or induction of apoptosis. See, e.g., Hayami, S., et al., *Overexpression of LSD1 contributes to human carcinogenesis through chromatin regulation in various cancers*. Int J Cancer, 2011. 128(3): p. 574-86; Lv, T., et al., *Over-expression of LSD1 promotes proliferation, migration and invasion in non-small cell lung cancer*. PLoS One, 2012. 7(4): p. e35065; Serce, N., et al., *Elevated expression of LSD1 (Lysine-specific demethylase 1) during tumour progression from pre-invasive to invasive ductal carcinoma of the breast*. BMC Clin Pathol, 2012. 12: p. 13; Lim, S., et al., *Lysine-specific demethylase 1 (LSD1) is highly expressed in ER-negative breast cancers and a biomarker predicting aggressive biology*. Carcinogenesis, 2010. 31(3): p. 512-20; Konovalov, S. and I. Garcia-Bassets, *Analysis of the levels of lysine-specific demethylase 1 (LSD1) mRNA in human ovarian tumors and the effects of chemical LSD1 inhibitors in ovarian cancer cell lines*. J Ovarian Res, 2013. 6(1): p. 75; Sareddy, G. R., et al., *KDM1 is a novel therapeutic target for the treatment of gliomas*. Oncotarget, 2013. 4(1): p. 18-28; Ding, J., et al., *LSD1-mediated epigenetic modification contributes to proliferation and metastasis of colon cancer*. Br J Cancer, 2013. 109(4): p. 994-1003; Bennani-Baiti, I. M., et al., *Lysine-specific demethylase 1 (LSD1/KDM1A/AOF2/BHC110) is expressed and is an epigenetic drug target in chondrosarcoma, Ewing's sarcoma, osteosarcoma, and rhabdomyosarcoma*. Hum Pathol, 2012. 43(8): p. 1300-7; Schulte, J. H., et al., *Lysine-specific demethylase 1 is strongly expressed in poorly differentiated neuroblastoma: implications for therapy*. Cancer Res, 2009. 69(5): p. 2065-71; Crea, F., et al., *The emerging role of histone lysine demethylases in prostate cancer*. Mol Cancer, 2012. 11: p. 52; Suikki, H. E., et al., *Genetic alterations and changes in expression of histone demethylases in prostate cancer*. Prostate, 2010. 70(8): p. 889-98; Yu, Y., et al., *High expression of lysine-specific demethylase 1 correlates with poor prognosis of patients with esophageal squamous cell carcinoma*. Biochem Biophys Res Commun, 2013. 437(2): p. 192-8; Kong, L., et al., *Immunohistochemical expression of RBP2 and LSD1 in papillary thyroid carcinoma*. Rom J Morphol Embryol, 2013. 54(3): p. 499-503.

Recently, the induction of CD86 expression by inhibiting LSD1 activity was reported (Lynch, J. T., et al., *CD86 expression as a surrogate cellular biomarker for pharmacological inhibition of the histone demethylase lysine-specific demethylase 1*. Anal Biochem, 2013. 442(1): p. 104-6). CD86 expression is a marker of maturation of dendritic cells (DCs) which are involved in antitumor immune response. Notably, CD86 functions as a co-stimulatory factor to activate T cell proliferation (Greaves, P. and J. G. Gribben, *The role of B7 family molecules in hematologic malignancy*. Blood, 2013. 121(5): p. 734-44; Chen, L. and D. B. Flies, *Molecular mechanisms of T cell co-stimulation and co-inhibition*. Nat Rev Immunol, 2013. 13(4): p. 227-42).

In addition to playing a role in cancer, LSD1 activity has also been associated with viral pathogenesis. Particularly, LSD1 activity appears to be linked with viral replications and expressions of viral genes. For example, LSD1 functions as a co-activator to induce gene expression from the viral immediate early genes of various type of herpes virus including herpes simplex virus (HSV), varicella zoster virus (VZV), and β-herpesvirus human cytomegalovirus (Liang, Y., et al., *Targeting the JMJD2 histone demethylases to epigenetically control herpesvirus infection and reactivation from latency*. Sci Transl Med, 2013. 5(167): p. 167ra5; Liang, Y., et al., *Inhibition of the histone demethylase LSD1 blocks alpha-herpesvirus lytic replication and reactivation from latency*. Nat Med, 2009. 15(11): p. 1312-7). In this setting, a LSD1 inhibitor showed antiviral activity by blocking viral replication and altering virus associated gene expression.

Recent studies have also shown that the inhibition of LSD1 by either genetic depletion or pharmacological intervention increased fetal globin gene expression in erythroid cells (Shi, L., et al., *Lysine-specific demethylase 1 is a therapeutic target for fetal hemoglobin induction*. Nat Med, 2013. 19(3): p. 291-4; Xu, J., et al., *Corepressor-dependent silencing of fetal hemoglobin expression by BCL11A*. Proc Natl Acad Sci USA, 2013. 110(16): p. 6518-23). Inducing fetal globin gene would be potentially therapeutically beneficial for the disease of β-globinopathies, including β-thalassemia and sickle cell disease where the production of normal β-globin, a component of adult hemoglobin, is impaired (Sankaran, V. G. and S. H. Orkin, *The switch from fetal to adult hemoglobin*. Cold Spring Harb Perspect Med, 2013. 3(1): p. a011643; Bauer, D. E., S. C. Kamran, and S. H. Orkin, *Reawakening fetal hemoglobin: prospects for new therapies for the beta-globin disorders*. Blood, 2012. 120 (15): p. 2945-53). Moreover, LSD1 inhibition may potentiate other clinically used therapies, such as hydroxyurea or azacitidine. These agents may act, at least in part, by increasing γ-globin gene expression through different mechanisms.

In summary, LSD1 contributes to tumor development by altering epigenetic marks on histones and non-histone proteins. Accumulating data have validated that either genetic depletion or pharmacological intervention of LSD1 normalizes altered gene expressions, thereby inducing differentiation programs into mature cell types, decreasing cell proliferation, and promoting apoptosis in cancer cells. Therefore, LSD1 inhibitors alone or in combination with established therapeutic drugs would be effective to treat the diseases associated with LSD1 activity.

SUMMARY OF THE INVENTION

The present invention is directed to, inter alia, a compound of Formula I:

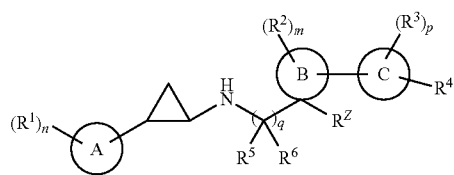

or a pharmaceutically acceptable salt thereof, wherein constituent variables are defined herein.

The present invention is further directed to a pharmaceutical composition comprising a compound of Formula I and at least one pharmaceutically acceptable carrier.

The present invention is further directed to a method of inhibiting LSD1 comprising contacting the LSD1 with a compound of Formula I.

The present invention is further directed to a method of treating an LSD1-mediated disease in a patient comprising administering to the patient a therapeutically effective amount of a compound of Formula I.

DETAILED DESCRIPTION

The present invention provides, inter alia, LSD1-inhibiting compounds such as a compound of Formula I:

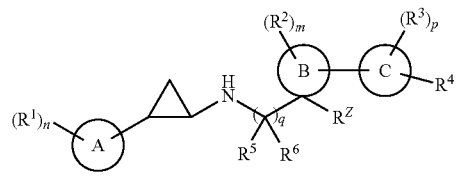

or a pharmaceutically acceptable salt thereof, wherein:
ring A is $C_{6-10}$ aryl or 5-10 membered heteroaryl having carbon and 1, 2, 3 or 4 heteroatoms selected from N, O, and S;
ring B is 4-10 membered heterocycloalkyl having carbon and 1, 2, or 3 heteroatoms selected from N, O, and S;
ring C is (1) monocyclic $C_{3-7}$ cycloalkyl, (2) monocyclic 4-7 membered heterocycloalkyl having carbon and 1, 2, 3 or 4 heteroatoms selected from N, O, and S, or (3) a fused bicyclic moiety having Formula (A):

wherein:
ring C1 is $C_{5-6}$ cycloalkyl or 5-6 membered heterocycloalkyl having carbon and 1, 2, 3 or 4 heteroatoms selected from N, O, and S;
ring C2 is (1) phenyl, (2) $C_{5-6}$ cycloalkyl, (3) 5-6 membered heteroaryl having carbon and 1, 2, 3 or 4 heteroatoms selected from N, O, and S, or (4) 5-6 membered heterocycloalkyl having carbon and 1, 2, 3 or 4 heteroatoms selected from N, O, and S;
wherein said fused bicyclic moiety of Formula (A) is bonded to ring B via ring C1, and wherein ring C substituents $R^3$ and $R^4$ are substituted on either or both of C1 and C2;
wherein ring C is substituted on any ring-forming atom of ring B except the ring-forming atom of ring B to which $R^Z$ is bonded;
each $R^1$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^2$ is independently selected from halo, $C_{1-6}$ alkyl, CN, $OR^{a1}$, $C(O)R^{b1}$, $C(O)NR^{c1}R^{d1}$, $C(O)OR^{a1}$, $NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

wherein each $R^2$ is substituted on any ring-forming atom of ring B except the ring-forming atom of ring B to which $R^Z$ is bonded;

each $R^3$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^4$ is halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, or $S(O)_2NR^{c3}R^{d3}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

$R^5$ and $R^6$ are each independently selected from H, halo, CN, $C_{1-4}$ alkyl, $C_{1-4}$ cyanoalkyl, $C_{1-4}$ haloalkyl, and —($C_{1-4}$ alkyl)-$OR^{a5}$;

$R^Z$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^a$, $R^b$, $R^c$, $R^d$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a1}$, $R^{b1}$, $R^{c1}$, $R^{d1}$ is independently selected from H and $C_{1-6}$ alkyl optionally substituted with 1, 2, 3, 4, or 5 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^e$, $R^{e1}$, $R^{e2}$, $R^{e3}$, $R^{e4}$, and $R^{e5}$ is independently selected from H, $C_{1-4}$ alkyl, and CN;

m is 0, 1, or 2;

n is 0, 1, 2, or 3;

p is 0, 1, 2, 3; and q is 0, 1, or 2.

In some embodiments, ring B is monocyclic 4-7 membered heterocycloalkyl having carbon and 1, 2, or 3 heteroatoms selected from N, O, and S.

In some embodiments, ring B is a 4-10 membered heterocycloalkyl having carbon and 1, 2, or 3 heteroatoms selected from N, O, and S wherein said ring B comprises at least one ring-forming N atom.

In some embodiments, ring B is a 4-7 membered heterocycloalkyl having carbon and 1, 2, or 3 heteroatoms selected from N, O, and S wherein said ring B comprises at least one ring-forming N atom.

In some embodiments, ring B is a 6-membered heterocycloalkyl ring having carbon and 1 or 2 heteroatoms selected from N, O, and S wherein said ring B comprises at least one ring-forming N atom.

In some embodiments, ring B is azetidine or piperidine.

In some embodiments, ring B is azetidine.

In some embodiments, ring B is piperidine.

In some embodiments, ring C is bound to a ring-forming N atom of ring B.

In some embodiments, ring A is $C_{6-10}$ aryl or 5-10 membered heteroaryl having carbon and 1, 2, 3 or 4 heteroatoms selected from N, O, and S.

In some embodiments, ring B is 4-10 membered heterocycloalkyl having carbon and 1, 2, or 3 heteroatoms selected from N, O, and S.

In some embodiments, ring C is (1) monocyclic $C_{3-7}$ cycloalkyl, (2) monocyclic 4-7 membered heterocycloalkyl having carbon and 1, 2, 3 or 4 heteroatoms selected from N, O, and S, or (3) a fused bicyclic moiety having Formula (A):

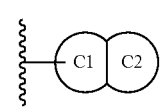

(A)

wherein:

ring C1 is $C_{5-6}$ cycloalkyl or 5-6 membered heterocycloalkyl having carbon and 1, 2, 3 or 4 heteroatoms selected from N, O, and S;

ring C2 is (1) phenyl, (2) $C_{5-6}$ cycloalkyl, (3) 5-6 membered heteroaryl having carbon and 1, 2, 3 or 4 heteroatoms selected from N, O, and S, or (4) 5-6 membered heterocycloalkyl having carbon and 1, 2, 3 or 4 heteroatoms selected from N, O, and S.

In some embodiments, the compounds of the invention include a compound of Formula II:

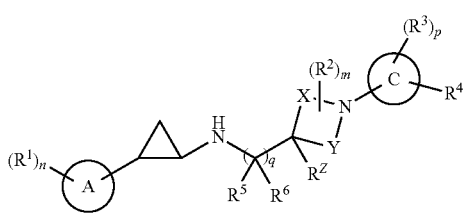

or a pharmaceutically acceptable salt thereof, wherein:

ring A is $C_{6-10}$ aryl or 5-10 membered heteroaryl having carbon and 1, 2, 3 or 4 heteroatoms selected from N, O, and S;

ring C is (1) monocyclic $C_{3-7}$ cycloalkyl, (2) monocyclic 4-7 membered heterocycloalkyl having carbon and 1, 2, 3 or 4 heteroatoms selected from N, O, and S, or (3) a fused bicyclic moiety having Formula (A):

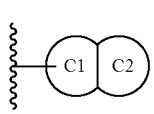

(A)

wherein:
ring C1 is $C_{5-6}$ cycloalkyl or 5-6 membered heterocycloalkyl having carbon and 1, 2, 3 or 4 heteroatoms selected from N, O, and S;
ring C2 is (1) phenyl, (2) $C_{5-6}$ cycloalkyl, (3) 5-6 membered heteroaryl having carbon and 1, 2, 3 or 4 heteroatoms selected from N, O, and S, or (4) 5-6 membered heterocycloalkyl having carbon and 1, 2, 3 or 4 heteroatoms selected from N, O, and S;
wherein said fused bicyclic moiety of Formula A is bonded to ring B via ring C1, and wherein ring C substituents $R^3$ and $R^4$ are substituted on either or both of C1 and C2;

X is —$CH_2$— or —$CH_2$—$CH_2$—;
Y is —$CH_2$— or —$CH_2$—$CH_2$—;

each $R^1$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^c$-$S(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS$ $(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^2$ is independently selected from halo, $C_{1-6}$ alkyl, CN, $OR^{a1}$, $C(O)R^{b1}$, $C(O)NR^{c1}R^{d1}$, $C(O)OR^{a1}$, $NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})$ $NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

wherein each $R^2$ is substituted any ring-forming carbon atom of the ring in Formula II containing X and Y except the ring-forming carbon atom to which $R^Z$ is bonded;

each $R^3$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^4$ is halo, $C_{1-6}$ alkyl, $C_{2-6}$ alkenyl, $C_{2-6}$ alkynyl, haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, haloalkyl, $C_{1-4}$ cyanoalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

$R^5$ and $R^6$ are each independently selected from H, halo, CN, $C_{1-4}$ alkyl, $C_{1-4}$ cyanoalkyl, $C_{1-4}$ haloalkyl, and —($C_{1-4}$ alkyl)-$OR^{a5}$;

$R^Z$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^a$, $R^b$, $R^c$, $R^d$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a1}$, $R^{b1}$, $R^{c1}$, $R^{d1}$ is independently selected from H and $C_{1-6}$ alkyl optionally substituted with 1, 2, 3, 4, or 5 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^e$, $R^{e1}$, $R^{e2}$, $R^{e3}$, $R^{e4}$, and $R^{e5}$ is independently selected from H, $C_{1-4}$ alkyl, and CN;

m is 0, 1, or 2;

n is 0, 1, 2, or 3;

p is 0, 1, 2, 3; and q is 0 or 1.

In some embodiments, the compounds of the invention include a compound of Formula IIIa or IIIb:

IIIa

IIIb or a pharmaceutically acceptable salt thereof, wherein:

ring A is $C_{6-10}$ aryl or 5-10 membered heteroaryl having carbon and 1, 2, 3 or 4 heteroatoms selected from N, O, and S;

ring C is (1) monocyclic $C_{3-7}$ cycloalkyl, (2) monocyclic 4-7 membered heterocycloalkyl having carbon and 1, 2, 3 or 4 heteroatoms selected from N, O, and S, or (3) a fused bicyclic moiety having Formula (A):

(A)

wherein:

ring C1 is $C_{5-6}$ cycloalkyl or 5-6 membered heterocycloalkyl having carbon and 1, 2, 3 or 4 heteroatoms selected from N, O, and S;

ring C2 is (1) phenyl, (2) $C_{5-6}$ cycloalkyl, (3) 5-6 membered heteroaryl having carbon and 1, 2, 3 or 4 heteroatoms selected from N, O, and S, or (4) 5-6 membered heterocycloalkyl having carbon and 1, 2, 3 or 4 heteroatoms selected from N, O, and S;

wherein said fused bicyclic moiety of Formula A is bonded to ring B via ring C1, and wherein ring C substituents $R^3$ and $R^4$ are substituted on either or both of C1 and C2;

each $R^1$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^2$ is independently selected from halo, $C_{1-6}$ alkyl, CN, $OR^{a1}$, $C(O)R^{b1}$, $C(O)NR^{c1}R^{d1}$, $C(O)OR^{a1}$, $NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})$ $NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

wherein each $R^2$ is substituted on any ring-forming carbon atom of the azetidine ring depicted in Formula IIIa or the piperidine ring depicted in Formula IIIb except the ring-forming carbon atom to which $R^Z$ is bonded;

each $R^3$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^4$ is halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, S(O)NR$^{c3}$R$^{d3}$, S(O)$_2$R$^{b3}$, and S(O)$_2$NR$^{c3}$R$^{d3}$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, or 4 substituents independently selected from halo, C$_{1-4}$ alkyl, C$_{1-4}$ haloalkyl, C$_{1-4}$ cyanoalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

R$^5$ and R$^6$ are each independently selected from H, halo, CN, C$_{1-4}$ alkyl, C$_{1-4}$ cyanoalkyl, C$_{1-4}$ haloalkyl, and —(C$_{1-4}$ alkyl)-OR$^{a5}$;

R$^Z$ is H, halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, or 4 substituents independently selected from halo, C$_{1-4}$ alkyl, C$_{1-4}$ haloalkyl, C$_{1-4}$ cyanoalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each R$^a$, R$^b$, R$^c$, R$^d$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, and R$^{d4}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- is optionally substituted with 1, 2, 3, 4, or 5 substituents independently selected from C$_{1-4}$ alkyl, C$_{1-4}$ haloalkyl, C$_{1-4}$ cycanoalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^c$ and R$^d$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, and 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c3}$ and R$^{d3}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O) NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c4}$ and R$^{d4}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O) NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$ S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, C$_{1-4}$ alkyl, C$_{1-4}$ haloalkyl, C$_{1-4}$ cyanoalkyl, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^{a1}$, R$^{b1}$, R$^{c1}$, R$^{d1}$ is independently selected from H and C$_{1-6}$ alkyl optionally substituted with 1, 2, 3, 4, or 5 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^{a5}$, R$^{b5}$, R$^{c5}$, and R$^{d5}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl, is optionally substituted with 1, 2, or 3 substituents independently selected from OH, CN, amino, halo, C$_{1-4}$ alkyl, C$_{1-4}$ alkoxy, C$_{1-4}$ alkylthio, C$_{1-4}$ alkylamino, di(C$_{1-4}$ alkyl)amino, C$_{1-4}$ haloalkyl, and C$_{1-4}$ haloalkoxy; and each R$^e$, R$^{e1}$, R$^{e2}$, R$^{e3}$, R$^{e4}$, and R$^{e5}$ is independently selected from H, C$_{1-4}$ alkyl, and CN;

m is 0, 1, or 2;

n is 0, 1, 2, or 3;

p is 0, 1, 2, 3; and q is 0, 1, or 2.

In some embodiments, the compounds of the invention include a compound of Formula IVa or IVb:

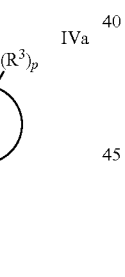

IVa

IVb

In some embodiments, the compounds of the invention include a compound of Formula Va or Vb:

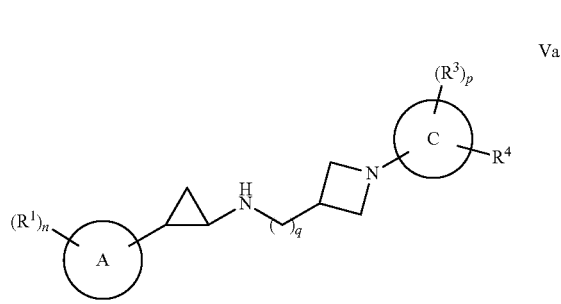

Va

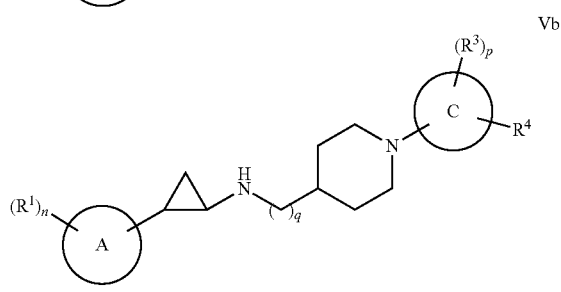

Vb or a pharmaceutically acceptable salt thereof, wherein:

ring A is C$_{6-10}$ aryl or 5-10 membered heteroaryl having carbon and 1, 2, 3 or 4 heteroatoms selected from N, O, and S;

ring C is (1) monocyclic C$_{3-7}$ cycloalkyl, (2) monocyclic 4-7 membered heterocycloalkyl having carbon and 1, 2, 3 or 4 heteroatoms selected from N, O, and S, or (3) a fused bicyclic moiety having Formula (A):

(A)

wherein:
ring C1 is C$_{5-6}$ cycloalkyl or 5-6 membered heterocycloalkyl having carbon and 1, 2, 3 or 4 heteroatoms selected from N, O, and S;
ring C2 is (1) phenyl, (2) C$_{5-6}$ cycloalkyl, (3) 5-6 membered heteroaryl having carbon and 1, 2, 3 or 4 heteroatoms selected from N, O, and S, or (4) 5-6 membered heterocycloalkyl having carbon and 1, 2, 3 or 4 heteroatoms selected from N, O, and S;
wherein said fused bicyclic moiety of Formula A is bonded to ring B via ring C1, and wherein Ring C substituents R$^3$ and R$^4$ are substituted on either or both of C1 and C2;

each R$^1$ is independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^3$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^4$ is halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^a$, $R^b$, $R^c$, $R^d$, $R^{a2}$, $R^{b2}$, $R^{c2}$, $R^{d2}$, $R^{a3}$, $R^{b3}$, $R^{c3}$ and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heterocloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^e$, $R^{e2}$, $R^{e3}$, and $R^{e5}$ is independently selected from H, $C_{1-4}$ alkyl, and CN;

n is 0, 1, 2, or 3;

p is 0, 1, 2, 3; and q is 0, 1, or 2.

In some embodiments, q is 0.

In some embodiments, q is 1.

In some embodiments, ring A is phenyl.

In some embodiments, n is 0.

In some embodiments, n is 1.

In some embodiments, $R^1$ is halo.

In some embodiments, $R^1$ is F.

In some embodiments, both $R^5$ and $R^6$ are H.

In some embodiments, ring C is monocyclic $C_{3-7}$ cycloalkyl.

In some embodiments, ring C is monocyclic 4-7 membered heterocycloalkyl having carbon and 1, 2, 3 or 4 heteroatoms selected from N, O, and S.

In some embodiments, ring C is cyclopropyl, cyclobutyl, cyclohexyl, azetidinyl, or piperidinyl.

In some embodiments, ring C is cyclopropyl, cyclohexyl, azetidinyl, or piperidinyl.

In some embodiments, $R^4$ is $C_{1-6}$ alkyl, $C_{6-10}$ aryl, 5-10 membered heteroaryl, $C(O)R^{b3}$, $C(O)NR^{c3}R^{d3}$, $C(O)OR^{a3}$, or $S(O)_2R^{b3}$, wherein said $C_{1-6}$ alkyl, $C_{6-10}$ aryl, and 5-10 membered heteroaryl are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{b3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a2}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^4$ is $C_{1-4}$ alkyl optionally substituted by CN, $C(O)NR^{c3}R^{d3}$, $OR^{a3}$, or $C(O)OR^{a3}$.

In some embodiments, $R^4$ is $C_{1-4}$ alkyl optionally substituted by CN, $C(O)NR^{c3}R^{d3}$, or $C(O)OR^{a3}$.

In some embodiments, $R^4$ is $C_{1-4}$ alkyl.

In some embodiments, $R^4$ is methyl.

In some embodiments, $R^4$ is phenyl.

In some embodiments, $R^4$ is CN.

In some embodiments, $R^4$ is —CH$_2$—CN, —CH$_2$—C(=O)OH, —CH$_2$—C(=O)NH(CH$_3$), —CH$_2$—C(=O)N(CH$_3$)$_2$, or —CH$_2$CH$_2$OH.

In some embodiments, $R^4$ is —CH$_2$—CN, —CH$_2$—C(=O)OH, —CH$_2$—C(=O)NH(CH$_3$), or —CH$_2$—C(=O)N(CH$_3$)$_2$.

In some embodiments, $R^4$ is —CH$_2$—CN.

In some embodiments, each $R^3$ is independently selected from $C_{1-6}$ alkyl, $C_{6-10}$ aryl, 5-10 membered heteroaryl, $C_{3-10}$ cycloalkyl, 4-10 membered heterocycloalkyl, $C(O)R^{b2}$, $C(O)NR^{c2}R^{d2}$, $C(O)OR^{a2}$, $S(O)_2R^{b2}$, and $S(O)_2NR^{c2}R^{d2}$, wherein said $C_{1-6}$ alkyl, $C_{6-10}$ aryl, and 5-10 membered heteroaryl, $C_{3-10}$ cycloalkyl, 4-10 membered heterocycloalkyl are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, each $R^3$ is independently selected from $C_{1-6}$ alkyl, $C_{6-10}$ aryl, 5-10 membered heteroaryl, $C(O)R^{b2}$, $C(O)NR^{c2}R^{d2}$, $C(O)OR^{a2}$, $S(O)_2R^{b2}$, and $S(O)_2NR^{c2}R^{d2}$, wherein said $C_{1-6}$ alkyl, $C_{6-10}$ aryl, and 5-10 membered heteroaryl are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, each $R^3$ is independently selected from $C_{1-6}$ alkyl, $C_{6-10}$ aryl, 5-10 membered heteroaryl, $C(O)R^{b2}$, $C(O)NR^{c2}R^{d2}$, $C(O)OR^{a2}$, and $S(O)_2R^{b2}$, wherein said $C_{1-6}$ alkyl, $C_{6-10}$ aryl, and 5-10 membered heteroaryl are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

In some embodiments, each $R^3$ is independently selected from $C_{1-6}$ alkyl, $C_{6-10}$ aryl, 5-10 membered heteroaryl, $C_{3-10}$ cycloalkyl, 4-10 membered heterocycloalkyl, $C(O)R^{b2}$, $C(O)NR^{c2}R^{d2}$, $C(O)OR^{a2}$, $S(O)_2R^{b2}$, and $S(O)_2NR^{c2}R^{d2}$, wherein said $C_{1-6}$ alkyl, $C_{6-10}$ aryl, 5-10 membered heteroaryl, $C_{3-10}$ cycloalkyl, and 4-10 membered heterocycloalkyl are each optionally substituted with 1, 2, 3, or 4 substituents independently selected from F, Cl, CF$_3$, CN, OH, C(O)OH, C(O)OCH$_3$, C(O)NH$_2$, C(O)NHCH$_3$, C(O)N(CH$_3$)$_2$, C(O)NH(i-Pr), CONH(CH(CH$_3$)(CF$_3$)), phenyl, cyclopropyl, pyrimidinyl, and thaizolyl.

In some embodiments, $R^Z$ is H, $C_{1-4}$ alkyl, or $C_{6-10}$ aryl-$C_{1-4}$ alkyl-, wherein said $C_{1-4}$ alkyl and $C_{6-10}$ aryl-$C_{1-4}$ alkyl- are each optionally substituted by halo or $OR^{a4}$.

In some embodiments, $R^Z$ is $C_{1-4}$ alkyl.

In some embodiments, $R^Z$ is $C_{1-4}$ alkyl substituted by methoxy.

In some embodiments, $R^Z$ is $C_{6-10}$ aryl-$C_{1-4}$ alkyl-substituted by fluoro.

In some embodiments, $R^Z$ is H, methyl, methoxymethyl, or 4-fluorophenylmethyl.

In some embodiments, $R^Z$ is H.

In some embodiments, p is 0.

In some embodiments, p is 1.

In some embodiments, p is 2.

In some embodiments, m is 0.

In some embodiments, the compound has a trans configuration with respect to the di-substituted cyclopropyl group depicted in Formula I (or any of Formulas II, IIIa, IIIb, IVa, IVb, Va, and Vb).

In some embodiments, each $R^a$, $R^b$, $R^c$, and $R^d$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

In some embodiments, each $R^{a2}$, $R^{b2}$, $R^{c2}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

In some embodiments, each $R^{a3}$, $R^{b3}$, $R^{c3}$, and $R^{d3}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c2}S(O)_2R^{b5}$, $NR^{c5}S(O)_2NR^{c5}R^{d5}$, and $S(O)_2NR^{c5}R^{d5}$.

In some embodiments, each $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}$, $C(O)R^{b5}$, $C(O)NR^{c5}R^{d5}$, $C(O)OR^{a2}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

In some embodiments, each $R^a$, $R^b$, $R^c$, and $R^d$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

In some embodiments, each $R^{a2}$, $R^{b2}$, $R^{c2}$, and $R^{d2}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

In some embodiments, each $R^{a3}$, $R^{b3}$, $R^{c3}$, and $R^{d3}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered hetero aryl)-$C_{1-4}$ alkyl-, and (4-10 membered heterocycloalkyl)-$C_{1-4}$ alkyl- is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

In some embodiments, each $R^{a4}$, $R^{b4}$, $R^{c4}$, and $R^{d4}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered hetero aryl)-$C_{1-4}$ alkyl-, and (4-10 membered heterocycloalkyl)-$C_{1-4}$ alkyl-, wherein said $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered hetero aryl)-$C_{1-4}$ alkyl-, and (4-10 membered heterocycloalkyl)-$C_{1-4}$ alkyl- is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy.

In some embodiments, each $R^a$, $R^b$, $R^c$, and $R^d$ is independently selected from H and $C_{1-6}$ alkyl.

In some embodiments, each $R^{a2}$, $R^{b2}$, $R^{c2}$, and $R^{d2}$ is independently selected from H and $C_{1-6}$ alkyl.

In some embodiments, each $R^{a3}$, $R^{b3}$, $R^{c3}$, and $R^{d3}$ is independently selected from H and $C_{1-6}$ alkyl.

In some embodiments, each $R^{a4}$, $R^{b4}$, $R^{c4}$, and $R^{d4}$ is independently selected from H and $C_{1-6}$ alkyl.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

A floating bond crossing a ring moiety in any structure or formula depicted herein is intended to show, unless otherwise indicated, that the bond can connect to any ring-forming atom of the ring moiety. For example, where ring A in Formula I is a naphthyl group, an $R^1$ substituent, if present, can be substituted on either of the two rings forming the naphthyl group.

In embodiments when ring C is a fused bicyclic moiety of Formula (A), the phrase "wherein said fused bicyclic moiety of Formula (A) is bonded to ring B via ring C1, and wherein Ring C substituents $R^3$ and $R^4$ are substituted on either or both of C1 and C2" is intended to denote that (1) ring B of Formula I is connected to ring C1 and not to ring C2, (2) $R^4$ is substituted on either ring C1 or ring C2, and (3) any $R^3$ that is present is substituted on either ring C1 or ring C2. The floating bond over ring C1 in Formula (A) is intended to show that ring C1 (not ring C2) connects to ring B.

As used herein, the phrase "optionally substituted" means unsubstituted or substituted. As used herein, the term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-6}$, and the like.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

The term "carbon" refers to one or more carbon atoms.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms. Exemplary alkylamino groups include methylamino, ethylamino, and the like.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. In some embodiments, the dialkylamino group is N($C_{1-4}$ alkyl)$_2$ such as, for example, dimethylamino or diethylamino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1-4}$ alkylthio such as, for example, methylthio or ethylthio.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "carbonyl", employed alone or in combination with other terms, refers to a —C(O)— group.

As used herein, the term "$C_{i-j}$ cyanoalkyl," employed alone or in combination with other terms, refers to an alkyl group substituted by a CN group.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl.

As used herein, "$C_{i-j}$ haloalkoxy," employed alone or in combination with other terms, refers to a group of formula —O-haloalkyl having i to j carbon atoms. An example haloalkoxy group is $OCF_3$. An additional example haloalkoxy group is $OCHF_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$ haloalkoxy.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. In some embodiments, the heteroaryl ring has or comprises carbon and 1, 2, 3 or 4 heteroatoms selected from N, O, and S. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridinyl, pyrimidinyl, pyrazinyl, pyridazinyl, pyrrolyl, pyrazolyl, azolyl, oxazolyl, isoxazolyl, thiazolyl, isothiazolyl, imidazoluyl, furanyl, thiophenyl, triazolyl, tetrazolyl, thiadiazolyl, quinolinyl, isoquinolinyl, indoleyl benzothiophenyl, benzofuranyl, benzisoxazolyl, imidazo[1,2-b]thiazolyl, purinyl, triazinyl, and the like.

A 5-membered heteroaryl is a heteroaryl group having five ring-forming atoms wherein one or more of the ring-forming atoms are independently selected from N, O, and S. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming members include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl.

As used herein, the term "heterocycloalkyl," employed alone or in combination with other terms, refers to non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. In some embodiments, the heterocycloalkyl group has or comprises carbon and 1, 2, or 3 heteroatoms selected from N, O, and S. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1,2,3,4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, the heterocycloalkyl is 5- to 10-membered, 4- to 10-membered, 4- to 7-membered, 5-membered, or 6-membered. Examples of heterocycloalkyl groups include 1,2,3,4-tetrahydro-quinolinyl, dihydrobenzofuranyl, azetidinyl, azepanyl, pyrrolidinyl, piperidinyl, piperazinyl, morpholinyl, thiomorpholinyl, and pyranyl.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002).

The following abbreviations may be used herein: AcOH (acetic acid); Ac$_2$O (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N,N'-diisopropyl azidodicarboxylate); DIEA (N,N-diisopropylethylamine); DIPEA (N,N-diisopropylethylamine); DMF (N,N-dimethylformamide); EA (ethyl acetate); Et (ethyl); EtOAc (ethyl acetate); g (gram(s)); h (hour(s)); HATU (N,N,N',N'-tetramethyl-O-(7-azabenzotriazol-1-yl) uronium hexafluorophosphate); HCl (hydrochloric acid); HPLC (high performance liquid chromatography); Hz (hertz); J (coupling constant); LCMS (liquid chromatography mass spectrometry); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); nM (nanomolar); NMP (N-methyl-pyrrolidinone); NMR (nuclear magnetic resonance spectroscopy); OTf (trifluoromethanesulfonate); Ph (phenyl); pM (picomolar); RP-HPLC (reverse phase high performance liquid chromatography); s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety. Protecting groups in the synthetic schemes are typically represented by "PG."

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compounds of formula 3 can be prepared by the methods outlined in Scheme 1. The cyclopropylamine derivative of formula 1 can react with aldehydes of formula 2 under reductive amination conditions well known in the art of organic synthesis to give the corresponding products of formula 3. For example, the reductive amination reaction can be performed in a suitable solvent such as DCM or THF using a reducing agent such as, but not limited to, sodium triacetoxyborohydride, optionally in the presence of an acid such as acetic acid. If any functional groups in compound 1 or 2 are protected to avoid any side reactions, a subsequent deprotection step can be performed to obtain the final product of formula 3. The deprotection conditions can be found in the literature or detailed in the specific examples described below. The starting materials of formula 1 or 2 are either commercially available, or can be prepared as described herein, or prepared following methods disclosed in the literature.

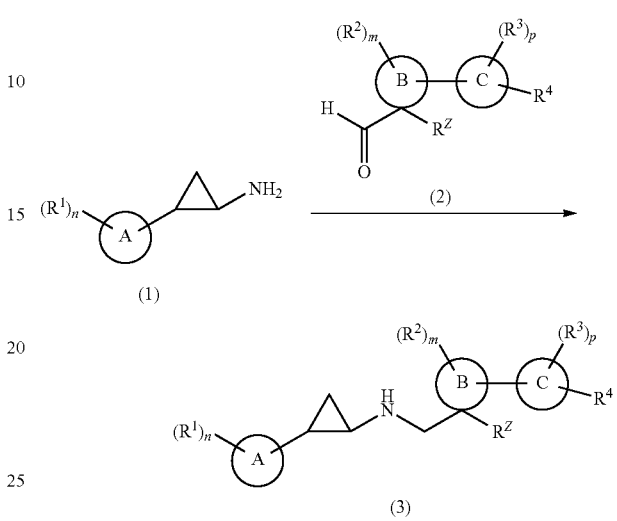

Compounds of formula 3a can be alternatively synthesized by the methods outlined in Scheme 2. Reductive amination of cyclopropylamine derivatives of formula 1 with aldehydes of formula 4 using similar conditions as described in Scheme 1 can give compounds of formula 5. The free amine group in compound 5 can then be protected with a suitable protecting group (PG) such as, but not limited to, CF$_3$CO and Cbz, followed by selective removal of the Boc protecting group by acid to give compound 6. Reductive amination of compound 6 with ketone 7 in a suitable solvent such as DCM with a reducing agent such as sodium triacetoxyborohydride can give compound 8, which can be deprotected to give compounds of formula 3a.

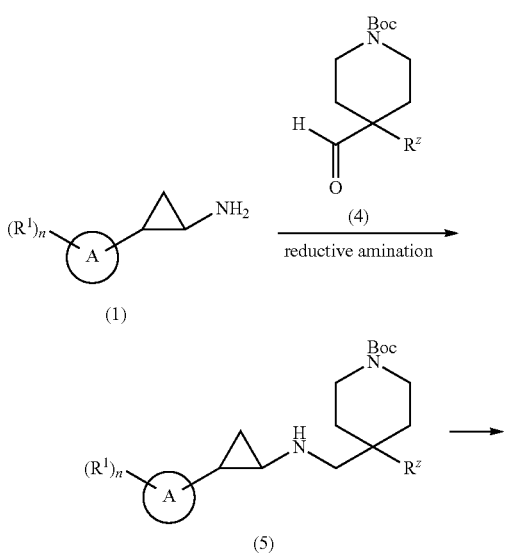

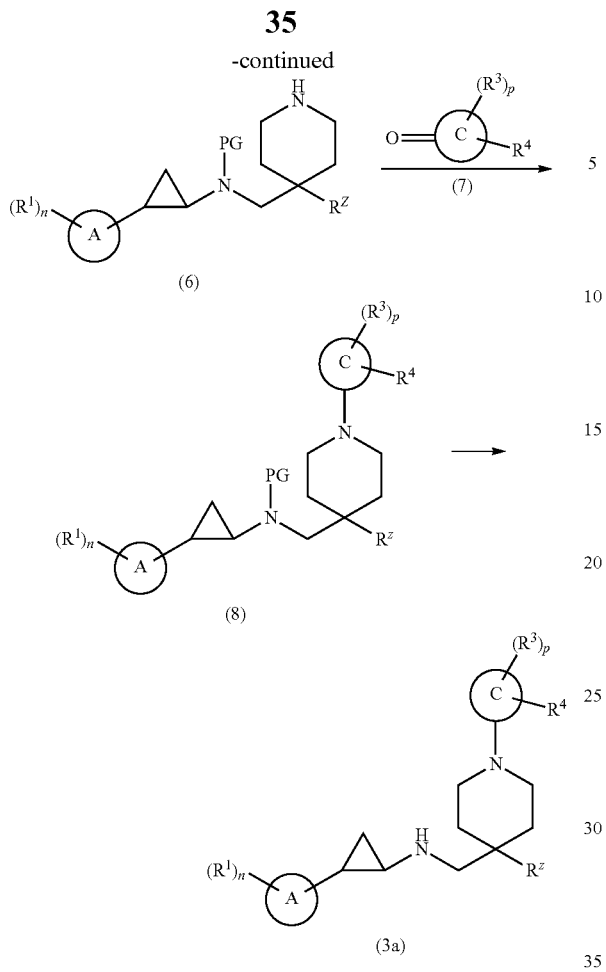

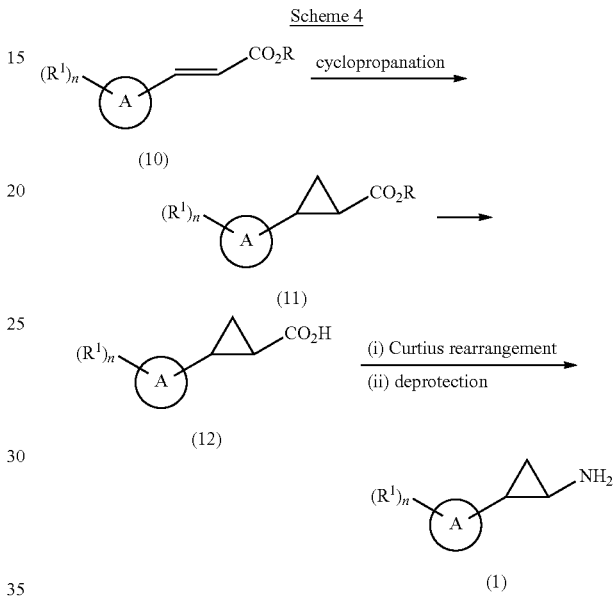

α,β-unsaturated esters of formula 10 (where R is alkyl such as ethyl) which are either commercially available or prepared using methods disclosed in the literature or detailed herein. Cyclopropanation of compound 10 under standard conditions such as Corey-Chaykovsky reaction can give the cyclopropyl derivatives of formula 11. The ester can be saponified to give acids of formula 12, which can be subjected to standard Curtius rearrangement conditions followed by deprotection to give cyclopropylamine derivatives of formula 1.

Compounds of formula 3b can be prepared by the methods outlined in Scheme 3 starting from compounds of formula 1 and compound 9 by reductive amination in a suitable solvent such as DCM or THF using a reducing agent such as, but not limited to, sodium triacetoxyborohydride, optionally in the presence of an acid such as acetic acid. If any functional groups in compound 1 or 9 are protected to avoid any side reactions, a subsequent deprotection step can be performed to obtain the final product of formula 3b.

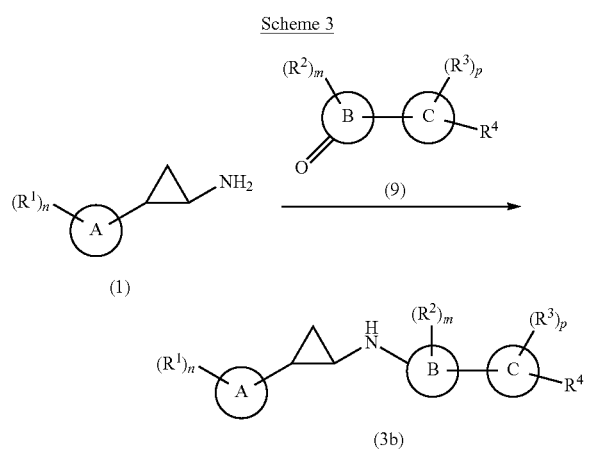

Cyclopropylamine derivatives of formula 1 can be prepared using methods outlined in Scheme 4, starting from the Methods of Use Compounds of the invention are LSD1 inhibitors and, thus, are useful in treating diseases and disorders associated with activity of LSD1. For the uses described herein, any of the compounds of the invention, including any of the embodiments thereof, may be used.

In some embodiments, the compounds of the invention are selective for LSD1 over LSD2, meaning that the compounds bind to or inhibit LSD1 with greater affinity or potency, compared to LSD2. In general, selectivity can be at least about 5-fold, at least about 10-fold, at least about 20-fold, at least about 50-fold, at least about 100-fold, at least about 200-fold, at least about 500-fold or at least about 1000-fold.

As inhibitors of LSD1, the compounds of the invention are useful in treating LSD1-mediated diseases and disorders. The term "LSD1-mediated disease" or "LSD1-mediated disorder" refers to any disease or condition in which LSD1 plays a role, or where the disease or condition is associated with expression or activity of LSD1. The compounds of the invention can therefore be used to treat or lessen the severity of diseases and conditions where LSD1 is known to play a role.

Diseases and conditions treatable using the compounds of the invention include generally cancers, inflammation, autoimmune diseases, viral induced pathogenesis, beta-globinopathies, and other diseases linked to LSD1 activity.

Cancers treatable using compounds according to the present invention include, for example, hematological cancers, sarcomas, lung cancers, gastrointestinal cancers, genitourinary tract cancers, liver cancers, bone cancers, nervous system cancers, gynecological cancers, and skin cancers.

Example hematological cancers include, for example, lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), and multiple myeloma.

Example sarcomas include, for example, chondrosarcoma, Ewing's sarcoma, osteosarcoma, rhabdomyosarcoma, angiosarcoma, fibrosarcoma, liposarcoma, myxoma, rhabdomyoma, fibroma, lipoma, harmatoma, and teratoma.

Example lung cancers include, for example, non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Example gastrointestinal cancers include, for example, cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Example genitourinary tract cancers include, for example, cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Example liver cancers include, for example, hepatoma (hepatocellular carcinoma), cholangiocarcinoma, hepatoblastoma, angiosarcoma, hepatocellular adenoma, and hemangioma.

Example bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Example nervous system cancers include, for example, cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Example gynecological cancers include, for example, cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Example skin cancers include, for example, melanoma, basal cell carcinoma, squamous cell carcinoma, Kaposi's sarcoma, moles dysplastic nevi, lipoma, angioma, dermatofibroma, and keloids.

The compounds of the invention can further be used to treat cancer types where LSD1 may be overexpressed including, for example, breast, prostate, head and neck, laryngeal, oral, and thyroid cancers (e.g., papillary thyroid carcinoma).

The compounds of the invention can further be used to treat genetic disorders such as Cowden syndrome and Bannayan-Zonana syndrome.

The compounds of the invention can further be used to treat viral diseases such as herpes simplex virus (HSV), varicella zoster virus (VZV), human cytomegalovirus, hepatitis B virus (HBV), and adenovirus.

The compounds of the invention can further be used to treat beta-globinopathies including, for example, beta-thalassemia and sickle cell anemia.

As used herein, the term "contacting" refers to the bringing together of indicated moieties in an in vitro system or an in vivo system. For example, "contacting" a LSD1 protein with a compound of the invention includes the administration of a compound of the present invention to an individual or patient, such as a human, having a LSD1 protein, as well as, for example, introducing a compound of the invention into a sample containing a cellular or purified preparation containing the LSD1 protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e. arresting further development of the pathology and/or symptomatology) or ameliorating the disease; for example, ameliorating a disease, condition or disorder in an individual who is experiencing or displaying the pathology or symptomatology of the disease, condition or disorder (i.e. reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, JAK, PIM, PI3K inhibitors for treatment of LSD1-mediated diseases, disorders or conditions. The one or more additional pharmaceutical agents can be administered to a patient simultaneously or sequentially.

In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, panobinostat, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating cancer and other proliferative diseases, the compounds of the invention can be used in combination with targeted therapies, including JAK kinase inhibitors (Ruxolitinib, JAK1-selective), Pim kinase inhibitors, PI3 kinase inhibitors including PI3K-delta selective and broad spectrum PI3K inhibitors, MEK inhibitors, Cyclin Dependent kinase inhibitors, b-RAF inhibitors, mTOR inhibitors, Proteasome inhibitors (Bortezomib, Carfilzomib), HDAC-inhibitors (Panobinostat, Vorinostat), DNA methyl transferase inhibitors, dexamethasone, bromo and extra terminal family members inhibitors and indoleamine 2,3-dioxygenase inhibitors.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine;

an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Biological drugs, such as antibodies and cytokines, used as anticancer agents, can be combined with the compounds of the invention. In addition, drugs modulating microenvironment or immune responses can be combined with the compounds of the invention. Examples of such drugs are anti-Her2 antibodies, anti-CD20 antibodies, anti-CTLA1, anti-PD-1, anti-PDL1, and other immunotherapeutic drugs.

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

The compounds of the invention can be provided with or used in combination with a companion diagnostic. As used herein, the term "companion diagnostic" refers to a diagnostic device useful for determining the safe and effective use of a therapeutic agent. For example, a companion diagnostic may be used to customize dosage of a therapeutic agent for a given subject, identify appropriate subpopulations for treatment, or identify populations who should not receive a particular treatment because of an increased risk of a serious side effect.

In some embodiments, the companion diagnostic is used to monitor treatment response in a patient. In some embodiments, the companion diagnostic is used to identify a subject that is likely to benefit from a given compound or therapeutic agent. In some embodiments, the companion diagnostic is used to identify a subject having an increased risk of adverse side effects from administration of a therapeutic agent, compared to a reference standard. In some embodiments, the companion diagnostic is an in vitro diagnostic or imaging tool selected from the list of FDA cleared or approved companion diagnostic devices. In some embodiments, the companion diagnostic is selected from the list of tests that have been cleared or approved by the Center for Devices and Radiological Health.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating LSD1 in tissue samples, including human, and for identifying LSD1 ligands by inhibition binding of a labeled compound. Accordingly, the present invention includes LSD1 assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind LSD1 by monitoring its concentration variation when contacting with LSD1, through tracking of the labeling. For example, a test compound (labeled) can be evaluated for its ability to reduce binding of another compound which is known to bind to LSD1 (i.e., standard compound). Accordingly, the ability of a test compound to compete with the standard compound for binding to LSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of LSD1 as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ C$_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ C$_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge C$_{18}$ 5 μm particle size, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

(1-{4-[(trans-2-Phenylcyclopropyl)amino]piperidin-1-yl}cyclobutyl)acetonitrile

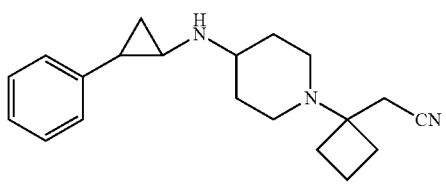 [SMILES: N#CCC1(N2CCC(NC3CC3c3ccccc3)CC2)CCC1]

47

Step 1: [1-(4-oxopiperidin-1-yl)cyclobutyl]acetonitrile

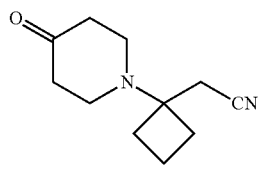 [SMILES: N#CCC1(N2CCC(=O)CC2)CCC1]

To the mixture of piperidin-4-one hydrochloride hydrate (154 mg, 1.00 mmol, Aldrich, cat#151769) in acetonitrile (2 mL, 40 mmol) was added DBU (225 μL, 1.50 mmol), followed by cyclobutylideneacetonitrile (187 mg, 2.00 mmol, prepared using methods disclosed in the literature such as WO 2009/114512). The resulting mixture was heated to 70° C. and stirred overnight. The reaction mixture was then cooled to room temperature and diluted with EtOAc. The mixture was then washed with water and brine. The organic layer was dried over $Na_2SO_4$ then concentrated. The residue (yellow oil) was used in the next step without further purification. LC-MS calculated for $C_{11}H_{17}N_2O$ $(M+H)^+$: m/z=193.1; found 193.2.

Step 2: (1-{4-[(trans-2-phenylcyclopropyl)amino]piperidin-1-yl}cyclobutyl)acetonitrile To a solution of 2-phenylcyclopropanamine hydrochloride (36 mg, 0.21 mmol) (trans, racemic, Acros: Cat#130470050, Lot: A0295784) and [1-(4-oxopiperidin-1-yl)cyclobutyl]acetonitrile (41 mg, 0.21 mmol) (crude product from Step 1) in DCM (2 mL) was added acetic acid (36 μL, 0.64 mmol). The resulting yellow solution was stirred at room temperature for 2 h. Then $Na(OAc)_3BH$ (140 mg, 0.64 mmol) was added. The reaction mixture was stirred at room temperature overnight. The reaction mixture was diluted with DCM then washed with saturated $Na_2CO_3$, water and brine. The organic layer was dried over $Na_2SO_4$ then concentrated. The residue was purified by prep. HPLC (pH=10, acetonitrile/water+$NH_4OH$) to give the product as a white solid (trans, racemic). LC-MS calculated for $C_{20}H_{28}N_3$ $(M+H)^+$: m/z=310.2; found 310.2.

Example 2

(1-Methyl-3-{4-[(trans-2-phenylcyclopropyl)amino]piperidin-1-yl}azetidin-3-yl)acetonitrile

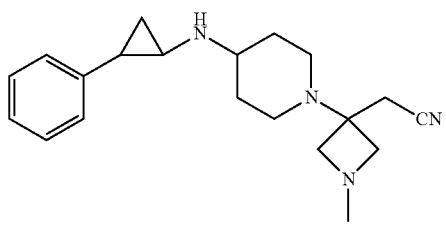 [SMILES: CN1CC(CC#N)(N2CCC(NC3CC3c3ccccc3)CC2)C1]

48

Step 1: tert-butyl 3-(cyanomethyl)-3-(4-oxopiperidin-1-yl)azetidine-1-carboxylate

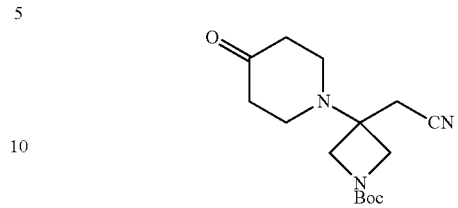

To a solution of piperidin-4-one hydrochloride hydrate (1.08 g, 7.00 mmol) and tert-butyl 3-(cyanomethylene)azetidine-1-carboxylate (2.04 g, 10.5 mmol, prepared using similar methods as disclosed in the literature such as WO 2009/114512) in acetonitrile (7 mL) was added DBU (1.36 mL, 9.10 mmol). The resulting mixture was stirred at room temperature for 15 min until all the solid dissolved. Then the resulting solution was heated to 70° C. and stirred for 48 h. The mixture was cooled to room temperature, diluted with EtOAc then washed with water and brine. The organic layer was dried over $Na_2SO_4$ then concentrated. The residue was purified by with silica gel column eluting with 0 to 7% MeOH/DCM to give the product (844 mg, 41%) as a yellow oil. LC-MS calculated for $C_{11}H_{16}N_3O_3$ $(M-^tBu+2H)^+$: m/z=238.1; found 238.2.

Step 2: tert-butyl 3-(cyanomethyl)-3-{4-[(trans-2-phenylcyclopropyl)amino]piperidin-1-yl}azetidine-1-carboxylate

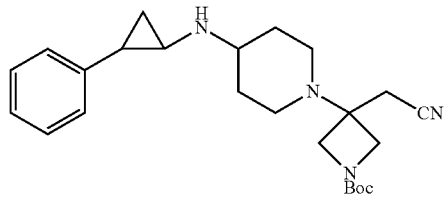 [SMILES: CC(C)(C)OC(=O)N1CC(CC#N)(N2CCC(NC3CC3c3ccccc3)CC2)C1]

To a solution of 2-phenylcyclopropanamine hydrochloride (540 mg, 3.2 mmol, Acros: Cat#130470050, Lot: A0295784) and tert-butyl 3-(cyanomethyl)-3-(4-oxopiperidin-1-yl)azetidine-1-carboxylate (937 mg, 3.19 mmol) in DCM (15 mL) was added acetic acid (540 μL, 9.6 mmol). The resulting yellow solution was stirred at room temperature overnight then $Na(OAc)_3BH$ (1.4 g, 6.4 mmol) was added. The reaction mixture was stirred at room temperature for 2 h then diluted with DCM and washed with saturated $Na_2CO_3$, water and brine. The organic layer was dried over $Na_2SO_4$ then concentrated. The residue was purified on a silica gel column eluting with 0 to 10% MeOH/DCM to give the desired product (1.07 g, 82%) as a yellow oil. LC-MS calculated for $C_{24}H_{35}N_4O_2$ $(M+H)^+$: m/z=411.3; found 411.3.

Step 3: tert-butyl 3-(cyanomethyl)-3-{4-[(trans-2-phenylcyclopropyl)(trifluoroacetyl)amino]piperidin-1-yl}azetidine-1-carboxylate

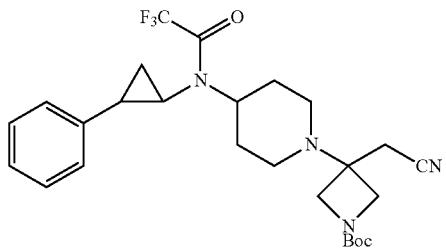 [SMILES: CC(C)(C)OC(=O)N1CC(CC#N)(N2CCC(N(C(=O)C(F)(F)F)C3CC3c3ccccc3)CC2)C1]

To a solution of tert-butyl 3-(cyanomethyl)-3-{4-[(trans-2-phenylcyclopropyl)amino]piperidin-1-yl}azetidine-1-carboxylate (1.07 g, 2.61 mmol) in DCM (15 mL) at 0° C. was added DIEA (1.4 mL, 7.8 mmol), followed by dropwise addition of trifluoroacetic anhydride (0.41 mL, 2.87 mmol). The resulting yellow solution was stirred at 0° C. for 1 h then the reaction was quenched with saturated NaHCO$_3$ solution and extracted with DCM. The combined extracts were dried over Na$_2$SO$_4$ then filtered and concentrated. The residue was purified on silica gel column eluting with 0 to 60% EtOAc/Hexanes to give the desired product (922 mg, 70%) as a yellow oil which solidified on standing to give a light yellow solid. LC-MS calculated for C$_{26}$H$_{34}$F$_3$N$_4$O$_3$ (M+H)$^+$: m/z=507.3; found 507.4.

Step 4: N-{1-[3-(cyanomethyl)azetidin-3-yl]piperidin-4-yl}-2,2,2-trifluoro-N-(trans-2-phenylcyclopropyl)acetamide

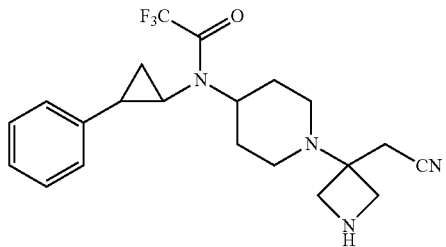 [SMILES: N#CCC1(N2CCC(N(C(=O)C(F)(F)F)C3CC3c3ccccc3)CC2)CNC1]

To a solution of tert-butyl 3-(cyanomethyl)-3-{4-[(trans-2-phenylcyclopropyl)(trifluoroacetyl)amino]piperidin-1-yl}azetidine-1-carboxylate (922 mg, 1.82 mmol) in DCM (7.2 mL) was added TFA (2.80 mL, 36.4 mmol). The resulting yellow solution was stirred at room temperature for 1 h then concentrated. The residue was dissolved in EtOAc then washed with saturated NaHCO$_3$ solution and brine. The organic layer was dried over Na$_2$SO$_4$ then concentrated. The residue was purified on a silica gel column eluting with 0 to 20% MeOH/DCM to give the desired product (700 mg, 95%) as a yellow oil which solidified on standing to give a light yellow solid. LC-MS calculated for C$_{21}$H$_{26}$F$_3$N$_4$O (M+H)$^+$: m/z=407.2; found 407.2.

Step 5: N-{1-[3-(cyanomethyl)-1-methylazetidin-3-yl]piperidin-4-yl}-2,2,2-trifluoro-N-(trans-2-phenylcyclopropyl)acetamide

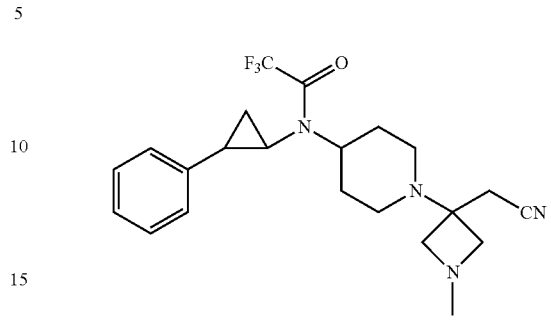

To a solution of N-{1-[3-(cyanomethyl)azetidin-3-yl]piperidin-4-yl}-2,2,2-trifluoro-N-(trans-2-phenylcyclopropyl)acetamide (24 mg, 0.059 mmol) in DCM (2 mL) was added formaldehyde (37 wt % in water, 22 µL, 0.30 mmol), followed by acetic acid (10. µL, 0.18 mmol). The resulting mixture was stirred at room temperature overnight, then Na(OAc)$_3$BH (38 mg, 0.18 mmol) was added. The reaction mixture was stirred at room temperature for 2 h then neutralized with saturated Na$_2$CO$_3$ solution and extracted with DCM. The combined extracts were dried over Na$_2$SO$_4$ then concentrated. The residue was used in the next step without further purification. LC-MS calculated for C$_{22}$H$_{28}$F$_3$N$_4$O (M+H)$^+$: m/z=421.2; found 421.2.

Step 6: (1-methyl-3-{4-[(trans-2-phenylcyclopropyl)amino]piperidin-1-yl}azetidin-3-yl)acetonitrile The crude product from Step 5 was dissolved in THF (1 mL) and MeOH (1 mL) then 2.0 M sodium hydroxide in water (0.15 mL, 0.30 mmol) was added. The resulting mixture was stirred at 30° C. for 1 h, cooled to room temperature, diluted with acetonitrile, then filtered and purified by prep. HPLC (pH=2, acetonitrile/water+TFA) to give the product in the form of a TFA salt as a white solid. LC-MS calculated for C$_{20}$H$_{29}$N$_4$ (M+H)$^+$: m/z=325.2; found 325.2.

Example 3

(3-{4-[(trans-2-Phenylcyclopropyl)amino]piperidin-1-yl}azetidin-3-yl)acetonitrile

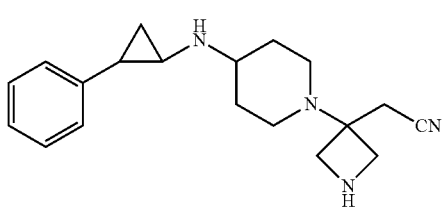 [SMILES: N#CCC1(N2CCC(NC3CC3c3ccccc3)CC2)CNC1]

To a solution of tert-butyl 3-(cyanomethyl)-3-{4-[(trans-2-phenylcyclopropyl)amino]piperidin-1-yl}azetidine-1-carboxylate (20 mg, 0.049 mmol, prepared as described in Example 2, Step 2) in DCM (1 mL) was added TFA (0.5 mL). The resulting yellow solution was stirred at room temperature for 1 h then concentrated. The residue was dissolved in acetonitrile then purified by prep. HPLC (pH=2, acetonitrile/water+TFA) to give the desired product in the form of TFA salt as a white solid. LC-MS calculated for $C_{19}H_{27}N_4$ (M+H)$^+$: m/z=311.2; found 311.2.

Example 4

(1-Benzyl-3-{4-[(trans-2-phenylcyclopropyl)amino]piperidin-1-yl}azetidin-3-yl)acetonitrile

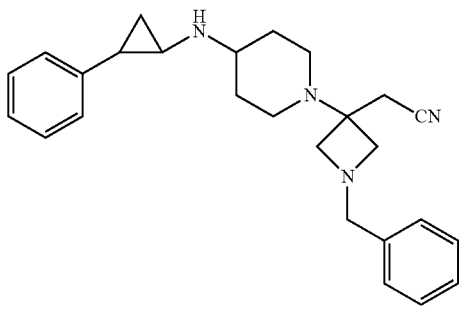 [SMILES: N#CCC1(N2CCC(NC3CC3c3ccccc3)CC2)CN(Cc2ccccc2)C1]

To a solution of N-{1-[3-(cyanomethyl)azetidin-3-yl]piperidin-4-yl}-2,2,2-trifluoro-N-(trans-2-phenylcyclopropyl)acetamide (24 mg, 0.059 mmol, prepared as described in Example 2, Step 4) in DCM (2 mL) was added benzaldehyde (30 μL, 0.29 mmol), followed by acetic acid (10 μL, 0.18 mmol). The resulting mixture was stirred at room temperature overnight, then Na(OAc)$_3$BH (38 mg, 0.18 mmol) was added. The reaction mixture was stirred at room temperature for 2 h at which time LC-MS indicated the reaction was complete. The mixture was then neutralized with saturated Na$_2$CO$_3$ solution and extracted with DCM. The combined extracts were dried over Na$_2$SO$_4$ then concentrated. The residue was dissolved in THF (1 mL) and MeOH (1 mL) then 2.0 M sodium hydroxide in water (0.15 mL, 0.30 mmol) was added. The resulting mixture was stirred at 30° C. for 1.5 h then cooled to room temperature and diluted with acetonitrile. The mixture was then filtered and purified by prep. HPLC (pH=2, acetonitrile/water+TFA) to give the desired product in the form of TFA salt as a white solid. LC-MS calculated for $C_{26}H_{33}N_4$ (M+H)$^+$: m/z=401.3; found 401.2.

Example 5

3-(3-(Cyanomethyl)-3-{4-[(trans-2-phenylcyclopropyl)amino]piperidin-1-yl}azetidin-1-yl)propanoic acid

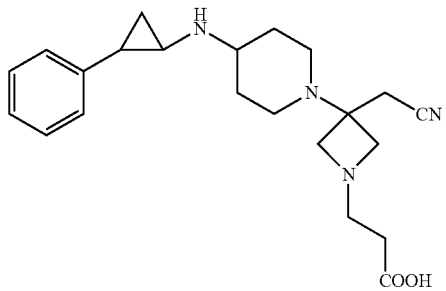 [SMILES: N#CCC1(N2CCC(NC3CC3c3ccccc3)CC2)CN(CCC(=O)O)C1]

To a solution of N-{1-[3-(cyanomethyl)azetidin-3-yl]piperidin-4-yl}-2,2,2-trifluoro-N-(trans-2-phenylcyclopropyl) acetamide (33 mg, 0.081 mmol, prepared as described in Example 2, Step 4) in acetonitrile (1 mL) was added methyl acrylate (36 μL, 0.40 mmol), followed by DBU (12 μL, 0.081 mmol). The resulting mixture was stirred at room temperature overnight then diluted with water and extracted with DCM. The combined extracts were dried over Na$_2$SO$_4$ then concentrated. The residue was dissolved in THF (1 mL) and MeOH (1 mL) then 2.0 M sodium hydroxide in water (0.30 mL, 0.60 mmol) was added. The resulting mixture was stirred at 30° C. for 1 h then diluted with MeOH/acetonitrile. The mixture was then filtered and purified by prep. HPLC (pH=2, acetonitrile/water+TFA) to give the desired product in the form of TFA salt as a white solid. LC-MS calculated for $C_{22}H_{31}N_4O_2$ (M+H)$^+$: m/z=383.2; found 383.3.

Example 6

(1-Acetyl-3-{4-[(trans-2-phenylcyclopropyl)amino]piperidin-1-yl}azetidin-3-yl)acetonitrile

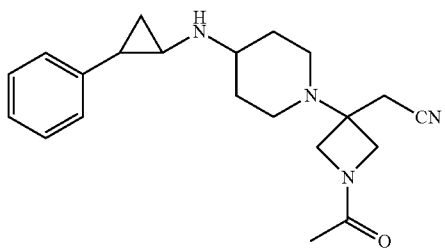 [SMILES: CC(=O)N1CC(CC#N)(N2CCC(NC3CC3c3ccccc3)CC2)C1]

To a solution of N-{1-[3-(cyanomethyl)azetidin-3-yl]piperidin-4-yl}-2,2,2-trifluoro-N-(trans-2-phenylcyclopropyl) acetamide (22 mg, 0.054 mmol, prepared as described in Example 2, Step 4) in THF (1.0 mL) was added DIEA (47 μL, 0.27 mmol), followed by acetyl chloride (7.7 μL, 0.11 mmol). The resulting mixture was stirred at room temperature for 1 h then MeOH (1.0 mL) was added, followed by 2.0 M sodium hydroxide in water (0.14 mL, 0.27 mmol). The resulting mixture was stirred at room temperature for 2 h at which time LC-MS indicated the reaction completed to the desired product. The reaction mixture was diluted with acetonitrile then purified by prep. HPLC (pH=2, acetonitrile/water+TFA) to give the desired product in the form of TFA salt as a white solid. LC-MS calculated for $C_{21}H_{29}N_4O$ (M+H)$^+$: m/z=353.2; found 353.3.

Example 7

(1-Benzoyl-3-{4-[(trans-2-phenylcyclopropyl)amino]piperidin-1-yl}azetidin-3-yl)acetonitrile

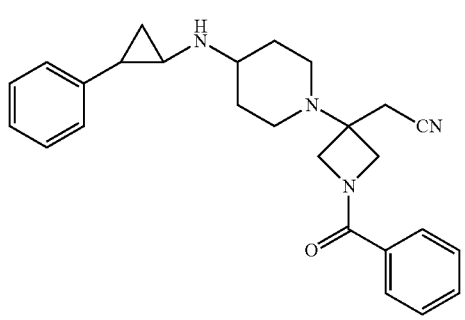 [SMILES: N#CCC1(N2CCC(NC3CC3c3ccccc3)CC2)CN(C(=O)c2ccccc2)C1]

To a solution of N-{1-[3-(cyanomethyl)azetidin-3-yl]piperidin-4-yl}-2,2,2-trifluoro-N-(trans-2-phenylcyclopropyl)acetamide (22 mg, 0.054 mmol, prepared as described in Example 2, Step 4) in THF (1.0 mL) was added DIEA (47 µL, 0.27 mmol), followed by benzoyl chloride (12 µL, 0.11 mmol). The resulting mixture was stirred at room temperature for 1 h then MeOH (1.0 mL) was added, followed by 2.0 M sodium hydroxide in water (0.14 mL, 0.27 mmol). The mixture was stirred at room temperature for 2 h then diluted with acetonitrile and purified by prep. HPLC (pH=2, acetonitrile/water+TFA) to give the desired product in the form of TFA salt as a white solid. LC-MS calculated for $C_{26}H_{31}N_4O$ (M+H)$^+$: m/z=415.2; found 415.3.

Example 8

Methyl 3-(cyanomethyl)-3-{4-[(trans-2-phenylcyclopropyl)amino]piperidin-1-yl}azetidine-1-carboxylate

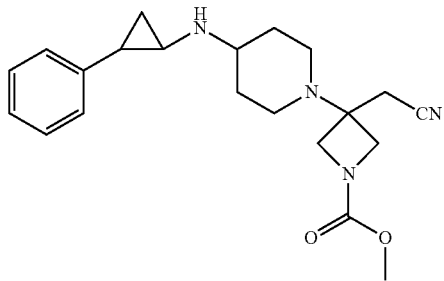 [SMILES: COC(=O)N1CC(CC#N)(N2CCC(NC3CC3c3ccccc3)CC2)C1]

To a solution of N-{1-[3-(cyanomethyl)azetidin-3-yl]piperidin-4-yl}-2,2,2-trifluoro-N-(trans-2-phenylcyclopropyl)acetamide (20. mg, 0.049 mmol, prepared as described in Example 2, Step 4) in THF (1.0 mL) was added DIEA (43 µL, 0.25 mmol), followed by methyl chloroformate (7.6 µL, 0.098 mmol). The resulting mixture was stirred at room temperature for 1.5 h then MeOH (1.0 mL) was added, followed by 2.0 M sodium hydroxide in water (0.12 mL, 0.25 mmol). The mixture was stirred at room temperature for 2 h then diluted with acetonitrile and purified by prep. HPLC (pH=2, acetonitrile/water+TFA) to give the desired product in the form of TFA salt as a white solid. LC-MS calculated for $C_{21}H_{29}N_4O_2$ (M+H)$^+$: m/z=369.2; found 369.3.

Example 9

(1-(Methylsulfonyl)-3-{4-[(trans-2-phenylcyclopropyl)amino]piperidin-1-yl}azetidin-3-yl)acetonitrile

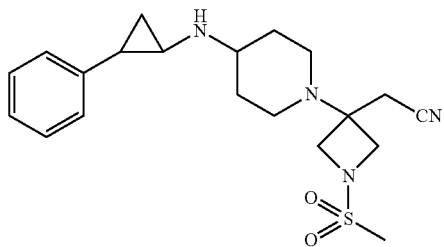 [SMILES: CS(=O)(=O)N1CC(CC#N)(N2CCC(NC3CC3c3ccccc3)CC2)C1]

To a solution of N-{1-[3-(cyanomethyl)azetidin-3-yl]piperidin-4-yl}-2,2,2-trifluoro-N-(trans-2-phenylcyclopropyl)acetamide (20. mg, 0.049 mmol, prepared as described in Example 2, Step 4) in THF (1.0 mL) was added DIEA (43 µL, 0.25 mmol), followed by methanesulfonyl chloride (7.6 µL, 0.098 mmol). The resulting mixture was stirred at room temperature for 1.5 h then MeOH (1.0 mL) was added, followed by 2.0 M sodium hydroxide in water (0.12 mL, 0.25 mmol). The reaction mixture was stirred at room temperature for 2 h then diluted with acetonitrile and purified by prep. HPLC (pH=2, acetonitrile/water+TFA) to give the desired product in the form of TFA salt as a white solid. LC-MS calculated for $C_{20}H_{29}N_4O_2S$ (M+H)$^+$: m/z=389.2; found 389.2.

Example 10

2-(3-(Cyanomethyl)-3-{4-[(trans-2-phenylcyclopropyl)amino]piperidin-1-yl}azetidin-1-yl)nicotinonitrile

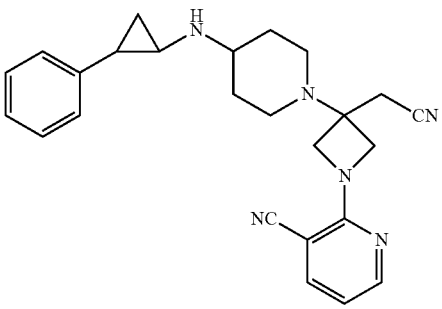 [SMILES: N#CCC1(N2CCC(NC3CC3c3ccccc3)CC2)CN(c2ncccc2C#N)C1]

To a solution of N-{1-[3-(cyanomethyl)azetidin-3-yl]piperidin-4-yl}-2,2,2-trifluoro-N-(trans-2-phenylcyclopropyl)acetamide (23 mg, 0.056 mmol, prepared as described in Example 2, Step 4) and 2-fluoronicotinonitrile (14 mg, 0.11 mmol) in NMP (1.0 mL, 10. mmol) was added DIEA (39 µL, 0.23 mmol). The resulting mixture was heated to 120° C. and stirred for 1 h at which time LC-MS indicated the reaction was complete to give the desired intermediate. The reaction mixture was cooled to room temperature then MeOH (1.0 mL) was added, followed by 2.0 M sodium hydroxide in water (0.14 mL, 0.28 mmol). The resulting mixture was stirred at room temperature for 2.5 h then diluted with acetonitrile and purified by prep. HPLC (pH=2, acetonitrile/water+TFA) to give the desired product in the form of TFA salt as a yellow solid. LC-MS calculated for $C_{25}H_{29}N_6$ (M+H)$^+$: m/z=413.2; found 413.3.

Example 11

3-Cyano-4-(3-(cyanomethyl)-3-{4-[(trans-2-phenyl-cyclopropyl)amino]piperidin-1-yl}azetidin-1-yl)benzoic acid

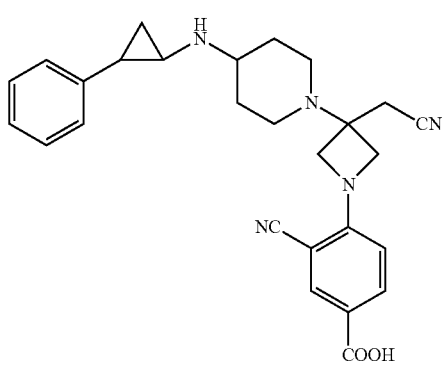 [SMILES: N#CCC1(N2CCC(NC3CC3c3ccccc3)CC2)CN(c2ccc(C(=O)O)cc2C#N)C1]

This compound was prepared using procedures analogous to those described for Example 10 with 3-cyano-4-fluorobenzoic acid replacing 2-fluoronicotinonitrile. The product was purified by prep. HPLC (pH=2, acetonitrile/water+TFA) to give the compound in the form of TFA salt as a white solid. LC-MS calculated for $C_{27}H_{30}N_5O_2$ (M+H)$^+$: m/z=456.2; found 456.3.

Example 12

2-(3-(Cyanomethyl)-3-{4-[(trans-2-phenylcyclopropyl)amino]piperidin-1-yl}azetidin-1-yl)benzonitrile

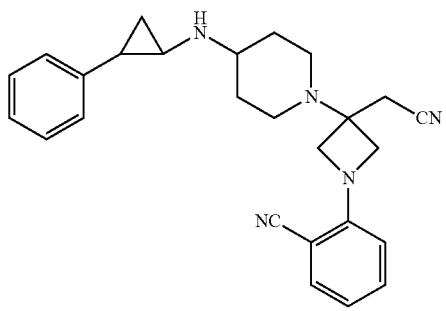 [SMILES: N#CCC1(N2CCC(NC3CC3c3ccccc3)CC2)CN(c2ccccc2C#N)C1]

This compound was prepared using procedures analogous to those described for Example 10 with 2-fluorobenzonitrile replacing 2-fluoronicotinonitrile. The product was purified by prep. HPLC (pH=2, acetonitrile/water+TFA) to give the compound in the form of TFA salt as a white solid. LC-MS calculated for $C_{26}H_{30}N_5$ (M+H)$^+$: m/z=412.2; found 412.3.

Example 13

4-(3-(Cyanomethyl)-3-{4-[(trans-2-phenylcyclopropyl)amino]piperidin-1-yl}azetidin-1-yl)benzonitrile

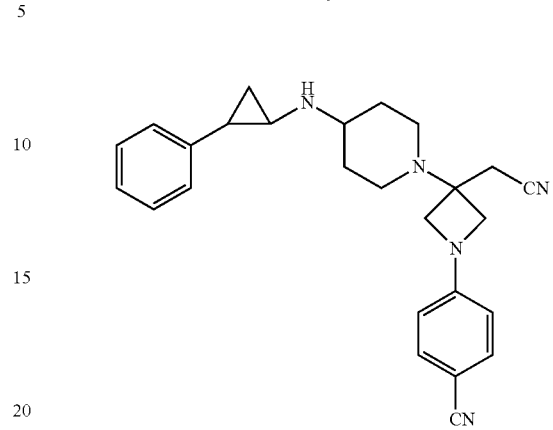

This compound was prepared using procedures analogous to those described for Example 10 with 4-fluorobenzonitrile replacing 2-fluoronicotinonitrile. The product was purified by prep. HPLC (pH=2, acetonitrile/water+TFA) to give the compound in the form of TFA salt as a white solid. LC-MS calculated for $C_{26}H_{30}N_5$ (M+H)$^+$: m/z=412.2; found 412.3.

Example 14

[1-(3-{[(trans-2-Phenylcyclopropyl)amino]methyl}azetidin-1-yl)cyclobutyl]acetonitrile

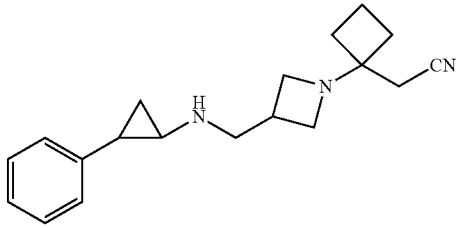 [SMILES: N#CCC1(N2CC(CNC3CC3c3ccccc3)C2)CCC1]

Step 1: tert-butyl 3-{[(trans-2-phenylcyclopropyl)amino]methyl}azetidine-1-carboxylate

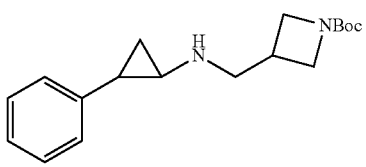 [SMILES: CC(C)(C)OC(=O)N1CC(CNC2CC2c2ccccc2)C1]

To a solution of tert-butyl 3-formylazetidine-1-carboxylate (556 mg, 3.00 mmol, Alfa Aesar: Cat# H52794) and 2-phenylcyclopropanamine hydrochloride (600. mg, 3.54 mmol, trans, racemic, J&W PharmLab: Cat#20-0073S, Lot: JW152-128A) in DCM (10 mL) was added acetic acid (510 μL, 9.0 mmol). The resulting yellow solution was stirred at room temperature overnight then Na(OAc)$_3$BH (1.9 g, 9.0 mmol) was added. The reaction mixture was stirred at room temperature for 1 h then diluted with DCM, washed with saturated Na$_2$CO$_3$, water and brine. The organic layer was dried over Na$_2$SO$_4$ then concentrated. The residue was purified on silica gel column eluting with 0 to 100% EtOAc/Hexanes to give the desired product (513 mg, 57%) as a light yellow oil. LC-MS calculated for C$_{14}$H$_{19}$N$_2$O$_2$ (M-$^t$Bu+2H)$^+$: m/z=247.1; found 247.2.

Step 2: tert-butyl 3-{[[(allyloxy)carbonyl](trans-2-phenylcyclopropyl)amino]methyl}azetidine-1-carboxylate

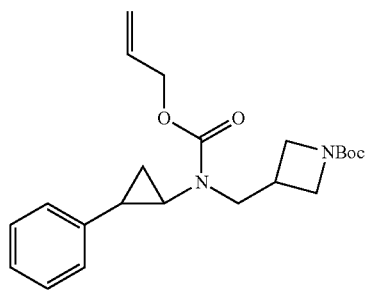 [SMILES: C=CCOC(=O)N(CC1CN(C(=O)OC(C)(C)C)C1)C1CC1c1ccccc1]

To a solution of tert-butyl 3-{[(trans-2-phenylcyclopropyl)amino]methyl}azetidine-1-carboxylate (513 mg, 1.70 mmol, prepared in Step 1) in DCM (5 mL, 80 mmol) was added DIEA (890 μL, 5.1 mmol), followed by dropwise addition of allyl chloroformate (234 μL, 2.20 mmol). The resulting mixture was stirred at room temperature for 40 min then quenched with water and extracted with DCM. The combined extracts were dried over Na$_2$SO$_4$ then concentrated. The residue was purified on silica gel column eluting with 0 to 60% EtOAc/Hexanes to give the desired product (632 mg, 96%) as a light yellow oil. LC-MS calculated for C$_{22}$H$_{31}$N$_2$O$_4$ (M+H)$^+$: m/z=387.2; found 387.2.

Step 3: allyl(azetidin-3-ylmethyl)(trans-2-phenylcyclopropyl)carbamate

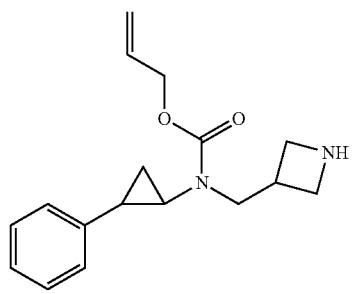 [SMILES: C=CCOC(=O)N(CC1CNC1)C1CC1c1ccccc1]

To a solution of tert-butyl 3-{[[(allyloxy)carbonyl](trans-2-phenylcyclopropyl)amino]methyl}azetidine-1-carboxylate (632 mg, 1.64 mmol) in DCM (3 mL) was added TFA (3 mL). The resulting mixture was stirred at room temperature for 1 h then concentrated. The residue was dissolved in EtOAc then washed with saturated NaHCO$_3$ solution and brine. The organic layer was dried over Na$_2$SO$_4$ then concentrated. The residue was used in the next step without further purification. LC-MS calculated for C$_{17}$H$_{23}$N$_2$O$_2$ (M+H)$^+$: m/z=287.2; found 287.2.

Step 4: allyl({1-[1-(cyanomethyl)cyclobutyl]azetidin-3-yl}methyl)(trans-2-phenylcyclopropyl)carbamate

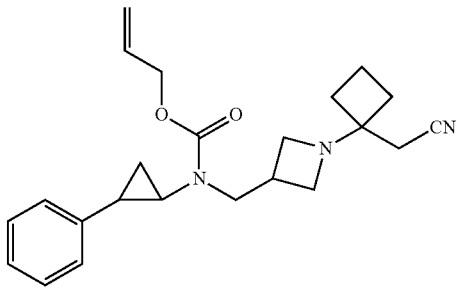 [SMILES: C=CCOC(=O)N(CC1CN(C2(CC#N)CCC2)C1)C1CC1c1ccccc1]

To a solution of allyl(azetidin-3-ylmethyl)(trans-2-phenylcyclopropyl)carbamate (48 mg, 0.17 mmol) and cyclobutylideneacetonitrile (31 mg, 0.34 mmol, prepared using methods disclosed in the literature such as WO 2009/114512) in acetonitrile (0.5 mL) was added DBU (10 μL, 0.08 mmol). The resulting mixture was stirred at room temperature overnight then concentrated. The residue was purified on silica gel column eluting with 0 to 10% MeOH/DCM to give the desired product (26 mg, 41%) as a yellow oil. LC-MS calculated for C$_{23}$H$_{30}$N$_3$O$_2$ (M+H)$^+$: m/z=380.2; found 380.2.

Step 5: [1-(3-{[(trans-2-phenylcyclopropyl)amino]methyl}azetidin-1-yl)cyclobutyl]acetonitrile A mixture of allyl({1-[1-(cyanomethyl)cyclobutyl]azetidin-3-yl}methyl)(trans-2-phenylcyclopropyl)carbamate (26 mg, 0.068 mmol) and tetrakis(triphenylphosphine)-palladium(0) (4 mg, 0.003 mmol) in THF (3 mL) was degassed then refilled with nitrogen. Then N-ethylethanamine (71 μL, 0.68 mmol) was added. The resulting mixture was heated to 85° C. and stirred for 2 h at which time LS-MS indicated the reaction was complete. The mixture was cooled to room temperature then diluted with acetonitrile, filtered and purified by prep. HPLC (pH=2, acetonitrile/water+TFA) to give the desired product in the form of TFA salt as a white solid. LC-MS calculated for C$_{19}$H$_{26}$N$_3$ (M+H)$^+$: m/z=296.2; found 296.2.

Example 15

(1'-(Ethylsulfonyl)-3-{[(trans-2-phenylcyclopropyl)amino]methyl}-1,3'-biazetidin-3'-yl)acetonitrile

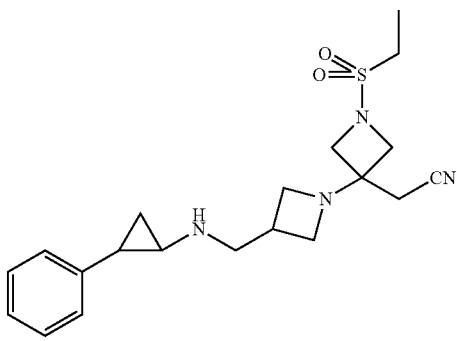 [SMILES: CCS(=O)(=O)N1CC(CC#N)(N2CC(CNC3CC3c3ccccc3)C2)C1]

This compound was prepared using procedures analogous to those as described for Example 14 with [1-(ethylsulfonyl)azetidin-3-ylidene]acetonitrile (prepared using similar conditions disclosed in the literature such as WO 2009/114512) replacing cyclobutylideneacetonitrile in Step 4. The product was purified by prep. HPLC (pH=2, acetonitrile/water+TFA) to give the compound in the form of TFA salt as a white solid. LC-MS calculated for $C_{20}H_{29}N_4O_2S$ (M+H)$^+$: m/z=389.2; found 389.2.

Example 16

[4-(3-{[(trans-2-Phenylcyclopropyl)amino]methyl}azetidin-1-yl)piperidin-4-yl]acetonitrile

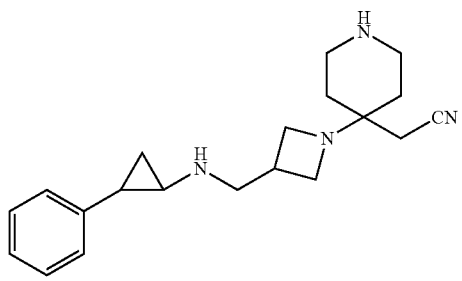 [SMILES: N#CCC1(N2CC(CNC3CC3c3ccccc3)C2)CCNCC1]

Step 1: tert-butyl 4-(cyanomethyl)-4-(3-{[(trans-2-phenylcyclopropyl)amino]methyl}azetidin-1-yl)piperidine-1-carboxylate

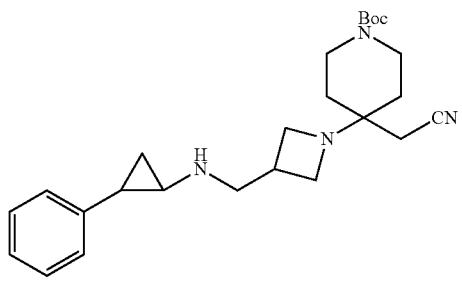 [SMILES: CC(C)(C)OC(=O)N1CCC(CC#N)(N2CC(CNC3CC3c3ccccc3)C2)CC1]

This compound was prepared using procedures analogous to those as described for Example 14 with tert-butyl 4-(cyanomethylene)piperidine-1-carboxylate (prepared using similar conditions disclosed in the literature such as WO 2008/064157) replacing cyclobutylideneacetonitrile in Step 4 and the reaction in Step 4 was carried out at 60° C. for 48 h. LC-MS calculated for $C_{25}H_{37}N_4O_2$ (M+H)$^+$: m/z=425.3; found 425.3.

Step 2: [4-(3-{[(trans-2-phenylcyclopropyl)amino]methyl}azetidin-1-yl)piperidin-4-yl]acetonitrile The crude product from Step 1 was dissolved in DCM (1 mL) then TFA (1 mL) was added. The mixture was stirred at room temperature for 1 h then concentrated. The residue was dissolved in MeOH then purified by prep. HPLC (pH=2, acetonitrile/water+TFA) to give the desired product in the form of TFA salt. LC-MS calculated for $C_{20}H_{29}N_4$ (M+H)$^+$: m/z=325.2; found 325.2.

Example 17

[1-Methyl-4-(3-{[(trans-2-phenylcyclopropyl)amino]methyl}azetidin-1-yl)piperidin-4-yl]acetonitrile

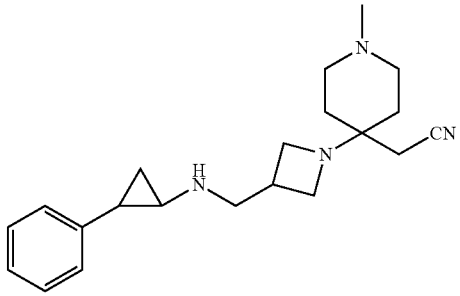 [SMILES: CN1CCC(CC#N)(N2CC(CNC3CC3c3ccccc3)C2)CC1]

Step 1: tert-butyl 3-{[(trans-2-phenylcyclopropyl)(trifluoroacetyl)amino]methyl}azetidine-1-carboxylate

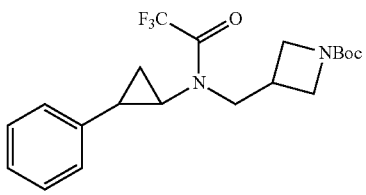 [SMILES: CC(C)(C)OC(=O)N1CC(CN(C(=O)C(F)(F)F)C2CC2c2ccccc2)C1]

To a solution of tert-butyl 3-{[(trans-2-phenylcyclopropyl)amino]methyl}azetidine-1-carboxylate (187 mg, 0.618 mmol, prepared as described in Example 14, Step 1) in DCM (5 mL) at 0° C. was added triethylamine (0.431 mL, 3.09 mmol), followed by dropwise addition of trifluoroacetic anhydride (114 μL, 0.804 mmol). The resulting yellow solution was stirred at 0° C. for 1 h then quenched with saturated NaHCO$_3$ solution and extracted with DCM. The combined extracts were dried over Na$_2$SO$_4$ then concentrated. The residue was purified on silica gel column eluting with 0 to 60% EtOAc/Hexanes to give the desired product (228 mg, 93%) as a yellow oil. LC-MS calculated for $C_{16}H_{18}F_3N_2O_3$ (M-$^t$Bu+2H)$^+$: m/z=343.1; found 343.2.

Step 2: N-(azetidin-3-ylmethyl)-2,2,2-trifluoro-N-(trans-2-phenylcyclopropyl)acetamide

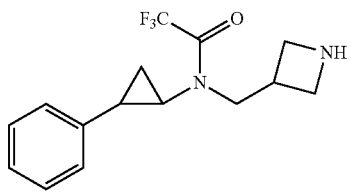 [SMILES: O=C(N(CC1CNC1)C1CC1c1ccccc1)C(F)(F)F]

To a solution of tert-butyl 3-{[(trans-2-phenylcyclopropyl)-(trifluoroacetyl)amino]methyl}azetidine-1-carboxylate (228 mg, 0.572 mmol) in DCM (3 mL) was added TFA (3 mL). The resulting light yellow solution was stirred at room temperature for 1 h then concentrated. The residue (TFA salt) was used in the next step without further purification. LC-MS calculated for $C_{15}H_{18}F_3N_2O$ (M+H)$^+$: m/z=299.1; found 299.2.

Step 3: tert-butyl 4-(cyanomethyl)-4-(3-{[(trans-2-phenylcyclopropyl)(trifluoroacetyl)amino]methyl}azetidin-1-yl)piperidine-1-carboxylate

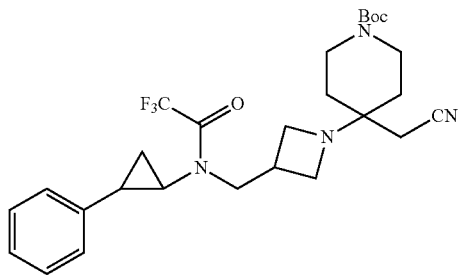 [SMILES: CC(C)(C)OC(=O)N1CCC(CC#N)(N2CC(CN(C(=O)C(F)(F)F)C3CC3c3ccccc3)C2)CC1]

To a solution of N-(azetidin-3-ylmethyl)-2,2,2-trifluoro-N-(trans-2-phenylcyclopropyl)acetamide (TFA salt: 0.93 g, 2.2 mmol), tert-butyl 4-(cyanomethylene)piperidine-1-carboxylate (0.50 g, 2.2 mmol, prepared using similar conditions disclosed in the literature such as WO 2008/064157) in acetonitrile (5 mL) was added DBU (0.7 mL, 4 mmol). The resulting mixture was stirred at room temperature overnight. The reaction mixture was quenched with saturated aqueous NaHCO$_3$, and extracted with EtOAc. The combined organic layers were washed with brine, dried over Na$_2$SO$_4$, filtered and concentrated under reduced pressure. The residue was purified by flash chromatography on a silica gel column eluting with ethyl acetate in hexanes (0-50%) to afford the desired product (95 mg, 8%). LC-MS calculated for $C_{27}H_{36}F_3N_4O_3$ (M+H)$^+$: m/z=521.3; found 521.2.

Step 4: N-({1-[4-(cyanomethyl)piperidin-4-yl]azetidin-3-yl}methyl)-2,2,2-trifluoro-N-(trans-2-phenylcyclopropyl)acetamide

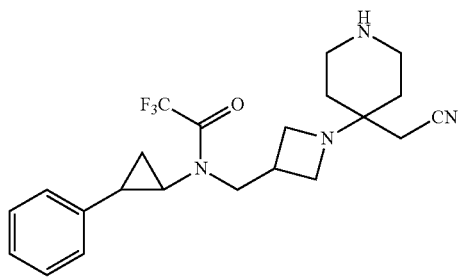 [SMILES: N#CCC1(N2CC(CN(C(=O)C(F)(F)F)C3CC3c3ccccc3)C2)CCNCC1]

To a solution of tert-butyl 4-(cyanomethyl)-4-(3-{[(trans-2-phenylcyclopropyl)(trifluoroacetyl)amino]methyl}azetidin-1-yl)piperidine-1-carboxylate (95 mg, 0.18 mmol) in DCM (1 mL) was added TFA (1 mL). The resulting mixture was stirred at room temperature for 1 h then concentrated. The residue was used in the next step without further purification. LC-MS calculated for $C_{22}H_{28}F_3N_4O$ (M+H)$^+$: m/z=421.2; found 421.2.

Step 5: [1-methyl-4-(3-{[(trans-2-phenylcyclopropyl)amino]methyl}azetidin-1-yl)piperidin-4-yl]acetonitrile To a solution of N-({1-[4-(cyanomethyl)piperidin-4-yl]azetidin-3-yl}methyl)-2,2,2-trifluoro-N-(trans-2-phenylcyclopropyl)acetamide (TFA salt, 10 mg, 0.02 mmol) in THF (0.5 mL) was added a solution of 10.0 M formaldehyde in water (10 μL, 0.1 mmol), followed by acetic acid (5.8 μL, 0.10 mmol). The reaction mixture was stirred at room temperature for 2 h then sodium triacetoxyborohydride (22 mg, 0.10 mmol) was added. The resulting mixture was stirred at room temperature for 2 h then MeOH (1 mL) and 2N NaOH in water (0.2 mL) were added. The reaction mixture was stirred at 40° C. for 1 h then cooled to room temperature, filtered and purified by prep. HPLC (pH=10, acetonitrile/water+NH$_4$OH) to afford the desired product. LC-MS calculated for $C_{21}H_{31}N_4$ (M+H)$^+$: m/z=339.3; found 339.3.

Example 18

[1-Acetyl-4-(3-{[(trans-2-phenylcyclopropyl)amino]methyl}azetidin-1-yl)piperidin-4-yl]acetonitrile

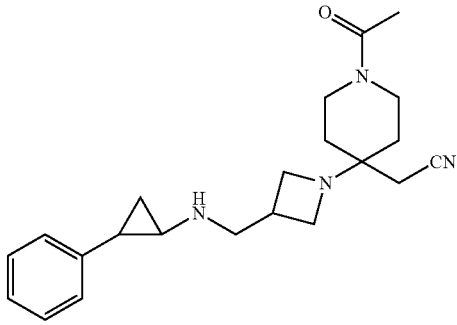 [SMILES: CC(=O)N1CCC(CC#N)(N2CC(CNC3CC3c3ccccc3)C2)CC1]

To a solution of N-({1-[4-(cyanomethyl)piperidin-4-yl]azetidin-3-yl}methyl)-2,2,2-trifluoro-N-(trans-2-phenylcyclopropyl)acetamide (TFA salt, prepared as described for Example 17, Step 4: 9 mg, 0.02 mmol) and DIEA (8.8 μL, 0.05 mmol) in THF (1 mL) was added acetic anhydride (3.2 μL, 0.034 mmol). The reaction mixture was stirred at room temperature for 1 h then 1N NaOH in water (0.5 mL) and MeOH (1 mL) were added. The resulting mixture was stirred at room temperature for 1 h then purified by prep. HPLC (pH=10, acetonitrile/water+NH$_4$OH) to afford the desired product. LC-MS calculated for $C_{22}H_{31}N_4O$ (M+H)$^+$: m/z=367.2; found 367.3.

Example 19

[1-(4-Fluorobenzoyl)-4-(3-{[(trans-2-phenylcyclopropyl)amino]methyl}azetidin-1-yl)piperidin-4-yl]acetonitrile

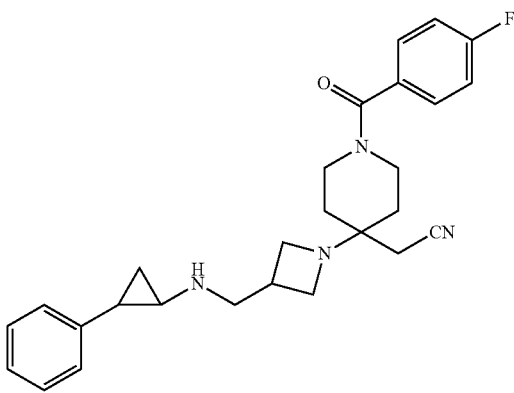 [SMILES: N#CCC1(N2CC(CNC3CC3c3ccccc3)C2)CCN(C(=O)c2ccc(F)cc2)CC1]

This compound was prepared by using procedures analogous to those described for the synthesis of Example 18 with 4-fluoro-benzoyl chloride replacing acetic anhydride. LC-MS calculated for $C_{27}H_{32}FN_4O$ (M+H)$^+$: m/z=447.3; found 447.3.

Example 20

[1-(Methylsulfonyl)-4-(3-{[(trans-2-phenylcyclopropyl)amino]methyl}azetidin-1-yl)piperidin-4-yl]acetonitrile

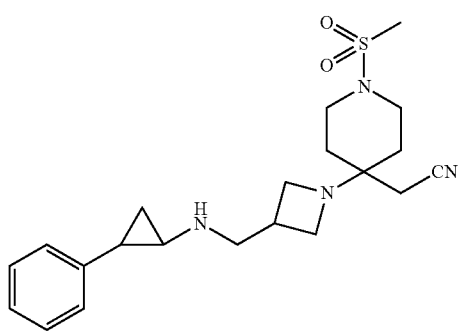 [SMILES: CS(=O)(=O)N1CCC(CC#N)(N2CC(CNC3CC3c3ccccc3)C2)CC1]

This compound was prepared by using procedures analogous to those described for the synthesis of Example 18 with methanesulfonyl chloride replacing acetic anhydride. LC-MS calculated for $C_{21}H_{31}N_4O_2S$ (M+H)$^+$: m/z=403.2; found 403.2.

Example 21

[4-(3-{[(trans-2-Phenylcyclopropyl)amino]methyl}azetidin-1-yl)-1-(phenylsulfonyl)piperidin-4-yl]acetonitrile

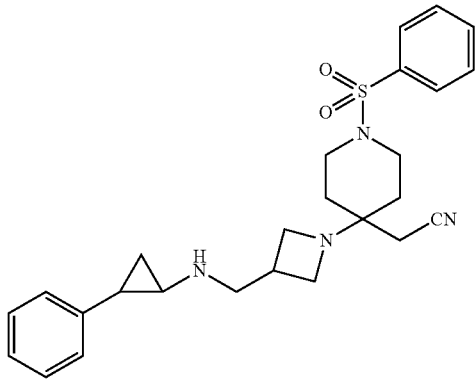 [SMILES: N#CCC1(N2CC(CNC3CC3c3ccccc3)C2)CCN(S(=O)(=O)c2ccccc2)CC1]

This compound was prepared by using procedures analogous to those described for the synthesis of Example 18 with benzenesulfonyl chloride replacing acetic anhydride. LC-MS calculated for $C_{26}H_{33}N_4O_2S$ (M+H)$^+$: m/z=465.2; found 465.2.

Example 22

Ethyl 4-(cyanomethyl)-4-(3-{[(trans-2-phenylcyclopropyl)amino]methyl}azetidin-1-yl)piperidine-1-carboxylate

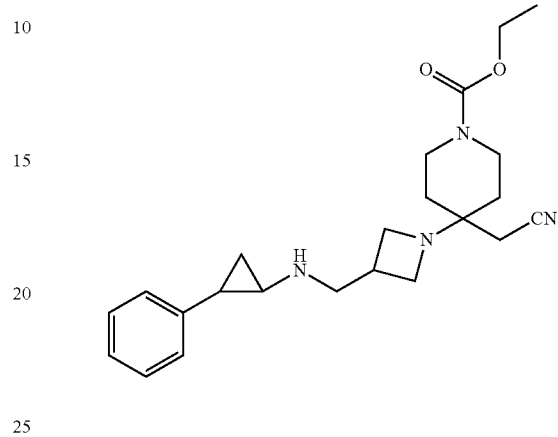

This compound was prepared by using procedures analogous to those described for the synthesis of Example 18 with ethyl chloroformate replacing acetic anhydride. LC-MS calculated for $C_{23}H_{33}N_4O_2$ (M+H)$^+$: m/z=397.3; found 397.2.

Example 23

4-(Cyanomethyl)-N,N-dimethyl-4-(3-{[(trans-2-phenylcyclopropyl)amino]methyl}azetidin-1-yl)piperidine-1-carboxamide

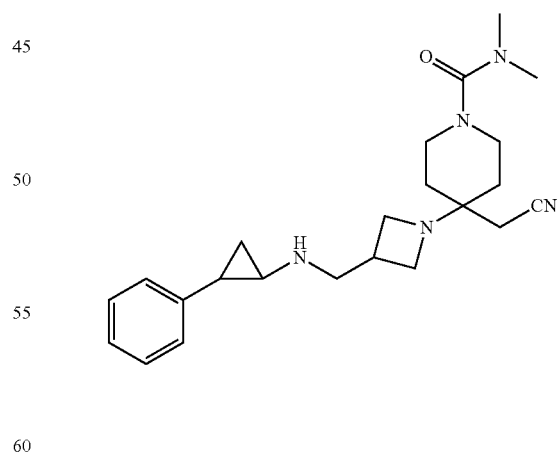

This compound was prepared using procedures analogous to those described for the synthesis of Example 18 with N,N-dimethylcarbamoyl chloride replacing acetic anhydride. LC-MS calculated for $C_{23}H_{34}N_5O$ (M+H)$^+$: m/z=396.3; found 396.3.

Example 24

4-(Cyanomethyl)-N-isopropyl-4-(3-{[(trans-2-phenylcyclopropyl)amino]methyl}azetidin-1-yl)piperidine-1-carboxamide

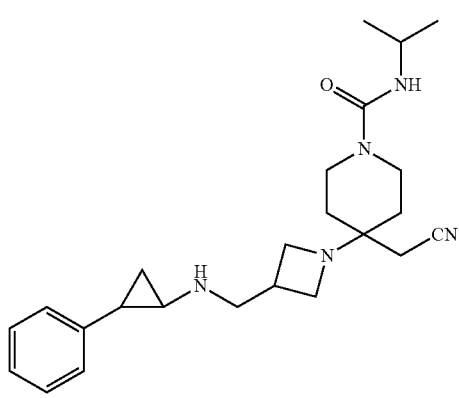 [SMILES: CC(C)NC(=O)N1CCC(CC#N)(N2CC(CNC3CC3c3ccccc3)C2)CC1]

This compound was prepared by using procedures analogous to those described for the synthesis of Example 18 with 2-isocyanatopropane replacing acetic anhydride. LC-MS calculated for $C_{24}H_{36}N_5O$ $(M+H)^+$: m/z=410.3; found 410.3.

Example 25

4-(Cyanomethyl)-N-(4-fluorophenyl)-4-(3-{[(trans-2-phenylcyclopropyl)amino]methyl}azetidin-1-yl)piperidine-1-carboxamide

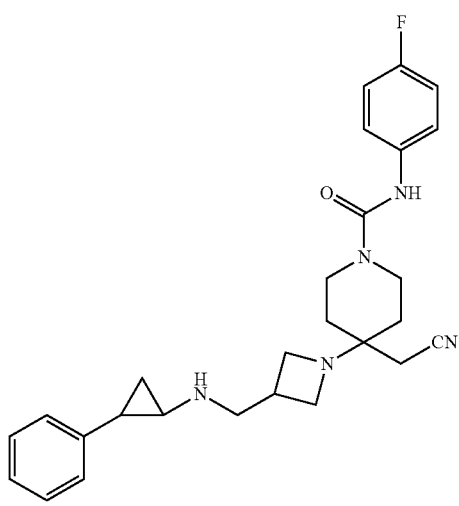 [SMILES: N#CCC1(N2CC(CNC3CC3c3ccccc3)C2)CCN(C(=O)Nc2ccc(F)cc2)CC1]

This compound was prepared by using procedures analogous to those described for the synthesis of Example 18 with 1-fluoro-4-isocyanatobenzene replacing acetic anhydride. LC-MS calculated for $C_{27}H_{33}FN_5O$ $(M+H)^+$: m/z=462.3; found 462.2.

Example 26

(3-{[(trans-2-Phenylcyclopropyl)amino]methyl}-1,3'-biazetidin-3'-yl)acetonitrile

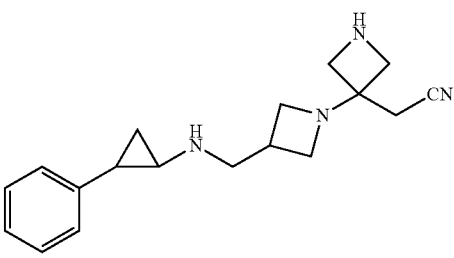 [SMILES: N#CCC1(N2CC(CNC3CC3c3ccccc3)C2)CNC1]

Step 1: tert-butyl 3'-(cyanomethyl)-3-{[(trans-2-phenylcyclopropyl) (trifluoroacetyl)amino]methyl}-1,3'-biazetidine-1'-carboxylate

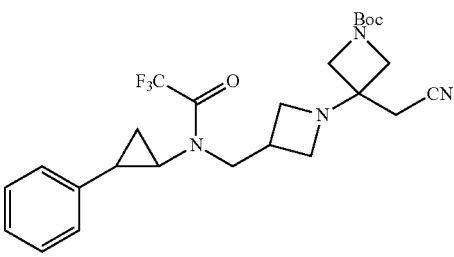 [SMILES: CC(C)(C)OC(=O)N1CC(CC#N)(N2CC(CN(C(=O)C(F)(F)F)C3CC3c3ccccc3)C2)C1]

To a solution of N-(azetidin-3-ylmethyl)-2,2,2-trifluoro-N-(trans-2-phenylcyclopropyl)acetamide (30 mg, 0.07 mmol, prepared as described for Example 17, Step 2), tert-butyl 3-(cyanomethylene)azetidine-1-carboxylate (27 mg, 0.14 mmol, prepared using similar methods as disclosed in the literature such as WO 2009/114512) in acetonitrile (1.0 mL) was added DBU (20 µL, 0.1 mmol). The resulting mixture was stirred at room temperature overnight. The mixture was diluted with EtOAc then washed with water and brine. The organic layer was dried over $Na_2SO_4$ then filtered and concentrated. The residue was used in the next step without further purification. LC-MS calculated for $C_{25}H_{32}F_3N_4O_3$ $(M+H)^+$: m/z=493.2; found 493.2.

Step 2: (3-{[(trans-2-Phenylcyclopropyl)amino]methyl}-1,3'-biazetidin-3'-yl)acetonitrile To a solution of the crude product from Step 1 in THF (1 mL) and MeOH (1 mL) was added 2N NaOH solution in water (0.5 mL). The resulting mixture was stirred at 30° C. for 1 h then cooled to room temperature and concentrated. The residue was dissolved in DCM then filtered and concentrated. The residue was then dissolved in DCM (1 mL) and TFA (1 mL) was added. The mixture was stirred at room temperature for 1 h then concentrated. The residue was dissolved in acetonitrile then purified by prep. HPLC (pH=2, acetonitrile/water+TFA) to give the desired product in the form of TFA salt. LC-MS calculated for $C_{18}H_{25}N_4$ $(M+H)^+$: m/z=297.2; found 297.2.

Example 27

4-(3'-(Cyanomethyl)-3-{[(trans-2-phenylcyclopropyl)amino]methyl}-1,3'-biazetidin-1'-yl)-2,5-difluoro-N-[(1S)-2,2,2-trifluoro-1-methylethyl]benzamide

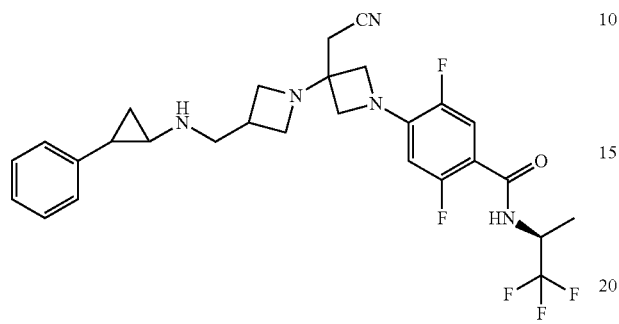

To a solution of N-(azetidin-3-ylmethyl)-2,2,2-trifluoro-N-(trans-2-phenylcyclopropyl)acetamide TFA salt (25 mg, 0.061 mmol, prepared as described for Example 17, Step 2) and 4-[3-(cyanomethylene)azetidin-1-yl]-2,5-difluoro-N-[(1S)-2,2,2-trifluoro-1-methylethyl]benzamide (24 mg, 0.070 mmol, prepared using similar methods as disclosed in the literature such as WO 2012/177606) in acetonitrile (1.0 mL) was added DBU (12 mg, 0.08 mmol). The resulting mixture was stirred at room temperature overnight then 2N NaOH (1 mL) and MeOH (1 mL) were added. The reaction mixture was stirred at room temperature overnight then filtered and purified by prep. HPLC (pH=10, acetonitrile/water+NH$_4$OH) to afford the desired product. LC-MS calculated for C$_{28}$H$_{31}$F$_5$N$_5$O (M+H)$^+$: m/z=548.2; found 548.2.

Example 28

N-{[1-(1-Methylpiperidin-4-yl)azetidin-3-yl]methyl}-trans-2-phenylcyclopropanamine

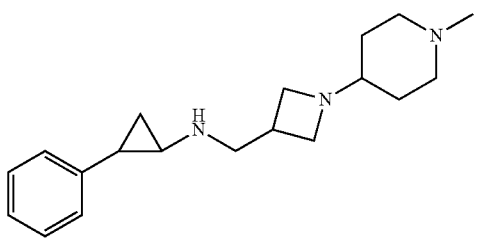 [SMILES: CN1CCC(N2CC(CNC3CC3c3ccccc3)C2)CC1]

To a solution of N-(azetidin-3-ylmethyl)-2,2,2-trifluoro-N-(trans-2-phenylcyclopropyl)acetamide TFA salt (30 mg, 0.07 mmol, prepared as described for Example 17, Step 2), and 1-methyl-4-piperidinone (11 mg, 0.10 mmol) in THF (1.0 mL) was added acetic acid (17 µL, 0.30 mmol). The reaction mixture was stirred at room temperature overnight then Na(OAc)$_3$BH (64 mg, 0.30 mmol) was added. The reaction mixture was stirred at room temperature for 1 h then 2N NaOH in water (0.5 mL) and MeOH (1 mL) were added. The resulting mixture was stirred at 40° C. for 1 h then cooled to room temperature, filtered and purified by RP-HPLC (pH=10, acetonitrile/water+NH$_4$OH) to afford the desired product. LC-MS calculated for C$_{19}$H$_{30}$N$_3$ (M+H)$^+$: m/z=300.2; found 300.2.

Example 29

Trans-2-phenyl-N-{[1-(1-phenylpiperidin-4-yl)azetidin-3-yl]methyl}cyclopropanamine

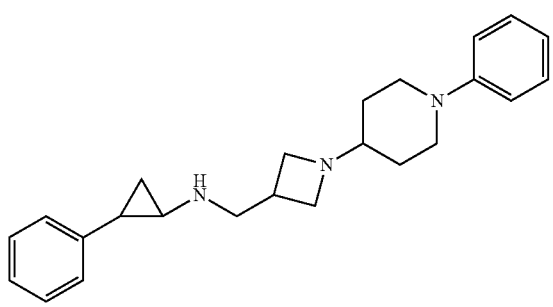 [SMILES: c1ccc(C2CC2NCC2CN(C3CCN(c4ccccc4)CC3)C2)cc1]

This compound was prepared using procedures analogous to those described for the synthesis of Example 28 with 1-phenylpiperidin-4-one replacing 1-methyl-4-piperidinone. LC-MS calculated for C$_{24}$H$_{32}$N$_3$ (M+H)$^+$: m/z=362.3; found 362.2.

Example 30

1-Phenyl-4-(3-{[(trans-2-phenylcyclopropyl)amino]methyl}azetidin-1-yl)cyclohexanecarbonitrile

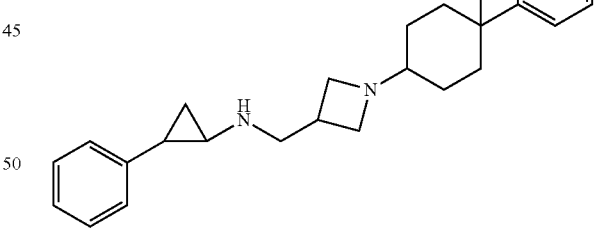

This compound was prepared using procedures analogous to those described for the synthesis of Example 28 with 4-oxo-1-phenylcyclohexanecarbonitrile (Lancaster, cat#5281) replacing 1-methyl-4-piperidinone. The product was purified by prep. HPLC (pH=10, acetonitrile/water+NH$_4$OH) to give two isomers corresponding to the trans- and cis-cyclohexyl. LC-MS calculated for C$_{26}$H$_{32}$N$_3$ (M+H)$^+$: m/z=386.3.

Isomer (I): LC-MS (pH=2, acetonitrile/water+TFA): found m/z=386.2; retention time=1.45 min.

Isomer (II): LC-MS (pH=2, acetonitrile/water+TFA): found m/z=386.2; retention time=1.55 min.

Example 31

[1-(Ethylsulfonyl)-3-(4-{[(trans-2-phenylcyclopropyl)amino]methyl}piperidin-1-yl)azetidin-3-yl]acetonitrile

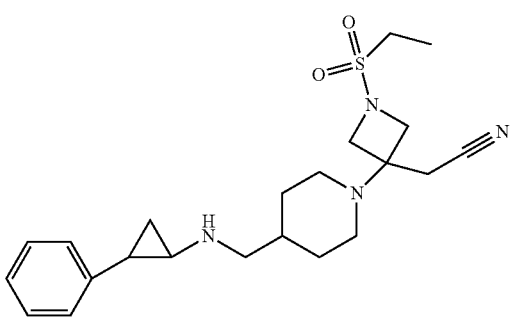 [SMILES: CCS(=O)(=O)N1CC(CC#N)(N2CCC(CNC3CC3c3ccccc3)CC2)C1]

Step 1: {1-(Ethylsulfonyl)-3-[4-(hydroxymethyl)piperidin-1-yl]azetidin-3-yl}acetonitrile

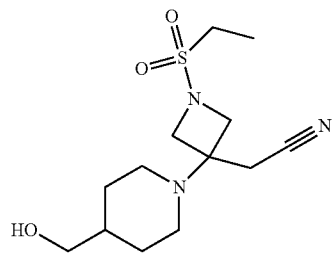 [SMILES: CCS(=O)(=O)N1CC(CC#N)(N2CCC(CO)CC2)C1]

To a solution of 4-piperidinemethanol (60 mg, 0.5 mmol) and [1-(ethylsulfonyl)azetidin-3-ylidene]acetonitrile (110 mg, 0.60 mmol, prepared using similar conditions as disclosed in the literature such as WO 2009/114512) in acetonitrile (1.0 mL) was added DBU (20 µL, 0.1 mmol). The resulting mixture was stirred at room temperature for 3 h then diluted with DCM, washed with water and brine. The organic layer was dried over $Na_2SO_4$, filtered and then concentrated. The residue was purified by flash chromatography on a silica gel column eluting with MeOH in DCM (0-8%) to give the desired product. LC-MS calculated for $C_{13}H_{24}N_3O_3S$ $(M+H)^+$: m/z=302.2; found 302.1.

Step 2: [1-(Ethylsulfonyl)-3-(4-formylpiperidin-1-yl)azetidin-3-yl]acetonitrile

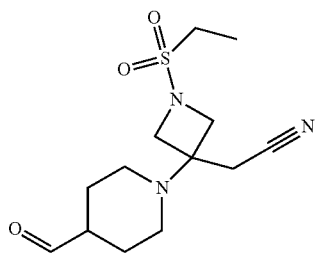 [SMILES: CCS(=O)(=O)N1CC(CC#N)(N2CCC(C=O)CC2)C1]

To a solution of {1-(ethylsulfonyl)-3-[4-(hydroxymethyl)piperidin-1-yl]azetidin-3-yl}acetonitrile (200 mg, 0.66 mmol) in methylene chloride (4.0 mL) was added Dess-Martin periodinane (420 mg, 1.0 mmol). The reaction mixture was at r.t. for 3 h then saturated $Na_2S_2O_3$ aqueous solution was added and stirred for 10 min. The mixture was diluted with DCM, washed with 1N NaOH, water and brine. The organic layer was dried over $Na_2SO_4$, filtered and then concentrated. The residue was purified by flash chromatography on a silica gel column eluting with MeOH in DCM (0-8%). LC-MS calculated for $C_{13}H_{22}N_3O_3S$ $(M+H)^+$: m/z=300.1; found 300.1.

Step 3: [1-(Ethylsulfonyl)-3-(4-{[(trans-2-phenylcyclopropyl)amino]methyl}piperidin-1-yl)azetidin-3-yl]acetonitrile To solution of [1-(ethylsulfonyl)-3-(4-formylpiperidin-1-yl)azetidin-3-yl]acetonitrile (15.0 mg, 0.050 mmol) and 2-phenylcyclopropanamine (10.0 mg, 0.075 mmol, trans, racemic, Acros: Cat#130470050) in DCM (0.5 mL) was added acetic acid (4.3 µL, 0.075 mmol). The mixture was stirred at r.t. for 2 h then sodium triacetoxyborohydride (32 mg, 0.15 mmol) was added. The reaction mixture was stirred at r.t. for 1 h then diluted with DCM and washed with saturated $NaHCO_3$ solution, water and brine. The organic layer was dried over $Na_2SO_4$ then concentrated. The residue was dissolved in acetonitrile then purified by prep. HPLC (pH=2, acetonitrile/water+TFA) to give the product in the form of TFA salt. LC-MS calculated for $C_{22}H_{33}N_4O_2S$ $(M+H)^+$: m/z=417.2; found 417.1.

Example 32

[1-(4-{[(trans-2-Phenylcyclopropyl)amino]methyl}piperidin-1-yl)cyclobutyl]acetonitrile

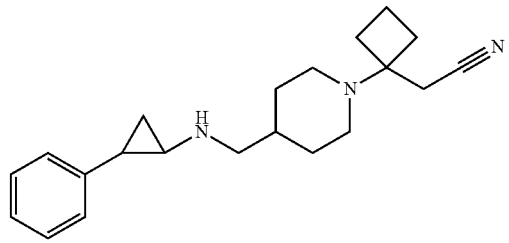 [SMILES: N#CCC1(N2CCC(CNC3CC3c3ccccc3)CC2)CCC1]

Step 1: {1-[4-(Hydroxymethyl)piperidin-1-yl]cyclobutyl}acetonitrile

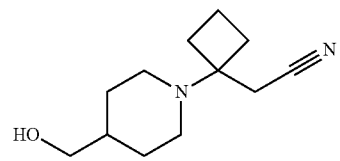 [SMILES: N#CCC1(N2CCC(CO)CC2)CCC1]

To a solution of 4-piperidinemethanol (230 mg, 2.0 mmol) and cyclobutylideneacetonitrile (280 mg, 3.0 mmol, prepared using methods disclosed in the literature such as WO 2009/114512) in acetonitrile (2.0 mL) was added DBU (90 µL, 0.6 mmol). The reaction mixture was stirred at 65° C. overnight. The mixture was cooled to room temperature then diluted with DCM, and washed with water and brine. The organic layer was dried over Na$_2$SO$_4$, filtered and then concentrated. The residue was purified by flash chromatography on a silica gel column eluting with MeOH in DCM (0-8%). LC-MS calculated for C$_{12}$H$_{21}$N$_2$O (M+H)$^+$: m/z=209.2; found 209.2.

Step 2: [1-(4-Formylpiperidin-1-yl)cyclobutyl]acetonitrile

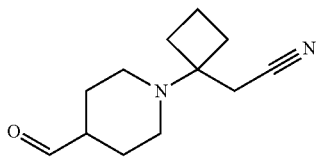 [SMILES: N#CCC1(N2CCC(C=O)CC2)CCC1]

This compound was prepared using procedures analogous to those described for the synthesis of Example 31, Step 2 starting from {1-[4-(hydroxymethyl)piperidin-1-yl]cyclobutyl}acetonitrile. LC-MS calculated for C$_{12}$H$_{19}$N$_2$O (M+H)$^+$: m/z=207.1; found 207.1.

Step 3: [1-(4-{[(trans-2-Phenylcyclopropyl)amino]methyl}piperidin-1-yl)cyclobutyl]acetonitrile The compound was prepared by using procedure analogous to those described for the synthesis of Example 31, Step 3 starting from [1-(4-formylpiperidin-1-yl)cyclobutyl]acetonitrile. The product was purified by prep. HPLC (pH=2, acetonitrile/water+TFA) to give the desired product in the form of TFA salt. LC-MS calculated for C$_{21}$H$_{30}$N$_3$ (M+H)$^+$: m/z=324.2; found 324.3.

Example 33

[3-(4-{[(trans-2-Phenylcyclopropyl)amino]methyl}piperidin-1-yl)azetidin-3-yl]acetonitrile

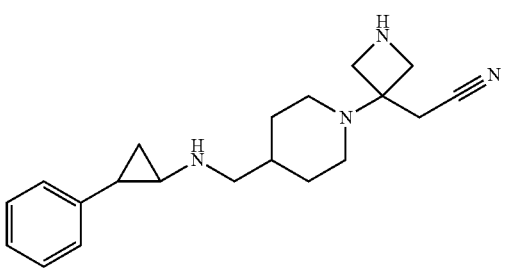 [SMILES: N#CCC1(N2CCC(CNC3CC3c3ccccc3)CC2)CNC1]

Step 1: tert-Butyl 4-{[(trans-2-phenylcyclopropyl)amino]methyl}piperidine-1-carboxylate

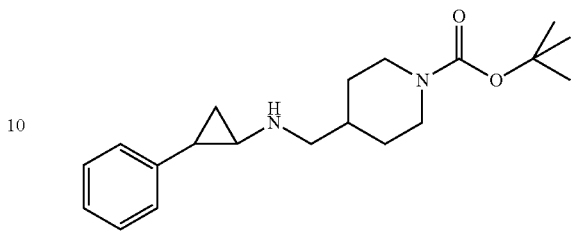

To a solution of tert-butyl 4-formylpiperidine-1-carboxylate (430 mg, 2.0 mmol), and trans-2-phenylcyclopropanamine (0.35 g, 2.6 mmol, Acros: Cat#130470050) in DCM (9 mL) was added acetic acid (0.17 mL, 3.0 mmol). The resulting mixture was stirred at r.t. for 2 h then sodium triacetoxyborohydride (1.3 g, 6.0 mmol) was added and the reaction mixture was stirred at r.t. for 1 h. The mixture was diluted with DCM, washed with 1N NaOH, water and brine. The organic layer was dried over Na$_2$SO$_4$, filtered and then concentrated. The residue was purified by flash chromatography on a silica gel column eluting with MeOH in DCM (0-10%). LC-MS calculated for C$_{16}$H$_{23}$N$_2$O$_2$ (M-$^t$Bu+2H)$^+$: m/z=275.2; found 275.2.

Step 2: tert-Butyl 4-{[[(allyloxy)carbonyl](trans-2-phenylcyclopropyl)amino]methyl}piperidine-1-carboxylate

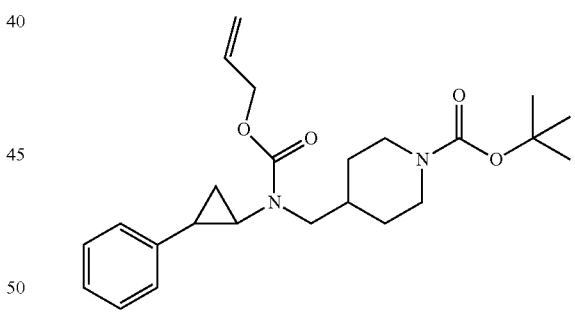

Allyl chloroformate (0.23 mL, 2.2 mmol) was added to a solution of tert-butyl 4-{[(trans-2-phenylcyclopropyl)amino]methyl}piperidine-1-carboxylate (0.59 g, 1.8 mmol) and N,N-diisopropylethylamine (0.63 mL, 3.6 mmol) in DCM (9.0 mL) at 0° C. and then the reaction mixture was stirred at r.t. for 1 h. The mixture was diluted with DCM, washed with saturated NaHCO$_3$, water and brine. The organic layer was dried over Na$_2$SO$_4$, filtered and concentrated. The residue was purified by flash chromatography on a silica gel column eluting with EtOAc in hexane (0-20%). LC-MS calculated for C$_{24}$H$_{34}$N$_2$NaO$_4$ (M+Na)$^+$: m/z=437.2; found 437.3.

Step 3: Allyl(trans-2-phenylcyclopropyl)(piperidin-4-ylmethyl)carbamate

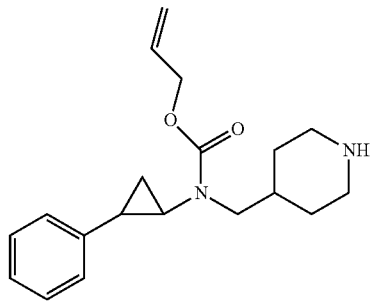 [SMILES: C=CCOC(=O)N(CC1CCNCC1)C1CC1c1ccccc1]

To a solution of tert-butyl 4-{[[(allyloxy)carbonyl](trans-2-phenylcyclopropyl)amino]methyl}piperidine-1-carboxylate (225.0 mg, 0.5428 mmol) in DCM (2 mL) was added 4.0 M hydrogen chloride in dioxane (2 mL). The resulting mixture was stirred at r.t. for 30 min then concentrated. The residue was dissolved in DCM, washed with 1 N NaOH and brine. The organic layer was dried over $Na_2SO_4$, filtered and then concentrated. The residue was purified by flash chromatography on a silica gel column eluting with methanol in DCM (0-10%) to give the desired product. LC-MS calculated for $C_{19}H_{27}N_2O_2$ $(M+H)^+$: m/z=315.2; found 315.2.

Step 4: tert-Butyl 3-(4-{[[(allyloxy)carbonyl](trans-2-phenylcyclopropyl)amino]methyl}piperidin-1-yl)-3-(cyanomethyl)azetidine-1-carboxylate

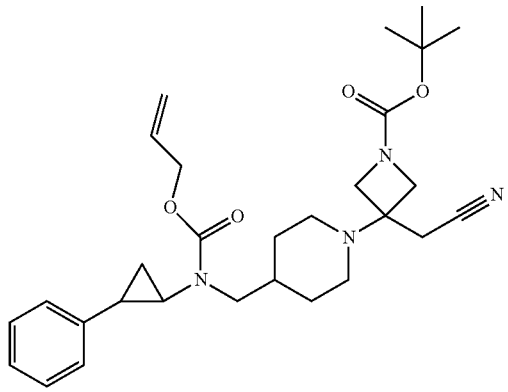 [SMILES: C=CCOC(=O)N(CC1CCN(C2(CC#N)CN(C(=O)OC(C)(C)C)C2)CC1)C1CC1c1ccccc1]

To a solution of allyl(trans-2-phenylcyclopropyl)(piperidin-4-ylmethyl)carbamate (80.0 mg, 0.254 mmol) and tert-butyl 3-(cyanomethylene)azetidine-1-carboxylate (59 mg, 0.30 mmol) in acetonitrile (0.5 mL) was added DBU (10 µL, 0.08 mmol). The resulting mixture was stirred at r.t. for 3 h then diluted with DCM, washed with water and brine. The organic layer was dried over $Na_2SO_4$, filtered and concentrated. The residue was purified by flash chromatography on a silica gel column eluting with EtOAc in DCM (0-20%) to give the desired product. LC-MS calculated for $C_{29}H_{41}N_4O_4$ $(M+H)^+$: m/z=509.3; found 509.3.

Step 5: Allyl({1-[3-(cyanomethyl)azetidin-3-yl]piperidin-4-yl}methyl)(trans-2-phenylcyclopropyl)carbamate

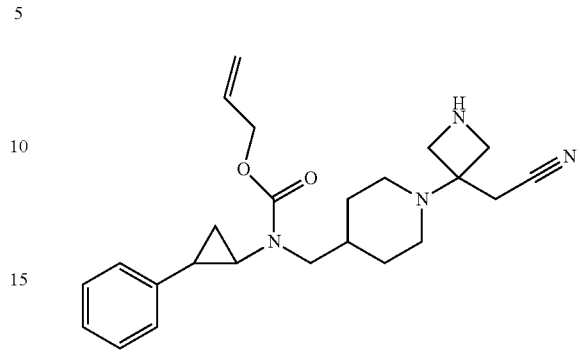

To a solution of tert-butyl 3-(4-{[[(allyloxy)carbonyl](trans-2-phenylcyclopropyl)amino]methyl}piperidin-1-yl)-3-(cyanomethyl)azetidine-1-carboxylate (100.0 mg, 0.1966 mmol) in DCM (0.5 mL) was added 4.0 M hydrogen chloride in dioxane (0.5 mL, 2 mmol). The resulting mixture was stirred at r.t. for 30 min then concentrated. The residue was used in the next step without further purification. LC-MS calculated for $C_{24}H_{33}N_4O_2$ $(M+H)^+$: m/z=409.3; found 409.3.

Step 6: [3-(4-{[(trans-2-Phenylcyclopropyl)amino]methyl}piperidin-1-yl)azetidin-3-yl]acetonitrile A mixture of allyl({1-[3-(cyanomethyl)azetidin-3-yl]piperidin-4-yl}methyl)(trans-2-phenylcyclopropyl)carbamate (30.1 mg, 0.0736 mmol), tetrakis(triphenylphosphine)palladium(0) (8.5 mg, 0.0074 mmol) and N,N-diethylamine (0.0761 mL, 0.736 mmol) in THF (1.0 mL) was stirred at 85° C. for 2 h under nitrogen then cooled to room temperature and filtered. The filtrate was purified by prep. HPLC (pH=2, acetonitrile/water+TFA) to afford the desired product as the TFA salt. LC-MS calculated for $C_{20}H_{29}N_4$ $(M+H)^+$: m/z=325.2; found 325.3.

Example 34

2-[3-(Cyanomethyl)-3-(4-{[(trans-2-phenylcyclopropyl)amino]methyl}piperidin-1-yl)azetidin-1-yl]nicotinonitrile

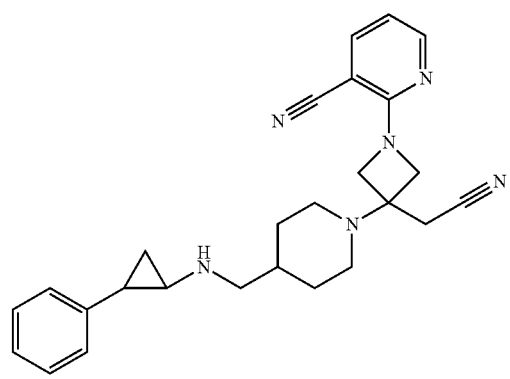 [SMILES: N#CCC1(N2CCC(CNC3CC3c3ccccc3)CC2)CN(c2ncccc2C#N)C1]

Step 1: Allyl({1-[3-(cyanomethyl)-1-(3-cyanopyridin-2-yl)azetidin-3-yl]piperidin-4-yl}methyl)(trans-2-phenylcyclopropyl)carbamate

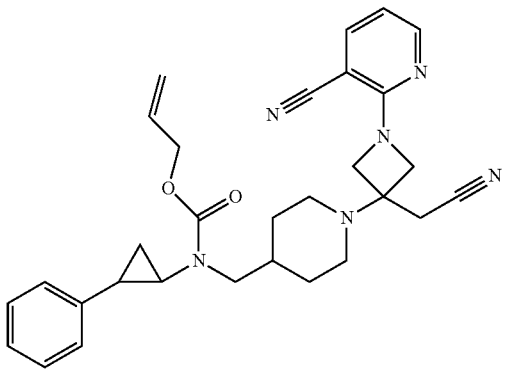 [SMILES: C=CCOC(=O)N(CC1CCN(C2(CC#N)CN(c3ncccc3C#N)C2)CC1)C1CC1c1ccccc1]

To a solution of allyl({1-[3-(cyanomethyl)azetidin-3-yl]piperidin-4-yl}methyl)(trans-2-phenylcyclopropyl)carbamate (25.0 mg, 0.0612 mmol, prepared as described in Example 33, Step 5) and 2-fluoronicotinonitrile (15 mg, 0.12 mmol) in NMP (0.6 mL) was added DIEA (43 μL, 0.24 mmol). The reaction mixture was stirred at 120° C. for 2 h then cooled to room temperature and diluted with methylene chloride. The mixture was then washed with saturated NaHCO$_3$, water and brine. The organic layer was dried over Na$_2$SO$_4$, filtered and concentrated. The residue was used in the next step without further purification. LC-MS calculated for C$_{30}$H$_{35}$N$_6$O$_2$ (M+H)$^+$: m/z=511.3; found 511.3.

Step 2: 2-[3-(Cyanomethyl)-3-(4-{[(trans-2-phenylcyclopropyl)amino]methyl}piperidin-1-yl)azetidin-1-yl]nicotinonitrile The crude product from Step 1 was dissolve in THF (0.5 mL) and then diethylamine (60 μL) was added, followed by Pd(PPh$_3$)$_4$ (10 mg). The container with the resulting mixture was evacuated then filled with nitrogen and stirred at 80° C. for 2 h. The mixture was cooled to room temperature, filtered then purified by prep. HPLC (pH=2, acetonitrile/water+TFA) to afford the desired product as a TFA salt. LC-MS calculated for C$_{26}$H$_{31}$N$_6$ (M+H)$^+$: m/z=427.3; found 427.3.

Example 35

4-[3-(Cyanomethyl)-3-(4-{[(trans-2-phenylcyclopropyl)amino]methyl}piperidin-1-yl)azetidin-1-yl]-2,5-difluoro-N-isopropylbenzamide

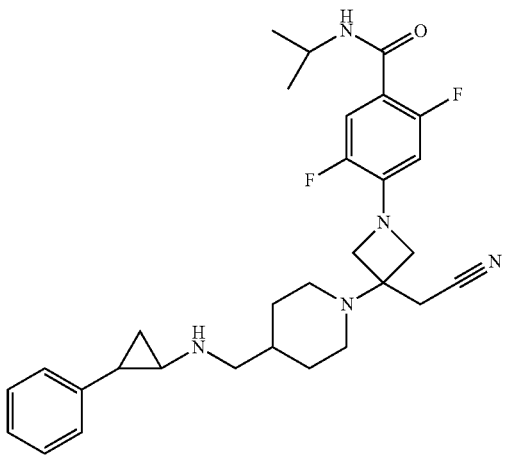 [SMILES: CC(C)NC(=O)c1cc(F)c(N2CC(CC#N)(N3CCC(CNC4CC4c4ccccc4)CC3)C2)cc1F]

This compound was prepared using procedures analogous to those described for the synthesis of Example 34 with 2,4,5-trifluoro-N-isopropylbenzamide replacing 2-fluoronicotinonitrile in Step 1. LC-MS calculated for C$_{30}$H$_{38}$F$_2$N$_5$O (M+H)$^+$: m/z=522.3; found 522.4.

Example 36

{3-(4-{[(trans-2-Phenylcyclopropyl)amino]methyl}piperidin-1-yl)-1-[3-(trifluoromethyl)pyridin-2-yl]azetidin-3-yl}acetonitrile

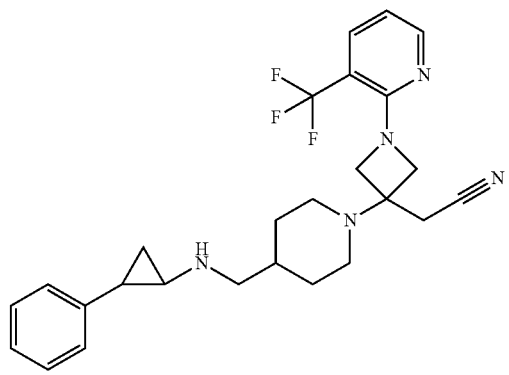 [SMILES: N#CCC1(N2CCC(CNC3CC3c3ccccc3)CC2)CN(c2ncccc2C(F)(F)F)C1]

This compound was prepared using procedures analogous to those described for the synthesis of Example 34 with 2-fluoro-3-(trifluoromethyl)pyridine replacing 2-fluoronicotinonitrile in Step 1. LC-MS calculated for C$_{26}$H$_{31}$F$_3$N$_5$ (M+H)$^+$: m/z=470.3; found 470.2.

Example 37

{3-(4-{[(trans-2-Phenylcyclopropyl)amino]methyl}piperidin-1-yl)-1-[5-(trifluoromethyl)pyridin-2-yl]azetidin-3-yl}acetonitrile

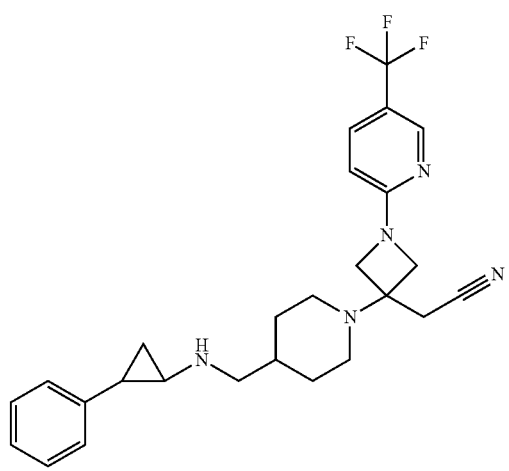 [SMILES: N#CCC1(N2CCC(CNC3CC3c3ccccc3)CC2)CN(c2ccc(C(F)(F)F)cn2)C1]

This compound was prepared using procedures analogous to those described for the synthesis of Example 34 with 2-fluoro-5-(trifluoromethyl)pyridine replacing 2-fluoronicotinonitrile in Step 1. LC-MS calculated for C$_{26}$H$_{31}$F$_3$N$_5$ (M+H)$^+$: m/z=470.3; found 470.2.

Example 38

2-Chloro-6-[3-(cyanomethyl)-3-(4-{[(trans-2-phenylcyclopropyl)amino]methyl}piperidin-1-yl)azetidin-1-yl]benzonitrile

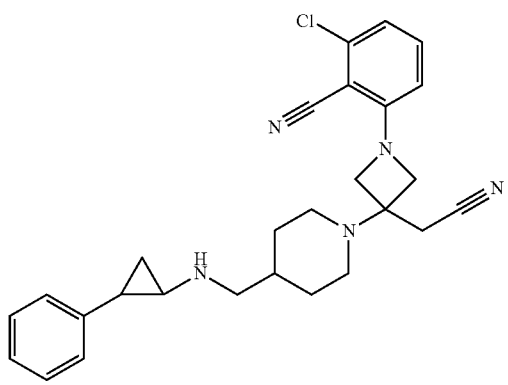 [SMILES: N#CCC1(N2CCC(CNC3CC3c3ccccc3)CC2)CN(c2cccc(Cl)c2C#N)C1]

This compound was prepared using procedures analogous to those described for the synthesis of Example 34 with 2-chloro-6-fluorobenzonitrile replacing 2-fluoronicotinonitrile in Step 1. LC-MS calculated for $C_{27}H_{31}ClN_5$ (M+H)$^+$: m/z=460.2; found 460.1.

Example 39

2-[3-(Cyanomethyl)-3-(4-{[(trans-2-phenylcyclopropyl)amino]methyl}piperidin-1-yl)azetidin-1-yl]benzonitrile

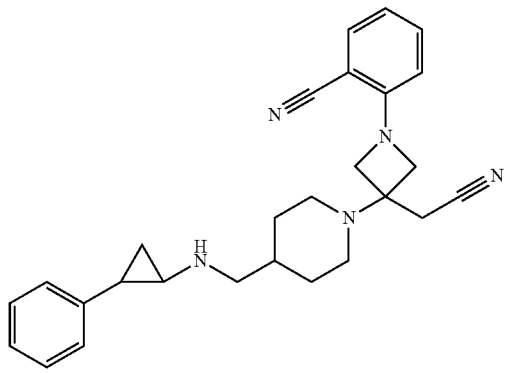 [SMILES: N#CCC1(N2CCC(CNC3CC3c3ccccc3)CC2)CN(c2ccccc2C#N)C1]

This compound was prepared using procedures analogous to those described for the synthesis of Example 34 with 2-fluorobenzonitrile replacing 2-fluoronicotinonitrile in Step 1. LC-MS calculated for $C_{27}H_{32}N_5$ (M+H)$^+$: m/z=426.3; found 426.3.

Example 40

4-[3-(Cyanomethyl)-3-(4-{[(trans-2-phenylcyclopropyl)amino]methyl}piperidin-1-yl)azetidin-1-yl]benzonitrile

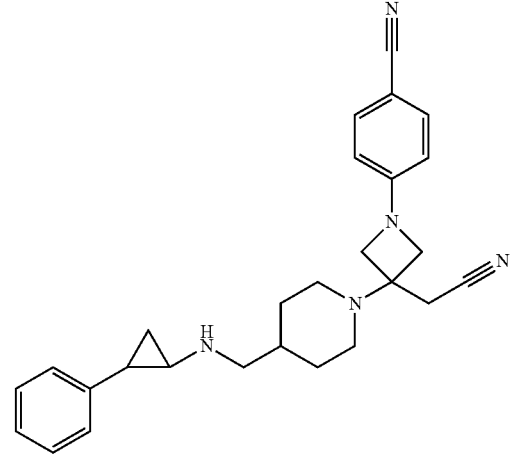 [SMILES: N#CCC1(N2CCC(CNC3CC3c3ccccc3)CC2)CN(c2ccc(C#N)cc2)C1]

This compound was prepared using procedures analogous to those described for the synthesis of Example 34 with 2-fluorobenzonitrile replacing 4-fluoronicotinonitrile in Step 1. LC-MS calculated for $C_{27}H_{32}N_5$ (M+H)$^+$: m/z=426.3; found 426.3.

Example 41

Methyl 3-(cyanomethyl)-3-(4-{[(trans-2-phenylcyclopropyl)amino]methyl}piperidin-1-yl)azetidine-1-carboxylate

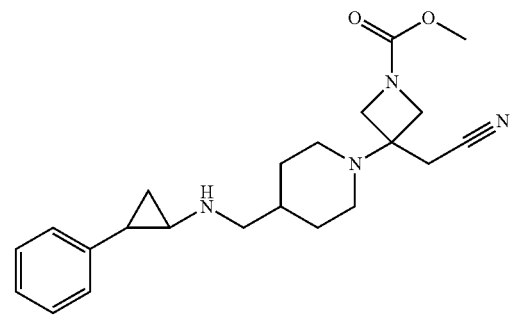 [SMILES: COC(=O)N1CC(CC#N)(N2CCC(CNC3CC3c3ccccc3)CC2)C1]

Methyl chloroformate (7.6 μL, 0.098 mmol) was added to a solution of allyl({1-[3-(cyanomethyl)azetidin-3-yl]piperidin-4-yl}methyl)(trans-2-phenylcyclopropyl)carbamate (20.0 mg, 0.0490 mmol, prepared as described in Example 33, Step 5) and triethylamine (27 μL, 0.20 mmol) in DCM (0.5 mL) at 0° C. The resulting mixture was stirred for 30 min at 0° C. then diluted with DCM, and washed with saturated NaHCO$_3$, water and brine. The organic layer was dried over Na$_2$SO$_4$, filtered and concentrated. The residue was dissolved in THF (0.5 mL) and then diethylamine (60 μL) was added, followed by Pd(PPh$_3$)$_4$ (10 mg). A container with the resulting mixture was evacuated then filled with nitrogen and the mixture was stirred at 80° C. for 2 h. The mixture was cooled to room temperature, filtered then purified by prep. HPLC (pH=2, acetonitrile/water+TFA) to afford the desired product as a TFA salt. LC-MS calculated for $C_{22}H_{31}N_4O_2$ (M+H)+: m/z=383.2; found 383.3.

Example 42

3-(Cyanomethyl)-N-(2,4-difluorophenyl)-3-(4-{[(trans-2-phenylcyclopropyl)amino]methyl}piperidin-1-yl)azetidine-1-carboxamide

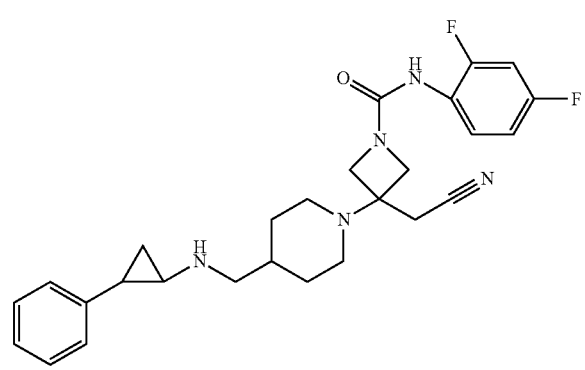 [SMILES: N#CCC1(N2CCC(CNC3CC3c3ccccc3)CC2)CN(C(=O)Nc2ccc(F)cc2F)C1]

This compound was prepared using procedures analogous to those described for the synthesis of Example 41 with 2,4-difluoro-1-isocyanatobenzene replacing methyl chloroformate. LC-MS calculated for $C_{27}H_{32}F_2N_5O$ (M+H)+: m/z=480.3; found 480.3.

Example 43

N-(3-Chloro-2-fluorophenyl)-3-(cyanomethyl)-3-(4-{[(trans-2-phenylcyclopropyl)amino]methyl}piperidin-1-yl)azetidine-1-carboxamide

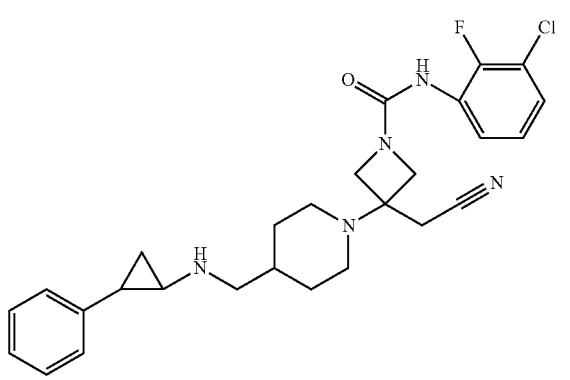 [SMILES: N#CCC1(N2CCC(CNC3CC3c3ccccc3)CC2)CN(C(=O)Nc2cccc(Cl)c2F)C1]

This compound was prepared using procedures analogous to those described for the synthesis of Example 41 with 1-chloro-2-fluoro-3-isocyanatobenzene replacing methyl chloroformate. LC-MS calculated for $C_{27}H_{32}ClFN_5O$ (M+H)+: m/z=496.2; found 496.2.

Example 44

[1-(3,5-Difluorobenzoyl)-3-(4-{[(trans-2-phenylcyclopropyl)amino]methyl}piperidin-1-yl)azetidin-3-yl]acetonitrile

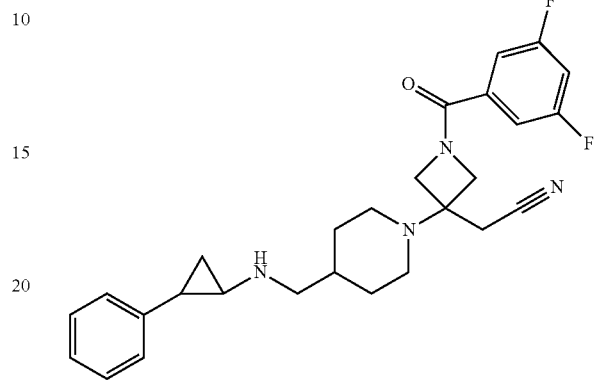

This compound was prepared using procedure analogous to those described for the synthesis of Example 41 with 3,5-difluorobenzoyl chloride replacing methyl chloroformate. LC-MS calculated for $C_{27}H_{31}F_2N_4O$ (M+H)+: m/z=465.2; found 465.2.

Example 45

[1-Benzoyl-3-(4-{[(trans-2-phenylcyclopropyl)amino]methyl}piperidin-1-yl)azetidin-3-yl]acetonitrile

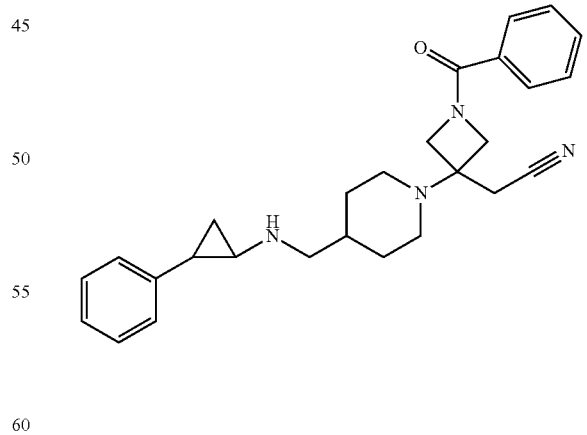

This compound was prepared using procedures analogous to those described for the synthesis of Example 41 with benzoyl chloride replacing methyl chloroformate. LC-MS calculated for $C_{27}H_{33}N_4O$ (M+H)+: m/z=429.3; found 429.2.

Example 46

[1-(2-Fluorobenzoyl)-3-(4-{[(trans-2-phenylcyclopropyl)amino]methyl}piperidin-1-yl)azetidin-3-yl]acetonitrile

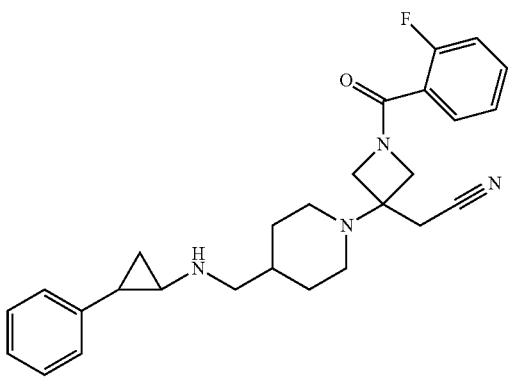 [SMILES: N#CCC1(N2CCC(CNC3CC3c3ccccc3)CC2)CN(C(=O)c2ccccc2F)C1]

This compound was prepared using procedures analogous to those described for the synthesis of Example 41 with 2-fluorobenzoyl chloride replacing methyl chloroformate. LC-MS calculated for $C_{27}H_{32}FN_4O$ $(M+H)^+$: m/z=447.3; found 447.3.

Example 47

[1-(3-Fluorobenzoyl)-3-(4-{[(trans-2-phenylcyclopropyl)amino]methyl}piperidin-1-yl)azetidin-3-yl]acetonitrile

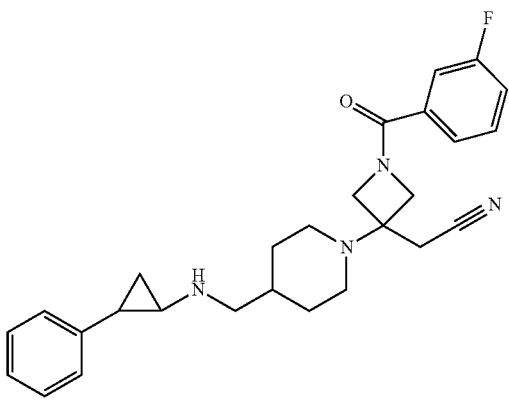 [SMILES: N#CCC1(N2CCC(CNC3CC3c3ccccc3)CC2)CN(C(=O)c2cccc(F)c2)C1]

This compound was prepared using procedures analogous to those described for the synthesis of Example 41 with 3-fluorobenzoyl chloride replacing methyl chloroformate. LC-MS calculated for $C_{27}H_{32}FN_4O$ $(M+H)^+$: m/z=447.3; found 447.3.

Example 48

[1-(4-Fluorobenzoyl)-3-(4-{[(trans-2-phenylcyclopropyl)amino]methyl}piperidin-1-yl)azetidin-3-yl]acetonitrile

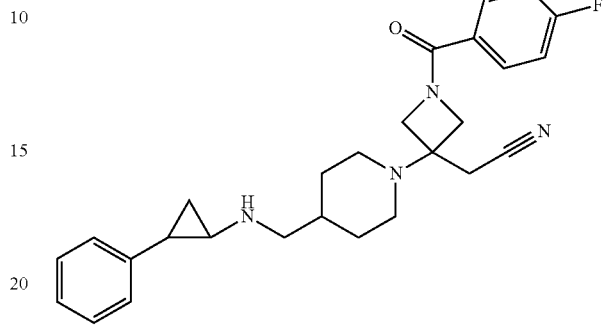

This compound was prepared using procedures analogous to those described for the synthesis of Example 41 with 4-fluorobenzoyl chloride replacing methyl chloroformate. LC-MS calculated for $C_{27}H_{32}FN_4O$ $(M+H)^+$: m/z=447.3; found 447.3.

Example 49

[1-Methyl-3-(4-{[(trans-2-phenylcyclopropyl)amino]methyl}piperidin-1-yl)azetidin-3-yl]acetonitrile

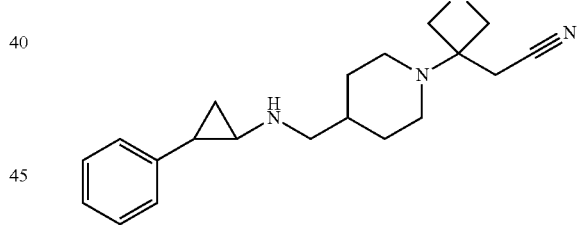

To a solution of allyl({1-[3-(cyanomethyl)azetidin-3-yl]piperidin-4-yl}methyl)(trans-2-phenylcyclopropyl)carbamate (20.0 mg, 0.0490 mmol, prepared as described in Example 33, Step 5) in DCM (0.5 mL) was added 7.0 M formaldehyde in water (2.7 µL, 0.019 mmol). The resulting mixture was stirred at room temperature for 1 h then sodium triacetoxyborohydride (16 mg, 0.076 mmol) was added. The reaction mixture was stirred for another 1 h at room temperature then diluted with DCM, and washed with saturated NaHCO$_3$, water and brine. The organic layer was dried over Na$_2$SO$_4$, then filtered and concentrated. The residue was dissolved in THF (0.5 mL) and then diethyl amine (60 uL) was added, followed by addition of Pd(PPh$_3$)$_4$ (10 mg). A container with the mixture was evacuated then filled with nitrogen then the mixture was stirred at 80° C. for 2 h. The mixture was cooled to room temperature, filtered then purified by prep. HPLC (pH=2, acetonitrile/water+TFA) to afford the desired product as a TFA salt. LC-MS calculated for $C_{21}H_{31}N_4$ $(M+H)^+$: m/z=339.3; found 339.3.

Example 50

[3-(4-{[(trans-2-Phenylcyclopropyl)amino]methyl}piperidin-1-yl)azetidin-3-yl]acetic acid

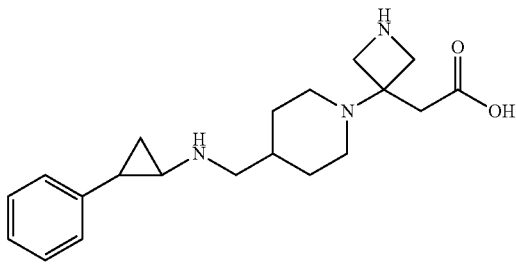 [SMILES: O=C(O)CC1(N2CCC(CNC3CC3c3ccccc3)CC2)CNC1]

Step 1: tert-Butyl 3-(2-tert-butoxy-2-oxoethylidene)azetidine-1-carboxylate

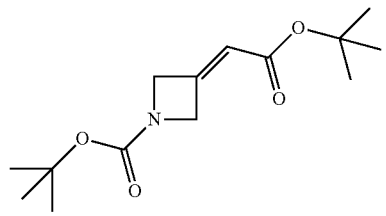 [SMILES: CC(C)(C)OC(=O)C=C1CN(C(=O)OC(C)(C)C)C1]

To a solution of tert-butyl(diethoxyphosphoryl)acetate (Aldrich, cat#348333: 1.1 g, 4.6 mmol) in THF (15 mL) at 0° C. was added 1.0 M potassium tert-butoxide in THF (4.6 mL, 4.6 mmol). The resulting mixture was warmed to room temperature and stirred for 30 min. The reaction mixture was cooled to 0° C. then a solution of tert-butyl 3-oxoazetidine-1-carboxylate (Aldrich, cat#696315: 0.6 g, 4 mmol) in THF (5 mL) was added. The mixture was warmed to room temperature, stirred overnight, then diluted with ethyl acetate, and washed with saturated NaHCO₃, water and brine. The organic layer was dried over Na₂SO₄, filtered and concentrated. The residue was purified by flash chromatography on a silica gel column eluting with EtOAc in hexane (0-20%) to give the desired product. LC-MS calculated for $C_6H_8NO_4$ (M-2ᵗBu+3H)⁺: m/z=158.0; found 158.1.

Step 2: tert-Butyl 3-(4-{[[(allyloxy)carbonyl](trans-2-phenylcyclopropyl)amino]methyl}piperidin-1-yl)-3-(2-tert-butoxy-2-oxoethyl)azetidine-1-carboxylate

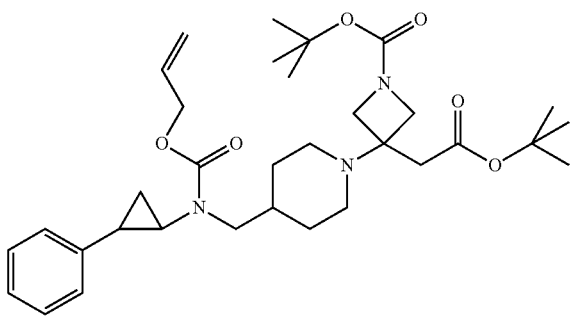 [SMILES: C=CCOC(=O)N(CC1CCN(C2(CC(=O)OC(C)(C)C)CN(C(=O)OC(C)(C)C)C2)CC1)C1CC1c1ccccc1]

To a solution of allyl(trans-2-phenylcyclopropyl)(piperidin-4-ylmethyl)carbamate (80.0 mg, 0.254 mmol, prepared as described in Example 33, Step 3) and tert-butyl 3-(2-tert-butoxy-2-oxoethylidene)azetidine-1-carboxylate (82 mg, 0.30 mmol) in acetonitrile (0.5 mL) was added DBU (10 μL, 0.08 mmol). The resulting mixture was stirred at 65° C. overnight then cooled to room temperature, diluted with DCM, washed with water and brine. The organic layer was dried over Na₂SO₄, filtered and concentrated. The residue was purified by flash chromatography on a silica gel column eluting with EtOAc in hexane (0-30%) to give the desired product. LC-MS calculated for $C_{33}H_{50}N_3O_6$ (M+H)⁺: m/z=584.4; found 584.3.

Step 3: [3-(4-{[(trans-2-phenylcyclopropyl)amino]methyl}piperidin-1-yl)azetidin-3-yl]acetic acid Tetrakis(triphenylphosphine)palladium(0) (8.5 mg) was added to a mixture of tert-butyl 3-(4-{[[(allyloxy)carbonyl](trans-2-phenylcyclopropyl)amino]methyl}piperidin-1-yl)-3-(2-tert-butoxy-2-oxoethyl)azetidine-1-carboxylate (43.0 mg, 0.0736 mmol) and diethylamine (0.0761 mL, 0.736 mmol) in THF (1.0 mL). A container with the resulting mixture was evacuated then filled with nitrogen and the mixture was stirred at 85° C. for 2 h. The mixture was cooled to room temperature then concentrated. The residue was dissolved in CH₂Cl₂ (0.5 mL) then TFA (0.5 mL) was added. The resulting mixture was stirred at room temperature for 3 h then concentrated. The residue was dissolved in acetonitrile then purified by prep. HPLC (pH=2, acetonitrile/water+TFA) to afford the desired product as a TFA salt. LC-MS calculated for $C_{20}H_{30}N_3O_2$ (M+H)⁺: m/z=344.2; found 344.2.

Example 51

N-Methyl-2-(3-(4-((trans-2-phenylcyclopropylamino)methyl)piperidin-1-yl)azetidin-3-yl)acetamide

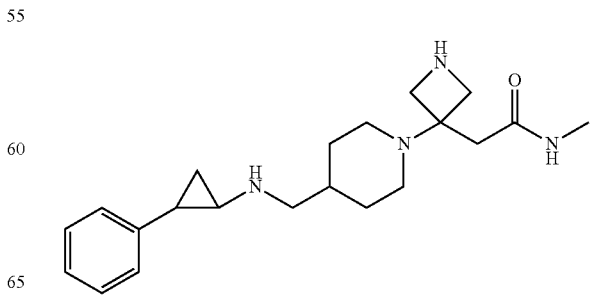

Step 1: [3-(4-{[[(Allyloxy)carbonyl](trans-2-phenyl-cyclopropyl)amino]methyl}piperidin-1-yl)-1-(tert-butoxycarbonyl)azetidin-3-yl]acetic acid

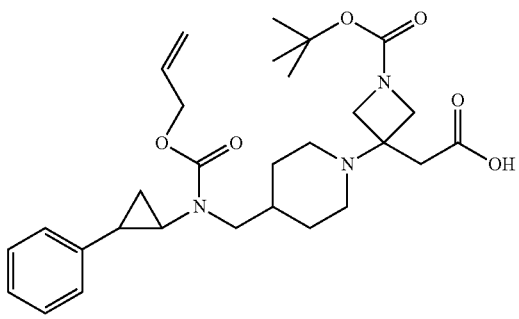 [SMILES: C=CCOC(=O)N(CC1CCN(C2(CC(=O)O)CN(C(=O)OC(C)(C)C)C2)CC1)C1CC1c1ccccc1]

To a solution of tert-butyl 3-(4-{[[(allyloxy)carbonyl](trans-2-phenylcyclopropyl)amino]methyl}piperidin-1-yl)-3-(2-tert-butoxy-2-oxoethyl)azetidine-1-carboxylate (0.10 g, 0.17 mmol, prepared as described in Example 50, Step 2) in DCM (1.0 mL) was added TFA (1.0 mL). The resulting mixture was stirred at room temperature for 5 h then concentrated. The residue was dissolved in THF (4 mL)/water (1 mL) then di-tert-butyldicarbonate (56 mg, 0.26 mmol) and sodium carbonate (73 mg, 0.68 mmol) was added. The reaction mixture was stirred at room temperature overnight then diluted with water and extracted with diethyl ether. The aqueous phase was then acidified by adding cold 1 N HCl and then extracted with ethyl acetate. The combined extracts were washed with brine, dried over $Na_2SO_4$ then concentrated. The residue was used in the next step without further purification. LC-MS calculated for $C_{29}H_{42}N_3O_6$ (M+H)$^+$: m/z=528.3; found 528.3.

Step 2: tert-Butyl 3-(4-(((allyloxycarbonyl)(trans-2-phenylcyclopropyl)amino)methyl)piperidin-1-yl)-3-(2-(methylamino)-2-oxoethyl)azetidine-1-carboxylate

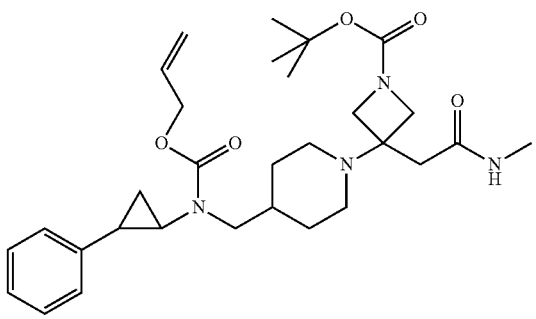 [SMILES: C=CCOC(=O)N(CC1CCN(C2(CC(=O)NC)CN(C(=O)OC(C)(C)C)C2)CC1)C1CC1c1ccccc1]

To a solution of [3-(4-{[[(allyloxy)carbonyl](trans-2-phenylcyclopropyl)amino]methyl}piperidin-1-yl)-1-(tert-butoxycarbonyl)azetidin-3-yl]acetic acid (20.0 mg, 0.0379 mmol) and BOP (27 mg, 0.060 mmol) in DMF (0.9 mL) was added 2.0 M methylamine in THF (0.4 mL, 0.7 mmol), followed by triethylamine (36.6 μL, 0.263 mmol). The resulting mixture was stirred at room temperature for 1 h then diluted with EtOAc, and washed with saturated $NaHCO_3$, water and brine. The organic layer was dried over $Na_2SO_4$, filtered and concentrated. The residue was used in the next step without further purification. LC-MS calculated for $C_{30}H_{45}N_4O_5$ (M+H)$^+$: m/z=541.3; found 541.3.

Step 3: N-Methyl-2-(3-(4-((trans-2-phenylcyclopropylamino)methyl)piperidin-1-yl)azetidin-3-yl)acetamide The crude product from Step 2 was dissolved in THF (1.0 mL) then Pd(PPh$_3$)$_4$ (10.0 mg) was added, followed by adding diethylamine (0.1 mL). A container with the mixture was evacuated the refilled with nitrogen and the mixture was stirred at 80° C. for 2 h. The reaction mixture was cooled to room temperature then concentrated. The residue was dissolved in $CH_2Cl_2$ (0.5 mL) then TFA (0.5 mL) was added. The mixture was stirred at room temperature for 1 h then concentrated. The residue was dissolved in acetonitrile then purified by prep. HPLC (pH=2, acetonitrile/water+TFA) to afford the desired product as a TFA salt. LC-MS calculated for $C_{21}H_{33}N_4O$ (M+H)$^+$: m/z=357.3; found 357.3.

Example 52

N,N-Dimethyl-2-(3-(4-((trans-2-phenylcyclopropylamino)methyl)piperidin-1-yl)azetidin-3-yl)acetamide

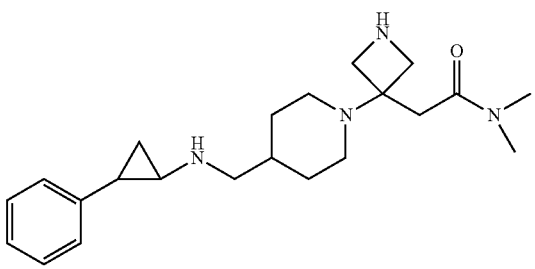 [SMILES: CN(C)C(=O)CC1(N2CCC(CNC3CC3c3ccccc3)CC2)CNC1]

This compound was prepared using procedures analogous to those described for the synthesis of Example 51 with N,N-dimethylamine replacing methylamine in Step 2. LC-MS calculated for $C_{22}H_{35}N_4O$ (M+H)$^+$: m/z=371.3; found 371.3.

Example 53

{1-[4-(4-fluorobenzyl)-4-({[(1R,2S)-2-phenylcyclopropyl]amino}methyl)piperidin-1-yl]cyclobutyl}acetic acid

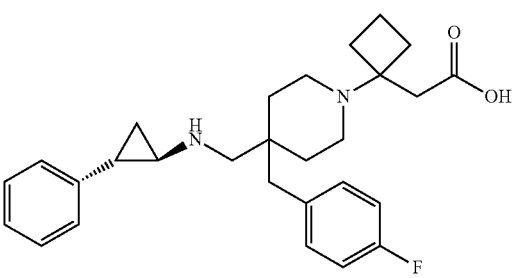

Step 1: 1-tert-butyl 4-methyl 4-(4-fluorobenzyl)piperidine-1,4-dicarboxylate

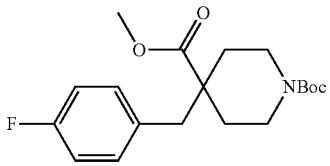

To a solution of N,N-diisopropylamine (4.9 mL, 35 mmol) in tetrahydrofuran (80 mL) at −78° C. was added n-butyllithium (2.5 M in hexanes, 14 mL, 35 mmol). The resulting mixture was warmed to −20° C. and stirred for 10 min then cooled to −78° C. and a solution of 1-tert-butyl 4-methyl piperidine-1,4-dicarboxylate (AstaTech, cat#B56857: 6.08 g, 25.0 mmol) in THF (10 mL) was slowly added. The reaction mixture was slowly warmed to −40° C. and stirred for 1 h. The mixture was then cooled to −78° C. and α-bromo-4-fluorotoluene (4.9 mL, 40. mmol) was added. The reaction mixture was stirred at −78° C. for 1 h then quenched with saturated NH$_4$Cl, warmed to room temperature and diluted with ethyl ether. The mixture was then washed with water, brine, dried over Na$_2$SO$_4$, filtered and concentrated. The residue was purified by flash chromatography on a silica gel column eluting with EtOAc in hexane (0-20%) to give the desired product (6.5 g, 74%). LC-MS calculated for $C_{15}H_{19}FNO_4$ (M-$^t$Bu+2H)$^+$: m/z=296.1; found 296.1.

Step 2: tert-butyl 4-(4-fluorobenzyl)-4-(hydroxymethyl)piperidine-1-carboxylate

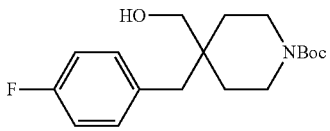 [SMILES: CC(C)(C)OC(=O)N1CCC(CO)(Cc2ccc(F)cc2)CC1]

To a solution of 1-tert-butyl 4-methyl 4-(4-fluorobenzyl) piperidine-1,4-dicarboxylate (6.5 g, 18 mmol) in tetrahydrofuran (90 mL) at 0° C. was added LiAlH$_4$ (1 M in THF, 24 mL, 24 mmol) slowly. The resulting mixture was stirred at 0° C. for 30 min then water (0.9 mL) was added, followed by NaOH (15 wt % in water, 0.9 mL) and water (0.9 mL). The mixture was stirred for 20 min then filtered and washed with THF. The filtrate was concentrated and the residue (5.8 g, 97%) was used in the next step without further purification. LC-MS calculated for $C_{14}H_{19}FNO_3$ (M-$^t$Bu+2H)$^+$: m/z=268.1; found 268.1.

Step 3: tert-butyl 4-(4-fluorobenzyl)-4-formylpiperidine-1-carboxylate

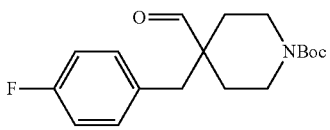 [SMILES: CC(C)(C)OC(=O)N1CCC(C=O)(Cc2ccc(F)cc2)CC1]

A solution of dimethyl sulfoxide (4.3 mL, 60. mmol) in methylene chloride (6 mL) was added to a solution of oxalyl chloride (2.6 mL, 30 mmol) in methylene chloride at −78° C. over 10 min and then the resulting mixture was warmed to −60° C. over 25 min. A solution of tert-butyl 4-(4-fluorobenzyl)-4-(hydroxymethyl)piperidine-1-carboxylate (5.2 g, 16 mmol) in methylene chloride (6 mL) was slowly added and then warmed to −45° C. over 30 mins. N,N-Diisopropylethylamine (21 mL, 120 mmol) was then added and the mixture was warmed to 0° C. over 15 min. The mixture was poured into a cold 1 N HCl aqueous solution and then extracted with ethyl ether. The combined extracts were dried over Na$_2$SO$_4$, filtered and concentrated. The residue was purified by flash chromatography on a silica gel column eluting with EtOAc in hexane (0-20%) to give the desired product (4.3 g, 83%). LC-MS calculated for $C_{14}H_{17}FNO_3$ (M-$^t$Bu+2H)$^+$: m/z=266.1; found 266.1.

Step 4: tert-butyl 4-(4-fluorobenzyl)-4-({[(1R,2S)-2-phenylcyclopropyl]amino}methyl)piperidine-1-carboxylate

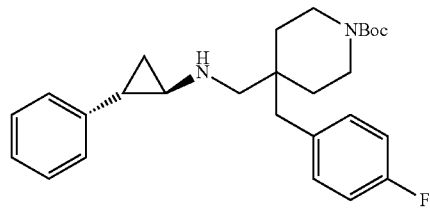

To a solution of tert-butyl 4-(4-fluorobenzyl)-4-formylpiperidine-1-carboxylate (4.2 g, 13 mmol) and (1R,2S)-2-phenylcyclopropanamine (1.96 g, 14.7 mmol) (prepared using procedures as described in *Bioorg. Med. Chem. Lett.*, 2011, 21, 4429) in 1,2-dichloroethane (50 mL) was added acetic acid (1.1 mL, 20. mmol). The resulting mixture was stirred at room temperature for 2 h then sodium triacetoxyborohydride (5.7 g, 27 mmol) was added. The reaction mixture was stirred at room temperature for 5 h then diluted with methylene chloride, washed with 1 N NaOH aqueous solution, water and brine. The organic layer was dried over Na$_2$SO$_4$, filtered and concentrated. The residue was purified by flash chromatography on a silica gel column eluting with MeOH in DCM (0-6%) to give the desired product (5.0 g, 87%). LC-MS calculated for $C_{27}H_{36}FN_2O_2$ (M+H)$^+$: m/z=439.3; found 439.2.

Step 5: tert-butyl 4-(4-fluorobenzyl)-4-{[(1R,2S)-2-phenylcyclopropyl-(trifluoroacetyl)amino]-methyl}piperidine-1-carboxylate

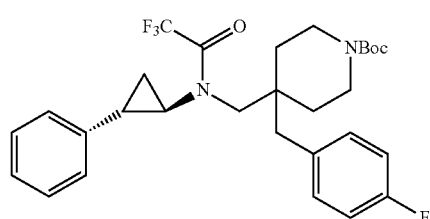

Trifluoroacetic anhydride (2.08 mL, 14.7 mmol) was added to a solution of tert-butyl 4-(4-fluorobenzyl)-4-({[(1R,2S)-2-phenylcyclopropyl]amino}methyl)piperidine-1-carboxylate (4.3 g, 9.8 mmol) and N,N-diisopropylethylamine (4.3 mL, 24 mmol) in methylene chloride (40 mL) at 0° C. The resulting mixture was stirred at 0° C. for 1 h then diluted with ether and washed with 1 N HCl, water and brine. The organic layer was dried over $Na_2SO_4$, filtered and concentrated. The residue was purified by flash chromatography on a silica gel column eluting with EtOAc in hexanes (0-30%) to give the desired product (4.6 g, 88%). LC-MS calculated for $C_{25}H_{27}F_4N_2O_3$ (M-$^t$Bu+2H)$^+$: m/z=479.2; found 479.2.

Step 6: 2,2,2-trifluoro-N-{[4-(4-fluorobenzyl)piperidin-4-yl]methyl}-N-[(1R,2S)-2-phenylcyclopropyl]acetamide

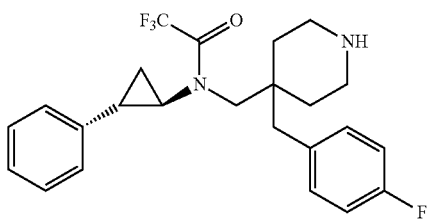

Hydrogen chloride (4 M in 1,4-dioxane, 20 mL, 80 mmol) was added to a solution of tert-butyl 4-(4-fluorobenzyl)-4-{[[(1R,2S)-2-phenylcyclopropyl](trifluoroacetyl)amino]methyl}-piperidine-1-carboxylate (4.6 g, 8.6 mmol) in methylene chloride (6 mL). The resulting mixture was stirred at room temperature for 30 min then concentrated. The residue was used in the next step without further purification. LC-MS calculated for $C_{24}H_{27}F_4N_2O$ (M+H)$^+$: m/z=435.2; found 435.2.

Step 7: tert-butyl cyclobutylideneacetate

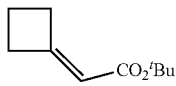

To a suspension of sodium hydride (1.2 g, 30 mmol) in tetrahydrofuran (20 mL) at 0° C. was added tert-butyl (diethoxyphosphoryl)acetate (6.8 g, 27 mmol). The resulting mixture was stirred at room temperature for 30 min then cyclobutanone (1.0 g, 14 mmol) was added. The mixture was stirred at room temperature for 2 hours then quenched with saturated $NaHCO_3$ aqueous solution and extracted with ethyl acetate. The combined extracts were washed with brine, dried over $Na_2SO_4$, filtered then concentrated. The residue was purified by flash chromatography on a silica gel column eluting with EtOAc in hexane (0-10%) to give the desired product (2.0 g, 84%). $^1$H NMR (400 MHz, $CDCl_3$) δ 5.50-5.46 (m, 1H), 3.14-3.05 (m, 2H), 2.84-2.76 (m, 2H), 2.11-2.02 (m, 2H), 1.46 (s, 9H).

Step 8: tert-butyl[1-(4-(4-fluorobenzyl)-4-{[[(1R,2S)-2-phenylcyclopropyl](trifluoroacetyl)amino]methyl}piperidin-1-yl)cyclobutyl]acetate

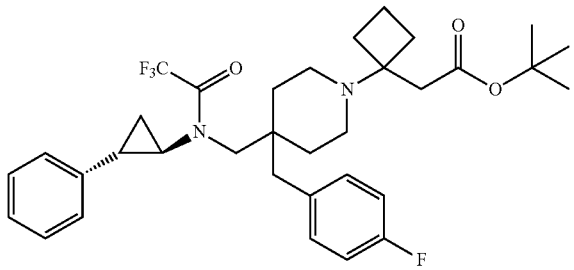

1,8-Diazabicyclo[5.4.0]undec-7-ene (57 μL, 0.38 mmol) was added to a mixture of 2,2,2-trifluoro-N-{[4-(4-fluorobenzyl)piperidin-4-yl]methyl}-N-[(1R,2S)-2-phenylcyclopropyl]acetamide (Step 6: 110. mg, 0.25 mmol) and tert-butyl cyclobutylideneacetate (64 mg, 0.38 mmol) in acetonitrile (0.6 mL, 10 mmol). The resulting mixture was stirred at 65° C. for 3 days then cooled to room temperature and concentrated. The residue was purified by flash chromatography on a silica gel column eluting with EtOAc in hexane (0-20%) to give the desired product (90 mg, 59%). LC-MS calculated for $C_{34}H_{43}F_4N_2O_3$ (M+H)$^+$: m/z=603.3; found 603.3.

Step 9: {1-[4-(4-fluorobenzyl)-4-({[(1R,2S)-2-phenylcyclopropyl]amino}methyl)piperidin-1-yl]cyclobutyl}acetic acid Trifluoroacetic acid (0.5 mL) was added to a solution of tert-butyl[1-(4-(4-fluorobenzyl)-4-{[[(1R,2S)-2-phenylcyclopropyl](trifluoroacetyl)amino]methyl}piperidin-1-yl)cyclobutyl]acetate (22.0 mg, 0.0364 mmol) in methylene chloride (0.5 mL). The mixture was stirred at room temperature for 4 h then concentrated. The residue was dissolved in THF/methanol (0.3/0.3 mL) and then NaOH (1 N in water, 1.0 mL) was added. The mixture was stirred at 40° C. for 2 h then cooled to room temperature and purified by prep HPLC (pH=2, acetonitrile/water+TFA) to give the desired product as the TFA salt. LC-MS calculated for $C_{28}H_{36}FN_2O_2$ (M+H)$^+$: m/z=451.3; found 451.3.

Example 54

{1-[4-(methoxymethyl)-4-({[(1R,2S)-2-phenylcyclopropyl]amino}methyl)piperidin-1-yl]cyclobutyl}acetic acid

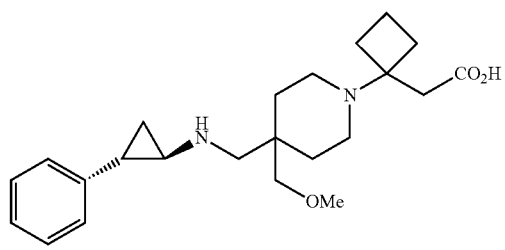

Step 1: 1-tert-butyl 4-methyl 4-(methoxymethyl)piperidine-1,4-dicarboxylate

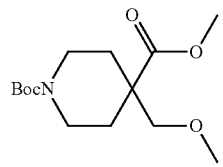 [SMILES: COCC1(C(=O)OC)CCN(C(=O)OC(C)(C)C)CC1]

To a solution of 1-tert-butyl 4-methyl piperidine-1,4-dicarboxylate (AstaTech, cat#B56857: 2.43 g, 10.0 mmol) in tetrahydrofuran (30 mL) at −40° C. was added lithium diisopropylamide (2 M in THF, 5.8 mL, 12 mmol). The resulting mixture was stirred at −40° C. for 30 min then chloromethyl methyl ether (1.2 mL, 16 mmol) was added. The reaction mixture was stirred at −40° C. for 1 h then quenched with saturated NH$_4$Cl aqueous solution and warmed to room temperature. The mixture was diluted with ethyl acetate, washed with saturated NaHCO$_3$ aqueous solution, water and brine. The organic layer was dried over Na$_2$SO$_4$, filtered and concentrated. The crude material was purified via flash chromatography on a silica gel column (0 to 20% EtOAc in hexanes) to give the desired product (2.6 g, 90%). LC-MS calculated for C$_9$H$_{18}$NO$_3$ (M-Boc+2H)$^+$: m/z=188.1; found 188.1.

Step 2: tert-butyl 4-(hydroxymethyl)-4-(methoxymethyl)piperidine-1-carboxylate

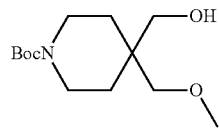

To a solution of 1-tert-butyl 4-methyl 4-(methoxymethyl) piperidine-1,4-dicarboxylate (2.3 g, 8.0 mmol) in tetrahydrofuran (40 mL) at 0° C. was added LiAlH$_4$ (1 M in THF, 10. mL, 10. mmol) slowly. The resulting mixture was stirred at 0° C. for 30 min then quenched with addition of water (0.1 mL), NaOH (15 wt % in water, 0.1 mL) and water (0.1 mL). The mixture was stirred for 10 min then filtered and washed with THF. The filtrate was concentrated and the residue was used in the next step without further purification. LC-MS calculated for C$_9$H$_{18}$NO$_4$ (M-tBu+2H)$^+$: m/z=204.1; found 204.1.

Step 3: tert-butyl 4-formyl-4-(methoxymethyl)piperidine-1-carboxylate

Dimethyl sulfoxide (1.7 mL, 24 mmol) in methylene chloride (2 mL) was added to a solution of oxalyl chloride (1.0 mL, 12 mmol) in methylene chloride (3 mL) at −78° C. over 10 min. The resulting mixture was warmed to −60° C. over 25 min then a solution of tert-butyl 4-(hydroxymethyl)-4-(methoxymethyl)piperidine-1-carboxylate (1.6 g, 6.0 mmol) in methylene chloride (5 mL) was slowly added. The mixture was warmed to −45° C. over 30 min then triethylamine (6.7 mL, 48 mmol) was added. The mixture was warmed to 0° C. over 15 min. The reaction mixture was then poured into a cold 1 N HCl aqueous solution and extracted with diethyl ether. The combined extracts were dried over Na$_2$SO$_4$, filtered and concentrated. The residue was purified via flash chromatography on a silica gel column eluting with 0 to 20% EtOAc in hexanes to give the desired product (1.3 g, 84%). LC-MS calculated for C$_8$H$_{16}$NO$_2$ (M-Boc+2H)$^+$: m/z=158.1; found 158.1.

Step 4: tert-butyl 4-(methoxymethyl)-4-({[(1R,2S)-2-phenylcyclopropyl]amino}methyl)-piperidine-1-carboxylate

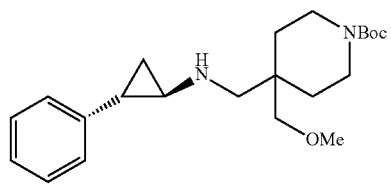

A mixture of tert-butyl 4-formyl-4-(methoxymethyl)piperidine-1-carboxylate (1.3 g, 5.0 mmol), acetic acid (0.43 mL, 7.5 mmol) and (1R,2S)-2-phenylcyclopropanamine (699 mg, 5.25 mmol) in 1,2-dichloroethane (20 mL) was stirred at room temperature for 1 h then sodium triacetoxyborohydride (2.1 g, 10. mmol) was added. The resulting mixture was stirred at room temperature for 2 h then diluted with methylene chloride, washed with saturated NaHCO$_3$ aqueous solution, water and brine. The organic layer was dried over Na$_2$SO$_4$, filtered and concentrated. The residue was purified via flash chromatography on a silica gel column eluting with 0 to 8% methanol in DCM to give the desired product (1.7 g, 91%). LC-MS calculated for C$_{22}$H$_{35}$N$_2$O$_3$ (M+H)$^+$: m/z=375.3; found 375.2.

Step 5: tert-butyl 4-(methoxymethyl)-4-{[[(1R,2S)-2-phenylcyclopropyl]-(trifluoroacetyl)amino]methyl}piperidine-1-carboxylate

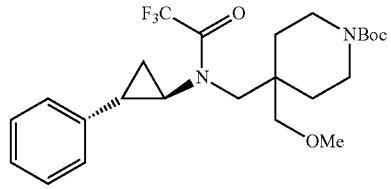

Trifluoroacetic anhydride (0.96 mL, 6.8 mmol) was added to a solution of tert-butyl 4-(methoxymethyl)-4-({[(1R,2S)-2-phenylcyclopropyl]amino}methyl)piperidine-1-carboxylate (1.7 g, 4.5 mmol) and N,N-diisopropylethylamine (1.6 mL, 9.1 mmol) in methylene chloride (25 mL) at 0° C. The resulting mixture was stirred at room temperature for 1 h then diluted with methylene chloride, washed with sat. NaHCO$_3$ aqueous solution, water, and brine. The organic Step 6: 2,2,2-trifluoro-N-{[4-(methoxymethyl)piperidin-4-yl]methyl}-N-[(1R,2S)-2-phenylcyclopropyl]acetamide

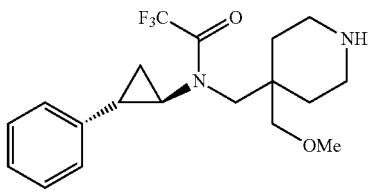

4.0 M Hydrogen chloride in dioxane (7 mL, 28 mmol) was added to a solution of tert-butyl 4-(methoxymethyl)-4-{[[(1R,2S)-2-phenylcyclopropyl](trifluoroacetyl)amino]methyl}-piperidine-1-carboxylate (1.8 g, 3.8 mmol) in methylene chloride (4 mL). The resulting mixture was stirred at room temperature for 30 min then concentrated. The residue was used in the next step without further purification. LC-MS calculated for $C_{19}H_{26}F_3N_2O_2$ (M+H)$^+$: m/z=371.2; found 371.2.

Step 7: methyl[1-(4-(methoxymethyl)-4-{[[(1R,2S)-2-phenylcyclopropyl](trifluoroacetyl)amino]-methyl}piperidin-1-yl)cyclobutyl]acetate

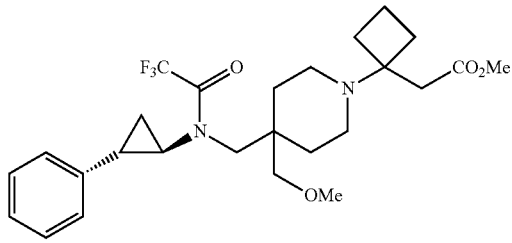

1,8-Diazabicyclo[5.4.0]undec-7-ene (40. μL, 0.26 mmol) was added to a mixture of 2,2,2-trifluoro-N-{[4-(methoxymethyl)piperidin-4-yl]methyl}-N-[(1R,2S)-2-phenylcyclopropyl]acetamide (65. mg, 0.17 mmol) and methyl cyclobutylideneacetate (SynChem, cat#SC-25429: 33 mg, 0.26 mmol) in acetonitrile (0.4 mL). The resulting mixture was stirred at 65° C. for 3 days then cooled to room temperature, diluted with methylene chloride, then washed with water and brine. The organic layer was dried over $Na_2SO_4$, filtered and concentrated. The residue was purified via flash chromatography on a silica gel column eluting with 0 to 50% EtOAc in hexanes to give the desired product. LC-MS calculated for $C_{26}H_{36}F_3N_2O_4$ (M+H)$^+$: m/z=497.3; found 497.2.

Step 8: {1-[4-(methoxymethyl)-4-({[(1R,2S)-2-phenylcyclopropyl]amino}methyl)piperidin-1-yl]cyclobutyl}acetic acid To the solution of methyl[1-(4-(methoxymethyl)-4-{[[(1R,2S)-2-phenylcyclopropyl](trifluoroacetyl)amino]methyl}piperidin-1-yl)cyclobutyl]acetate (60.0 mg, 0.12 mmol) in MeOH/THF (0.5/0.5 mL) was added 1 N NaOH (1 mL). The resulting mixture was stirred at 40° C. for 6 h then cooled to room temperature and purified by prep HPLC (pH=2, acetonitrile/water+TFA) to give the desired product as the TFA salt. LC-MS calculated for $C_{23}H_{35}N_2O_3$ (M+H)$^+$: m/z=387.3; found 387.3.

Example 55

{1-[4-methyl-4-({[(1R,2S)-2-phenylcyclopropyl]amino}methyl)piperidin-1-yl]cyclobutyl}acetic acid

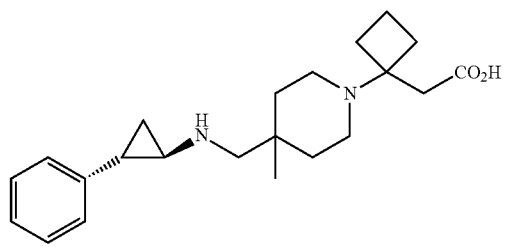

Step 1: tert-butyl 4-methyl-4-({[(1R,2S)-2-phenylcyclopropyl]amino}methyl)piperidine-1-carboxylate

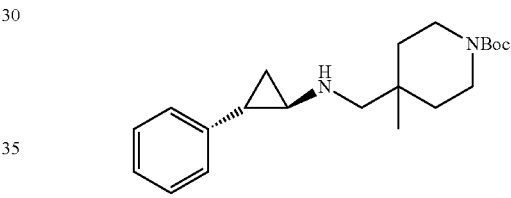

A mixture of tert-butyl 4-formyl-4-methylpiperidine-1-carboxylate (Synnovator, cat#PBN2011767: 2.50 g, 11.0 mmol), acetic acid (0.94 mL, 16 mmol) and (1R,2S)-2-phenylcyclopropanamine (1.54 g, 11.5 mmol) in 1,2-dichloroethane (40 mL) was stirred at room temperature for 1 h then sodium triacetoxyborohydride (4.7 g, 22 mmol) was added. The mixture was stirred at room temperature for 2 h then diluted with methylene chloride, washed with saturated $NaHCO_3$, water and brine. The organic layer was dried over $Na_2SO_4$, filtered and concentrated. The residue was purified via flash chromatography on a silica gel column eluting with 0 to 8% MeOH in DCM to give the desired product (3.4 g, 90%). LC-MS calculated for $C_{21}H_{33}N_2O_2$ (M+H)$^+$: m/z=345.3; found 345.2.

Step 2: tert-butyl 4-methyl-4-{[[(1R,2S)-2-phenylcyclopropyl](trifluoroacetyl)amino]methyl}-piperidine-1-carboxylate

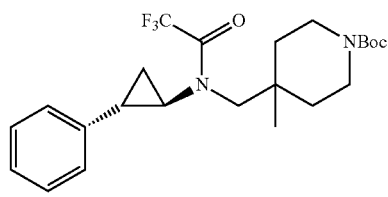

Trifluoroacetic anhydride (0.96 mL, 6.8 mmol) was added to a solution of tert-butyl 4-methyl-4-({[(1R,2S)-2-phenylcyclopropyl]amino}methyl)piperidine-1-carboxylate (1.6 g, 4.5 mmol) and N,N-diisopropylethylamine (1.6 mL, 9.1 mmol) in methylene chloride (25 mL) at 0° C. The resulting mixture was stirred at room temperature for 1 h then diluted with methylene chloride, washed with saturated NaHCO$_3$, water and brine. The organic layer was dried over Na$_2$SO$_4$, filtered and concentrated. The residue was purified via flash chromatography on a silica gel column eluting with 0 to 20% EtOAc in hexanes to give the desired product (1.8 g, 90%). LC-MS calculated for $C_{19}H_{24}F_3N_2O_3$ (M-$^t$Bu+2H)$^+$: m/z=385.2; found 385.2.

Step 3: 2,2,2-trifluoro-N-[(4-methylpiperidin-4-yl)methyl]-N-[(1R,2S)-2-phenylcyclopropyl]-acetamide

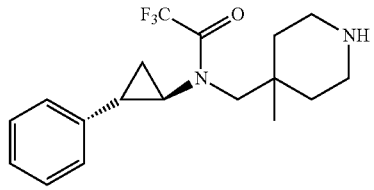

To a solution of tert-butyl 4-methyl-4-{[[(1R,2S)-2-phenylcyclopropyl](trifluoroacetyl)-amino]methyl}piperidine-1-carboxylate (1.5 g, 3.4 mmol) in methylene chloride (3 mL) was added hydrogen chloride (4 M in 1,4-dioxane, 6 mL, 24 mmol). The resulting mixture was stirred at room temperature for 1 h then concentrated. The residue was used in the next step without further purification. LC-MS calculated for $C_{18}H_{24}F_3N_2O$ (M+H)$^+$: m/z=341.2; found 341.2.

Step 4: tert-butyl[1-(4-methyl-4-{[[(1R,2S)-2-phenylcyclopropyl](trifluoroacetyl)amino]methyl}piperidin-1-yl)cyclobutyl]acetate

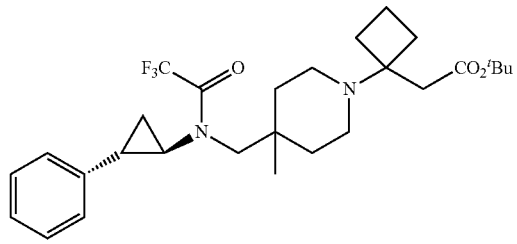

1,8-Diazabicyclo[5.4.0]undec-7-ene (40. μL, 0.26 mmol) was added to a mixture of 2,2,2-trifluoro-N-[(4-methylpiperidin-4-yl)methyl]-N-[(1R,2S)-2-phenylcyclopropyl]acetamide (60.0 mg, 0.176 mmol) and tert-butyl cyclobutylideneacetate (Example 53, Step 7: 44 mg, 0.26 mmol) in acetonitrile (0.4 mL). The resulting mixture was stirred at 65° C. for 3 days then cooled to room temperature and diluted with methylene chloride, washed with water and brine. The organic layer was dried over Na$_2$SO$_4$, filtered and concentrated. The residue was purified via flash chromatography on a silica gel column eluting with 0 to 30% EtOAc in hexanes to give the desired product (60 mg, 67%). LC-MS calculated for $C_{28}H_{40}F_3N_2O_3$ (M+H)$^+$: m/z=509.3; found 509.3.

Step 5: {1-[4-methyl-4-({[(1R,2S)-2-phenylcyclopropyl]amino}methyl)piperidin-1-yl]cyclobutyl}acetic acid To the solution of tert-butyl[1-(4-methyl-4-{[[(1R,2S)-2-phenylcyclopropyl](trifluoroacetyl)amino]methyl}piperidin-1-yl)cyclobutyl]acetate (60 mg) in methylene chloride (0.5 mL) was added trifluoroacetic acid (0.5 mL). The resulting mixture was stirred at room temperature for 4 h then concentrated. The residue was dissolved in methanol/THF (0.5/0.5 mL) then NaOH (15 wt % in water, 0.5 mL) was added. The reaction mixture was stirred at room temperature for 5 h then purified by prep-HPLC (pH=2, acetonitrile/water+TFA) to give the desired product as the TFA salt. LC-MS calculated for $C_{22}H_{33}N_2O_2$ (M+H)$^+$: m/z=357.3; found 357.2. $^1$H NMR (500 MHz, DMSO) δ 7.33-7.27 (m, 2H), 7.25-7.20 (m, 1H), 7.19-7.16 (m, 2H), 3.16-2.97 (m, 6H), 2.96-2.89 (m, 1H), 2.83 (s, 2H), 2.48-2.42 (m, 3H), 2.30-2.20 (m, 2H), 1.90-1.75 (m, 4H), 1.75-1.65 (m, 2H), 1.56-1.44 (m, 1H), 1.32-1.21 (m, 1H), 1.10 (s, 3H).

Example 56

N,N-dimethyl-2-{1-[4-methyl-4-({[(1R,2S)-2-phenylcyclopropyl]amino}methyl)piperidin-1-yl]cyclobutyl}acetamide

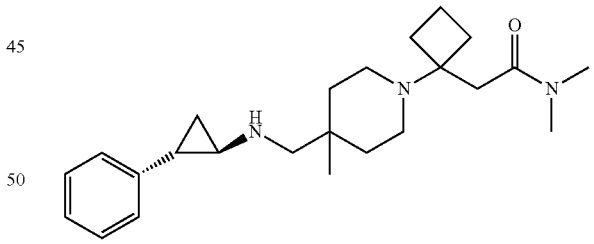

To a solution of {1-[4-methyl-4-({[(1R,2S)-2-phenylcyclopropyl]amino}methyl)piperidin-1-yl]cyclobutyl}acetic acid (Example 55: 9.0 mg, 0.025 mmol) and (benzotriazol-1-yloxy)tripyrrolidinophosphonium hexafluorophosphate (21 mg, 0.04 mmol) in N,N-dimethylformamide (0.6 mL) was added dimethylamine (2 M in THF, 0.2 mL, 0.5 mmol), followed by triethylamine (24. μL, 0.17 mmol). The resulting mixture was stirred at room temperature for 1 h then purified by prep-HPLC (pH=2, acetonitrile/water+TFA) to give the desired product as the TFA salt. LC-MS calculated for $C_{24}H_{38}N_3O$ (M+H)$^+$: m/z=384.3; found 384.3.

Example 57

N-methyl-2-{1-[4-methyl-4-({[(1R,2S)-2-phenylcyclopropyl]amino}methyl)piperidin-1-yl]cyclobutyl}acetamide

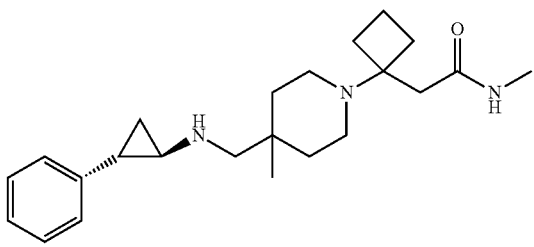

This compound was prepared using procedures analogous to those described for the synthesis of Example 56 with methylamine replacing dimethylamine. The reaction mixture was purified by prep-HPLC (pH=2, acetonitrile/water+TFA) to give the desired product as the TFA salt. LC-MS calculated for $C_{23}H_{36}N_3O$ $(M+H)^+$: m/z=370.3; found 370.3.

Example 58

[1-(methylsulfonyl)-3-(4-{[(1R,2S)-2-phenylcyclopropyl]amino}piperidin-1-yl)azetidin-3-yl]acetonitrile

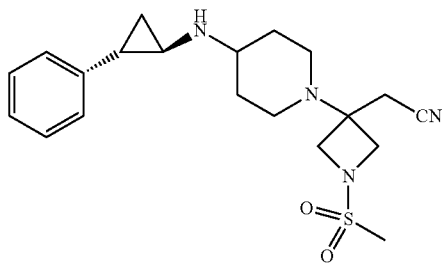

Step 1: tert-butyl 3-(cyanomethyl)-3-(4-oxopiperidin-1-yl)azetidine-1-carboxylate

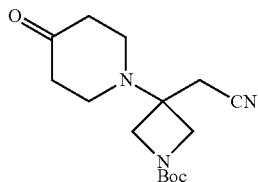 [SMILES: CC(C)(C)OC(=O)N1CC(CC#N)(N2CCC(=O)CC2)C1]

To the mixture of piperidin-4-one hydrochloride hydrate (Aldrich, cat#151769: 1.54 g, 10.0 mmol) and tert-butyl 3-(cyanomethylene)azetidine-1-carboxylate (prepared using similar methods as disclosed in the literature such as WO 2012/177606: 2.33 g, 12.0 mmol) in acetonitrile (10 mL) was added 1,8-diazabicyclo[5.4.0]undec-7-ene (1.94 mL, 13.0 mmol). The resulting mixture was heated to 75° C. and stirred for two days then cooled to room temperature and diluted with EtOAc then washed with water and brine. The organic layer was dried over $Na_2SO_4$ then concentrated. The residue was purified via flash chromatography on a silica gel column eluting with 0 to 60% EtOAc in hexanes to give the desired product (2.26 g, 77%). LC-MS calculated for $C_{11}H_{16}N_3O_3$ $(M-^tBu+2H)^+$: m/z=238.1; found 238.2.

Step 2: tert-butyl 3-(cyanomethyl)-3-(4-{[(1R,2S)-2-phenylcyclopropyl]amino}piperidin-1-yl)azetidine-1-carboxylate

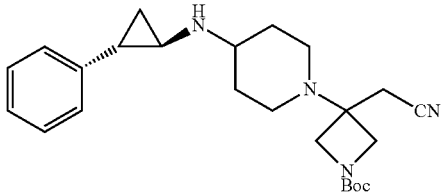

To the solution of (1R,2S)-2-phenylcyclopropanamine (2.16 g, 16.2 mmol) (prepared using procedures as described in *Bioorg. Med. Chem. Lett.*, 2011, 21, 4429) and tert-butyl 3-(cyanomethyl)-3-(4-oxopiperidin-1-yl)azetidine-1-carboxylate (4.77 g, 16.2 mmol) in methylene chloride (80 mL) was added acetic acid (1.85 mL, 32.5 mmol). The resulting mixture was stirred at room temperature for 7 h, then sodium triacetoxyborohydride (10.3 g, 48.8 mmol) was added portion-wise. The reaction mixture was stirred at room temperature for overnight then cooled to 0° C. and quenched with saturated $NaHCO_3$ aqueous solution. The mixture was extracted with DCM. The combined extracts were dried over $Na_2SO_4$ and concentrated. The residue was purified via flash chromatography on a silica gel column eluting with 0 to 10% MeOH in DCM to give the desired product (5.62 g, 84%). LC-MS calculated for $C_{24}H_{35}N_4O_2$ $(M+H)^+$: m/z=411.3; found 411.3.

Step 3: tert-butyl 3-(cyanomethyl)-3-{4-[[(1R,2S)-2-phenylcyclopropyl](trifluoroacetyl)amino]piperidin-1-yl}azetidine-1-carboxylate

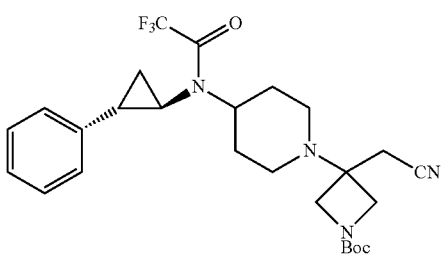

To the solution of tert-butyl 3-(cyanomethyl)-3-(4-{[(1R,2S)-2-phenylcyclopropyl]amino}piperidin-1-yl)azetidine-1-carboxylate (5.62 g, 13.7 mmol) in methylene chloride (80 mL) at 0° C. was added N,N-diisopropylethylamine (5.96 mL, 34.2 mmol), followed by trifluoroacetic anhydride (2.90 mL, 20.5 mmol). The resulting mixture was stirred at 0° C. for 1 h then quenched with saturated $NaHCO_3$ aqueous solution. The organic layer was dried over $Na_2SO_4$ and concentrated. The residue was purified via flash chromatography on a silica gel column eluting with 0 to 60% EtOAc in hexanes to give the desired product (5.66 g, 82%). LC-MS calculated for $C_{26}H_{34}F_3N_4O_3$ (M+H)$^+$: m/z=507.3; found 507.2.

Step 4: N-{1-[3-(cyanomethyl)azetidin-3-yl]piperidin-4-yl}-2,2,2-trifluoro-N-[(1R,2S)-2-phenylcyclopropyl]acetamide

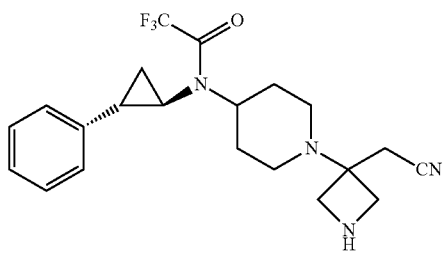

To a solution of the product (5.66 g) from Step 3 in methylene chloride (60 mL) at 0° C. was added trifluoroacetic acid (10.5 mL). The resulting yellow solution was stirred at room temperature overnight then concentrated. The residue was dissolved in 50 mL of DCM then cooled to 0° C. and neutralized with saturated NaHCO$_3$ aqueous solution. The organic layer was dried over Na$_2$SO$_4$ and concentrated. The residue was purified via flash chromatography on a silica gel column eluting with 0 to 20% MeOH in DCM to give the desired product (4.32 g). LC-MS calculated for $C_{21}H_{26}F_3N_4O$ (M+H)$^+$: m/z=407.2; found 407.2.

Step 5: N-{1-[3-(cyanomethyl)-1-(methylsulfonyl)azetidin-3-yl]piperidin-4-yl}-2,2,2-trifluoro-N-[(1R,2S)-2-phenylcyclopropyl]acetamide

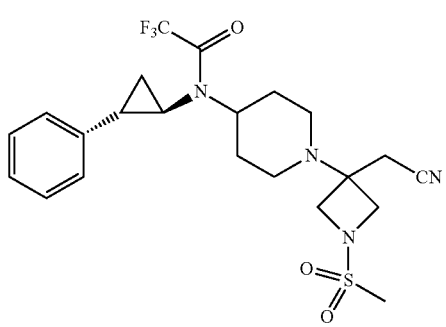

To a solution of N-{1-[3-(cyanomethyl)azetidin-3-yl]piperidin-4-yl}-2,2,2-trifluoro-N-[(1R,2S)-2-phenylcyclopropyl]acetamide (2.00 g, 4.92 mmol) in methylene chloride (30 mL) at 0° C. was added N,N-diisopropylethylamine (2.57 mL, 14.8 mmol), followed by methanesulfonyl chloride (0.57 mL, 7.38 mmol). The resulting yellow solution was stirred at 0° C. for 1 h then diluted with DCM and washed with saturated NaHCO$_3$ aqueous solution. The organic layer was dried over Na$_2$SO$_4$ and concentrated. The residue was purified via flash chromatography on a silica gel column eluting with 0 to 50% EtOAc in hexanes to give the desired product (2.13 g, 89%) as a white solid. LC-MS calculated for $C_{22}H_{28}F_3N_4O_3S$ (M+H)$^+$: m/z=485.2; found 485.1.

Step 6: [1-(methylsulfonyl)-3-(4-{[(1R,2S)-2-phenylcyclopropyl]amino}piperidin-1-yl)azetidin-3-yl]acetonitrile To a solution of product (2.13 g) from Step 5 in tetrahydrofuran (20 mL) and methanol (10 mL) was added sodium hydroxide (2M in water, 12 mL, 24 mmol). The resulting mixture was stirred at room temperature for overnight then quenched with saturated NH$_4$Cl aqueous solution and extracted with EtOAc. The combined extracts were washed with water and brine. The organic layer was dried over Na$_2$SO$_4$ and concentrated. The residue was purified via flash chromatography on a silica gel column eluting with 0 to 10% MeOH in DCM to give the desired product (1.48 g) as a white solid, which was further purified by prep-HPLC (pH=2, acetonitrile/water+TFA) to give the desired product as the TFA salt. LC-MS calculated for $C_{20}H_{29}N_4O_2S$ (M+H)$^+$: m/z=389.2; found 389.2. $^1$H NMR (500 MHz, DMSO) δ 9.07 (br, 2H), 7.33-7.27 (m, 2H), 7.24-7.20 (m, 1H), 7.19-7.15 (m, 2H), 3.91-3.81 (m, 2H), 3.75-3.68 (m, 2H), 3.29-3.17 (m, 1H), 3.02 (s, 3H), 3.00-2.92 (m, 3H), 2.86-2.75 (m, 2H), 2.45-2.36 (m, 1H), 2.27-2.12 (m, 2H), 2.09-1.96 (m, 2H), 1.63-1.49 (m, 2H), 1.48-1.38 (m, 1H), 1.37-1.28 (m, 1H).

Example 59

[1-methyl-3-(4-{[(1R,2S)-2-phenylcyclopropyl]amino}piperidin-1-yl)azetidin-3-yl]acetonitrile

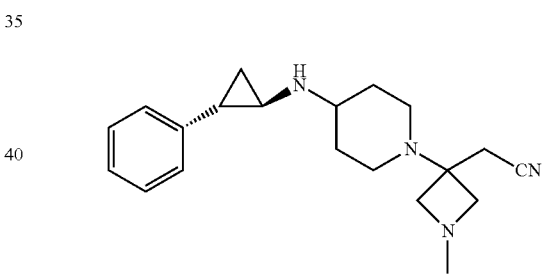

To the solution of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 50.0 mg, 0.123 mmol) in methylene chloride (4 mL) was added formaldehyde (37 wt % in water, 46 μL, 0.62 mmol), followed by acetic acid (21 μL, 0.37 mmol). The resulting mixture was stirred at room temperature for 1 h then sodium triacetoxyborohydride (78 mg, 0.37 mmol) was added. The reaction mixture was stirred at room temperature overnight then neutralized with saturated Na$_2$CO$_3$ aqueous solution and extracted with DCM. The combined extracts were dried over Na$_2$SO$_4$ then concentrated. The residue was dissolved in tetrahydrofuran (2 mL) and methanol (2 mL) then 2.0 M sodium hydroxide in water (0.31 mL, 0.62 mmol) was added. The resulting mixture was stirred at 30° C. for 5 h then cooled to room temperature and diluted with DCM. The mixture was washed with water and brine. The organic layer was dried over Na$_2$SO$_4$ then concentrated. The residue was dissolved in acetonitrile then purified by prep-HPLC (pH=2, acetonitrile/water+TFA) to give the desired product as the TFA salt. LC-MS calculated for $C_{20}H_{29}N_4$ $(M+H)^+$: m/z=325.2; found 325.2. $^1$H NMR (500 MHz, DMSO) δ 7.33-7.28 (m, 2H), 7.25-7.20 (m, 1H), 7.19-7.15 (m, 2H), 4.31-4.11 (m, 2H), 3.98-3.78 (m, 2H), 3.32-3.18 (m, 1H), 3.08-2.94 (m, 3H), 2.94-2.76 (m, 5H), 2.47-2.38 (m, 1H), 2.31-2.20 (m, 2H), 2.13-1.99 (m, 2H), 1.66-1.51 (m, 2H), 1.50-1.41 (m, 1H), 1.39-1.29 (m, 1H).

Example 60

[3-(4-{[(1R,2S)-2-phenylcyclopropyl]amino}piperidin-1-yl)azetidin-3-yl]acetonitrile

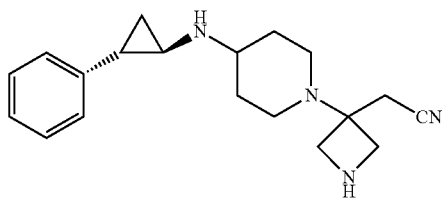

To the solution of tert-butyl 3-(cyanomethyl)-3-(4-{[(1R,2S)-2-phenylcyclopropyl]amino}piperidin-1-yl)azetidine-1-carboxylate (Example 58, Step 2: 20 mg) in DCM (0.5 mL) was added TFA (0.5 mL). The resulting mixture was stirred at room temperature for 1 h then concentrated. The residue was dissolved in acetonitrile then purified by prep-HPLC (pH=2, acetonitrile/water+TFA) to give the desired product as the TFA salt. LC-MS calculated for $C_{19}H_{27}N_4$ $(M+H)^+$: m/z=311.2; found 311.2.

Example 61

[3-(4-{[(1S,2R)-2-phenylcyclopropyl]amino}piperidin-1-yl)azetidin-3-yl]acetonitrile

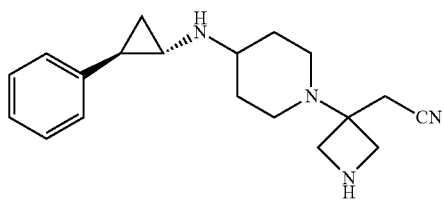 [SMILES: N#CCC1(N2CCC(N[C@H]3C[C@@H]3c3ccccc3)CC2)CNC1]

This compound was prepared using procedures analogous to those described for the synthesis of Example 60 with (1S,2R)-2-phenylcyclopropanamine (prepared using procedures as described in *Bioorg. Med. Chem. Lett.*, 2011, 21, 4429) replacing (1R,2S)-2-phenylcyclopropanamine. The reaction mixture was purified by prep-HPLC (pH=2, acetonitrile/water+TFA) to give the desired product as the TFA salt. LC-MS calculated for $C_{19}H_{27}N_4$ $(M+H)^+$: m/z=311.2; found 311.2.

Example 62

[1-(ethylsulfonyl)-3-(4-{[(1R,2S)-2-phenylcyclopropyl]amino}piperidin-1-yl)azetidin-3-yl]acetonitrile

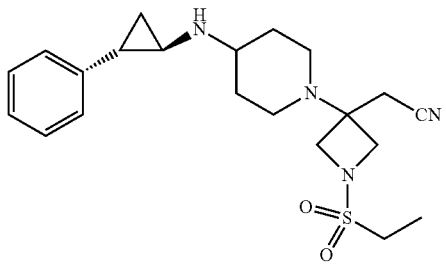

This compound was prepared using procedures analogous to those described for the synthesis of Example 58. The reaction mixture was purified by prep-HPLC (pH=2, acetonitrile/water+TFA) to give the desired product as the TFA salt. LC-MS calculated for $C_{21}H_{31}N_4O_2S$ $(M+H)^+$: m/z=403.2; found 403.2. $^1$H NMR (500 MHz, DMSO) δ 8.99 (br, 2H), 7.33-7.27 (m, 2H), 7.25-7.20 (m, 1H), 7.19-7.16 (m, 2H), 3.90-3.80 (m, 2H), 3.72-3.60 (m, 2H), 3.31-3.17 (m, 1H), 3.13 (q, J=7.3 Hz, 2H), 3.02-2.91 (m, 3H), 2.82-2.70 (m, 2H), 2.43-2.33 (m, 1H), 2.25-2.13 (m, 2H), 2.06-1.97 (m, 2H), 1.62-1.47 (m, 2H), 1.46-1.38 (m, 1H), 1.37-1.30 (m, 1H), 1.23 (t, J=7.3 Hz, 3H).

Example 63

3-(cyanomethyl)-N,N-dimethyl-3-(4-{[(1R,2S)-2-phenylcyclopropyl]amino}piperidin-1-yl)azetidine-1-sulfonamide

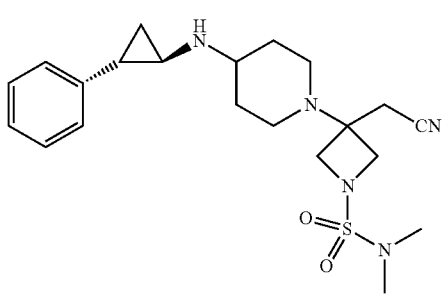

This compound was prepared using procedures analogous to those described for the synthesis of Example 58 with dimethylsulfamoyl chloride replacing methanesulfonyl chloride in Step 5. The reaction mixture was purified by prep-HPLC (pH=2, acetonitrile/water+TFA) to give the desired product as the TFA salt. LC-MS calculated for $C_{21}H_{32}N_5O_2S$ $(M+H)^+$: m/z=418.2; found 418.2.

Example 64

3-(cyanomethyl)-N-methyl-3-(4-{[(1R,2S)-2-phenyl-cyclopropyl]amino}piperidin-1-yl)azetidine-1-sulfonamide

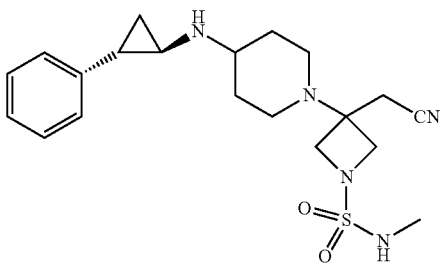

This compound was prepared using procedures analogous to those described for the synthesis of Example 58 with methylsulfamoyl chloride replacing methanesulfonyl chloride in Step 5. The reaction mixture was purified by prep-HPLC (pH=2, acetonitrile/water+TFA) to give the desired product as the TFA salt. LC-MS calculated for $C_{20}H_{30}N_5O_2S$ (M+H)$^+$: m/z=404.2; found 404.2. $^1$H NMR (500 MHz, CD$_3$CN) δ 7.37-7.29 (m, 2H), 7.28-7.22 (m, 1H), 7.19-7.12 (m, 2H), 3.81 (d, J=8.1 Hz, 2H), 3.63 (d, J=8.5 Hz, 2H), 3.38-3.22 (m, 1H), 2.89-2.76 (m, 5H), 2.67 (s, 3H), 2.60-2.48 (m, 1H), 2.38-2.24 (m, 2H), 2.19-2.05 (m, 2H), 1.78-1.62 (m, 2H), 1.63-1.51 (m, 1H), 1.42-1.29 (m, 1H).

Example 65

3-(cyanomethyl)-3-(4-{[(1R,2S)-2-phenylcyclopropyl]amino}piperidin-1-yl)azetidine-1-sulfonamide

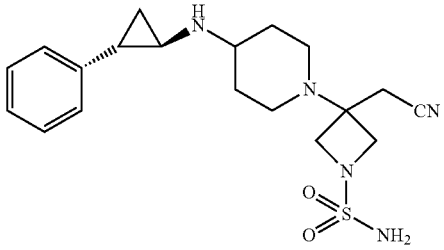

To the solution of chlorosulfonyl isocyanate (86 μL, 0.98 mmol) in methylene chloride (1.0 mL) at 0° C. was added a solution of tert-butyl alcohol (94 μL, 0.98 mmol) in methylene chloride (1.0 mL). The resulting mixture was stirred at 0° C. for 10 min then warmed to room temperature and stirred for 1 h. The mixture was then added to a solution of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 100. mg, 0.246 mmol) and N,N-diisopropylethylamine (210 μL, 1.2 mmol) in tetrahydrofuran (5 mL). The reaction mixture was stirred at 0° C. for 1 h then warmed to room temperature and stirred for 2 h. The reaction mixture was quenched with saturated NaHCO$_3$ solution then extracted with DCM. The combined extracts were dried over Na$_2$SO$_4$ and concentrated. The residue was dissolved in methylene chloride (1.5 mL) then trifluoroacetic acid (1.5 mL) was added. The resulting mixture was stirred at room temperature for 1 h then concentrated. The residue was dissolved in tetrahydrofuran (2.0 mL) then 2.0 M sodium hydroxide in water (1.8 mL, 3.7 mmol) was added, followed by methanol (2.0 mL). The resulting mixture was stirred at room temperature for overnight then purified with prep-HPLC (pH=10, acetonitrile/water+NH$_4$OH) to give the desired product as a white powder. LC-MS calculated for $C_{19}H_{28}N_5O_2S$ (M+H)$^+$: m/z=390.2; found 390.2. $^1$H NMR (500 MHz, DMSO) δ 7.23-7.18 (m, 2H), 7.12-7.06 (m, 1H), 7.02-6.98 (m, 2H), 6.94 (s, 2H), 3.68-3.62 (m, 2H), 3.50-3.45 (m, 2H), 2.94 (s, 2H), 2.64-2.55 (m, 2H), 2.55-2.50 (m, 1H), 2.37-2.28 (m, 1H), 2.21-2.11 (m, 3H), 1.81-1.70 (m, 3H), 1.30-1.18 (m, 2H), 0.96-0.90 (m, 2H).

Example 66

[1-methyl-3-(4-{[(1R,2S)-2-phenylcyclopropyl]amino}piperidin-1-yl)azetidin-3-yl]acetic acid

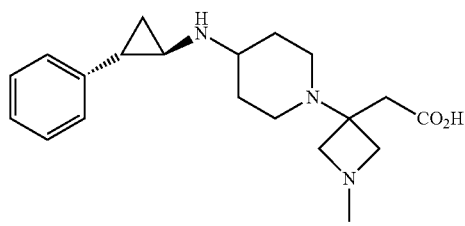

Step 1: tert-butyl 3-(2-tert-butoxy-2-oxoethylidene)azetidine-1-carboxylate

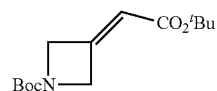

1.0 M Potassium tert-butoxide in THF (20.0 mL, 20.0 mmol) was added to a solution of tert-butyl(diethoxyphosphoryl)acetate (5.00 g, 19.8 mmol) in tetrahydrofuran (22.0 mL) at 0° C. The mixture was stirred at room temperature for 30 min then cooled to 0° C. and a solution of tert-butyl 3-oxoazetidine-1-carboxylate (2.83 g, 16.5 mmol) in 10 mL of THF was added. The reaction mixture was stirred at room temperature for overnight then diluted with ethyl acetate, washed with saturated NaHCO$_3$ aqueous solution, water and brine. The organic layer was dried over Na$_2$SO$_4$, filtered and concentrated. The residue was purified via flash chromatography on a silica gel column eluting with 0 to 20% EtOAc in hexanes to give the desired product (4.46 g, quant.).

Step 2: tert-butyl 3-(2-tert-butoxy-2-oxoethyl)-3-(4-oxopiperidin-1-yl)azetidine-1-carboxylate

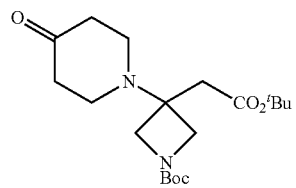 [SMILES: CC(C)(C)OC(=O)CC1(N2CCC(=O)CC2)CN(C(=O)OC(C)(C)C)C1]

To the mixture of piperidin-4-one hydrochloride hydrate (922 mg, 6.00 mmol) in acetonitrile (5.0 mL) was added 1,8-diazabicyclo[5.4.0]undec-7-ene (1.08 mL, 7.20 mmol), followed by tert-butyl 3-(2-tert-butoxy-2-oxoethylidene)azetidine-1-carboxylate (1080 mg, 4.00 mmol). The resulting mixture was heated to 75° C. and stirred for 2 days. The mixture was cooled to room temperature then diluted with EtOAc and washed with water and brine. The organic layer was dried over $Na_2SO_4$ and concentrated. The residue was purified via flash chromatography on a silica gel column eluting with 0 to 60% EtOAc in hexanes to give the desired product (424 mg, 29%). LC-MS calculated for $C_{19}H_{33}N_2O_5$ $(M+H)^+$: m/z=369.2; found 369.2.

Step 3: tert-butyl 3-(2-tert-butoxy-2-oxoethyl)-3-(4-{[(1R,2S)-2-phenylcyclopropyl]amino}-piperidin-1-yl)azetidine-1-carboxylate

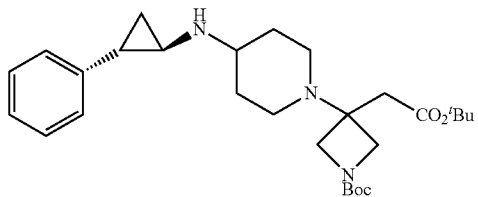

To the solution of (1R,2S)-2-phenylcyclopropanamine (173 mg, 1.30 mmol) and tert-butyl 3-(2-tert-butoxy-2-oxoethyl)-3-(4-oxopiperidin-1-yl)azetidine-1-carboxylate (479 mg, 1.30 mmol) in methylene chloride (6 mL) was added acetic acid (150 μL, 2.6 mmol). The resulting mixture was stirred at room temperature for overnight then sodium triacetoxyborohydride (550 mg, 2.6 mmol) was added. The reaction mixture was stirred at room temperature for 2 h then diluted with DCM, washed with saturated $NaHCO_3$ aqueous solution, water and brine. The organic layer was dried over $Na_2SO_4$ then concentrated. The residue was purified via flash chromatography on a silica gel column eluting with 0 to 10% MeOH in DCM to give the desired product (512 mg, 81%). LC-MS calculated for $C_{28}H_{44}N_3O_4$ $(M+H)^+$: m/z=486.3; found 486.4.

Step 4: tert-butyl 3-(2-tert-butoxy-2-oxoethyl)-3-{4-[[(1R,2S)-2-phenylcyclopropyl](trifluoroacetyl)amino]piperidin-1-yl}azetidine-1-carboxylate

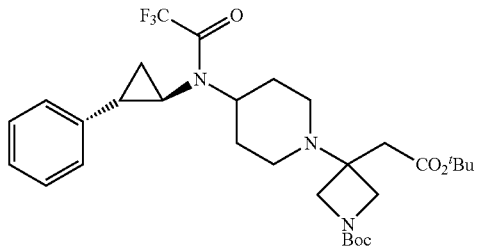

To the solution of tert-butyl 3-(2-tert-butoxy-2-oxoethyl)-3-(4-{[(1R,2S)-2-phenylcyclopropyl]amino}piperidin-1-yl)azetidine-1-carboxylate (497 mg, 1.02 mmol) in methylene chloride (8 mL) at 0° C. was added N,N-diisopropylethylamine (530 μL), followed by trifluoroacetic anhydride (190 μL, 1.3 mmol). The resulting yellow solution was stirred at 0° C. for 1 h then quenched with saturated $NaHCO_3$ solution. The resulting mixture was extracted with DCM. The combined extracts were dried over $Na_2SO_4$ then concentrated. The residue was purified via flash chromatography on a silica gel column eluting with 0 to 60% EtOAc in hexanes to give the desired product (583 mg, 98%). LC-MS calculated for $C_{30}H_{43}F_3N_3O_5$ $(M+H)^+$: m/z=582.3; found 582.3.

Step 5: (3-{4-[[(1R,2S)-2-phenylcyclopropyl](trifluoroacetyl)amino]piperidin-1-yl}azetidin-3-yl)acetic acid dihydrochloride

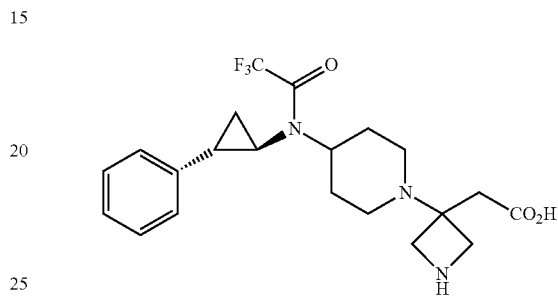

To a solution of the product from Step 4 in methylene chloride (6 mL) was added 4.0 M hydrogen chloride in 1,4-dioxane (2.0 mL, 8.0 mmol). The resulting mixture was stirred at room temperature for overnight then concentrated to give light yellow solid (548 mg) which was used in the next step without further purification. LC-MS calculated for $C_{21}H_{27}F_3N_3O_3$ $(M+H)^+$: m/z=426.2; found 426.1.

Step 6: [1-methyl-3-(4-{[(1R,2S)-2-phenylcyclopropyl]amino}piperidin-1-yl)azetidin-3-yl]acetic acid To a solution of (3-{4-[[(1R,2S)-2-phenylcyclopropyl](trifluoroacetyl)amino]piperidin-1-yl}azetidin-3-yl)acetic acid dihydrochloride (30. mg, 0.060 mmol) in methylene chloride (2 mL, 30 mmol) was added formaldehyde (37 wt % in water, 22 μL, 0.30 mmol), followed by acetic acid (10. μL, 0.18 mmol). The resulting mixture was stirred at room temperature for 1 h, then sodium triacetoxyborohydride (38 mg, 0.18 mmol) was added. The reaction mixture was stirred at room temperature for 2 h then concentrated. The residue was dissolved in tetrahydrofuran (1.0 mL) then 2.0 M sodium hydroxide in water (1.0 mL, 2.0 mmol) was added, followed by methanol (1.0 mL). The resulting mixture was stirred at room temperature for overnight then purified by prep-HPLC (pH=2, acetonitrile/water+TFA) to give the desired product as the TFA salt. LC-MS calculated for $C_{20}H_{30}N_3O_2$ $(M+H)^+$: m/z=344.2; found 344.3. $^1H$ NMR (500 MHz, DMSO) δ 7.33-7.27 (m, 2H), 7.25-7.20 (m, 1H), 7.19-7.14 (m, 2H), 4.40-4.28 (m, 1H), 4.15-4.03 (m, 1H), 3.99-3.87 (m, 1H), 3.84-3.70 (m, 1H), 3.31-3.17 (m, 1H), 3.03-2.75 (m, 6H), 2.74-2.59 (m, 2H), 2.47-2.36 (m, 1H), 2.18-2.08 (m, 2H), 2.07-1.96 (m, 2H), 1.65-1.49 (m, 2H), 1.50-1.40 (m, 1H), 1.38-1.25 (m, 1H).

Example 67

[1-ethyl-3-(4-{[(1R,2S)-2-phenylcyclopropyl]amino}piperidin-1-yl)azetidin-3-yl]acetic acid

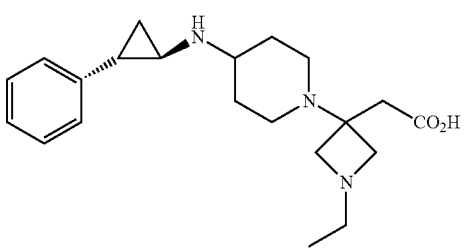

This compound was prepared using procedures analogous to those described for the synthesis of Example 66 with acetaldehyde (5 M in THF) replacing formaldehyde. The reaction mixture was purified by prep-HPLC (pH=2, acetonitrile/water+TFA) to give the desired product as the TFA salt. LC-MS calculated for $C_{21}H_{32}N_3O_2$ (M+H)$^+$: m/z=358.2; found 358.2.

Example 68

N,N-dimethyl-2-[1-(4-{[(1R,2S)-2-phenylcyclopropyl]amino}piperidin-1-yl)cyclobutyl]acetamide

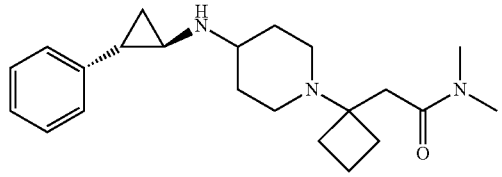

Step 1: tert-butyl[1-(4-oxopiperidin-1-yl)cyclobutyl]acetate

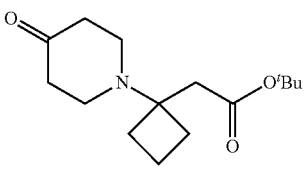 [SMILES: CC(C)(C)OC(=O)CC1(N2CCC(=O)CC2)CCC1]

To the mixture of piperidin-4-one hydrochloride hydrate (614 mg, 4.00 mmol) in acetonitrile (3.0 mL) was added 1,8-diazabicyclo[5.4.0]undec-7-ene (0.69 mL, 4.6 mmol), followed by tert-butyl cyclobutylideneacetate (336 mg, 2.00 mmol). The resulting mixture was heated to 75° C. and stirred for 2 days. The mixture was cooled to room temperature then diluted with EtOAc and washed with water and brine. The organic layer was dried over $Na_2SO_4$ and concentrated. The residue was purified via flash chromatography on a silica gel column eluting with 0 to 50% EtOAc in hexanes to give the desired product (57 mg, 11%). LC-MS calculated for $C_{15}H_{26}NO_3$ (M+H)$^+$: m/z=268.2; found 268.1.

Step 2: tert-butyl[1-(4-{[(1R,2S)-2-phenylcyclopropyl]amino}piperidin-1-yl)cyclobutyl]acetate

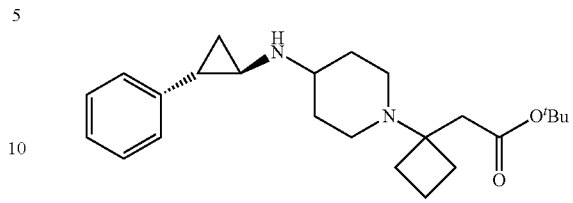

To the solution of (1R,2S)-2-phenylcyclopropanamine (28 mg, 0.21 mmol) and tert-butyl[1-(4-oxopiperidin-1-yl)cyclobutyl]acetate (57 mg, 0.21 mmol) in methylene chloride (3 mL) was added acetic acid (24 µL, 0.43 mmol). The resulting mixture was stirred at room temperature for overnight then sodium triacetoxyborohydride (90. mg, 0.43 mmol) was added. The reaction mixture was stirred at room temperature for 2 h then diluted with DCM and washed with saturated $NaHCO_3$ aqueous solution, water and brine. The organic layer was dried over $Na_2SO_4$ then concentrated. The residue was purified via flash chromatography on a silica gel column eluting with 0 to 10% MeOH in DCM to give the desired product (79 mg, 96%). LC-MS calculated for $C_{24}H_{37}N_2O_2$ (M+H)$^+$: m/z=385.3; found 385.3.

Step 3: [1-(4-{[(1R,2S)-2-phenylcyclopropyl]amino}piperidin-1-yl)cyclobutyl]acetic acid dihydrochloride

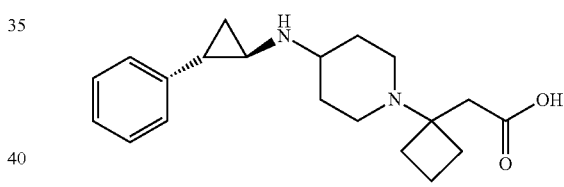

The product from Step 2 was dissolved in methylene chloride (3 mL) then 4.0 M hydrogen chloride in 1,4-dioxane (0.533 mL, 2.13 mmol) was added. The resulting mixture was stirred at room temperature for overnight then concentrated. The residue (73 mg, white solid) was used in the next step without further purification. LC-MS calculated for $C_{20}H_{29}N_2O_2$ (M+H)$^+$: m/z=329.2; found 329.2.

Step 4: N,N-dimethyl-2-[1-(4-{[(1R,2S)-2-phenylcyclopropyl]amino}piperidin-1-yl)cyclobutyl]acetamide To the solution of [1-(4-{[(1R,2S)-2-phenylcyclopropyl]amino}piperidin-1-yl)cyclobutyl]acetic acid dihydrochloride (24 mg, 0.060 mmol) in N,N-dimethylformamide (2 mL) was added N,N-diisopropylethylamine (100. µL, 0.574 mmol) and 2.0 M dimethylamine in THF (0.15 mL, 0.30 mmol). The mixture was stirred at room temperature for 5 min then benzotriazol-1-yloxytris(dimethylamino)phosphonium hexafluorophosphate (29. mg, 0.066 mmol) was added. The resulting mixture was stirred at room temperature for 2 h then diluted with acetonitrile and purified by prep-HPLC (pH=10, acetonitrile/water+$NH_4OH$) to give the desired product as a white solid. LC-MS calculated for $C_{22}H_{34}N_3O$ (M+H)$^+$: m/z=356.3; found 356.3.

Example 69

N-methyl-2-[1-(4-{[(1R,2S)-2-phenylcyclopropyl]amino}piperidin-1-yl)cyclobutyl]acetamide

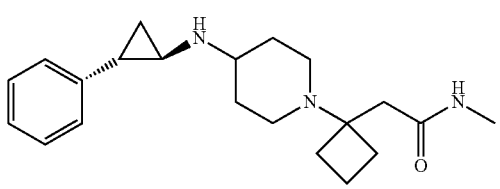

This compound was prepared using procedures analogous to those described for the synthesis of Example 68 with methylamine (2 M in THF) replacing dimethylamine. The resulting mixture was purified by prep-HPLC (pH=10, acetonitrile/water+NH$_4$OH) to give the desired product as a white solid. LC-MS calculated for C$_{21}$H$_{32}$N$_3$O (M+H)$^+$: m/z=342.3; found 342.3.

Example 70

2-[1-(ethylsulfonyl)-3-(4-{[(1R,2S)-2-phenylcyclopropyl]amino}piperidin-1-yl)azetidin-3-yl]-N,N-dimethylacetamide

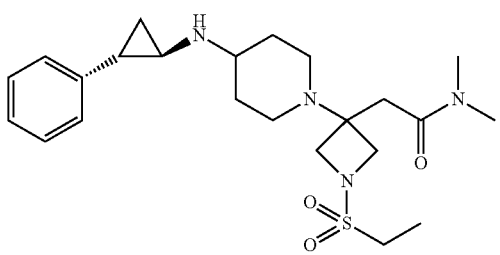

Step 1: tert-butyl 3-(2-methoxy-2-oxoethyl)-3-(4-oxopiperidin-1-yl)azetidine-1-carboxylate

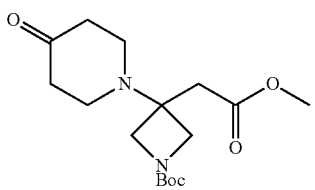 [SMILES: COC(=O)CC1(N2CCC(=O)CC2)CN(C(=O)OC(C)(C)C)C1]

To the mixture of piperidin-4-one hydrochloride hydrate (0.77 g, 5.0 mmol) and tert-butyl 3-(2-methoxy-2-oxoethylidene)azetidine-1-carboxylate (MolBridge, cat#MB00001187: 1.2 g, 5.5 mmol) in acetonitrile (5 mL) was added 1,8-diazabicyclo[5.4.0]undec-7-ene (0.90 mL, 6.0 mmol). The resulting mixture was heated to 75° C. and stirred for two days. The mixture was diluted with EtOAc then washed with water and brine. The organic layer was dried over Na$_2$SO$_4$ then concentrated. The residue was purified via flash chromatography on a silica gel column eluting with 0 to 70% EtOAc in hexanes to give the desired product (1.08 g, 66%). LC-MS calculated for C$_{12}$H$_{19}$N$_2$O$_5$ (M-$^t$Bu+2H)$^+$: m/z=271.1; found 271.2.

Step 2: tert-butyl 3-(2-methoxy-2-oxoethyl)-3-(4-{[(1R,2S)-2-phenylcyclopropyl]amino}-piperidin-1-yl)azetidine-1-carboxylate

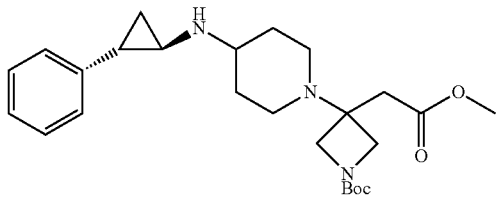

To the solution of (1R,2S)-2-phenylcyclopropanamine (133 mg, 1.00 mmol) and tert-butyl 3-(2-methoxy-2-oxoethyl)-3-(4-oxopiperidin-1-yl)azetidine-1-carboxylate (326 mg, 1.00 mmol) in methylene chloride (8 mL) was added acetic acid (110 µL, 2.0 mmol). The resulting mixture was stirred at room temperature for overnight then sodium triacetoxyborohydride (420 mg, 2.0 mmol) was added. The reaction mixture was stirred at room temperature for 3 h then diluted with DCM and washed with saturated NaHCO$_3$, water and brine. The organic layer was dried over Na$_2$SO$_4$ then concentrated. The residue was purified via flash chromatography on a silica gel column eluting with 0 to 10% MeOH in DCM to give the desired product (483 mg, quant.). LC-MS calculated for C$_{25}$H$_{38}$N$_3$O$_4$ (M+H)$^+$: m/z=444.3; found 444.3.

Step 3: tert-butyl 3-(2-methoxy-2-oxoethyl)-3-{4-[[(1R,2S)-2-phenylcyclopropyl](trifluoroacetyl)amino]piperidin-1-yl}azetidine-1-carboxylate

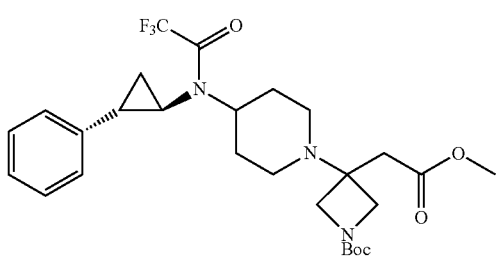

To the solution of tert-butyl 3-(2-methoxy-2-oxoethyl)-3-(4-{[(1R,2S)-2-phenylcyclopropyl]amino}piperidin-1-yl)azetidine-1-carboxylate (444 mg, 1.00 mmol) in methylene chloride (8 mL) was added N,N-diisopropylethylamine (520 µL, 3.0 mmol), followed by trifluoroacetic anhydride (180 µL, 1.3 mmol). The resulting yellow solution was stirred at room temperature for 1 h then quenched with saturated NaHCO$_3$ solution and extracted with DCM. The combined extracts were dried over Na$_2$SO$_4$ then concentrated. The residue was purified via flash chromatography on a silica gel column eluting with 0 to 60% EtOAc in hexanes to give the desired product (446 mg, 83%). LC-MS calculated for C$_{27}$H$_{37}$F$_3$N$_3$O$_5$ (M+H)$^+$: m/z=540.3; found 540.2.

Step 4: methyl(3-{4-[[(1R,2S)-2-phenylcyclopropyl](trifluoroacetyl)amino]piperidin-1-yl}azetidin-3-yl)acetate dihydrochloride

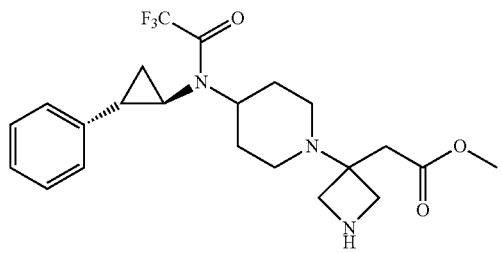

To the solution of the product from Step 3 in methylene chloride (6 mL) was added 4.0 M hydrogen chloride in 1,4-dioxane (2.50 mL, 10.0 mmol). The resulting mixture was stirred at room temperature overnight then concentrated to give 400 mg light yellow solid which was used in the next step without further purification. LC-MS calculated for $C_{22}H_{29}F_3N_3O_3$ (M+H)$^+$: m/z=440.2; found 440.2.

Step 5: methyl(1-(ethylsulfonyl)-3-{4-[[(1R,2S)-2-phenylcyclopropyl](trifluoroacetyl)amino]-piperidin-1-yl}azetidin-3-yl)acetate

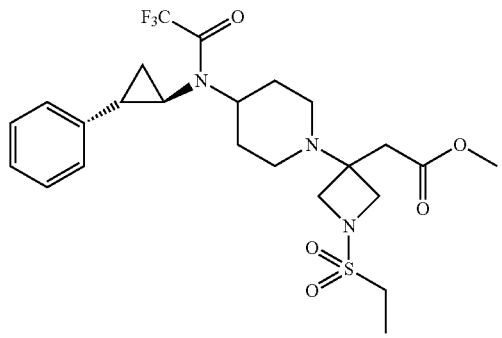

To the suspension of methyl(3-{4-[[(1R,2S)-2-phenylcyclopropyl](trifluoroacetyl)amino]piperidin-1-yl}azetidin-3-yl)acetate dihydrochloride (150 mg, 0.29 mmol) in tetrahydrofuran (5 mL) was added N,N-diisopropylethylamine (255 µL, 1.46 mmol), then ethanesulfonyl chloride (55.5 µL, 0.585 mmol) was added dropwise. The resulting mixture was stirred at room temperature for 1 h then quenched with water and extracted with DCM. The combined extracts were dried over $Na_2SO_4$ then concentrated. The residue was purified via flash chromatography on a silica gel column eluting with 0 to 60% EtOAc in Hexanes to give the desired product. LC-MS calculated for $C_{24}H_{33}F_3N_3O_5S$ (M+H)$^+$: m/z=532.2; found 532.2.

Step 6: [1-(ethylsulfonyl)-3-(4-{[(1R,2S)-2-phenylcyclopropyl]amino}piperidin-1-yl)azetidin-3-yl]acetic acid

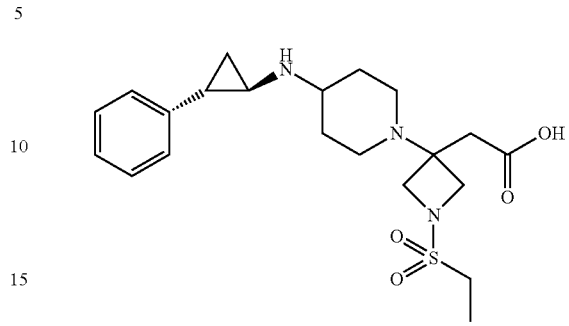

The product from Step 5 was dissolved in tetrahydrofuran (2.5 mL) and methanol (2.5 mL) then 2.0 M sodium hydroxide in water (1.0 mL, 2.0 mmol) was added. The resulting mixture was stirred at room temperature for 2 h then purified by prep HPLC (pH=2, acetonitrile/water+TFA) to give the desired product as the TFA salt. LC-MS calculated for $C_{21}H_{32}N_3O_4S$ (M+H)$^+$: m/z=422.2; found 422.1.

Step 7: 2-[1-(ethylsulfonyl)-3-(4-{[(1R,2S)-2-phenylcyclopropyl]amino}piperidin-1-yl)azetidin-3-yl]-N,N-dimethylacetamide To a solution of [1-(ethylsulfonyl)-3-(4-{[(1R,2S)-2-phenylcyclopropyl]amino}piperidin-1-yl)azetidin-3-yl]acetic acid bis(trifluoroacetate) (36 mg, 0.055 mmol) in tetrahydrofuran (2.0 mL) was added N,N-diisopropylethylamine (58 µL, 0.33 mmol), followed by 2.0 M dimethylamine in THF (150 µL, 0.30 mmol). Then benzotriazol-1-yloxytris-(dimethylamino)phosphonium hexafluorophosphate (27 mg, 0.061 mmol) was added. The resulting mixture was stirred at room temperature for 1 h then diluted with acetonitrile and purified by prep HPLC (pH=10, acetonitrile/water+NH$_4$OH) to give the desired product as a white solid. LC-MS calculated for $C_{23}H_{37}N_4O_3S$ (M+H)$^+$: m/z=449.3; found 449.3. $^1$H NMR (500 MHz, CD$_3$CN) δ 7.27-7.20 (m, 2H), 7.16-7.10 (m, 1H), 7.07-7.01 (m, 2H), 3.99-3.90 (m, 2H), 3.78-3.69 (m, 2H), 3.07-2.95 (m, 5H), 2.85 (s, 3H), 2.75-2.66 (m, 2H), 2.62 (s, 2H), 2.61-2.53 (m, 1H), 2.32-2.24 (m, 1H), 2.18-2.06 (m, 2H), 1.88-1.80 (m, 2H), 1.80-1.73 (m, 1H), 1.37-1.22 (m, 5H), 1.03-0.91 (m, 2H).

Example 71

2-[1-(ethylsulfonyl)-3-(4-{[(1R,2S)-2-phenylcyclopropyl]amino}piperidin-1-yl)azetidin-3-yl]-N-methylacetamide

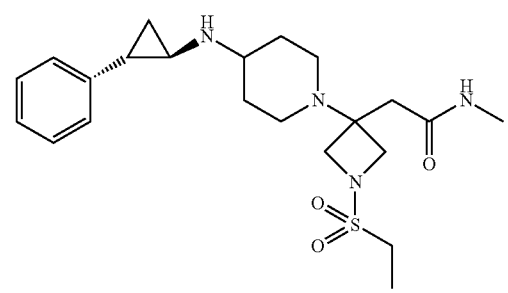

This compound was prepared using procedures analogous to those described for the synthesis of Example 70 with methylamine (2 M in THF) replacing dimethylamine in Step 7. The reaction mixture was prep HPLC (pH=10, acetonitrile/water+NH$_4$OH) to give the desired product as a white solid. LC-MS calculated for $C_{22}H_{35}N_4O_3S$ (M+H)$^+$: m/z=435.2; found 435.3.

Example 72

[1-(trans-4-hydroxycyclohexyl)-3-(4-{[(1R,2S)-2-phenylcyclopropyl]amino}piperidin-1-yl)azetidin-3-yl]acetonitrile

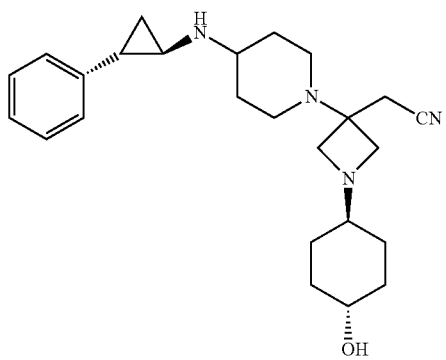

Step 1: N-{1-[1-(4-{[tert-butyl(dimethyl)silyl]oxy}cyclohexyl)-3-(cyanomethyl)azetidin-3-yl]piperidin-4-yl}-2,2,2-trifluoro-N-[(1R,2S)-2-phenylcyclopropyl]acetamide

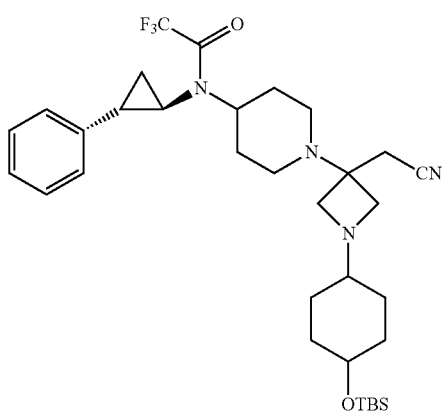

To the solution of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 20. mg, 0.049 mmol) in methylene chloride (2 mL) was added 4-{[tert-butyl(dimethyl)silyl]oxy}cyclohexanone (Aldrich, cat#638153: 62 µL 0.25 mmol), followed by acetic acid (8.4 µL, 0.15 mmol). The resulting mixture was stirred at room temperature for 1 h, then sodium triacetoxyborohydride (31 mg, 0.15 mmol) was added. The reaction mixture was stirred at room temperature for 1.5 h, then neutralized with saturated NaHCO$_3$ solution and extracted with DCM. The combined extracts were dried over Na$_2$SO$_4$ then concentrated. The residue was used in the next step without further purification. LC-MS calculated for $C_{33}H_{50}F_3N_4O_2Si$ (M+H)$^+$: m/z=619.4; found 619.3.

Step 2: N-{1-[3-(cyanomethyl)-1-(4-hydroxycyclohexyl)azetidin-3-yl]piperidin-4-yl}-2,2,2-trifluoro-N-[(1R,2S)-2-phenylcyclopropyl]acetamide

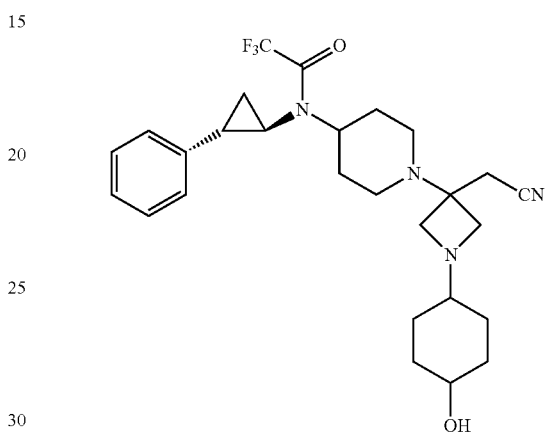

The crude product from Step 1 was dissolved in THF (1 mL) then 4.0 M Hydrogen chloride in 1,4-dioxane (0.5 mL, 2 mmol) was added. The resulting mixture was stirred at room temperature for 1 h then concentrated under reduced pressure. The residue was used in the next step without further purification. LC-MS calculated for $C_{27}H_{36}F_3N_4O_2$ (M+H)$^+$: m/z=505.3; found 505.3.

Step 3: [1-(trans-4-hydroxycyclohexyl)-3-(4-{[(1R,2S)-2-phenylcyclopropyl]amino}piperidin-1-yl)azetidin-3-yl]acetonitrile The crude product from Step 2 was dissolved in THF (1 mL) and MeOH (1 mL) then 2.0 M Sodium hydroxide in water (0.5 mL, 1 mmol) was added. The resulting mixture was stirred at room temperature for 2 h to give a mixture of cis- and trans-products which was separated and purified by prep-HPLC (pH=10, acetonitrile/water+NH$_4$OH). LC-MS calculated for $C_{25}H_{37}N_4O$ (M+H)$^+$: m/z=409.3; found 409.2.

For the trans-isomer: $^1$H NMR (500 MHz, CD$_3$CN) δ 7.26-7.21 (m, 2H), 7.15-7.10 (m, 1H), 7.06-7.01 (m, 2H), 3.50-3.40 (m, 1H), 3.22 (d, J=7.8 Hz, 2H), 2.83 (d, J=7.4 Hz, 2H), 2.75 (s, 2H), 2.66-2.53 (m, 3H), 2.29-2.18 (m, 3H), 2.03-1.95 (m, 1H), 1.86-1.68 (m, 7H), 1.30-1.11 (m, 4H), 1.02-0.90 (m, 4H). Trans-configuration of the cyclohexane ring was confirmed by 2D NMR. Analytical LC-MS (pH=10, acetonitrile/water+NH$_4$OH) retention time t=1.91 min.

Example 73

[1-(cis-4-hydroxycyclohexyl)-3-(4-{[(1R,2S)-2-phenylcyclopropyl]amino}piperidin-1-yl)azetidin-3-yl]acetonitrile

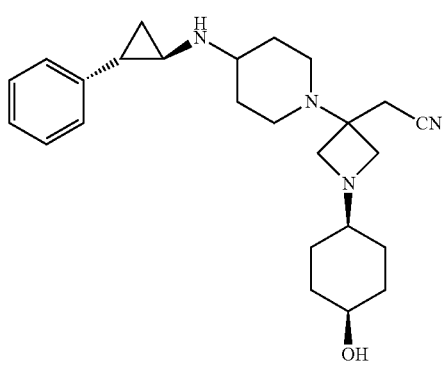

The cis-isomer was also formed in the reaction of Example 72, Step 3. It was isolated via prep-HPLC (pH=10, acetonitrile/water+NH$_4$OH) to give the desired product. LC-MS calculated for C$_{25}$H$_{37}$N$_4$O (M+H)$^+$: m/z=409.3; found 409.2. $^1$H NMR (500 MHz, CD$_3$CN) δ 7.29-7.24 (m, 2H), 7.18-7.13 (m, 1H), 7.09-7.05 (m, 2H), 3.68-3.61 (m, 1H), 3.30-3.24 (m, 2H), 2.85-2.80 (m, 4H), 2.71-2.56 (m, 3H), 2.33-2.22 (m, 4H), 1.89-1.78 (m, 3H), 1.66-1.59 (m, 2H), 1.54-1.44 (m, 4H), 1.44-1.36 (m, 2H), 1.32-1.22 (m, 2H), 1.02-0.96 (m, 2H). Analytical LC-MS (pH=10, acetonitrile/water+NH$_4$OH) retention time t=2.06 min.

Example 74

[1-(2-hydroxyethyl)-3-(4-{[(1R,2S)-2-phenylcyclopropyl]amino}piperidin-1-yl)azetidin-3-yl]acetonitrile

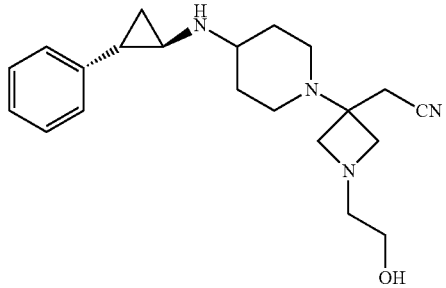

This compound was prepared according to the procedures of Example 72 with {[tert-butyl(dimethyl)silyl]oxy}acetaldehyde (Aldrich, cat#449458) replacing 4-{[tert-butyl(dimethyl)silyl]oxy}cyclohexanone in Step 1. The reaction mixture was purified by prep-HPLC (pH=10, acetonitrile/water+NH$_4$OH) to give the desired product. LC-MS calculated for C$_{21}$H$_{31}$N$_4$O (M+H)$^+$: m/z=355.2; found 355.2.

Example 75

[3-(4-{[(1R,2S)-2-phenylcyclopropyl]amino}piperidin-1-yl)-1-(tetrahydro-2H-pyran-4-yl)azetidin-3-yl]acetonitrile

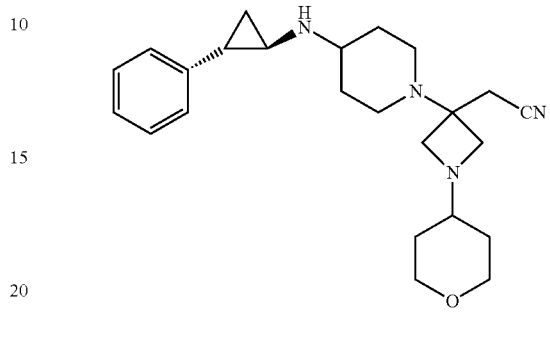

This compound was prepared according to the procedures of Example 72 with tetrahydro-4H-pyran-4-one (Aldrich, cat#198242) replacing 4-{[tert-butyl(dimethyl)silyl]oxy}-cyclohexanone in Step 1. The reaction mixture was purified by prep-HPLC (pH=10, acetonitrile/water+NH$_4$OH) to give the desired product. LC-MS calculated for C$_{24}$H$_{35}$N$_4$O (M+H)$^+$: m/z=395.3; found 395.2.

Example 76

[3-(4-{[(1R,2S)-2-phenylcyclopropyl]amino}piperidin-1-yl)-1-(tetrahydrofuran-3-yl)azetidin-3-yl]acetonitrile (mixture of diasteromers)

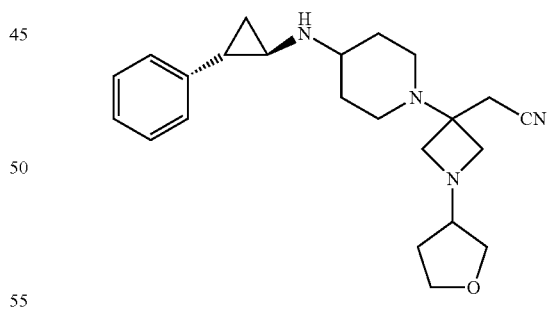

This compound was prepared according to the procedures of Example 72 with dihydrofuran-3(2H)-one (J&W PharmLab, cat#10-0169) replacing 4-{[tert-butyl(dimethyl)silyl]oxy}cyclohexanone in Step 1. The reaction mixture was purified by prep-HPLC (pH=10, acetonitrile/water+NH$_4$OH) to give the desired product. LC-MS calculated for C$_{23}$H$_{33}$N$_4$O (M+H)$^+$: m/z=381.3; found 381.2.

Example 77

2-(3-(cyanomethyl)-3-(4-(((1R,2S)-2-phenylcyclopropyl)amino)piperidin-1-yl)azetidin-1-yl)-N,N-dimethylacetamide

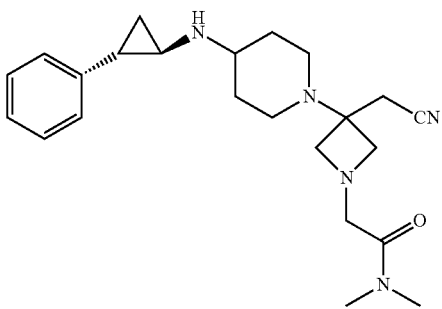

Step 1: [3-(cyanomethyl)-3-(4-{[(1R,2S)-2-phenylcyclopropyl]amino}piperidin-1-yl)azetidin-1-yl]acetic acid

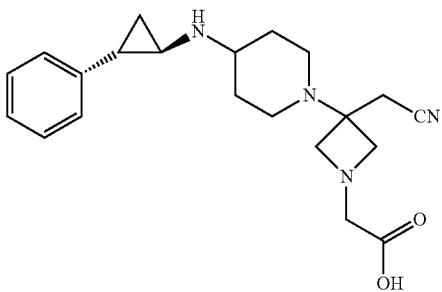

To the solution of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 150 mg, 0.37 mmol) and 5.0 M ethyl glyoxylate in toluene (88 µL, 0.44 mmol) in methylene chloride (2 mL) was added acetic acid (62.9 µL, 1.11 mmol). The resulting mixture was stirred at room temperature overnight then sodium triacetoxyborohydride (160 mg, 0.74 mmol) was added. The reaction mixture was stirred at room temperature for 2 h then diluted with DCM, washed with saturated NaHCO$_3$, water and brine. The organic layer was dried over Na$_2$SO$_4$, filtered and concentrated. The residue was dissolved in THF (2 mL) and MeOH (2 mL) then a solution of Lithium hydroxide, monohydrate (46 mg, 1.1 mmol) in water (1 mL) was added. The reaction mixture was stirred at 40° C. for 2 h. The reaction mixture was adjusted to pH=4 with HCl (aq.), and concentrated under reduced pressure to afford the crude product which was used in the next step without further purification. LC-MS calculated for C$_{21}$H$_{29}$N$_4$O$_2$ (M+H)$^+$: m/z=369.2; found 369.2.

Step 2: 2-(3-(cyanomethyl)-3-(4-(((1R,2S)-2-phenylcyclopropyl)amino)piperidin-1-yl)azetidin-1-yl)-N,N-dimethylacetamide 2.0 M Dimethylamine in THF (41 µL, 0.081 mmol) was added to a mixture of [3-(cyanomethyl)-3-(4-{[(1R,2S)-2-phenylcyclopropyl]amino}piperidin-1-yl)azetidin-1-yl]acetic acid (20 mg, 0.05 mmol) and benzotriazol-1-yloxytris(dimethylamino)phosphonium hexafluorophosphate (29 mg, 0.065 mmol) in DMF (1 mL), followed by triethylamine (20 µL, 0.2 mmol). The reaction mixture was stirred at room temperature for 1 h then adjusted to pH=2 with TFA, and purified by prep-HPLC (pH=2, acetonitrile/water+TFA) to give the desired product as the TFA salt. LC-MS calculated for C$_{23}$H$_{34}$N$_5$O (M+H)$^+$: m/z=396.3; found 396.2.

Example 78

2-[3-(cyanomethyl)-3-(4-{[(1R,2S)-2-phenylcyclopropyl]amino}piperidin-1-yl)azetidin-1-yl]-N-methylacetamide

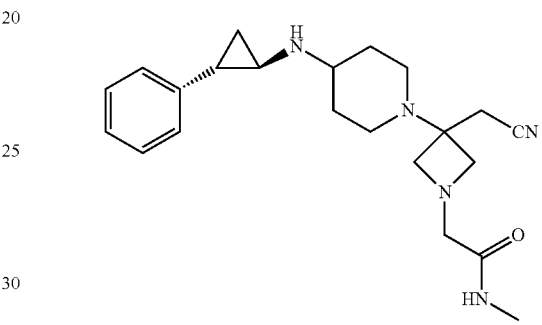

This compound was prepared according to the procedures of Example 77 with methylamine replacing dimethylamine in Step 2. The reaction mixture was purified by prep-HPLC (pH=2, acetonitrile/water+TFA) to give the desired product as the TFA salt. LC-MS calculated for C$_{22}$H$_{32}$N$_5$O (M+H)$^+$: m/z=382.3; found 382.2.

Example 79

2-[3-(cyanomethyl)-3-(4-{[(1R,2S)-2-phenylcyclopropyl]amino}piperidin-1-yl)azetidin-1-yl]acetamide

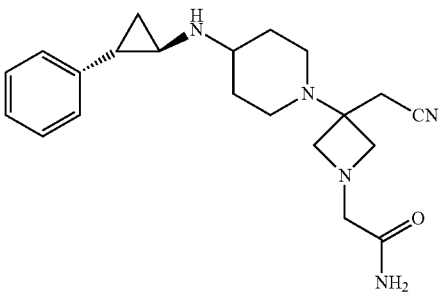

This compound was prepared according to the procedures of Example 77 with ammonium carbonate replacing dimethylamine in Step 2. The reaction mixture was purified by prep-HPLC (pH=2, acetonitrile/water+TFA) to give the desired product as the TFA salt. LC-MS calculated for C$_{21}$H$_{30}$N$_5$O (M+H)$^+$: m/z=368.2; found 368.2.

Example 80

[1-[(1-methyl-1H-pyrazol-4-yl)carbonyl]-3-(4-{[(1R,2S)-2-phenylcyclopropyl]amino}piperidin-1-yl)azetidin-3-yl]acetonitrile

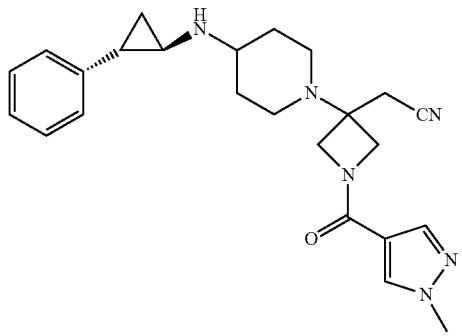

Benzotriazol-1-yloxytris(dimethylamino)phosphonium hexafluorophosphate (35 mg, 0.079 mmol) was added to a mixture of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 25 mg, 0.061 mmol), 1-methyl-1H-pyrazole-4-carboxylic acid (Aldrich, cat#682063: 9.9 mg, 0.079 mmol) in acetonitrile (1.0 mL), followed by triethylamine (25 µL, 0.18 mmol). The reaction mixture was stirred at room temperature overnight then quenched with saturated aqueous NaHCO$_3$, and extracted with ethyl acetate. The combined organic layers were washed with brine, dried over Na$_2$SO$_4$, filtered and concentrated. The residue was dissolved in THF (1 mL) and MeOH (1 mL) then 2 N NaOH (1 mL) was added. The resulting mixture was stirred at room temperature for 3 h then acidified with TFA and purified by prep-HPLC (pH=2, acetonitrile/water+TFA) to give the desired product as the TFA salt. LC-MS calculated for C$_{24}$H$_{31}$N$_6$O (M+H)$^+$: m/z=419.3; found 419.3. The TFA salt of the product was neutralized to obtain the free base form of the product which was used to obtain the NMR data. $^1$H NMR (500 MHz, DMSO) δ 8.15 (s, 1H), 7.74 (s, 1H), 7.21 (t, J=7.6 Hz, 2H), 7.09 (t, J=7.3 Hz, 1H), 7.00 (d, J=7.5 Hz, 2H), 4.26-4.13 (m, 2H), 3.88-3.76 (m, 5H), 2.94 (s, 2H), 2.72-2.62 (m, 2H), 2.56-2.50 (m, 1H), 2.22-2.10 (m, 3H), 1.84-1.70 (m, 3H), 1.34-1.20 (m, 2H), 0.99-0.89 (m, 2H).

Example 81

[1-[(1-methyl-1H-pyrazol-5-yl)carbonyl]-3-(4-{[(1R,2S)-2-phenylcyclopropyl]amino}piperidin-1-yl)azetidin-3-yl]acetonitrile

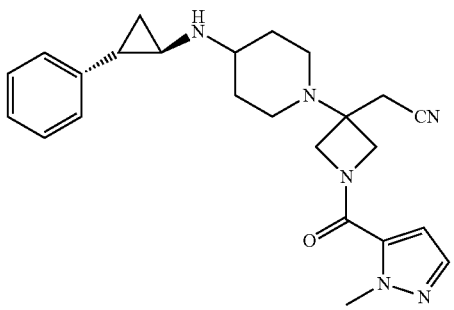

This compound was prepared according to the procedures of Example 80 with 1-methyl-1H-pyrazole-5-carboxylic acid replacing 1-methyl-1H-pyrazole-4-carboxylic acid. The reaction mixture was purified by prep-HPLC (pH=2, acetonitrile/water+TFA) to give the desired product as the TFA salt. LC-MS calculated for C$_{24}$H$_{31}$N$_6$O (M+H)$^+$: m/z=419.3; found 419.3.

Example 82

[1-[(trans-4-hydroxycyclohexyl)carbonyl]-3-(4-{[(1R,2S)-2-phenylcyclopropyl]amino}piperidin-1-yl)azetidin-3-yl]acetonitrile

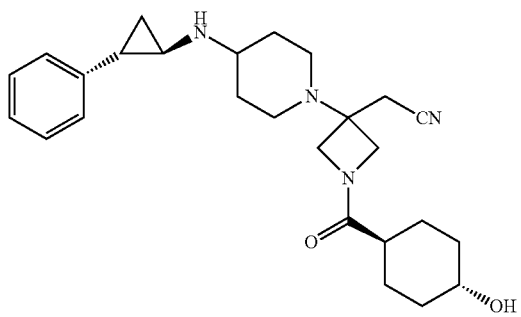

This compound was prepared according to the procedures of Example 80 with trans-4-hydroxycyclohexanecarboxylic acid replacing 1-methyl-1H-pyrazole-4-carboxylic acid. The reaction mixture was purified by prep-HPLC (pH=2, acetonitrile/water+TFA) to give the desired product as the TFA salt. LC-MS calculated for C$_{26}$H$_{37}$N$_4$O$_2$ (M+H)$^+$: m/z=437.3; found 437.3.

Example 83

[1-[(cis-4-hydroxycyclohexyl)carbonyl]-3-(4-{[(1R,2S)-2-phenylcyclopropyl]amino}piperidin-1-yl)azetidin-3-yl]acetonitrile

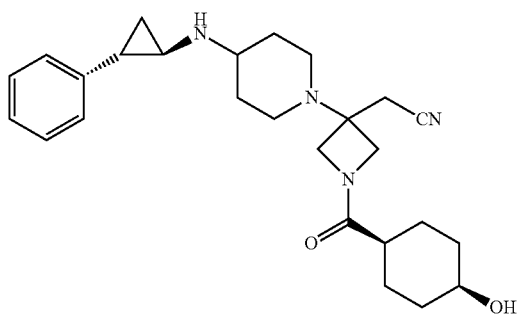

This compound was prepared according to the procedures of Example 80 with cis-4-hydroxycyclohexanecarboxylic acid replacing 1-methyl-1H-pyrazole-4-carboxylic acid. The reaction mixture was purified by prep-HPLC (pH=2, acetonitrile/water+TFA) to give the desired product as the TFA salt. LC-MS calculated for C$_{26}$H$_{37}$N$_4$O$_2$ (M+H)$^+$: m/z=437.3; found 437.3.

Example 84

[1-[(1-hydroxycyclopropyl)carbonyl]-3-(4-{[(1R,2S)-2-phenylcyclopropyl]amino}piperidin-1-yl)azetidin-3-yl]acetonitrile

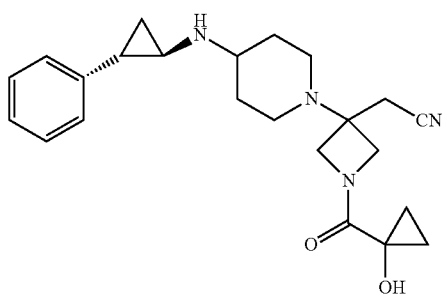

This compound was prepared according to the procedures of Example 80 with 1-hydroxycyclopropanecarboxylic acid replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{23}H_{31}N_4O_2$ $(M+H)^+$: m/z=395.2; found 395.2.

Example 85

[1-[(1-hydroxycyclopentyl)carbonyl]-3-(4-{[(1R,2S)-2-phenylcyclopropyl]amino}piperidin-1-yl)azetidin-3-yl]acetonitrile

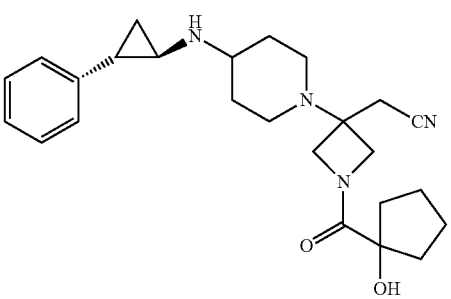

This compound was prepared according to the procedures of Example 80 with 1-hydroxycyclopentanecarboxylic acid replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{25}H_{35}N_4O_2$ $(M+H)^+$: m/z=423.3; found 423.3.

Example 86

[1-(morpholin-4-ylcarbonyl)-3-(4-{[(1R,2S)-2-phenylcyclopropyl]amino}piperidin-1-yl)azetidin-3-yl]acetonitrile

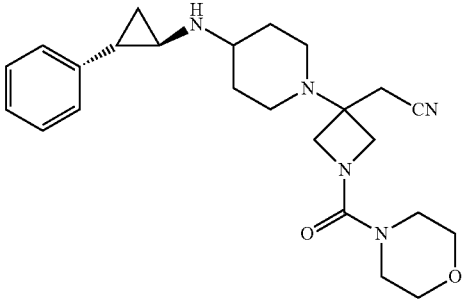

Phosgene (15 wt % in toluene, 80 μL, 0.1 mmol) was added to a mixture of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 30 mg, 0.08 mmol) and triethylamine (30 μL, 0.2 mmol) in acetonitrile (1 mL) at 0° C. The resulting mixture was stirred at room temperature for 1 h, then concentrated under reduced pressure. To the residue was added a solution of Morpholine (10. μL, 0.11 mmol) and triethylamine (20 μL, 0.2 mmol) in acetonitrile (1 mL). The reaction mixture was stirred at room temperature for 30 min then 2N NaOH (1 mL) was added. The reaction mixture was stirred at room temperature for 3 h then purified by prep-HPLC (pH=2, acetonitrile/water+TFA) to give the desired product as the TFA salt. LC-MS calculated for $C_{24}H_{34}N_5O_2$ $(M+H)^+$: m/z=424.3; found 424.3.

Example 87

[1-[(4-hydroxypiperidin-1-yl)carbonyl]-3-(4-{[(1R,2S)-2-phenylcyclopropyl]amino}piperidin-1-yl)azetidin-3-yl]acetonitrile

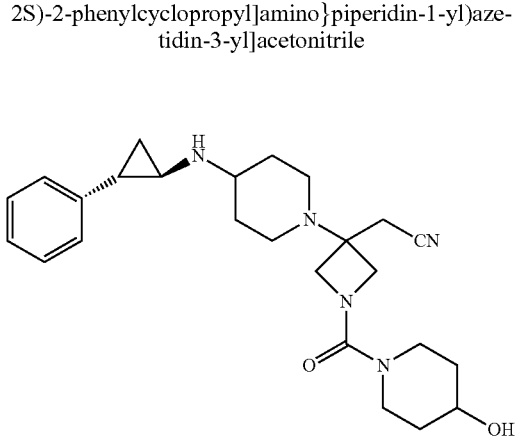

This compound was prepared using similar procedures as described for Example 86 with 4-hydroxypiperidine replacing morpholine. The reaction mixture was purified by prep-HPLC (pH=2, acetonitrile/water+TFA) to give the desired product as the TFA salt. LC-MS calculated for $C_{25}H_{36}N_5O_2$ $(M+H)^+$: m/z=438.3; found 438.3.

Example 88

[1-[(4-methoxypiperidin-1-yl)carbonyl]-3-(4-{[(1R,2S)-2-phenylcyclopropyl]amino}piperidin-1-yl)azetidin-3-yl]acetonitrile

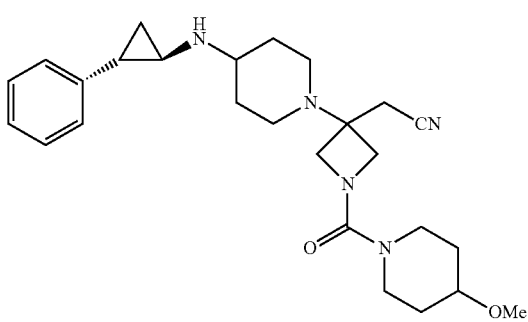

This compound was prepared according to the procedures of Example 86 with 4-methoxypiperidine replacing morpholine. The reaction mixture was purified by prep-HPLC (pH=2, acetonitrile/water+TFA) to give the desired product as the TFA salt. LC-MS calculated for $C_{26}H_{38}N_5O_2$ $(M+H)^+$: m/z=452.3; found 452.3.

Example 89

[1-[(3-hydroxyazetidin-1-yl)carbonyl]-3-(4-{[(1R,2S)-2-phenylcyclopropyl]amino}piperidin-1-yl)azetidin-3-yl]acetonitrile

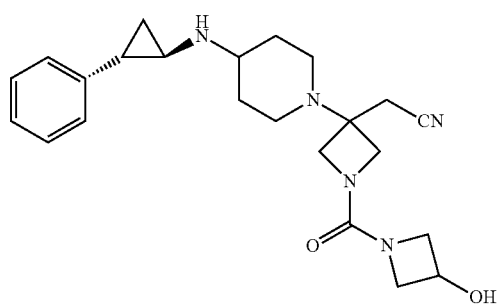

This compound was prepared according to the procedures of Example 86 with azetidin-3-ol hydrochloride replacing Morpholine. The reaction mixture was purified by prep-HPLC (pH=2, acetonitrile/water+TFA) to give the desired product as the TFA salt. LC-MS calculated for $C_{23}H_{32}N_5O_2$ $(M+H)^+$: m/z=410.3; found 410.3.

Example 90

N,N-dimethyl-2-(1-(methylsulfonyl)-3-(4-(((1R,2S)-2-phenylcyclopropyl)amino)piperidin-1-yl)azetidin-3-yl)acetamide

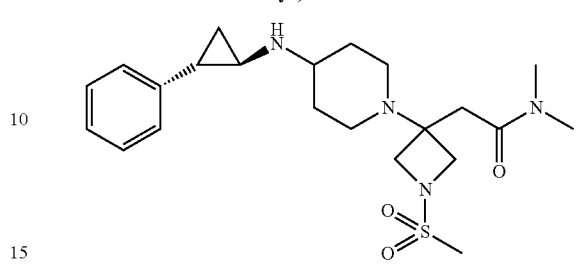

This compound was prepared according to the procedures of Example 70 with methanesulfonyl chloride replacing ethanesulfonyl chloride in Step 5. The reaction mixture was purified by prep-HPLC (pH=2, acetonitrile/water+TFA) to give the desired product as the TFA salt. LC-MS calculated for $C_{22}H_{35}N_4O_3S$ $(M+H)^+$: m/z=435.2; found 435.3.

Example 91

N-methyl-2-[1-(methylsulfonyl)-3-(4-{[(1R,2S)-2-phenylcyclopropyl]amino}piperidin-1-yl)azetidin-3-yl]acetamide

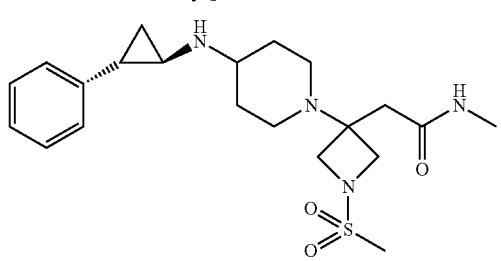

This compound was prepared according to the procedures of Example 70 with methanesulfonyl chloride replacing ethanesulfonyl chloride in Step 5; and methylamine replacing dimethylamine in Step 7. The reaction mixture was purified by prep-HPLC (pH=2, acetonitrile/water+TFA) to give the desired product as the TFA salt. LC-MS calculated for $C_{21}H_{33}N_4O_3S$ $(M+H)^+$: m/z=421.2; found 421.3.

Example 92

2-[1-(ethylsulfonyl)-3-(4-{[(1R,2S)-2-phenylcyclopropyl]amino}piperidin-1-yl)azetidin-3-yl]ethanol

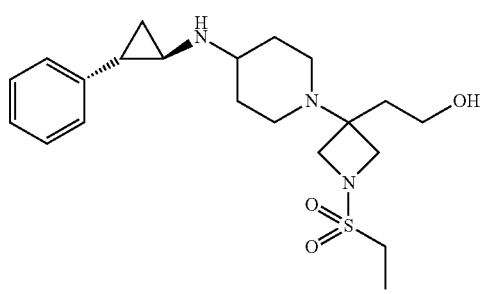

To the solution of [1-(ethylsulfonyl)-3-(4-{[(1R,2S)-2-phenylcyclopropyl]amino}piperidin-1-yl)azetidin-3-yl]acetic acid bis(trifluoroacetate) (Example 70, Step 6: 33 mg, 0.051 mmol) in tetrahydrofuran (1.5 mL) at 0° C. was added 1.0 M lithium tetrahydroaluminate in THF (300 µL, 0.30 mmol) dropwise. The resulting mixture was stirred at 0° C. for 1.5 h then quenched with 0.1 mL water, 0.1 mL NaOH (15% in water) then 0.3 mL water. The resulting mixture was stirred at 0° C. for 10 min then diluted with THF and filtered. The filtrate was purified by prep-HPLC (pH=2, acetonitrile/water+TFA) to give the desired product as the TFA salt. LC-MS calculated for $C_{21}H_{34}N_3O_3S$ (M+H)$^+$: m/z=408.2; found 408.2.

Example 93

2-[1-(methylsulfonyl)-3-(4-{[(1R,2S)-2-phenylcyclopropyl]amino}piperidin-1-yl)azetidin-3-yl]ethanol

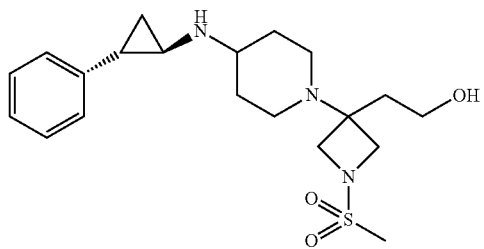

This compound was prepared according to the procedures of Example 70 (Steps 5, 6) and Example 92; with methanesulfonyl chloride replacing ethanesulfonyl chloride in Example 70, Step 5. The reaction mixture was purified by prep-HPLC (pH=2, acetonitrile/water+TFA) to give the desired product as the TFA salt. LC-MS calculated for $C_{20}H_{32}N_3O_3S$ (M+H)$^+$: m/z=394.2; found 394.2.

Example 94 methyl 3-[2-(dimethylamino)-2-oxoethyl]-3-(4-{[(1R,2S)-2-phenylcyclopropyl]amino}piperidin-1-yl)azetidine-1-carboxylate

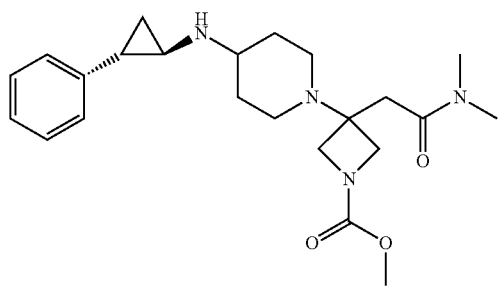

This compound was prepared according to the procedures of Example 70 with methyl chloroformate replacing ethanesulfonyl chloride. The reaction mixture was purified by prep-HPLC (pH=2, acetonitrile/water+TFA) to give the desired product as the TFA salt. LC-MS calculated for $C_{23}H_{35}N_4O_3$ (M+H)$^+$: m/z=415.3; found 415.3.

Example 95 methyl 3-[2-(methylamino)-2-oxoethyl]-3-(4-{[(1R,2S)-2-phenylcyclopropyl]amino}piperidin-1-yl)azetidine-1-carboxylate

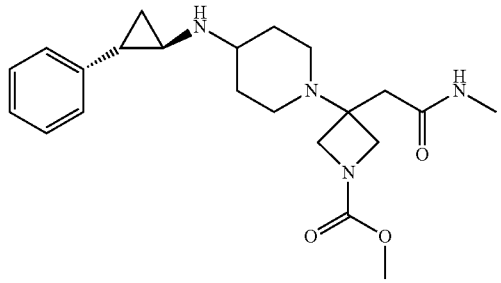

This compound was prepared according to the procedures of Example 70 with methylamine replacing dimethylamine. The reaction mixture was purified by prep-HPLC (pH=2, acetonitrile/water+TFA) to give the desired product as the TFA salt. LC-MS calculated for $C_{22}H_{33}N_4O_3$ (M+H)$^+$: m/z=401.3; found 401.2.

Example 96

3-[2-(dimethylamino)-2-oxoethyl]-N,N-dimethyl-3-(4-{[(1R,2S)-2-phenylcyclopropyl]amino}piperidin-1-yl)azetidine-1-carboxamide

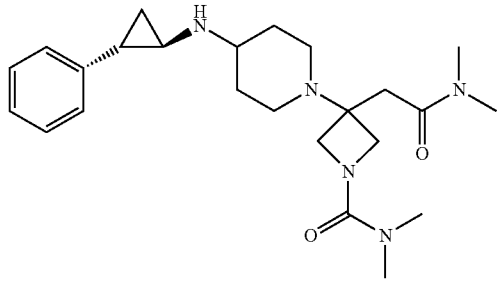

This compound was prepared according to the procedures of Example 70 with N,N-dimethylcarbamoyl chloride replacing ethanesulfonyl chloride in Step 5. The reaction mixture was purified by prep-HPLC (pH=2, acetonitrile/water+TFA) to give the desired product as the TFA salt. LC-MS calculated for $C_{24}H_{38}N_5O_2$ (M+H)$^+$: m/z=428.3; found 428.3.

Example 97

N,N-dimethyl-3-[2-(methylamino)-2-oxoethyl]-3-(4-{[(1R,2S)-2-phenylcyclopropyl]amino}piperidin-1-yl)azetidine-1-carboxamide

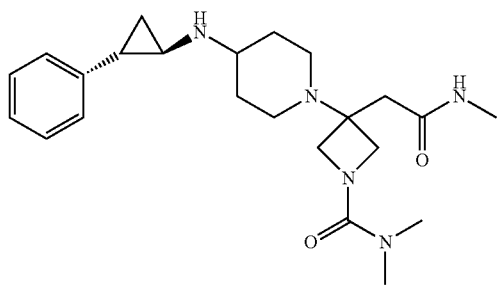

This compound was prepared according to the procedures of Example 70 with N,N-dimethylcarbamoyl chloride replacing ethanesulfonyl chloride in Step 5 and methylamine replacing dimethylamine in Step 7. The reaction mixture was purified by prep-HPLC (pH=2, acetonitrile/water+TFA) to give the desired product as the TFA salt. LC-MS calculated for $C_{23}H_{36}N_5O_2$ $(M+H)^+$: m/z=414.3; found 414.2.

Example 98

[1-(1-methyl-1H-pyrazol-4-yl)-3-(4-{[(1R,2S)-2-phenylcyclopropyl]amino}piperidin-1-yl)azetidin-3-yl]acetonitrile

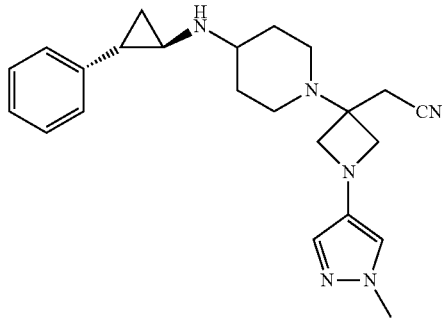

The mixture of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 40 mg, 0.1 mmol), 4-bromo-1-methyl-1H-pyrazole (24 mg, 0.15 mmol), tris(dibenzylideneacetone)dipalladium (0) (4 mg, 0.004 mmol), dicyclohexyl(2',4',6'-triisopropylbiphenyl-2-yl)phosphine (8.2 mg, 0.017 mmol) and cesium carbonate (70. mg, 0.22 mmol) in toluene (2 mL) was purged with nitrogen then stirred at 110° C. for overnight. The reaction mixture was cooled to room temperature then quenched with saturated aqueous $NaHCO_3$, and extracted with ethyl acetate. The combined organic layers were washed with brine, dried over $Na_2SO_4$, filtered and concentrated under reduced pressure. The residue was dissolved in THF (2 mL) then 2N NaOH (2 mL) was added. The reaction mixture was stirred at room temperature for 2 h then purified by prep-HPLC (pH=2, acetonitrile/water+TFA) to give the desired product as the TFA salt. LC-MS calculated for $C_{23}H_{31}N_6$ $(M+H)^+$: m/z=391.3; found 391.2.

Example 99 tetrahydrofuran-3-yl 3-(cyanomethyl)-3-(4-{[(1R,2S)-2-phenylcyclopropyl]amino}piperidin-1-yl)azetidine-1-carboxylate (mixture of diastereomers)

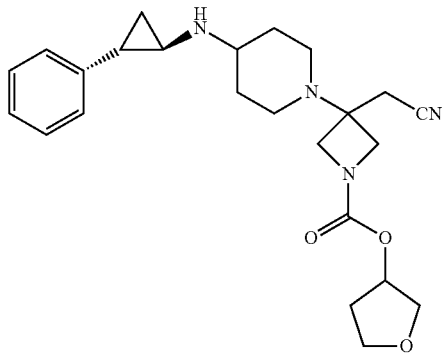

To a mixture of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 20 mg, 0.05 mmol) and triethylamine (20 μL, 0.14 mmol) in acetonitrile (0.8 mL) was added 4-nitrophenyl tetrahydrofuran-3-yl carbonate (prepared as described in WO 2010/108059: 16 mg, 0.063 mmol). The reaction mixture was stirred at room temperature for 1 h then quenched with saturated aqueous $NaHCO_3$, and extracted with ethyl acetate. The combined organic layers were washed with brine, dried over $Na_2SO_4$, filtered and concentrated under reduced pressure. The residue was dissolved in THF (1 mL) then 2N NaOH (1 mL) was added. The reaction mixture was stirred at room temperature for 2 h then purified by prep-HPLC (pH=2, acetonitrile/water+TFA) to give the desired product as the TFA salt. LC-MS calculated for $C_{24}H_{33}N_4O_3$ $(M+H)^+$: m/z=425.3; found 425.3.

Example 100

[1-[(1-methyl-1H-pyrazol-4-yl)sulfonyl]-3-(4-{[(1R,2S)-2-phenylcyclopropyl]amino}piperidin-1-yl)azetidin-3-yl]acetonitrile

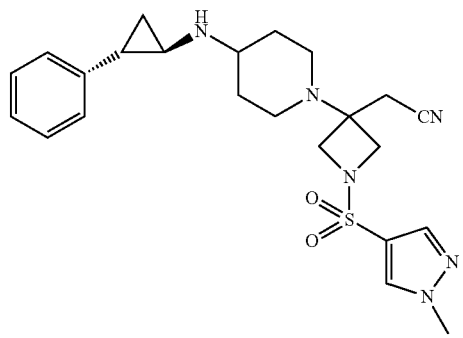

This compound was prepared according to the procedures of Example 58 with 1-methyl-1H-pyrazole-4-sulfonyl chloride replacing methanesulfonyl chloride in Step 5. The reaction mixture was purified by prep-HPLC (pH=2, acetonitrile/water+TFA) to give the desired product as the TFA salt. LC-MS calculated for $C_{23}H_{31}N_6O_2S$ $(M+H)^+$: m/z=455.2; found 455.2.

Example 101

[3-(4-{[(1R,2S)-2-(4-fluorophenyl)cyclopropyl]amino}piperidin-1-yl)-1-(methylsulfonyl)azetidin-3-yl]acetonitrile

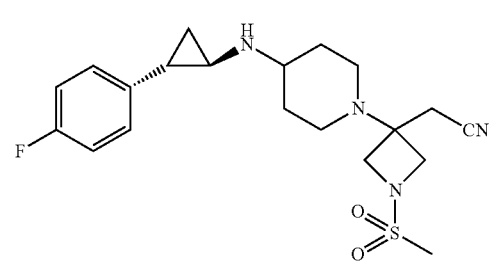

This compound was prepared according to the procedures of Example 58 with (1R,2S)-2-(4-fluorophenyl)cyclopropanamine (Enamine, cat#EN300-189082) replacing (1R,2S)-2-phenylcyclopropanamine in Step 2. The reaction mixture was purified by prep-HPLC (pH=2, acetonitrile/water+TFA) to give the desired product as the TFA salt. LC-MS calculated for $C_{20}H_{28}FN_4O_2S$ $(M+H)^+$: m/z=407.2; found 407.1.

Example 102

3-(cyanomethyl)-3-(4-{[(1R,2S)-2-(4-fluorophenyl)cyclopropyl]amino}piperidin-1-yl)azetidine-1-sulfonamide

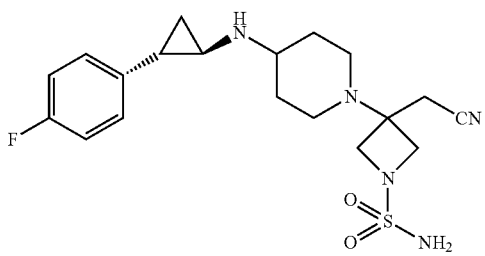

This compound was prepared according to the procedures of Example 65 with (1R,2S)-2-(4-fluorophenyl)cyclopropanamine (Enamine, cat#EN300-189082) replacing (1R,2S)-2-phenylcyclopropanamine. The reaction mixture was purified by prep-HPLC (pH=2, acetonitrile/water+TFA) to give the desired product as the TFA salt. LC-MS calculated for $C_{19}H_{27}FN_5O_2S$ $(M+H)^+$: m/z=408.2; found 408.1.

Example 103

[3-(4-{[(1R,2S)-2-(4-fluorophenyl)cyclopropyl]amino}piperidin-1-yl)-1-(4-hydroxycyclohexyl)azetidin-3-yl]acetonitrile (Isomer 1)

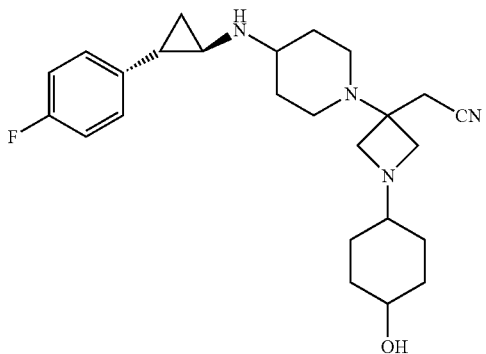

This compound was prepared according to the procedures of Example 72 with (1R,2S)-2-(4-fluorophenyl)cyclopropanamine (Enamine, cat#EN300-189082) replacing (1R,2S)-2-phenylcyclopropanamine. The reaction mixture was purified by prep-HPLC (pH=2, acetonitrile/water+TFA) to separate two isomers as their respective TFA salts. Isomer one was assigned as Example 103. LC-MS calculated for $C_{25}H_{36}FN_4O$ $(M+H)^+$: m/z=427.3; found 427.2.

Example 104

[3-(4-{[(1R,2S)-2-(4-fluorophenyl)cyclopropyl]amino}piperidin-1-yl)-1-(4-hydroxycyclohexyl)azetidin-3-yl]acetonitrile (Isomer 2)

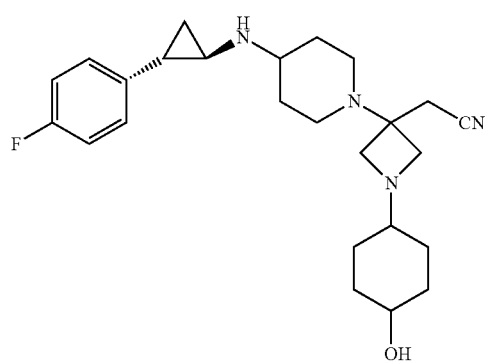

This compound was prepared according to the procedures of Example 72 with (1R,2S)-2-(4-fluorophenyl)cyclopropanamine (Enamine, cat#EN300-189082) replacing (1R,2S)-2-phenylcyclopropanamine. The reaction mixture was purified by prep-HPLC (pH=2, acetonitrile/water+TFA) to separate two isomers as their respective TFA salts. Isomer two was assigned as Example 104. LC-MS calculated for $C_{25}H_{36}FN_4O$ $(M+H)^+$: m/z=427.3; found 427.2.

Example 105

{1-[4-({[(1R,2S)-2-phenylcyclopropyl]amino}methyl)piperidin-1-yl]cyclobutyl}acetic acid

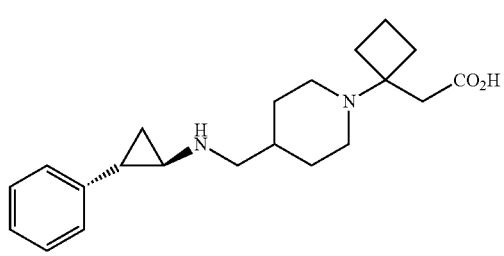

This compound was prepared according to the procedures of Example 55 with 1-boc-4-piperidinecarboxaldehyde (Ark pharm, cat#AK-21827) replacing tert-butyl 4-formyl-4-methylpiperidine-1-carboxylate in Step 1. The reaction mixture was purified by prep-HPLC (pH=2, acetonitrile/water+TFA) to give the desired product as the TFA salt. LC-MS calculated for $C_{21}H_{31}N_2O_2$ $(M+H)^+$: m/z=343.2; found 343.2.

Example 106

[1-(3-hydroxycyclobutyl)-3-(4-{[(1R,2S)-2-phenyl-cyclopropyl]amino}piperidin-1-yl)azetidin-3-yl]acetonitrile

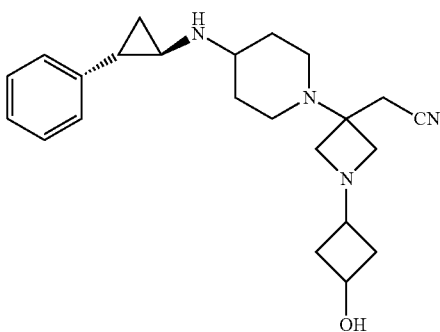

To the solution of N-{1-[3-(cyanomethyl)azetidin-3-yl]piperidin-4-yl}-2,2,2-trifluoro-N-[(1R,2S)-2-phenylcyclopropyl]acetamide (Example 58, Step 4: 20 mg, 0.05 mmol) in methylene chloride (2 mL) was added 3-oxocyclobutyl benzoate (19 mg, 0.098 mmol), followed by acetic acid (8.4 µL, 0.15 mmol). The resulting mixture was stirred at room temperature for 1 h, then sodium triacetoxyborohydride (31 mg, 0.15 mmol) was added. The reaction mixture was stirred at room temperature for 1.5 h then quenched with saturated aqueous NaHCO$_3$, and extracted with ethyl acetate. The combined organic layers were washed with brine, dried over Na$_2$SO$_4$, filtered and concentrated under reduced pressure. The residue was dissolved in acetonitrile (1 mL) then 4N NaOH (1 mL) was added. The reaction mixture was stirred at room temperature for 2 h then purified by prep-HPLC (pH=2, acetonitrile/water+TFA) to give the desired product as the TFA salt. LC-MS calculated for C$_{23}$H$_{33}$N$_4$O (M+H)$^+$: m/z=381.3; found 381.2.

Example 107

2-(3-(4-(((1R,2S)-2-phenylcyclopropyl)amino)piperidin-1-yl)-1-(tetrahydrofuran-2-carbonyl)azetidin-3-yl)acetonitrile

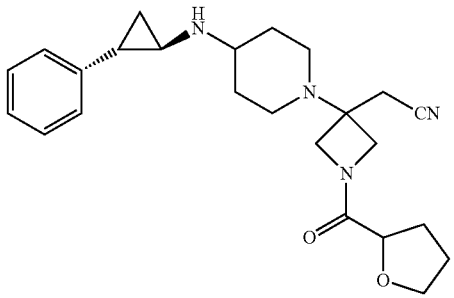

This compound was prepared according to the procedures of Example 80 with tetrahydrofuran-2-carboxylic acid replacing 1-methyl-1H-pyrazole-4-carboxylic acid. The reaction mixture was purified by prep-HPLC (pH=2, acetonitrile/water+TFA) to give the desired product as the TFA salt. LC-MS calculated for C$_{24}$H$_{33}$N$_4$O$_2$ (M+H)$^+$: m/z=409.3; found 409.2.

Example 108

[3-(4-{[(1R,2S)-2-phenylcyclopropyl]amino}piperidin-1-yl)-1-(tetrahydrofuran-3-ylcarbonyl)azetidin-3-yl]acetonitrile

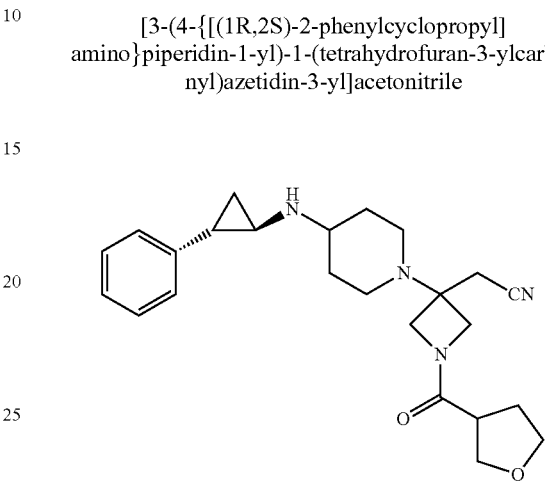

This compound was prepared according to the procedures of Example 80 with tetrahydrofuran-3-carboxylic acid replacing 1-methyl-1H-pyrazole-4-carboxylic acid. The reaction mixture was purified by prep-HPLC (pH=2, acetonitrile/water+TFA) to give the desired product as the TFA salt. LC-MS calculated for C$_{24}$H$_{33}$N$_4$O$_2$ (M+H)$^+$: m/z=409.3; found 409.3.

Example 109

[3-(4-{[(1R,2S)-2-phenylcyclopropyl]amino}piperidin-1-yl)-1-(1,3-thiazol-5-ylcarbonyl)azetidin-3-yl]acetonitrile

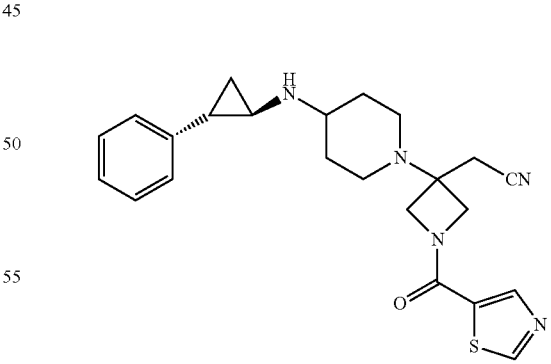

This compound was prepared according to the procedures of Example 80 with Thiazole-5-carboxylic acid (AstaTech, cat#69866) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for C$_{23}$H$_{28}$N$_5$OS (M+H)$^+$: m/z=422.2; found 422.2.

Example 110

[1-(isothiazol-5-ylcarbonyl)-3-(4-{[(1R,2S)-2-phenylcyclopropyl]amino}piperidin-1-yl)azetidin-3-yl]acetonitrile

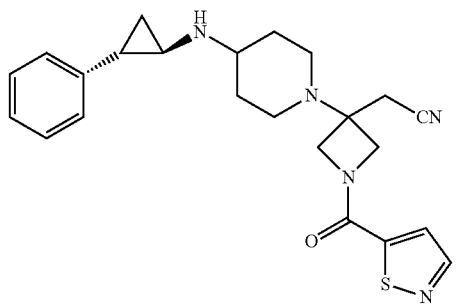

This compound was prepared according to the procedures of Example 80 with isothiazole-5-carboxylic acid (AstaTech, cat#62856) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{23}H_{28}N_5OS$ (M+H)$^+$: m/z=422.2; found 422.2.

Example 111

[3-(4-{[(1R,2S)-2-phenylcyclopropyl]amino}piperidin-1-yl)-1-(pyrazin-2-ylcarbonyl)azetidin-3-yl]acetonitrile

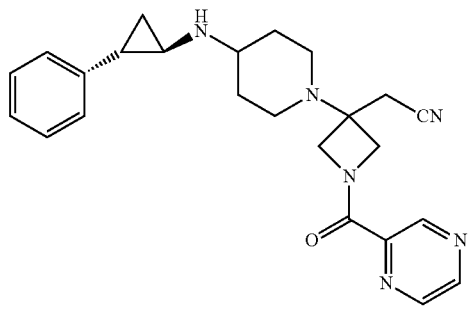

This compound was prepared according to the procedures of Example 80 with 2-pyrazinecarboxylic acid (Aldrich, cat#P56100) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{24}H_{29}N_6O$ (M+H)$^+$: m/z=417.2; found 417.2.

Example 112

[3-(4-{[(1R,2S)-2-phenylcyclopropyl]amino}piperidin-1-yl)-1-(1H-pyrazol-4-ylcarbonyl)azetidin-3-yl]acetonitrile

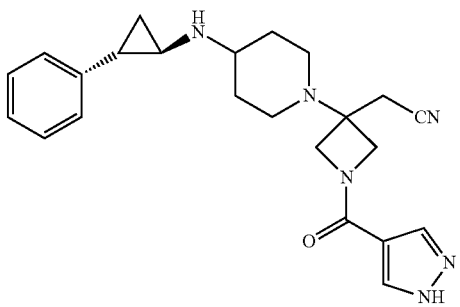

This compound was prepared according to the procedures of Example 80 with 1H-pyrazole-4-carboxylic acid (Ark Pharm, cat#AK-25877) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{23}H_{29}N_6O$ (M+H)$^+$: m/z=405.2; found 405.3.

Example 113

[3-(4-{[(1R,2S)-2-phenylcyclopropyl]amino}piperidin-1-yl)-1-(1H-pyrazol-5-ylcarbonyl)azetidin-3-yl]acetonitrile This compound was prepared according to the procedures of Example 80 with 1H-pyrazole-5-carboxylic acid (Oakwood, cat#014533) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{23}H_{29}N_6O$ (M+H)$^+$: m/z=405.2; found 405.2.

Example 114

{3-(4-{[(1R,2S)-2-phenylcyclopropyl]amino}piperidin-1-yl)-1-[(3R)-tetrahydrofuran-3-ylcarbonyl]azetidin-3-yl}acetonitrile

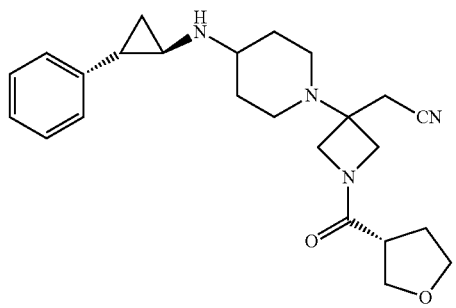

This compound was prepared according to the procedures of Example 80 with (R)-tetrahydrofuran-3-carboxylic acid (Aldrich, cat#712280) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{24}H_{33}N_4O_2$ (M+H)$^+$: m/z=409.3; found 409.4.

Example 115

{3-(4-{[(1R,2S)-2-phenylcyclopropyl]amino}piperidin-1-yl)-1-[(3S)-tetrahydrofuran-3-ylcarbonyl]azetidin-3-yl}acetonitrile

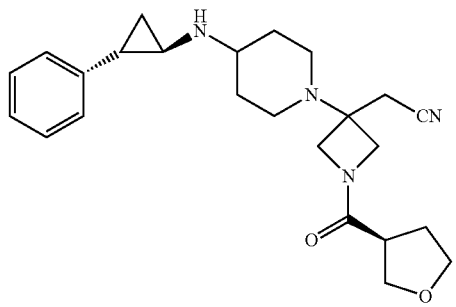

This compound was prepared according to the procedures of Example 80 with (S)-tetrahydrofuran-3-carboxylic acid (Astech, cat#66517) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{24}H_{33}N_4O_2$ (M+H)$^+$: m/z=409.3; found 409.3.

Example 116

{3-(4-{[(1R,2S)-2-phenylcyclopropyl]amino}piperidin-1-yl)-1-[(2S)-tetrahydrofuran-2-ylcarbonyl]azetidin-3-yl}acetonitrile

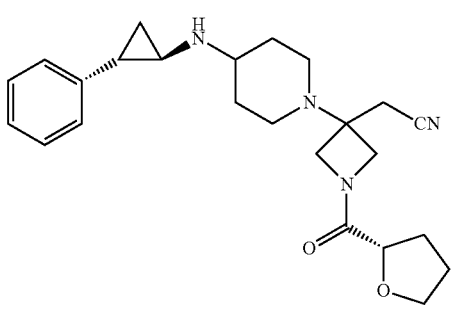

This compound was prepared according to the procedures of Example 80 with (S)-2-tetrahydrofuroic acid (Aldrich, cat#527890) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{24}H_{33}N_4O_2$ (M+H)$^+$: m/z=409.3; found 409.3.

Example 117

{3-(4-{[(1R,2S)-2-phenylcyclopropyl]amino}piperidin-1-yl)-1-[(2R)-tetrahydrofuran-2-ylcarbonyl]azetidin-3-yl}acetonitrile

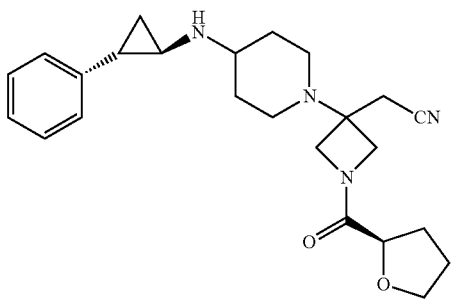

This compound was prepared according to the procedures of Example 80 with (R)-2-tetrahydrofuroic acid (Aldrich, cat#479292) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{24}H_{33}N_4O_2$ (M+H)$^+$: m/z=409.3; found 409.2.

Example 118

[3-(4-{[(1R,2S)-2-phenylcyclopropyl]amino}piperidin-1-yl)-1-(pyridin-2-ylacetyl)azetidin-3-yl]acetonitrile

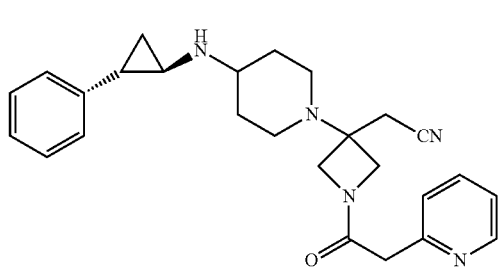

This compound was prepared according to the procedures of Example 80 with 2-pyridylacetic acid hydrochloride (Aldrich, cat#P65606) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{26}H_{32}N_5O$ (M+H)$^+$: m/z=430.3; found 430.3.

Example 119

[3-(4-{[(1R,2S)-2-phenylcyclopropyl]amino}piperidin-1-yl)-1-(1,3-thiazol-4-ylcarbonyl)azetidin-3-yl]acetonitrile

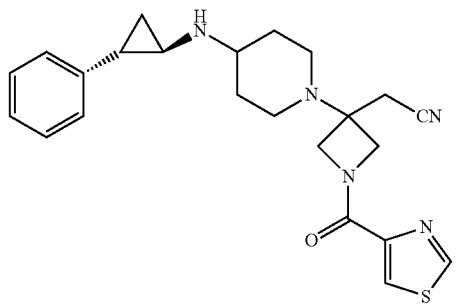

This compound was prepared according to the procedures of Example 80 with thiazole-4-carboxylic acid (Aldrich, cat#633658) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{23}H_{28}N_5OS$ (M+H)$^+$: m/z=422.2; found 422.2.

Example 120

[3-(4-{[(1R,2S)-2-phenylcyclopropyl]amino}piperidin-1-yl)-1-(1,3-thiazol-2-ylcarbonyl)azetidin-3-yl]acetonitrile

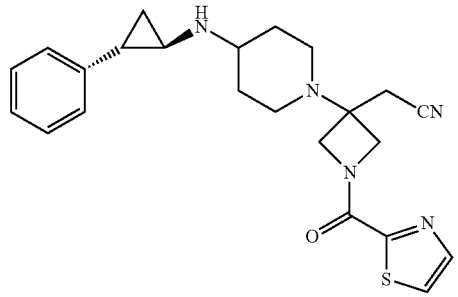

This compound was prepared according to the procedures of Example 80 with thiazole-2-carboxylic acid (Ark Pharm, cat#AK-21895) replacing 1-methyl-1H-pyrazole-4-carboxylic acid. The reaction mixture was purified by prep-HPLC (pH=2, acetonitrile/water+TFA) to give the desired product as the TFA salt. LC-MS calculated for $C_{23}H_{28}N_5OS$ (M+H)$^+$: m/z=422.2; found 422.2.

Example 121

N,N-dimethyl-2-[3-(4-{[(1R,2S)-2-phenylcyclopropyl]amino}piperidin-1-yl)-1-(tetrahydro-2H-pyran-4-yl)azetidin-3-yl]acetamide

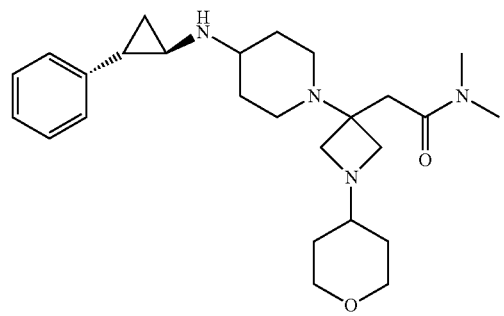

Step 1: [3-(4-{[(1R,2S)-2-phenylcyclopropyl]amino}piperidin-1-yl)-1-(tetrahydro-2H-pyran-4-yl)azetidin-3-yl]acetic acid

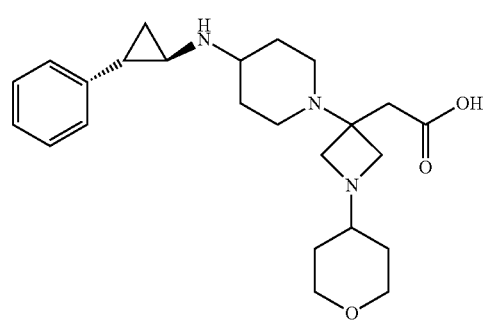

To a solution of methyl(3-{4-[[(1R,2S)-2-phenylcyclopropyl](trifluoroacetyl)amino]piperidin-1-yl}azetidin-3-yl)acetate (Example 70, Step 4: 150 mg, 0.29 mmol) in methylene chloride (10 mL) was added tetrahydro-4H-pyran-4-one (Aldrich, cat#198242: 100 µL, 1 mmol), followed by acetic acid (100 µL, 2 mmol). The resulting mixture was stirred at room temperature for 1 h, then sodium triacetoxyborohydride (190 mg, 0.88 mmol) was added. The reaction mixture was stirred at room temperature for 2 h then diluted with DCM and washed with saturated NaHCO$_3$, water and brine. The organic layer was dried over Na$_2$SO$_4$, filtered and concentrated. The residue was dissolved in tetrahydrofuran (2 mL) then 2.0 M sodium hydroxide in water (2 mL, 4 mmol) was added, followed by methanol (5 mL). The resulting mixture was stirred at room temperature for overnight then diluted with MeOH, filtered and purified by prep-HPLC (pH=2, acetonitrile/water+TFA) to give the desired product as the TFA salt. LC-MS calculated for C$_{24}$H$_{36}$N$_3$O$_3$ (M+H)$^+$: m/z=414.3; found 414.3.

Step 2: N,N-dimethyl-2-[3-(4-{[(1R,2S)-2-phenylcyclopropyl]amino}piperidin-1-yl)-1-(tetrahydro-2H-pyran-4-yl)azetidin-3-yl]acetamide

[3-(4-{[(1R,2S)-2-Phenylcyclopropyl]amino}piperidin-1-yl)-1-(tetrahydro-2H-pyran-4-yl)azetidin-3-yl]acetic acid (TFA salt, 20 mg) was dissolved in tetrahydrofuran (1 mL) then (benzotriazol-1-yloxy)tripyrrolidinophosphonium hexafluorophosphate (19 mg, 0.037 mmol), N,N-diisopropylethylamine (150 µL, 0.86 mmol) and 2.0 M dimethylamine in THF (80 µL, 0.2 mmol) were added. The mixture was stirred at room temperature for 2 h then diluted with MeOH and purified by prep-HPLC (pH=2, acetonitrile/water+TFA) to give the desired product as the TFA salt. LC-MS calculated for C$_{26}$H$_{41}$N$_4$O$_2$ (M+H)$^+$: m/z=441.3; found 441.3.

Example 122

N-methyl-2-[3-(4-{[(1R,2S)-2-phenylcyclopropyl]amino}piperidin-1-yl)-1-(tetrahydro-2H-pyran-4-yl)azetidin-3-yl]acetamide

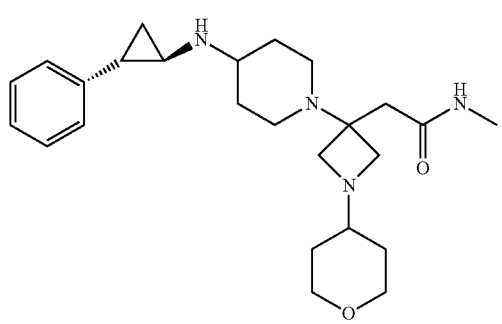

This compound was prepared according to the procedures of Example 121 with methylamine replacing dimethylamine in Step 2. The reaction mixture was purified by prep-HPLC (pH=2, acetonitrile/water+TFA) to give the desired product as the TFA salt. LC-MS calculated for C$_{25}$H$_{39}$N$_4$O$_2$ (M+H)$^+$: m/z=427.3; found 427.3.

Example 123

2-[1-(cyclopropylmethyl)-3-(4-{[(1R,2S)-2-phenylcyclopropyl]amino}piperidin-1-yl)azetidin-3-yl]-N,N-dimethylacetamide

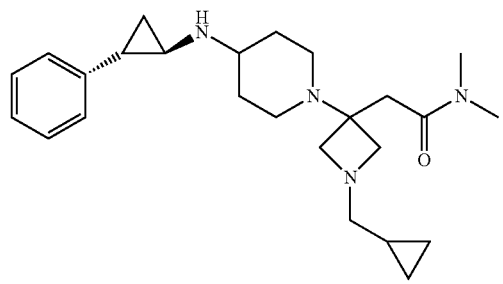

This compound was prepared according to the procedures of Example 121 with cyclopropanecarboxaldehyde replacing tetrahydro-4H-pyran-4-one in Step 1. The reaction mixture was purified by prep-HPLC (pH=2, acetonitrile/water+TFA) to give the desired product as the TFA salt. LC-MS calculated for C$_{25}$H$_{39}$N$_4$O (M+H)$^+$: m/z=411.3; found 411.4.

Example 124

2-[1-(cyclopropylmethyl)-3-(4-{[(1R,2S)-2-phenylcyclopropyl]amino}piperidin-1-yl)azetidin-3-yl]-N-methylacetamide

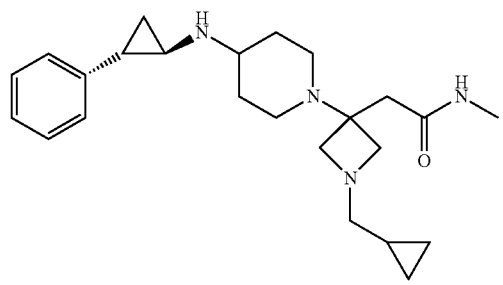

This compound was prepared according to the procedures of Example 123 with methylamine replacing dimethylamine. The reaction mixture was purified by prep-HPLC (pH=2, acetonitrile/water+TFA) to give the desired product as the TFA salt. LC-MS calculated for C$_{24}$H$_{37}$N$_4$O (M+H)$^+$: m/z=397.3; found 397.3.

Example 125

[3-(4-{[(1R,2S)-2-phenylcyclopropyl]amino}piperidin-1-yl)-1-(pyrimidin-2-ylmethyl)azetidin-3-yl]acetic acid

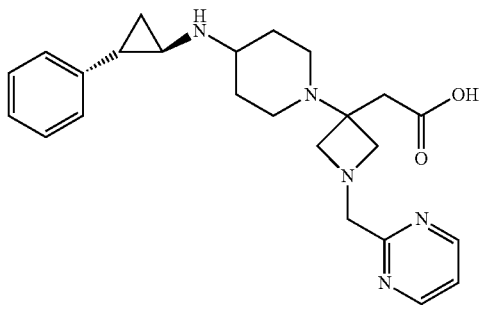

This compound was prepared according to the procedures of Example 121, Step 1 with pyrimidine-2-carbaldehyde (Synnovator, cat#PB00379) replacing tetrahydro-4H-pyran-4-one. The reaction mixture was purified by prep-HPLC (pH=2, acetonitrile/water+TFA) to give the desired product as the TFA salt. LC-MS calculated for $C_{24}H_{32}N_5O_2$ $(M+H)^+$: m/z=422.3; found 422.2.

Example 126

[3-(4-{[(1R,2S)-2-phenylcyclopropyl]amino}piperidin-1-yl)-1-(pyrimidin-5-ylmethyl)azetidin-3-yl]acetic acid

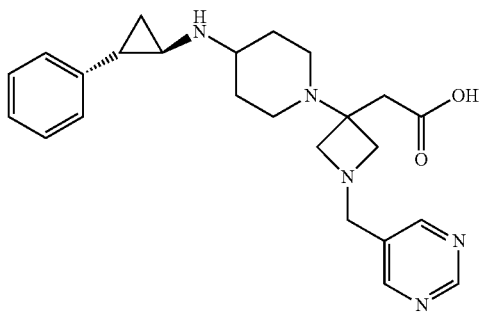

This compound was prepared according to the procedures of Example 121, Step 1 with pyrimidine-5-carbaldehyde (Matrix Scientific, cat#007321) replacing tetrahydro-4H-pyran-4-one. The reaction mixture was purified by prep-HPLC (pH=2, acetonitrile/water+TFA) to give the desired product as the TFA salt. LC-MS calculated for $C_{24}H_{32}N_5O_2$ $(M+H)^+$: m/z=422.3; found 422.2.

Example 127

[3-(4-{[(1R,2S)-2-phenylcyclopropyl]amino}piperidin-1-yl)-1-(1,3-thiazol-4-ylmethyl)azetidin-3-yl]acetic acid

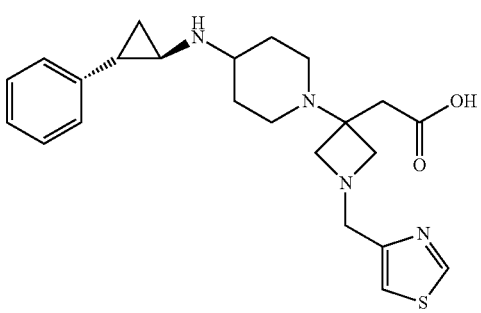

This compound was prepared according to the procedures of Example 121, Step 1 with thiazole-4-carboxaldehyde (Aldrich, cat#681105) replacing tetrahydro-4H-pyran-4-one. The reaction mixture was purified by prep-HPLC (pH=2, acetonitrile/water+TFA) to give the desired product as the TFA salt. LC-MS calculated for $C_{23}H_{31}N_4O_2S$ $(M+H)^+$: m/z=427.2; found 427.2.

Example 128

[3-(4-{[(1R,2S)-2-phenylcyclopropyl]amino}piperidin-1-yl)-1-(1,3-thiazol-5-ylmethyl)azetidin-3-yl]acetic acid

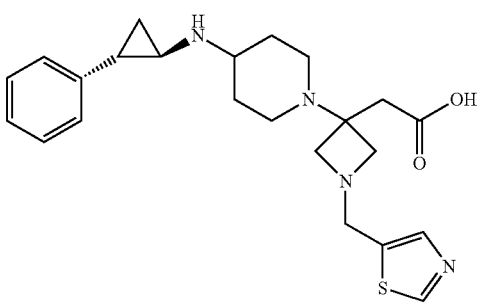

This compound was prepared according to the procedures of Example 121, Step 1 with thiazole-5-carboxaldehyde (Aldrich, cat#658103) replacing tetrahydro-4H-pyran-4-one. The reaction mixture was purified by prep-HPLC (pH=2, acetonitrile/water+TFA) to give the desired product as the TFA salt. LC-MS calculated for $C_{23}H_{31}N_4O_2S$ $(M+H)^+$: m/z=427.2; found 427.2.

Example 129

[3-(4-{[(1R,2S)-2-phenylcyclopropyl]amino}piperidin-1-yl)-1-(1,3-thiazol-2-ylmethyl)azetidin-3-yl]acetic acid

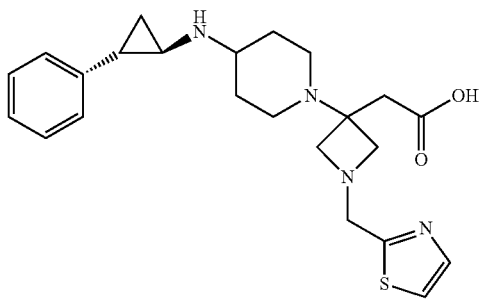

This compound was prepared according to the procedures of Example 121, Step 1 with thiazole-2-carboxaldehyde (Aldrich, cat#422460) replacing tetrahydro-4H-pyran-4-one. The reaction mixture was purified by prep-HPLC (pH=2, acetonitrile/water+TFA) to give the desired product as the TFA salt. LC-MS calculated for $C_{23}H_{31}N_4O_2S$ (M+H)$^+$: m/z=427.2; found 427.2.

Example 130

[3-(4-{[(1R,2S)-2-phenylcyclopropyl]amino}piperidin-1-yl)-1-(3,3,3-trifluoropropyl)azetidin-3-yl]acetic acid

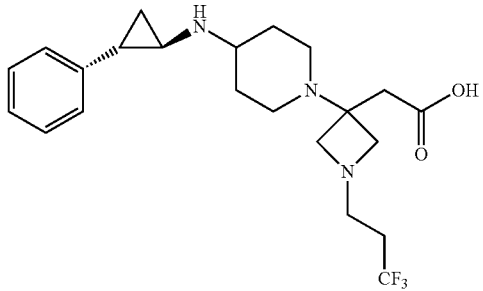

This compound was prepared according to the procedures of Example 121, Step 1 with 3,3,3-trifluoropropanal (Alfa Aesar, cat#H50472) replacing tetrahydro-4H-pyran-4-one. The reaction mixture was purified by prep-HPLC (pH=2, acetonitrile/water+TFA) to give the desired product as the TFA salt. LC-MS calculated for $C_{22}H_{31}F_3N_3O_2$ (M+H)$^+$: m/z=426.2; found 426.2.

Example A

LSD1 Histone Demethylase Biochemical Assay

LANCE LSD1/KDM1A demethylase assay—10 μL of 1 nM LSD-1 enzyme (ENZO BML-SE544-0050) in the assay buffer (50 mM Tris, pH 7.5, 0.01% Tween-20, 25 mM NaCl, 5 mM DTT) were preincubated for 1 hour at 25° C. with 0.8 μL compound/DMSO dotted in black 384 well polystyrene plates. Reactions were started by addition of 10 μL of assay buffer containing 0.4 μM Biotin-labeled Histone H3 peptide substrate: ART-K(Me1)-QTARKSTGGKAPRKQLA-GGK (Biotin) SEQ ID NO:1 (AnaSpec 64355) and incubated for 1 hour at 25° C. Reactions were stopped by addition of 10 μL 1× LANCE Detection Buffer (PerkinElmer CR97-100) supplemented with 1.5 nM Eu-anti-unmodified H3K4 Antibody (PerkinElmer TRF0404), and 225 nM LANCE Ultra Streptavidin (PerkinElmer TRF102) along with 0.9 mM Tranylcypromine-HCl (Millipore 616431). After stopping the reactions plates were incubated for 30 minutes and read on a PHERAstar FS plate reader (BMG Labtech). Compounds having an $IC_{50}$ of 1 μM or less were considered active. $IC_{50}$ data for the example compounds is provided in Table 1 (+ refers to $IC_{50} \leq 100$ nM; ++ refers to $IC_{50} > 100$ nM and $\leq 500$ nM).

TABLE 1

| Example No. | $IC_{50}$ (nM) |
| --- | --- |
| 1 | + |
| 2 | + |
| 3 | + |
| 4 | + |
| 5 | + |
| 6 | + |
| 7 | + |
| 8 | + |
| 9 | + |
| 10 | + |
| 11 | ++ |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | ++ |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |

TABLE 1-continued

| Example No. | IC$_{50}$ (nM) |
|---|---|
| 59 | + |
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |

TABLE 1-continued

| Example No. | IC$_{50}$ (nM) |
|---|---|
| 96 | + |
| 97 | + |
| 98 | + |
| 99 | + |
| 100 | + |
| 101 | + |
| 102 | + |
| 103 | + |
| 104 | + |
| 105 | + |
| 106 | + |

TABLE 1-continued

| Example No. | IC$_{50}$ (nM) |
|---|---|
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

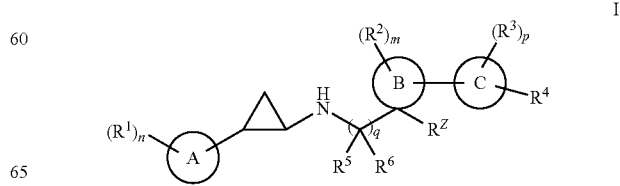

or a pharmaceutically acceptable salt thereof, wherein:
  ring A is a phenyl ring;
  ring B is a piperidinyl ring;
  ring C is an azetidinyl ring;
  wherein ring C is substituted on any ring-forming atom of ring B except the ring-forming atom of ring B to which $R^Z$ is bonded;
  each $R^1$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, OR$^a$, SR$^a$, C(O)R$^b$, C(O)NR$^cR^d$, C(O)OR$^a$, OC(O)R$^b$, OC(O)NR$^cR^d$, NR$^cR^d$, NR$^cC(O)R^b$, NR$^cC(O)OR^a$, NR$^cC(O)NR^cR^d$, C(=NR$^e$)R$^b$, C(=NR$^e$)NR$^cR^d$, NR$^cC(=NR^e)NR^cR^d$, NR$^cS(O)R^b$, NR$^cS(O)_2R^b$, NR$^cS(O)_2NR^cR^d$, S(O)R$^b$, S(O)NR$^cR^d$, S(O)$_2R^b$, and S(O)$_2$NR$^cR^d$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, OR$^a$, SR$^a$, C(O)R$^b$, C(O)NR$^cR^d$, C(O)OR$^a$, OC(O)R$^b$, OC(O)NR$^cR^d$, C(=NR$^e$)NR$^cR^d$, NR$^cC(=NR^e)$ NR$^cR^d$, NR$^cR^d$, NR$^cC(O)R^b$, NR$^cC(O)OR^a$, NR$^cC(O)$ NR$^cR^d$, NR$^cS(O)R^b$, NR$^cS(O)_2R^b$, NR$^cS(O)_2NR^cR^d$, S(O)R$^b$, S(O)NR$^cR^d$, S(O)$_2R^b$, and S(O)$_2NR^cR^d$;
  each $R^2$ is independently selected from halo, $C_{1-6}$ alkyl, CN, OR$^{a1}$, C(O)R$^{b1}$, C(O)NR$^{c1}R^{d1}$, C(O)OR$^{a1}$, NR$^{c1}R^{d1}$, S(O)R$^{b1}$, S(O)NR$^{c1}R^{d1}$, S(O)$_2R^{b1}$, and S(O)$_2$NR$^{c1}R^{d1}$, wherein said $C_{1-6}$ alkyl is optionally substituted with 1, 2, or 3 substituents independently selected from halo, CN, OR$^{a1}$, SR$^{a1}$, C(O)R$^{b1}$, C(O)NR$^{c1}R^{d1}$, C(O)OR$^{a1}$, OC(O)R$^{b1}$, OC(O)NR$^{c1}R^{d1}$, C(=NR$^{e1}$)NR$^{c1}R^{d1}$, NR$^{c1}C(=NR^{e1})NR^{c1}R^{d1}$, NR$^{c1}R^{d1}$, NR$^{c1}C(O)R^{b1}$, NR$^{c1}C(O)OR^{a1}$, NR$^{c1}C(O)$ NR$^{c1}R^{d1}$, NR$^{c1}S(O)R^{b1}$, NR$^{c1}S(O)_2R^{b1}$, NR$^{c1}$ S(O)$_2NR^{c1}R^{d1}$, S(O)R$^{b1}$, S(O)NR$^{c1}R^{d1}$, S(O)$_2R^{b1}$, and S(O)$_2NR^{c1}R^{d1}$;
  wherein each $R^2$ is substituted on any ring-forming atom of ring B except the ring-forming atom of ring B to which $R^Z$ is bonded;
  each $R^3$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, OR$^{a2}$, SR$^{a2}$, C(O)R$^{b2}$, C(O)NR$^{c2}R^{d2}$, C(O)OR$^{a2}$, OC(O)R$^{b2}$, OC(O)NR$^{c2}R^{d2}$, NR$^{c2}R^{d2}$, NR$^{c2}R^{d2}$, NR$^{c2}C(O)R^{b2}$, NR$^{c2}C(O)OR^{a2}$, NR$^{c2}C(O)NR^{c2}R^{d2}$, C(=NR$^{e2}$)R$^{b2}$, C(=NR$^{e2}$) NR$^{c2}R^{d2}$, NR$^{c2}C(=NR^{e2})NR^{c2}R^{d2}$, NR$^{c2}S(O)R^{b2}$, NR$^{c2}S(O)_2R^{b2}$, NR$^{c2}S(O)_2NR^{c2}R^{d2}$, S(O)R$^{b2}$, S(O) NR$^{c2}R^{d2}$, S(O)$_2R^{b2}$, and S(O)$_2$NR$^{c2}R^{d2}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, OR$^{a2}$, SR$^{a2}$, C(O)R$^{b2}$, C(O)NR$^{c2}R^{d2}$, C(O)OR$^{a2}$, OC(O)R$^{b2}$, OC(O)NR$^{c2}R^{d2}$, C(=NR$^{e2}$)NR$^{c2}R^{d2}$, NR$^{c2}C(=NR^{e2})$ NR$^{c2}R^{d2}$, NR$^{c2}R^{d2}$, NR$^{c2}C(O)R^{b2}$, NR$^{c2}C(O)OR^{a2}$, NR$^{c2}C(O)NR^{c2}R^{d2}$, NR$^{c2}S(O)R^{b2}$, NR$^{c2}S(O)_2R^{b2}$, NR$^{c2}S(O)_2NR^{c2}R^{d2}$, S(O)R$^{b2}$, S(O)NR$^{c2}R^{d2}$, S(O)$_2R^{b2}$, and S(O)$_2$NR$^{c2}R^{d2}$;
  $R^4$ is halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, OR$^{a3}$, SR$^{a3}$, C(O)R$^{b3}$, C(O)NR$^{c3}R^{d3}$, C(O)OR$^{a3}$, OC(O)R$^{b3}$, OC(O)NR$^{c3}R^{d3}$, NR$^{c3}R^{d3}$, NR$^{c3}C(O)R^{b3}$, NR$^{c3}C(O) OR^{a3}$, NR$^{c3}C(O)NR^{c3}R^{d3}$, C(=NR$^{e3}$)R$^{b3}$, C(=NR$^{e3}$) NR$^{c3}R^{d3}$, NR$^{c3}C(=NR^{e3})NR^{c3}R^{d3}$, NR$^{c3}S(O)R^{b3}$, NR$^{c3}S(O)_2R^{b3}$, NR$^{c3}S(O)_2NR^{c3}R^{d3}$, S(O)R$^{b3}$, S(O) NR$^{c3}R^{d3}$, S(O)$_2R^{b3}$, or S(O)$_2$NR$^{c3}R^{d3}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, OR$^{a3}$, SR$^{a3}$, C(O)R$^{b3}$, C(O)NR$^{c3}R^{d3}$, C(O)OR$^{a3}$, OC(O)R$^{b3}$, OC(O)NR$^{c3}R^{d3}$, C(=NR$^{e3}$)NR$^{c3}R^{d3}$, NR$^{c3}C(=NR^{e3})$ NR$^{c3}R^{d3}$, NR$^{c3}R^{d3}$, NR$^{c3}C(O)R^{b3}$, NR$^{c3}C(O)OR^{a3}$, NR$^{c3}C(O)NR^{c3}R^{d3}$, NR$^{c3}S(O)R^{b3}$, NR$^{c3}S(O)_2R^{b3}$, NR$^{c3}S(O)_2NR^{c3}R^{d3}$, S(O)R$^{b3}$, S(O)NR$^{c3}R^{d3}$, S(O)$_2R^{b3}$, and S(O)$_2$NR$^{c3}R^{d3}$;
  $R^5$ and $R^6$ are each independently selected from H, halo, CN, $C_{1-4}$ alkyl, $C_{1-4}$ cyanoalkyl, $C_{1-4}$ haloalkyl, and —($C_{1-4}$ alkyl)-OR$^{a5}$;
  $R^Z$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NO$_2$, OR$^{a4}$, SR$^{a4}$, C(O)R$^{b4}$, C(O)NR$^{c4}R^{d4}$, C(O)OR$^{a4}$, OC(O)R$^{b4}$, OC(O)NR$^{c4}R^{d4}$, NR$^{c4}R^{d4}$, NR$^{c4}C(O)R^{b4}$, NR$^{c4}C(O) OR^{a4}$, NR$^{c4}C(O)NR^{c4}R^{d4}$, C(=NR$^{e4}$)R$^{b4}$, C(=NR$^{e4}$) NR$^{c4}R^{d4}$, NR$^{c4}C(=NR^{e4})NR^{c4}R^{d4}$, NR$^{c4}S(O)R^{b4}$, NR$^{c4}S(O)_2R^{b4}$, NR$^{c4}S(O)_2NR^{c4}R^{d4}$, S(O)R$^{b4}$, S(O) NR$^{c4}R^{d4}$, S(O)$_2R^{b4}$, and S(O)$_2$NR$^{c4}R^{d4}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- are each optionally substituted with 1, 2, 3, or 4 substituents independently selected from halo, $C_{1-4}$ alkyl, $C_{1-4}$ haloalkyl, $C_{1-4}$ cyanoalkyl, CN, NO$_2$, OR$^{a4}$, SR$^{a4}$, C(O)R$^{b4}$, C(O)NR$^{c4}R^{d4}$, C(O)OR$^{a4}$, OC(O)R$^{b4}$, OC(O)NR$^{c4}R^{d4}$, C(=NR$^{e4}$)NR$^{c4}R^{d4}$, NR$^{c4}C(=NR^{e4})$ NR$^{c4}R^{d4}$, NR$^{c4}R^{d4}$, NR$^{c4}C(O)R^{b4}$, NR$^{c4}C(O)OR^{a4}$, NR$^{c4}C(O)NR^{c4}R^{d4}$, NR$^{c4}S(O)R^{b4}$, NR$^{c4}S(O)_2R^{b4}$, NR$^{c4}S(O)_2NR^{c4}R^{d4}$, S(O)R$^{b4}$, S(O)NR$^{c4}R^{d4}$, S(O)$_2R^{b4}$, and S(O)$_2$NR$^{c4}R^{d4}$;
  each $R^a$, $R^b$, $R^c$, $R^d$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- is optionally substituted with 1, 2, 3, 4, or 5 substituents independently selected from $C_{1-4}$ alkyl, $C_{1-4}$ haloalkyl, $C_{1-4}$ cycanoalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$$C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$ cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, $C_{1-4}$ alkyl, $C_{1-4}$ haloalkyl, $C_{1-4}$-cyanoalkyl, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a1}$, $R^{b1}$, $R^{c1}$, $R^{d1}$ is independently selected from H and $C_{1-6}$ alkyl optionally substituted with 1, 2, 3, 4, or 5 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^e$, $R^{e1}$, $R^{e2}$, $R^{e3}$, $R^{e4}$, and $R^{e5}$ is independently selected from H, $C_{1-4}$ alkyl, and CN;

m is 0, 1, or 2;

n is 0, 1, 2, or 3;

p is 0, 1, 2, 3; and q is 0, 1, or 2.

2. The compound of claim 1 having Formula IIIb:

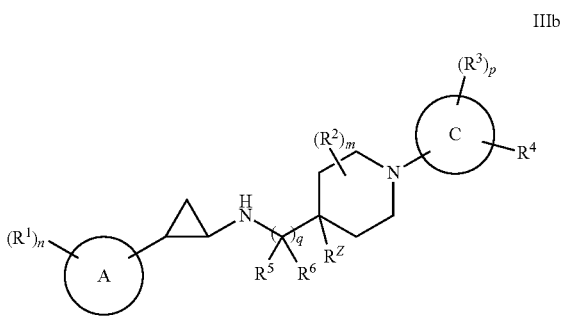

or a pharmaceutically acceptable salt thereof, wherein each $R^2$ is substituted on any ring-forming carbon atom of the piperidine ring depicted in Formula IIIb except the ring-forming carbon atom to which $R^Z$ is bonded.

3. The compound of claim 2, or a pharmaceutically acceptable salt thereof, having Formula IVb:

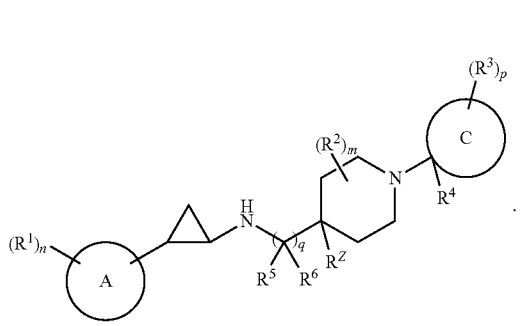

4. The compound of claim 1 having Formula Vb:

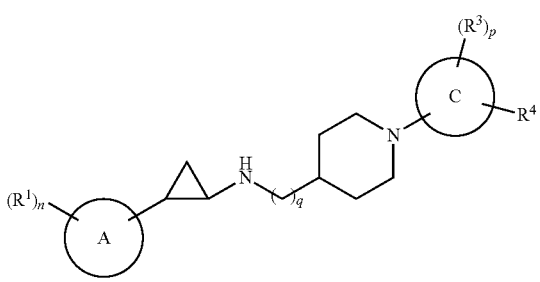

or a pharmaceutically acceptable salt thereof.

5. The compound of claim 1, or a pharmaceutically acceptable salt thereof, wherein q is 0.

6. The compound of claim 1, or a pharmaceutically acceptable salt thereof, wherein q is 1.

7. The compound of claim 1, or a pharmaceutically acceptable salt thereof, wherein n is 0.

8. The compound of claim 1, or a pharmaceutically acceptable salt thereof, wherein n is 1.

9. The compound of claim 1, or a pharmaceutically acceptable salt thereof, wherein $R^1$ is halo.

10. The compound of claim 1, or a pharmaceutically acceptable salt thereof, wherein $R^1$ is F.

11. The compound of claim 1, or a pharmaceutically acceptable salt thereof, wherein both $R^5$ and $R^6$ are H.

12. The compound of claim 1, or a pharmaceutically acceptable salt thereof, wherein $R^4$ is $C_{1-6}$ alkyl, $C_{6-10}$ aryl, 5-10 membered heteroaryl, $C(O)R^{b3}$, $C(O)NR^{c3}R^{d3}$, $C(O)OR^{a3}$, or $S(O)_2R^{b3}$, wherein said $C_{1-6}$ alkyl, $C_{6-10}$ aryl, and 5-10 membered heteroaryl are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

13. The compound of claim 1, or a pharmaceutically acceptable salt thereof, wherein $R^4$ is $C_{1-4}$ alkyl optionally substituted by CN, $C(O)NR^{c3}R^{d3}$, $OR^{a3}$, or $C(O)OR^{a3}$.

14. The compound of claim 1, or a pharmaceutically acceptable salt thereof, wherein $R^4$ is $C_{1-4}$ alkyl optionally substituted by CN, $C(O)NR^{c3}R^{d3}$, or $C(O)OR^{a3}$.

15. The compound of claim 1, or a pharmaceutically acceptable salt thereof, wherein $R^4$ is —$CH_2$—CN, —$CH_2$—C(=O)OH, —$CH_2$—C(=O)NH(CH_3), —$CH_2$—C(=O)N(CH_3)_2, or —$CH_2CH_2OH$.

16. The compound of claim 1, or a pharmaceutically acceptable salt thereof, wherein each $R^3$ is independently selected from $C_{1-6}$ alkyl, $C_{6-10}$ aryl, 5-10 membered heteroaryl, $C_{3-10}$ cycloalkyl, 4-10 membered heterocycloalkyl, $C(O)R^{b2}$, $C(O)NR^{c2}R^{d2}$, $C(O)OR^{a2}$, $S(O)_2R^{b2}$, and $S(O)_2NR^{c2}R^{d2}$, wherein said $C_{1-6}$ alkyl, $C_{6-10}$ aryl, 5-10 membered heteroaryl, $C_{3-10}$ cycloalkyl, and 4-10 membered heterocycloalkyl are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

17. The compound of claim 1, or a pharmaceutically acceptable salt thereof, wherein each $R^3$ is independently selected from $C_{1-6}$ alkyl, $C_{6-10}$ aryl, 5-10 membered heteroaryl, $C(O)R^{b2}$, $C(O)NR^{c2}R^{d2}$, $C(O)OR^{a2}$, $S(O)_2R^{b2}$, and $S(O)_2NR^{c2}R^{d2}$, wherein said $C_{1-6}$ alkyl, $C_{6-10}$ aryl, and 5-10 membered heteroaryl are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

18. The compound of claim 1, or a pharmaceutically acceptable salt thereof, wherein each $R^3$ is independently selected from $C_{1-6}$ alkyl, $C_{6-10}$ aryl, 5-10 membered heteroaryl, $C(O)R^{b2}$, $C(O)NR^{c2}R^{d2}$, $C(O)OR^{a2}$, and $S(O)_2R^{b2}$, wherein said $C_{1-6}$ alkyl, $C_{6-10}$ aryl, and 5-10 membered heteroaryl are each optionally substituted with 1, 2, 3, or 4 substituents independently selected from halo, $C_{1-4}$ alkyl, $C_{1-4}$ haloalkyl, $C_{1-4}$ cyanoalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)$ NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

19. The compound of claim 1, or a pharmaceutically acceptable salt thereof, wherein R$^Z$ is H, C$_{1-4}$ alkyl, or C$_{6-10}$ aryl-C$_{1-4}$ alkyl-, wherein said C$_{1-4}$ alkyl and C$_{6-10}$ aryl-C$_{1-4}$ alkyl- are each optionally substituted by halo or OR$^{a4}$.

20. The compound of claim 1, or a pharmaceutically acceptable salt thereof, wherein R$^Z$ is C$_{1-4}$ alkyl.

21. The compound of claim 1, or a pharmaceutically acceptable salt thereof, wherein R$^Z$ is C$_{1-4}$ alkyl substituted by methoxy.

22. The compound of claim 1, or a pharmaceutically acceptable salt thereof, wherein R$^Z$ is C$_{6-10}$ aryl-C$_{1-4}$ alkyl- substituted by fluoro.

23. The compound of claim 1, or a pharmaceutically acceptable salt thereof, wherein R$^Z$ is H, methyl, methoxymethyl, or 4-fluorophenylmethyl.

24. The compound of claim 1, or a pharmaceutically acceptable salt thereof, wherein R$^Z$ is H.

25. The compound of claim 1, or a pharmaceutically acceptable salt thereof, wherein p is 0.

26. The compound of claim 1, or a pharmaceutically acceptable salt thereof, wherein p is 1.

27. The compound of claim 1, or a pharmaceutically acceptable salt thereof, wherein p is 2.

28. The compound of claim 1, or a pharmaceutically acceptable salt thereof, wherein m is 0.

29. The compound of claim 1, or a pharmaceutically acceptable salt thereof, having a trans configuration with respect to the di-substituted cyclopropyl group depicted in Formula I.

30. The compound of claim 1 selected from:
(1-Methyl-3-{4-[(trans-2-phenylcyclopropyl)amino]piperidin-1-yl}azetidin-3-yl)acetonitrile;
(3-{4-[(trans-2-Phenylcyclopropyl)amino]piperidin-1-yl}azetidin-3-yl)acetonitrile;
(1-Benzyl-3-{4-[(trans-2-phenylcyclopropyl)amino]piperidin-1-yl}azetidin-3-yl)acetonitrile;
3-(3-(Cyanomethyl)-3-{4-[(trans-2-phenylcyclopropyl)amino]piperidin-1-yl}azetidin-1-yl)propanoic acid;
(1-Acetyl-3-{4-[(trans-2-phenylcyclopropyl)amino]piperidin-1-yl}azetidin-3-yl)acetonitrile;
(1-Benzoyl-3-{4-[(trans-2-phenylcyclopropyl)amino]piperidin-1-yl}azetidin-3-yl)acetonitrile;
Methyl 3-(cyanomethyl)-3-{4-[(trans-2-phenylcyclopropyl)amino]piperidin-1-yl}azetidine-1-carboxylate;
(1-(Methylsulfonyl)-3-{4-[(trans-2-phenylcyclopropyl)amino]piperidin-1-yl}azetidin-3-yl)acetonitrile;
2-(3-(Cyanomethyl)-3-{4-[(trans-2-phenylcyclopropyl)amino]piperidin-1-yl}azetidin-1-yl)nicotinonitrile;
3-Cyano-4-(3-(cyanomethyl)-3-{4-[(trans-2-phenylcyclopropyl)amino]piperidin-1-yl}azetidin-1-yl)benzoic acid;
2-(3-(Cyanomethyl)-3-{4-[(trans-2-phenylcyclopropyl)amino]piperidin-1-yl}azetidin-1-yl)benzonitrile;
4-(3-(Cyanomethyl)-3-{4-[(trans-2-phenylcyclopropyl)amino]piperidin-1-yl}azetidin-1-yl)benzonitrile;
[1-(Ethylsulfonyl)-3-(4-{[(trans-2-phenylcyclopropyl)amino]methyl}piperidin-1-yl)azetidin-3-yl]acetonitrile;
[3-(4-{[(trans-2-Phenylcyclopropyl)amino]methyl}piperidin-1-yl)azetidin-3-yl]acetonitrile;
2-[3-(Cyanomethyl)-3-(4-{[(trans-2-phenylcyclopropyl)amino]methyl}piperidin-1-yl)azetidin-1-yl]nicotinonitrile;
4-[3-(Cyanomethyl)-3-(4-{[(trans-2-phenylcyclopropyl)amino]methyl}piperidin-1-yl)azetidin-1-yl]-2,5-difluoro-N-isopropylbenzamide;
{3-(4-{[(trans-2-Phenylcyclopropyl)amino]methyl}piperidin-1-yl)-1-[3-(trifluoromethyl)pyridin-2-yl]azetidin-3-yl}acetonitrile;
{3-(4-{[(trans-2-Phenylcyclopropyl)amino]methyl}piperidin-1-yl)-1-[5-(trifluoromethyl)pyridin-2-yl]azetidin-3-yl}acetonitrile;
2-Chloro-6-[3-(cyanomethyl)-3-(4-{[(trans-2-phenylcyclopropyl)amino]methyl}piperidin-1-yl)azetidin-1-yl]benzonitrile;
2-[3-(Cyanomethyl)-3-(4-{[(trans-2-phenylcyclopropyl)amino]methyl}piperidin-1-yl)azetidin-1-yl]benzonitrile;
4-[3-(Cyanomethyl)-3-(4-{[(trans-2-phenylcyclopropyl)amino]methyl}piperidin-1-yl)azetidin-1-yl]benzonitrile;
Methyl 3-(cyanomethyl)-3-(4-{[(trans-2-phenylcyclopropyl)amino]methyl}piperidin-1-yl)azetidine-1-carboxylate;
3-(Cyanomethyl)-N-(2,4-difluorophenyl)-3-(4-{[(trans-2-phenylcyclopropyl)amino]methyl}piperidin-1-yl)azetidine-1-carboxamide;
N-(3-Chloro-2-fluorophenyl)-3-(cyanomethyl)-3-(4-{[(trans-2-phenylcyclopropyl)amino]methyl}piperidin-1-yl)azetidine-1-carboxamide;
[1-(3,5-Difluorobenzoyl)-3-(4-{[(trans-2-phenylcyclopropyl)amino]methyl}piperidin-1-yl)azetidin-3-yl]acetonitrile;
[1-Benzoyl-3-(4-{[(trans-2-phenylcyclopropyl)amino]methyl}piperidin-1-yl)azetidin-3-yl]acetonitrile;
[1-(2-Fluorobenzoyl)-3-(4-{[(trans-2-phenylcyclopropyl)amino]methyl}piperidin-1-yl)azetidin-3-yl]acetonitrile;
[1-(3-Fluorobenzoyl)-3-(4-{[(trans-2-phenylcyclopropyl)amino]methyl}piperidin-1-yl)azetidin-3-yl]acetonitrile;
[1-(4-Fluorobenzoyl)-3-(4-{[(trans-2-phenylcyclopropyl)amino]methyl}piperidin-1-yl)azetidin-3-yl]acetonitrile;
[1-Methyl-3-(4-{[(trans-2-phenylcyclopropyl)amino]methyl}piperidin-1-yl)azetidin-3-yl]acetonitrile;
[3-(4-{[(trans-2-Phenylcyclopropyl)amino]methyl}piperidin-1-yl)azetidin-3-yl]acetic acid;
N-Methyl-2-(3-(4-((trans-2-phenylcyclopropylamino)methyl)piperidin-1-yl)azetidin-3-yl)acetamide; and
N,N-Dimethyl-2-(3-(4-((trans-2-phenylcyclopropylamino)methyl)piperidin-1-yl)azetidin-3-yl)acetamide,
or a pharmaceutically acceptable salt of any of the aforementioned.

31. The compound of claim 1 selected from:
[1-(methylsulfonyl)-3-(4-{[(1R,2S)-2-phenylcyclopropyl]amino}piperidin-1-yl)azetidin-3-yl]acetonitrile;
[1-methyl-3-(4-{[(1R,2S)-2-phenylcyclopropyl]amino}piperidin-1-yl)azetidin-3-yl]acetonitrile;
[3-(4-{[(1R,2S)-2-phenylcyclopropyl]amino}piperidin-1-yl)azetidin-3-yl]acetonitrile;
[3-(4-{[(1S,2R)-2-phenylcyclopropyl]amino}piperidin-1-yl)azetidin-3-yl]acetonitrile;
[1-(ethylsulfonyl)-3-(4-{[(1R,2S)-2-phenylcyclopropyl]amino}piperidin-1-yl)azetidin-3-yl]acetonitrile;
3-(cyanomethyl)-N,N-dimethyl-3-(4-{[(1R,2S)-2-phenylcyclopropyl]amino}piperidin-1-yl)azetidine-1-sulfonamide;

3-(cyanomethyl)-N-methyl-3-(4-{[(1R,2S)-2-phenylcyclopropyl]amino}piperidin-1-yl)azetidine-1-sulfonamide;

3-(cyanomethyl)-3-(4-{[(1R,2S)-2-phenylcyclopropyl]amino}piperidin-1-yl)azetidine-1-sulfonamide;

[1-methyl-3-(4-{[(1R,2S)-2-phenylcyclopropyl]amino}piperidin-1-yl)azetidin-3-yl]acetic acid;

[1-ethyl-3-(4-{[(1R,2S)-2-phenylcyclopropyl]amino}piperidin-1-yl)azetidin-3-yl]acetic acid;

2-[1-(ethylsulfonyl)-3-(4-{[(1R,2S)-2-phenylcyclopropyl]amino}piperidin-1-yl)azetidin-3-yl]-N,N-dimethylacetamide; and 2-[1-(ethylsulfonyl)-3-(4-{[(1R,2S)-2-phenylcyclopropyl]amino}piperidin-1-yl)azetidin-3-yl]-N-methylacetamide;

or a pharmaceutically acceptable salt of any of the aforementioned.

32. The compound of claim 1 selected from:

[1-(1-methyl-1H-pyrazol-4-yl)-3-(4-{[(1R,2S)-2-phenylcyclopropyl]amino}piperidin-1-yl)azetidin-3-yl]acetonitrile;

[1-(2-hydroxyethyl)-3-(4-{[(1R,2S)-2-phenylcyclopropyl]amino}piperidin-1-yl)azetidin-3-yl]acetonitrile;

[1-(3-hydroxycyclobutyl)-3-(4-{[(1R,2S)-2-phenylcyclopropyl]amino}piperidin-1-yl)azetidin-3-yl]acetonitrile;

[1-(cis-4-hydroxycyclohexyl)-3-(4-{[(1R,2S)-2-phenylcyclopropyl]amino}piperidin-1-yl)azetidin-3-yl]acetonitrile;

[1-(isothiazol-5-ylcarbonyl)-3-(4-{[(1R,2S)-2-phenylcyclopropyl]amino}piperidin-1-yl)azetidin-3-yl]acetonitrile;

[1-(morpholin-4-ylcarbonyl)-3-(4-{[(1R,2S)-2-phenylcyclopropyl]amino}piperidin-1-yl)azetidin-3-yl]acetonitrile;

[1-(trans-4-hydroxycyclohexyl)-3-(4-{[(1R,2S)-2-phenylcyclopropyl]amino}piperidin-1-yl)azetidin-3-yl]acetonitrile;

[1-[(1-hydroxycyclopentyl)carbonyl]-3-(4-{[(1R,2S)-2-phenylcyclopropyl]amino}piperidin-1-yl)azetidin-3-yl]acetonitrile;

[1-[(1-hydroxycyclopropyl)carbonyl]-3-(4-{[(1R,2S)-2-phenylcyclopropyl]amino}piperidin-1-yl)azetidin-3-yl]acetonitrile;

[1-[(1-methyl-1H-pyrazol-4-yl)carbonyl]-3-(4-{[(1R,2S)-2-phenylcyclopropyl]amino}piperidin-3-yl]acetonitrile;

[1-[(1-methyl-1H-pyrazol-4-yl)sulfonyl]-3-(4-{[(1R,2S)-2-phenylcyclopropyl]amino}piperidin-1-yl)azetidin-3-yl]acetonitrile;

[1-[(1-methyl-1H-pyrazol-5-yl)carbonyl]-3-(4-{[(1R,2S)-2-phenylcyclopropyl]amino}piperidin-3-yl]acetonitrile;

[1-[(3-hydroxyazetidin-1-yl)carbonyl]-3-(4-{[(1R,2S)-2-phenylcyclopropyl]amino}piperidin-1-yl)azetidin-3-yl]acetonitrile;

[1-[(4-hydroxypiperidin-1-yl)carbonyl]-3-(4-{[(1R,2S)-2-phenylcyclopropyl]amino}piperidin-1-yl)azetidin-3-yl]acetonitrile;

[1-[(4-methoxypiperidin-1-yl)carbonyl]-3-(4-{[(1R,2S)-2-phenylcyclopropyl]amino}piperidin-1-yl)azetidin-3-yl]acetonitrile;

[1-[(cis-4-hydroxycyclohexyl)carbonyl]-3-(4-{[(1R,2S)-2-phenylcyclopropyl]amino}piperidin-1-yl)azetidin-3-yl]acetonitrile;

[1-[(trans-4-hydroxycyclohexyl)carbonyl]-3-(4-{[(1R,2S)-2-phenylcyclopropyl]amino}piperidin-1-yl)azetidin-3-yl]acetonitrile;

[3-(4-{[(1R,2S)-2-(4-fluorophenyl)cyclopropyl]amino}piperidin-1-yl)-1-(4-hydroxycyclohexyl)azetidin-3-yl]acetonitrile;

[3-(4-{[(1R,2S)-2-(4-fluorophenyl)cyclopropyl]amino}piperidin-1-yl)-1-(methylsulfonyl)azetidin-3-yl]acetonitrile;

[3-(4-{[(1R,2S)-2-phenylcyclopropyl]amino}piperidin-1-yl)-1-(1,3-thiazol-5-ylcarbonyl)azetidin-3-yl]acetonitrile;

[3-(4-{[(1R,2S)-2-phenylcyclopropyl]amino}piperidin-1-yl)-1-(1H-pyrazol-4-ylcarbonyl)azetidin-3-yl]acetonitrile;

[3-(4-{[(1R,2S)-2-phenylcyclopropyl]amino}piperidin-1-yl)-1-(pyrazin-2-ylcarbonyl)azetidin-3-yl]acetonitrile;

[3-(4-{[(1R,2S)-2-phenylcyclopropyl]amino}piperidin-1-yl)-1-(tetrahydro-2H-pyran-4-yl)azetidin-3-yl]acetonitrile;

[3-(4-{[(1R,2S)-2-phenylcyclopropyl]amino}piperidin-1-yl)-1-(tetrahydrofuran-3-yl)azetidin-3-yl]acetonitrile;

[3-(4-{[(1R,2S)-2-phenylcyclopropyl]amino}piperidin-1-yl)-1-(tetrahydrofuran-3-ylcarbonyl)azetidin-3-yl]acetonitrile;

2-(3-(4-(((1R,2S)-2-phenylcyclopropyl)amino)piperidin-1-yl)-1-(tetrahydrofuran-2-carbonyl)azetidin-3-yl)acetonitrile;

2-(3-(cyanomethyl)-3-(4-(((1R,2S)-2-phenylcyclopropyl)amino)piperidin-1-yl)azetidin-1-yl)-N,N-dimethylacetamide;

2-[1-(ethylsulfonyl)-3-(4-{[(1R,2S)-2-phenylcyclopropyl]amino}piperidin-1-yl)azetidin-3-yl]ethanol;

2-[1-(methylsulfonyl)-3-(4-{[(1R,2S)-2-phenylcyclopropyl]amino}piperidin-1-yl)azetidin-3-yl]ethanol;

2-[3-(cyanomethyl)-3-(4-{[(1R,2S)-2-phenylcyclopropyl]amino}piperidin-1-yl)azetidin-1-yl]acetamide;

2-[3-(cyanomethyl)-3-(4-{[(1R,2S)-2-phenylcyclopropyl]amino}piperidin-1-yl)azetidin-1-yl]-N-methylacetamide;

3-(cyanomethyl)-3-(4-{[(1R,2S)-2-(4-fluorophenyl)cyclopropyl]amino}piperidin-1-yl)azetidine-1-sulfonamide;

3-[2-(dimethylamino)-2-oxoethyl]-N,N-dimethyl-3-(4-{[(1R,2S)-2-phenylcyclopropyl]amino}piperidin-1-yl)azetidine-1-carboxamide;

methyl 3-[2-(dimethylamino)-2-oxoethyl]-3-(4-{[(1R,2S)-2-phenylcyclopropyl]amino}piperidin-1-yl)azetidine-1-carboxylate;

methyl 3-[2-(methylamino)-2-oxoethyl]-3-(4-{[(1R,2S)-2-phenylcyclopropyl]amino}piperidin-1-yl)azetidine-1-carboxylate;

N,N-dimethyl-2-(1-(methylsulfonyl)-3-(4-(((1R,2S)-2-phenylcyclopropyl)amino)piperidin-1-yl)azetidin-3-yl)acetamide;

N,N-dimethyl-3-[2-(methylamino)-2-oxoethyl]-3-(4-{[(1R,2S)-2-phenylcyclopropyl]amino}piperidin-1-yl)azetidine-1-carboxamide;

N-methyl-2-[1-(methylsulfonyl)-3-(4-{[(1R,2S)-2-phenylcyclopropyl]amino}piperidin-1-yl)azetidin-3-yl]acetamide;

tetrahydrofuran-3-yl 3-(cyanomethyl)-3-(4-{[(1R,2S)-2-phenylcyclopropyl]amino}piperidin-1-yl)azetidine-1-carboxylate;

[3-(4-{[(1R,2S)-2-phenylcyclopropyl]amino}piperidin-1-yl)-1-(1H-pyrazol-5-ylcarbonyl)azetidin-3-yl]acetonitrile;

{3-(4-{[(1R,2S)-2-phenylcyclopropyl]amino}piperidin-1-yl)-1-[(3R)-tetrahydrofuran-3-ylcarbonyl]azetidin-3-yl}acetonitrile;

{3-(4-{[(1R,2S)-2-phenylcyclopropyl]amino}piperidin-1-yl)-1-[(3S)-tetrahydrofuran-3-ylcarbonyl]azetidin-3-yl}acetonitrile;

{3-(4-{[(1R,2S)-2-phenylcyclopropyl]amino}piperidin-1-yl)-1-[(2S)-tetrahydrofuran-2-ylcarbonyl]azetidin-3-yl}acetonitrile;

{3-(4-{[(1R,2S)-2-phenylcyclopropyl]amino}piperidin-1-yl)-1-[(2R)-tetrahydrofuran-2-ylcarbonyl]azetidin-3-yl}acetonitrile;

[3-(4-{[(1R,2S)-2-phenylcyclopropyl]amino}piperidin-1-yl)-1-(pyridin-2-ylacetyl)azetidin-3-yl]acetonitrile;

[3-(4-{[(1R,2S)-2-phenylcyclopropyl]amino}piperidin-1-yl)-1-(1,3-thiazol-4-ylcarbonyl)azetidin-3-yl]acetonitrile;

[3-(4-{[(1R,2S)-2-phenylcyclopropyl]amino}piperidin-1-yl)-1-(1,3-thiazol-2-ylcarbonyl)azetidin-3-yl]acetonitrile;

N,N-dimethyl-2-[3-(4-{[(1R,2S)-2-phenylcyclopropyl]amino}piperidin-1-yl)-1-(tetrahydro-2H-pyran-4-yl)azetidin-3-yl]acetamide;

N-methyl-2-[3-(4-{[(1R,2S)-2-phenylcyclopropyl]amino}piperidin-1-yl)-1-(tetrahydro-2H-pyran-4-yl)azetidin-3-yl]acetamide;

2-[1-(cyclopropylmethyl)-3-(4-{[(1R,2S)-2-phenylcyclopropyl]amino}piperidin-1-yl)azetidin-3-yl]-N,N-dimethylacetamide;

2-[1-(cyclopropylmethyl)-3-(4-{[(1R,2S)-2-phenylcyclopropyl]amino}piperidin-1-yl)azetidin-3-yl]-N-methylacetamide;

[3-(4-{[(1R,2S)-2-phenylcyclopropyl]amino}piperidin-1-yl)-1-(pyrimidin-2-ylmethyl)azetidin-3-yl]acetic acid;

[3-(4-{[(1R,2S)-2-phenylcyclopropyl]amino}piperidin-1-yl)-1-(pyrimidin-5-ylmethyl)azetidin-3-yl]acetic acid;

[3-(4-{[(1R,2S)-2-phenylcyclopropyl]amino}piperidin-1-yl)-1-(1,3-thiazol-4-ylmethyl)azetidin-3-yl]acetic acid;

[3-(4-{[(1R,2S)-2-phenylcyclopropyl]amino}piperidin-1-yl)-1-(1,3-thiazol-5-ylmethyl)azetidin-3-yl]acetic acid;

[3-(4-{[(1R,2S)-2-phenylcyclopropyl]amino}piperidin-1-yl)-1-(1,3-thiazol-2-ylmethyl)azetidin-3-yl]acetic acid; and

[3-(4-{[(1R,2S)-2-phenylcyclopropyl]amino}piperidin-1-yl)-1-(3,3,3-trifluoropropyl)azetidin-3-yl]acetic acid, or a pharmaceutically acceptable salt of any of the aforementioned.

33. A pharmaceutical composition comprising a compound of claim 1, or a pharmaceutically acceptable salt thereof, and at least one pharmaceutically acceptable carrier.

* * * * *